(12) United States Patent
Choong et al.

(10) Patent No.: US 8,975,247 B2
(45) Date of Patent: Mar. 10, 2015

(54) METHODS AND COMPOSITIONS OF TREATING A FLAVIVIRIDAE FAMILY VIRAL INFECTION

(75) Inventors: Ingrid C. Choong, Los Altos, CA (US); David Cory, Redwood City, CA (US); Jeffrey S. Glenn, Palo Alto, CA (US); Wenjin Yang, Foster City, CA (US)

(73) Assignee: The Board of Trustees of the Leland Stanford Junion University, Palo Alto, CA (US)

( * ) Notice: Subject to any disclaimer, the term of this patent is extended or adjusted under 35 U.S.C. 154(b) by 0 days.

(21) Appl. No.: 13/376,483

(22) PCT Filed: Mar. 16, 2010

(86) PCT No.: PCT/US2010/027400
§ 371 (c)(1),
(2), (4) Date: Jul. 16, 2012

(87) PCT Pub. No.: WO2010/107739
PCT Pub. Date: Sep. 23, 2010

(65) Prior Publication Data
US 2012/0276050 A1 Nov. 1, 2012

Related U.S. Application Data

(63) Continuation-in-part of application No. 12/383,030, filed on Mar. 18, 2009, and a continuation-in-part of application No. 12/383,071, filed on Mar. 18, 2009.

(60) Provisional application No. 61/299,886, filed on Jan. 29, 2010.

(51) Int. Cl.
| | |
|---|---|
| A01N 43/52 | (2006.01) |
| A61K 31/415 | (2006.01) |
| A01N 43/40 | (2006.01) |
| A61K 31/445 | (2006.01) |
| A01N 43/04 | (2006.01) |
| A61K 31/70 | (2006.01) |
| A01N 43/00 | (2006.01) |
| A61K 31/55 | (2006.01) |
| A61K 31/4184 | (2006.01) |
| A61K 31/437 | (2006.01) |
| A61K 31/4965 | (2006.01) |
| A61K 45/06 | (2006.01) |
| C07D 235/06 | (2006.01) |
| C07D 235/08 | (2006.01) |
| C07D 235/10 | (2006.01) |
| C07D 235/14 | (2006.01) |
| C07D 235/16 | (2006.01) |
| C07D 235/28 | (2006.01) |
| C07D 401/04 | (2006.01) |
| C07D 401/06 | (2006.01) |
| C07D 401/12 | (2006.01) |
| C07D 401/14 | (2006.01) |
| C07D 403/06 | (2006.01) |
| C07D 403/14 | (2006.01) |
| C07D 405/06 | (2006.01) |
| C07D 409/06 | (2006.01) |
| C07D 413/06 | (2006.01) |
| C07D 417/04 | (2006.01) |
| C07D 471/08 | (2006.01) |
| C07D 491/04 | (2006.01) |

(52) U.S. Cl.
CPC ........... *A61K 31/4184* (2013.01); *A61K 31/437* (2013.01); *A61K 31/4965* (2013.01); *A61K 45/06* (2013.01); *C07D 235/06* (2013.01); *C07D 235/08* (2013.01); *C07D 235/10* (2013.01); *C07D 235/14* (2013.01); *C07D 235/16* (2013.01); *C07D 235/28* (2013.01); *C07D 401/04* (2013.01); *C07D 401/06* (2013.01); *C07D 401/12* (2013.01); *C07D 401/14* (2013.01); *C07D 403/06* (2013.01); *C07D 403/14* (2013.01); *C07D 405/06* (2013.01); *C07D 409/06* (2013.01); *C07D 413/06* (2013.01); *C07D 417/04* (2013.01); *C07D 471/08* (2013.01); *C07D 491/04* (2013.01)
USPC ............ 514/183; 514/395; 514/322; 514/43; 514/217.09

(58) Field of Classification Search
None
See application file for complete search history.

(56) References Cited

U.S. PATENT DOCUMENTS

| | | | |
|---|---|---|---|
| 2,684,327 A | | 7/1954 | Passal et al. |
| 2,689,853 A | | 9/1954 | Schenck et al. |

(Continued)

FOREIGN PATENT DOCUMENTS

| | | |
|---|---|---|
| DE | 102007028521 A1 | 12/2008 |
| EP | 1400241 A1 | 3/2004 |

(Continued)

OTHER PUBLICATIONS

Patani et al., "Bioisosterism: A Rationale Approach in Drug Design," Chem. Rev. 1996, 96, 3147-3176.*
Einav et al., "Discovery of a Hepatitis C Target and Its Pharmacological Inhibitors by Microfluidic Affinity Analysis," Nature Biotechnology (Aug. 31, 2008), 26(9), 1019-1027.*
CAS RN: 872583-99-8 (entered STN Jan. 25, 2006).*
STN CAS RN: 7188-79-6 (entered Nov. 16, 1984).*
Echeverri, A.C. & Dasgupta, A. Amino Terminal Regions of Poliovirus 2C Protein Mediate Membrane Binding. Virology, 1995. vol. 208, pp. 540-553.

(Continued)

*Primary Examiner* — Craig Ricci
*Assistant Examiner* — Jared D Barsky
(74) *Attorney, Agent, or Firm* — Thomas|Horstemeyer, LLP

(57) ABSTRACT

Clemizole and clemizole analog compounds, and pharmaceutical compositions of the same, are useful in methods of treating a host infected with a virus from the Flaviviridae family of viruses, methods of inhibiting HCV replication in a host, methods of inhibiting the binding of NS4B polypeptide to the 3'UTR of HCV negative strand RNA in a host, and methods of treating liver fibrosis in a host.

5 Claims, No Drawings

(56) References Cited

U.S. PATENT DOCUMENTS

| | | | |
|---|---|---|---|
| 3,265,691 | A | 8/1966 | Richter et al. |
| 3,423,413 | A * | 1/1969 | Priewe et al. ............... 544/370 |
| 3,428,634 | A | 2/1969 | Palazzo |
| 4,011,322 | A | 3/1977 | Rahtz et al. |
| 4,269,835 | A | 5/1981 | Whittle |
| 5,552,426 | A | 9/1996 | Lunn et al. |
| 6,211,177 | B1 | 4/2001 | Sperl et al. |
| 6,369,235 | B1 | 4/2002 | Michejda et al. |
| 6,476,062 | B2 | 11/2002 | Chu |
| 7,495,015 | B2 | 2/2009 | Arora et al. |
| 2002/0128307 | A1 | 9/2002 | Chu |
| 2004/0092575 | A1 | 5/2004 | Peuvot et al. |
| 2004/0097438 | A1 | 5/2004 | Hashimoto et al. |
| 2004/0224876 | A1* | 11/2004 | Jost-Price et al. ............ 514/11 |
| 2005/0187261 | A1 | 8/2005 | Verner et al. |
| 2005/0192261 | A1* | 9/2005 | Jost-Price et al. ............ 514/171 |
| 2006/0052602 | A1 | 3/2006 | Kim et al. |
| 2008/0161324 | A1 | 7/2008 | Johansen |
| 2010/0028299 | A1 | 2/2010 | Einav et al. |

FOREIGN PATENT DOCUMENTS

| | | |
|---|---|---|
| KR | 10-1995-0031074 A | 12/1995 |
| WO | 0204425 A2 | 1/2002 |
| WO | 2002007761 A1 | 3/2002 |
| WO | 2003060475 A2 | 7/2003 |
| WO | 2005012288 A1 | 2/2005 |
| WO | 2005/032329 | 4/2005 |
| WO | 2006010446 A2 | 2/2006 |
| WO | 2006131737 | 12/2006 |
| WO | 2006131737 A2 | 12/2006 |
| WO | 2006135383 A2 | 12/2006 |
| WO | 2007103111 A2 | 9/2007 |
| WO | 2007115077 A2 | 10/2007 |
| WO | 2007117465 A2 | 10/2007 |
| WO | PCT/US2007/019932 | 3/2008 |
| WO | 2009039248 A2 | 3/2009 |

OTHER PUBLICATIONS

Rodriguez, P.L. & Carrasco L. Poliovirus Protein 2C Contains Two Regions Involved in RNA Binding Activity. J. Biol. Chem. 1995, vol. 270 (17), pp. 10105-10112.

Hadd, A.D. et al. Microchip Device for Performing Enzyme Assays. Anal. Chem. 1997, vol. 69, pp. 3407-3412.

El-Hage, N. & Luo, G. Replication of Hepatitis C Virus RNA Occurs in a Membrane-Bound Replication Complex Containing Nonstructural Viral Proteins and RNA. Journal of General Virology, 2003, vol. 84, pp. 2761-2769.

Park-Lee et al. Characterization of the Interaction between Neuronal RNA-binding Protein HuD and AU-rich RNA. Journal of Biological Chemistry, 2003, vol. 278(41) pp. 39801-39808.

Einav, S. et al. A Nucleotide Binding Motif in Hepatitis C Virus (HCV) NS4B Mediates HCV RNA Replication. Journal of Virology, 2004, vol. 78(20) pp. 11288-11295.

Lundin, M et al. Topology of the Membrane-Associated Hepatitis C Virus Protein NS4B. Journal of Virology, 2003, vol. 77(9), pp. 5428-5438.

Gosert, R. et al. Identification of the Hepatitis C Virus RNA Replication Complex in Huh-7 Cells Harboring Subgenomic Replicons. Journal of Virology, 2003, vol. 77(9), pp. 5487-5492.

Tscherne, D.M. Time- and Temperature-Dependent Activation of Hepatitis C Virus for Low-pH-Triggered Entry. Journal of Virology, 2006, vol. 80(4), pp. 1734-1741.

Elazar, M. et al. An N-Terminal Amphipathic Helix in Hepatitis C Virus (HCV) NS4B Mediates Membrane Association, Correct Localization of Replication Complex Proteins, and HCV RNA Replication. Journal of Virology, 2004, vol. 78(20), pp. 11393-11400.

Dimitrova M. et al. Protein-Protein Interactions between Hepatitis C Virus Nonstructural Proteins. Journal of Virology, 2003, vol. 77(9), pp. 5401-5414.

Glenn J.S. et al. In Vitro-Synthesized Hepatitis Delta Virus RNA Initiates Genome Replication in Cultured Cells. Journal of Virology, 1990, vol. 64(6), pp. 3104-3107.

Huang L. et al. Hepatitis C Virus Nonstructural Protein 5A (NS5A) Is an RNA-binding Protein. Journal of Biological Chemistry, 2005, vol. 280(43) pp. 36414-36428.

Elazar, M. et al. Amphipathic Helix-Dependent Localization of NS5A Mediates Hepatitis C Virus RNA Replication. Journal of Virology, 2003, vol. 77(70), pp. 6055-6061.

Egger D. et al. Expression of Hepatitis C Virus Proteins Induces Distinct Membrane Alterations Including a Candidate Viral Replication Complex. Journal of Virology, 2002, vol. 76(12), pp. 5974-5984.

Kang L. et al. Microfluidics for drug discovery and development: From target selection to product lifecycle management. Drug Discovery Today, 2008, vol. 13 (1/2), pp. 1-13.

Kusov YY. et al. Membrane association and RNA binding of recombinant hepatitis A virus protein 2C. Arch Virol. 1998, vol. 143, pp. 931-944.

Liang, T.J. et al. Pathogenesis, Natural History, Treatment, and Prevention of Hepatitis C, Ann. Intern. Med., 2000, vol. 132, pp. 296-305.

Park, S. et al. HuD RNA Recognition Motifs Play Distinct Roles in the Formation of a Stable Complex with AU-Rich RNA. Mol. Cell. Biol. 2000, vol. 20(13), pp. 4765-4772.

Lee, N. L. et al. Solvent Compatibility of Poly(dimethylsiloxane)-Based Microfluidic Devices. Anal. Chem., 2003, vol. 75, pp. 6544-6554.

Roosild, T.P. et al. NMR Structure of Mistic, a Membrane-Integrating Protein for Membrane Protein Expression. Science, 2005, vol. 307, pp. 1317.

Reed K.E. & Rice C.M. Overview of Hepatitis C Virus Genome Structure, Polyprotein Processing, and Protein Properties. The Hepatitis C Viruses, Current Topics in Microbiology and Immunology, 2000, vol. 242, pp. 55-84.

Overington, J.P. et al. How many drug targets are there? Nat Rev Drug Discov. 2006, vol. 5, pp. 993-996.

Maerkl, SJ. et al. A Systems Approach to Measuring the Binding Energy Landscapes of Transcription Factors. Science, 2007, vol. 315, pp. 233-237.

Toepke, MW, et al. PDMS absorption of small molecules and consequences in microfluidic applications. Lab on a Chip, 2006, vol. 6, pp. 1484-1483.

Whitesides, GM. The origins and the future of microfluidics. Nature 2006, vol. 442, pp. 368-373.

Myer, VE et al. Identification of HuR as a protein implicated in AUUUA-mediated mRNA decay. The EMBO Journal, 1997, vol. 16, pp. 2130-2139.

Glenn, JS. et al. In Vitro-Synthesized Hepatitis Delta Virus RNA Initiates Genome Replication in Cultured Cells. Journal of Virology, 1990, vol. 64(6), pp. 3104-3107.

Glenn, JS et al. Identification of a Prenylation Site in Delta Virus Large Antigen. Science, 1992, vol. 256, pp. 1331-1333.

Burd, CG & Dreyfuss G. Conserved Structures and Diversity of Functions of RNA-Binding Proteins. Science, 1994, vol. 265, pp. 615-621.

Wung, CH et al. Identification of the RNA-binding sites of the triple gene block protein 1 of bamboo mosaic potexvirus. J. Gen. Virol. 1999, vol. 80, pp. 1119-1126.

Spangberg, K et al. HuR, a Protein Implicated in Oncogene and Growth Factor mRNA Decay, Binds to the 39 Ends of Hepatitis C Virus Rna of Both Polarities. Virology, 2000, vol. 274, pp. 378-390.

Lindenbach et al. Complete Replication of Hepatitis C Virus in Cell Culture. Science, 2005, vol. 309, pp. 623-626.

Tong X et al. Identification and analysis of fitness of resistance mutations against the HCV protease inhibitor SCH 503034. Antiviral Research, 2006, vol. 70, pp. 28-38.

Blight KJ et al. Efficient Initiation of HCV RNA Replication in Cell Culture. Science, 2000, vol. 290, pp. 1972-1974.

Schilders G. et al. MPP6 is an exosome-associated RNA-binding protein involved in 5.8S rRNA maturation. Nucleic Acids Research, 2005, vol. 33(21), pp. 6795-6804.

Gupta AK et al. Antifungal Agents: An overview. Part I. Journal of the American Academy of Dermatology, 1994, vol. 30(5) Part 1, pp. 677-698.

The International Search Report and Written Opinion dated Aug. 13, 2009.

(56) References Cited

OTHER PUBLICATIONS

Testa; "Prodrug research: futile or fertile?", 2004, Biochemical Pharmacology; 68:2097-2106.
Selwood, D.L., et al. "Synthesis and Biological Evaluation of Novel Pyrazoles and Indazoles as Activators of the Nitric Oxide Receptor, Soluable Guanylate Cyclase", Journal of Medicinal Chemistry, 2001, vol. 44, pp. 78-93.
The International Search Report and Written Opinion dated Dec. 27, 2010.
Patel, PD, et al. 3D QSAR and Molecular Docking Studies of Benzimidazole Derivatives as Hepatitis C Virus NS5B Polymerase Inhibitors, Journal of Chemical Information and Modeling, 2008, vol. 48, pp. 42-55.
Einav, S., et al., "The Hepatitis C Virus (HCV) NS4B RNA Binding Inhibitor Clemizole is Highly Synergistic with HCV Protease Inhibitors," Anti-HCV Drug Synergy with Clemizole, JID 2010:202 (Jul. 1) pp. 65-74.
Cho, et al., "Identification of a Class of HCV Inhibitors Directed Against the Nonstructural Protein NS4B," www.scienceTranslationalMedicine.org, Jan. 20, 2010, vol. 2, Issue 15, pp. 1-8.
Cho, et al., Supplementary Materials for "Identification of a Class of HCV Inhibitors Directed Against the Nonstructural Protein NS4B," www.scienceTranslationalMedicine.org, Jan. 20, 2010, vol. 2, Issue 15, pp. 1-23.
International Search Report and Written Opinion dated Apr. 1, 2009.
Blight, K.J. et al., "Allelic Variation in the Hepatitis C Virus NS4B Protein Dramatically Influences RNA Replication," J. Virology, Jun 2007, vol. 81, No. 11, pp. 5724-5736.
Einav, S. et al., "A Nucleotide Binding Motif in Hepatitis C Virus (HCV) NS4B Mediates HCV RNA Replication, " J. Virology, Oct. 2004, vol.78, No. 20, pp. 11288-11295.
Puerstinger, G., et al., "Antiviral 2,5-disubstituted Imidazo[4,5-c]pyridines: From Anti-Pestivirus to Anti-Hepatitis C Virus Activity, " Bioorganic Medicinal Chemistry Letters, Jan. 2007, vol. 17, No. 2, pp. 390-393.
Hirashima, S., et al. "Benzimidazole Derivatives Bearing Substituted Biphenyls as Hepatitis C Virus NS5B RNA-Dependent RNA Polymerase Inhibitors: Structure-Activity Relationship Studies and Identification of a Potent and Highly Selective Inhibitor JTK-109," J. Medicinal Chemistry, Jun. 2006, vol. 49, No. 15, pp. 4721-4736.
Korba, B.E., et al. "Nitazoxanide, Tizoaxanide and Other Thiazolides are Potent Inhibitors of Hepatitis B Virus and Hepatitis C Virus Replication," Antiviral Research, Sep. 4, 2007, vol.77, No. 1, pp. 56-63.
Blight, et al.; Efficient Initiation of HCV RNA Replication in Cell Culture; Science; vol. 290; Dec. 8, 2009, 1972-1974.
Takhampunya, et al.; Inhibition of Dengue Virus Replication by Mycophenolic Acid and Ribavirin; Journal of General Virology; vol. 87; 2006; 1947-1952.
Hwang, et al.; Inhibition of Hepatitis C Virus Replication by Arsenic Trioxide; Antimicrobial Agents and Chemotheraphy; vol. 48, No. 8; Aug. 2004; p. 2876-2882.
Lohmann, et al.; Replication of Subgenomic Hepatitis C Virus RNAs in a Hepatoma Cell Line; Science; vol. 285; Jul. 2, 1999; pp. 110-113.

Maerkl, et al.; A Systems Approach to Measuring the Binding Energy Landscapes of Transcription Factors; Science; vol. 315; Jan. 12, 2007; pp. 233-237.
Voronina et al. "Synthesis and pharmaceutical properties of amidine analogs of pyracetatam". Khimiko-Farmatsevticheskii Zhurnal, 1990, vol. 24, 11:26-29. CAPLUS Abstract, AN 1991:101601.
The Supplemental European Search Report dated Jul. 2, 2012.
The Supplemental European Search Report dated Aug. 8, 2012.
Einav, et al., Discovery of a Hepatitis C Target and its Pharmacological Inhibitors by Microfluidic Affinity Analysis, Nature Biotechnology, Nature Publishing Group, New York, NY, vol. 26, No. 9, Sep. 1, 2008, pp. 1019-1027.
Caroti, et al., "Synthesis, Antilipidemic and Platelet Antiaggregatory Activity of 2-Aminobenzimidazole Amide Derivatives," II Farmaco, Elsevier France, Scientifiques Et Medicals, IT, vol. 44, No. 3, Jan. 1, 1989, pp. 227-255.
Tuncbilek, et al., "Synthesis and Antimicrobial Activity of Some New Anilino Benzimidazoles," Archiv Der Pharmazie, Wiley, VH Verlag GmBH & Co. KGAA, Dec. 1, 1997, pp. 372-376.
Manganaro, et al., "Activity of Antiinflammatory Steroidal and Nonsteroidal Compounds in Some Experimental Functions, II, Activity of Certain Nonsteroidal Antiinflammatory Agents as Compared with that of Prednisone in Murine Hepatitis Due to MHV3," Inflammation, Plenum Press, New York, NY, vol. Proc. Int. Symp. No. 1968, Jan. 1, 1968, pp. 67-71.
Anonymous, Registry, Dec. 8, 2008, XP007920913.
Anonymous, Registry, Dec. 18, 1984-Dec. 22, 2009, XP007920912.
Anonymous, Registry, Nov. 8, 2004, XP007920909.
The Office Action dated Sep. 9, 2013 for Chinese Application Serial No. 201080021845.9, 4 pages.
The Office Action dated Sep. 11, 2013 for Chinese Application Serial No. 201080021850.X, 3 pages.
Supplemental European Search Report dated Oct. 13, 2011.
Beaulieu, P.L., et al., "Non-nucleoside Inhibitors of the Hepatitis C Virus NS5B polymerase: Discovery and Preliminary SAR of Benzimidazolde Derivatives," Bioorganic & Medicinal Chemistry Letters, Pergamon, Elsevier Science, GB, vol. 14, no. 1, Jan. 1, 2004, pp. 119-124.
Beaulieu, P.L., et al., "Improved Replicon Cellular Activity of Non-Nucleoside Allosteric Inhibitors of HCV NS5B Polymerase: From Benzimidazole to Indole Scaffolds," Bioorganic & Medicinal Chemistry Letters, Pergamon, Elsevier Science, GB, vol. 16, No. 19, Oct. 1, 2006, pp. 4987-4993.
"Martindale, The Complete Drug Reference", 2000, Pharmaceutical Press, XP000002659125, Clemizole Hydrocholoride, p. 406.
Einav, Shirit, et al., "Discovery of a Hepatitis C Target and its Pharmacological Inhibitors of Microfluidic Affinity Analysis," Nature Biotechnology, Nature Publishing Group, NY, vol. 26, No. 9, Sep. 1, 2008, pp. 1019-1027.
International Search and Written Opinion dated Dec. 27, 2010.
Beaulieu, et al., "Benzimidazoles as new potent and selective DP antagonists for the treatment of allergic rhinitis," Bioorganic & Medicial Chemistry Letters, 2004, vol. 14, pp. 3195-3199.
Einay, et al.,"Discovery of Hepatitis C Target and its Pharmacological Inhibitors by Microfluidic affivity analysis," Nature Biotechnology, Sep. 2008, vol. 26, No. 9, pp. 1019-1027.
The International Preliminary Report on Patentability dated Sep. 29, 2011.

\* cited by examiner

METHODS AND COMPOSITIONS OF TREATING A FLAVIVIRIDAE FAMILY VIRAL INFECTION

CROSS-REFERENCE TO RELATED APPLICATION

This application is the 35 U.S.C. §371 national stage of PCT Application "Methods and Composition of Treating a Flaviviridae Family Viral Infection," having serial number PCT/US2010/027400, filed on Mar. 16, 2010. This application is a Continuation-in-Part of U.S. application Ser. No. 12/383,030, filed Mar. 18, 2009, and is a Continuation-in-Part of U.S. application Ser. No. 12/383,071, filed on Mar. 18, 2009 and claims benefit of and priority to U.S. Provisional Application No. 61/299,886, filed Jan. 29, 2010, all of which are entirely incorporated herein by reference.

STATEMENT REGARDING FEDERALLY SPONSORED RESEARCH OR DEVELOPMENT

This invention was made with Government support under contract DK066793 awarded by the National Institutes of Health. The Government has certain rights in this invention.

BACKGROUND

Over 150 million people are infected with Hepatitis C Virus (HCV) worldwide. Unfortunately, the current standard care, consisting of administration of a combination of interferon and ribavirin, is often unable to clear HCV infection in many infected individuals. Moreover, this treatment is associated with significant side effects, precluding its use by many individuals. Thus, current therapies are inadequate for the majority of the patients, and there is a pressing need for new drugs to treat HCV infection (See, *Annals Internal Med.* 132:296-305 (2000)).

The 9.6-kb positive single-stranded RNA HCV genome encodes a 3,000-amino-acid polyprotein that is proteolytically processed into structural proteins, which are components of the mature virus, and nonstructural proteins (NS), which are involved in replicating the viral genome (*Curr Top Microbiol Immunol* 242, 55-84 (2000)). Like other positive strand RNA viruses (B. N. Fields, D. M. Knipe, and P. M. Howley (ed.), Fields Virology (Lippincott-Raven Publications, Philadelphia, Pa., 1996, in "The viruses and their replication")), HCV appears to replicate in association with intracellular membrane structures. In the case of HCV, the structures are referred to as the membranous web (*J Virol* 76, 5974-5984 (2002)), the formation of which is believed to be induced by the NS4B protein. NS4B is also used to assemble the other viral NS proteins within the apparent sites of RNA replication (*J Virol* 78, 11393-11400 (2004)).

There is an ongoing need in the art for agents that treat HCV infection.

SUMMARY

Briefly described, aspects of this invention include compounds, compositions, pharmaceutical compositions, methods of treating a host infected with a virus from the Flaviviridae family of viruses, methods of treating HCV replication in a host, methods of inhibiting the binding of NS4B polypeptide to the 3'UTR of HCV negative strand RNA in a host, methods of treating liver fibrosis in a host, and the like.

In one aspect, the present invention provides a method of treating a subject infected with a virus from the Flaviviridae family. The method comprises administering to the subject clemizole or clemizole analog, or a pharmaceutically acceptable salt, isomer, tautomer or prodrug thereof, in an amount that is effective in reducing viral load of said virus in said subject.

In another aspect, the present invention provides a method of inhibiting formation of a complex between NS4B polypeptide and hepatitis C viral (HCV) RNA in a cell. The method comprises administering to the cell clemizole or clemizole analog, or a pharmaceutically acceptable salt, isomer, tautomer or prodrug thereof, in an amount that is effective in reducing binding of NS4B polypeptide to HCV RNA.

In another aspect, the present invention provides a method of treating liver fibrosis in a subject. The method comprises administering to the subject a therapeutically effective amount of clemizole or clemizole analog, or a pharmaceutically acceptable salt, isomer, tautomer or prodrug thereof.

In some embodiments, any of the methods of the present invention involves administration of clemizole or a clemizole analog (or a composition (e.g., pharmaceutical) including the compound or consisting essentially of the compound) having a structure of Formula I:

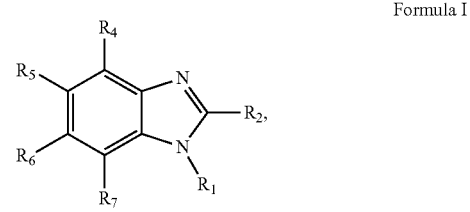

Formula I wherein $R_1$ is selected from the group consisting of: —H,

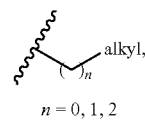

$n = 0, 1, 2$ and

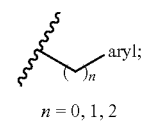

$n = 0, 1, 2$ wherein $R_2$ is selected from the group consisting of

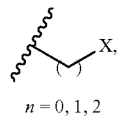

$n = 0, 1, 2$ wherein X is selected from the group consisting of: -alkyl, -aryl, CONH(alkyl), CONH(aryl),

or cycloalkyl or aryl or heteroaryl or heterocyclo,

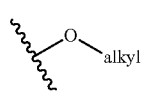

or cycloalkyl or aryl or heteroaryl or heterocyclo, —N-attached substituted heterocyclo, —N-attached halogen-substituted heterocyclo,

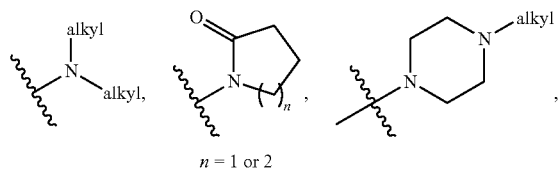

n = 1 or 2 or heteroaryl or aryl or cycloalkyl,

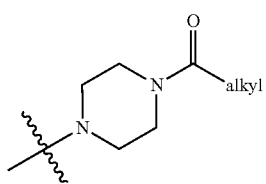

or aryl or heteroaryl or cycloalkyl,

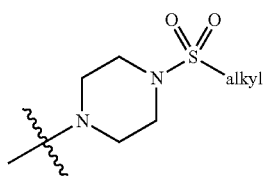

or aryl or heteroaryl or cycloalkyl —C-attached heterocyclo where heterocyclo contains at least 1 nitrogen, —O-Linker-C-attached heterocyclo where heterocyclo contains at least 1 nitrogen and Linker is substituted or unsubstituted $C_1$-$C_6$ or $C_2$-$C_6$ alkylene, heteroalkylene, alkenylene, or heteroalkenylene group, —N-Linker-C-attached heterocyclo where heterocyclo contains at least 1 nitrogen and the Linker is a substituted or an unsubstituted $C_1$-$C_6$ or $C_2$-$C_6$ alkylene, heteroalkylene, alkenylene, or heteroalkenylene group, or X is

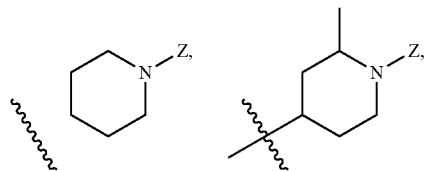

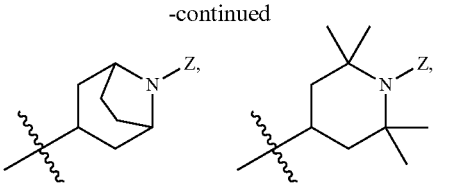

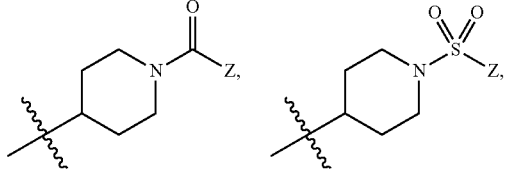

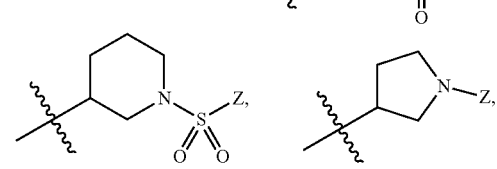

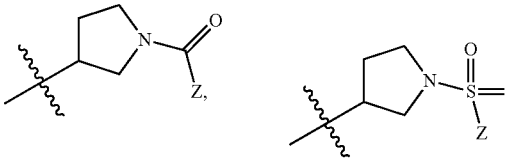

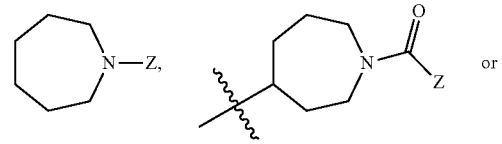

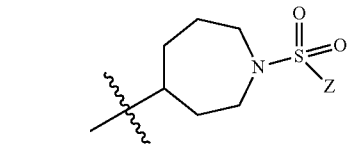

or

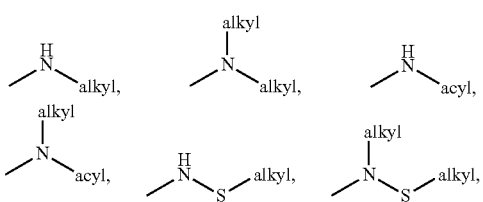

where Z is H, alkyl, aryl, heteroaryl, or cycloalkyl, —SH, —$SO_2$(alkyl), —S(alkyl), and —S(aralkyl);

each of $R_4$-$R_7$ is independently selected from the group consisting of: —H, —Cl, —F, —I, —Br, —$CH_3$, —$OCH_3$, —$NH_2$,

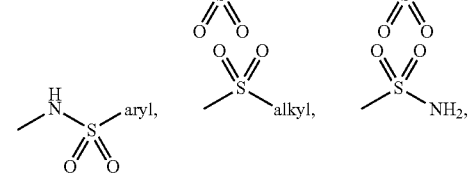

-continued

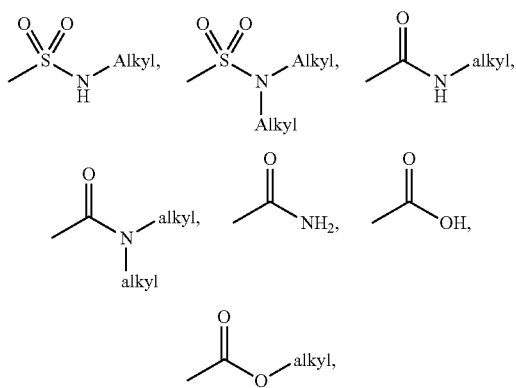

—NHC(O)aryl, —NHC(O)alkyl, —NHSO$_2$NH$_2$, —NHSO$_2$NH-alkyl, —NHC(O)NH$_2$, —NHC(O)NH-alkyl, —N(alkyl)C(O)aryl, —N(alkyl)C(O)alkyl, —N(alkyl)SO$_2$NH$_2$, —N(alkyl)SO$_2$NH-alkyl, —N(alkyl)C(O)NH$_2$, and —N(alkyl)C(O)NH-alkyl;

or, optionally, R$_4$ and R$_5$, R$_5$ and R$_6$, or R$_6$ and R$_7$ are joined together with a bond to form a 5, 6, or 7-membered ring; or, optionally, R$_4$ and R$_5$, R$_5$ and R$_6$, or R$_6$ and R$_7$ are joined together to form a 1,2-(methylenedioxy)benzene ring system; wherein the alkyl or Alkyl group as used herein includes cycloalkyl and is independently selected from the group consisting of —CH$_3$, —CH$_2$CH$_3$, —CH(CH$_3$)$_2$, —CF$_3$, cyclopropyl, cyclopentyl, and cyclohexyl; wherein the aryl group is independently selected from the group consisting of Group A to Group F:

Group A

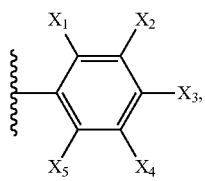

Group B

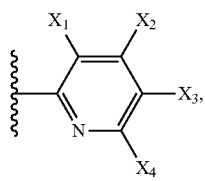

Group C

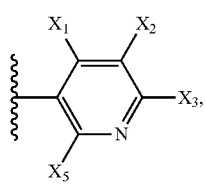

Group D

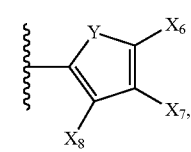

Group E

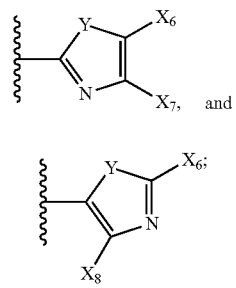

and

Group F wherein X$_1$-X$_5$ are each independently selected from the group consisting of —H, -alkyl, —I, —Br, —Cl, —F, —O-alkyl,

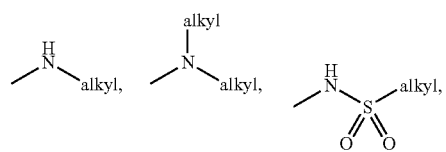

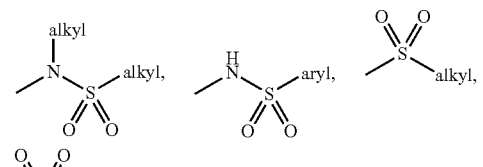

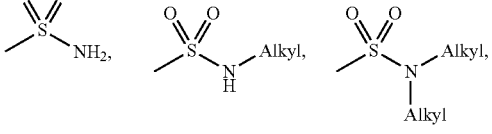

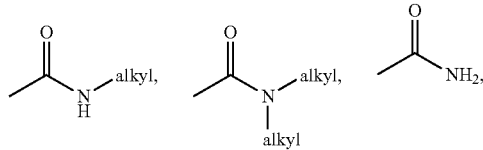

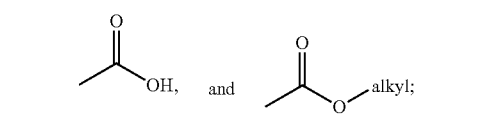

and wherein Y is selected from the group consisting of O, S, NH, N-alkyl, and N-acyl; X$_6$ is selected from the group consisting of —H, —CH$_3$, —I, —Br, —Cl, —F, —CF$_3$ and —OCH$_3$; and X$_7$ and X$_8$ are independently selected from H or CH$_3$.

Other compounds of the invention have the same structure but with an aza-benzimidazole core. Thus, in each of the formulae depicted herein, corresponding compounds of the invention include those with an aza-benzimidazole core (instead of the benzimidazole core depicted).

In other embodiments, any of the methods of the present invention involves administration of clemizole or clemizole analog (or a composition (e.g., pharmaceutical) including the compound or consisting essentially of the compound) having a structure of Formula I:

Formula I

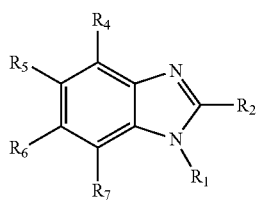

wherein R$_1$ is selected from the group consisting of: —H and

m = 0, 1, 2 wherein V is selected from alkyl, cycloalkyl, heterocyclo, aryl or heteroaryl, and m is 0, 1 or 2; R$_2$ is selected from the group consisting of:

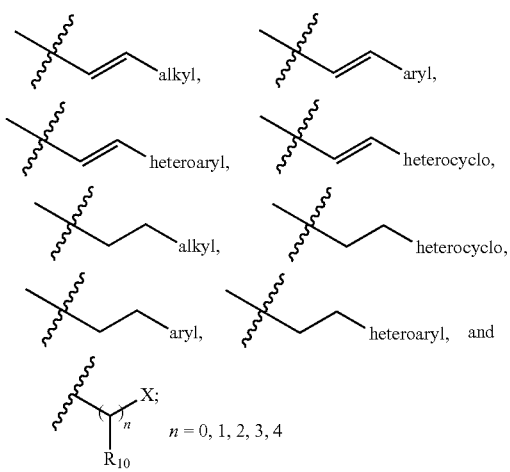

n = 0, 1, 2, 3, 4 wherein X is selected from the group consisting of:

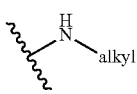

or cycloalkyl or aryl or heteroaryl or heterocyclo,

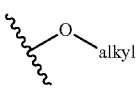

or cycloalkyl or aryl or heteroaryl or heterocyclo, —N-attached substituted heterocyclo, —N-attached halogen-substituted heterocyclo, —N(alkyl)$_2$, CONH(alkyl), COHC(aryl), -alkyl, -cycloalkyl, -alkenyl, -aryl, -heteroaryl, —C-attached heterocyclo where heterocyclo contains at least 1 nitrogen, —O-Linker-C-attached heterocyclo where heterocyclo contains at least 1 nitrogen, —N-Linker-C-attached heterocyclo where heterocyclo contains at least 1 nitrogen, where Linker is a substituted or an unsubstituted C$_1$-C$_6$ alkylene, heteroalkylene, alkenylene, or heteroalkenylene; each of R$_4$-R$_7$ is independently selected from the group consisting of: —H, —I, —Br, —Cl, —F, —CH$_3$, —CN, —OH, —OCH$_3$, —NO$_2$, —NH$_2$, or, optionally, R$_4$ and R$_5$, R$_5$ and R$_6$, or R$_6$ and R$_7$ are joined together with a bond to form a 5, 6, or 7-membered ring; or, optionally, R$_4$ and R$_5$, R$_5$ and R$_6$, or R$_6$ and R$_7$ are joined together to form a 1,2-(methylenedioxy)benzene ring system; and R$_{10}$ is hydrogen or alkyl. In some other embodiments of the methods of the invention, X is selected from the group consisting of: -alkyl, cycloalkyl, alkenyl, —O-alkyl, —O-cycloalkyl, —O-aryl, —O-heteroaryl, —O-heterocyclo, -aryl,

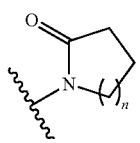

n = 1, 2, or 3,

N-attached substituted heterocyclo, N-attached halogen-substituted heterocyclo,

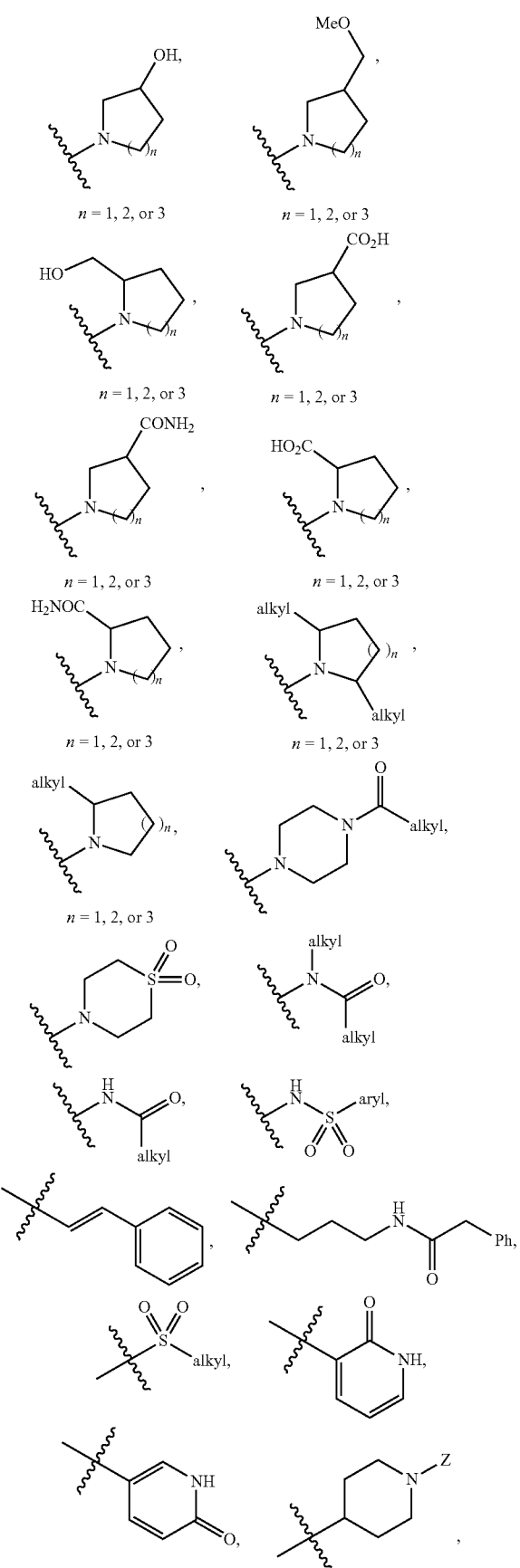
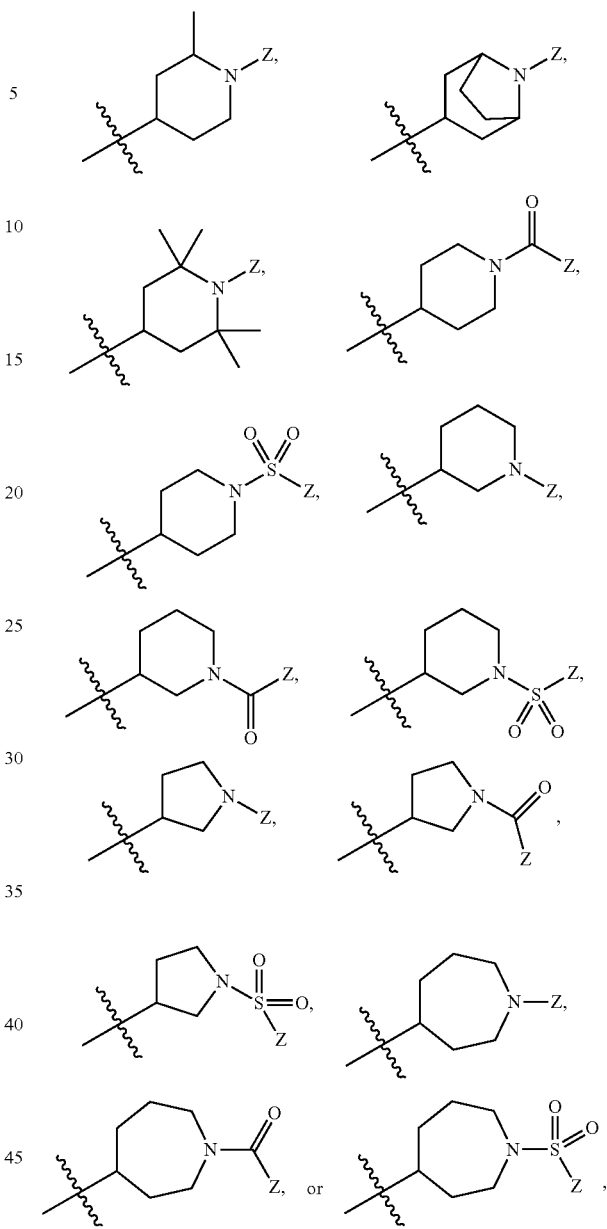
where Z is H, alkyl, aryl, heteroaryl, or cycloalkyl, provided that the compounds are not
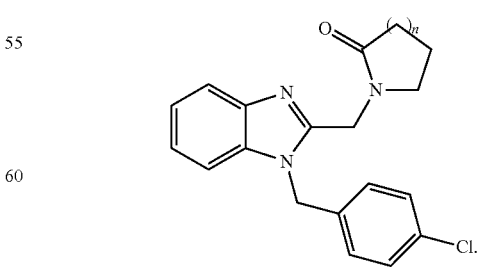
In various embodiments of the methods of the invention, the compound of Formula (I) has the structure:

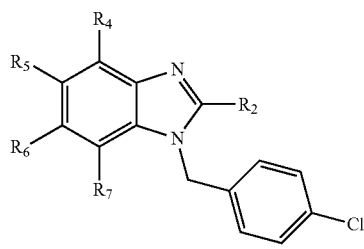

and, optionally, $R_4$ and $R_7$ are hydrogen, provided that the compounds are not

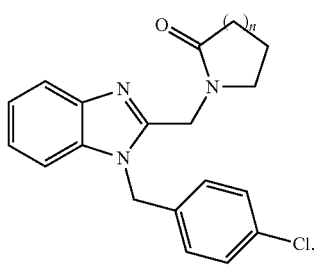

n = 1, 2

In one embodiment, the present invention provides a method of treating a subject infected with a virus from the Flaviviridae family, the method comprising administering to said subject a compound (or a composition (e.g., pharmaceutical) including the compound or consisting essentially of the compound) of Formula I, Formula I

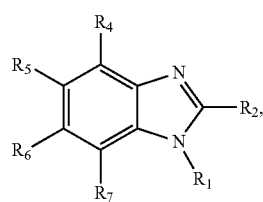

wherein $R_1$ is —CH$_2$-aryl;
$R_2$ is —CH$_2$—X;
X is selected from the group consisting of:

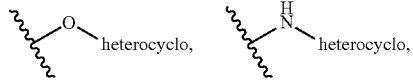

—N-attached substituted heterocycle where heterocycle contains at least 1 nitrogen, C-attached heterocycle where heterocycle contains at least 1 nitrogen,

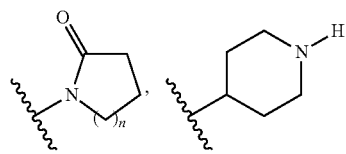

n = 1 or 2 or alkyl or aryl or heteroaryl,

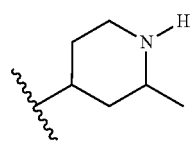 [SMILES: *C1CCNC(C)C1]

or alkyl or aryl or heteroaryl,

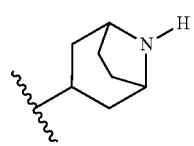 [SMILES: *C1CC2CCC(C1)N2]

or alkyl or aryl or heteroaryl,

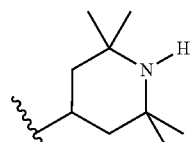

or alkyl or aryl or heteroaryl,

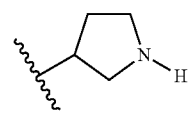 [SMILES: *C1CCNC1]

or alkyl,

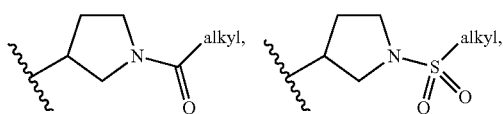

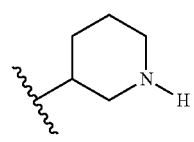

or alkyl or aryl or heteroaryl,

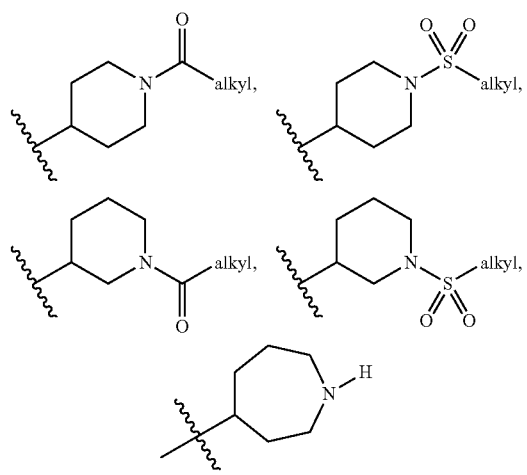

or alkyl or aryl or heteroaryl,

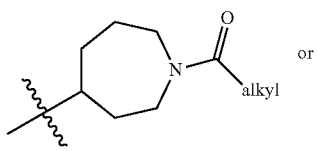

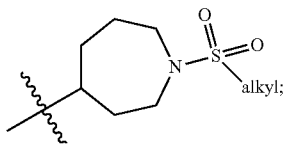

each of $R_4$-$R_7$ is independently selected from the group consisting of: —H, —Cl, —F, —I, —Br, —CH$_3$, —OCH$_3$, —NH$_2$,

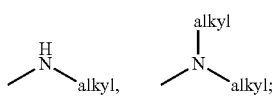

or a pharmaceutically acceptable salt, an isomer, a tautomer, or a prodrug thereof and wherein the compound of Formula I is administered in an amount that is effective in reducing viral load of said virus in said subject. In one embodiment, when aryl is a part of $R_1$, then aryl is a substituted or an unsubstituted phenyl. In another embodiment, the heterocycle that is part of $R_2$ is a C-attached, a substituted or an unsubstituted, 5, 6, or 7 membered heterocycle containing at least one nitrogen atom. In another embodiment, $R_4$ and $R_7$ are hydrogen.

In one embodiment, the present invention provides a method of treating a subject infected with a virus from the Flaviviridae family, the method comprising administering to said subject a compound (or a composition (e.g., pharmaceutical) including the compound or consisting essentially of the compound) of Formula (I), Formula I

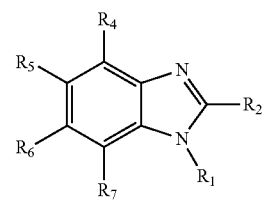

wherein $R_1$ is —CH$_2$—V;

V is aryl or heteroaryl;

$R_2$ is selected from the group consisting of:

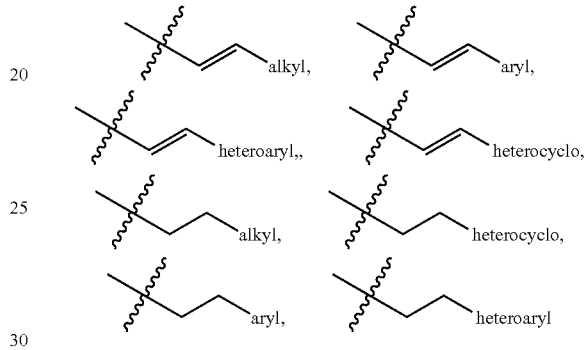

and —CH($R_{10}$)$_n$—X;

n=1 or 2;

X is selected from the group consisting of: substituted or unsubstituted

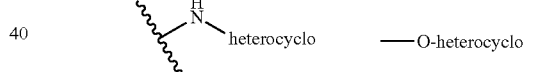

or C-attached heterocyclo, or substituted N-attached heterocyclo; each of $R_4$-$R_7$ is independently selected from the group consisting of: —H, —I, —Br, —Cl, —F, —CH$_3$, —CN, —OH, —OCH$_3$, —NO$_2$, —NH$_2$, ![](alkyl structures)

In one embodiment, X is —O-heterocyclo,

![](three pyrrolidine structures with n = 1, 2, or 3)

-continued

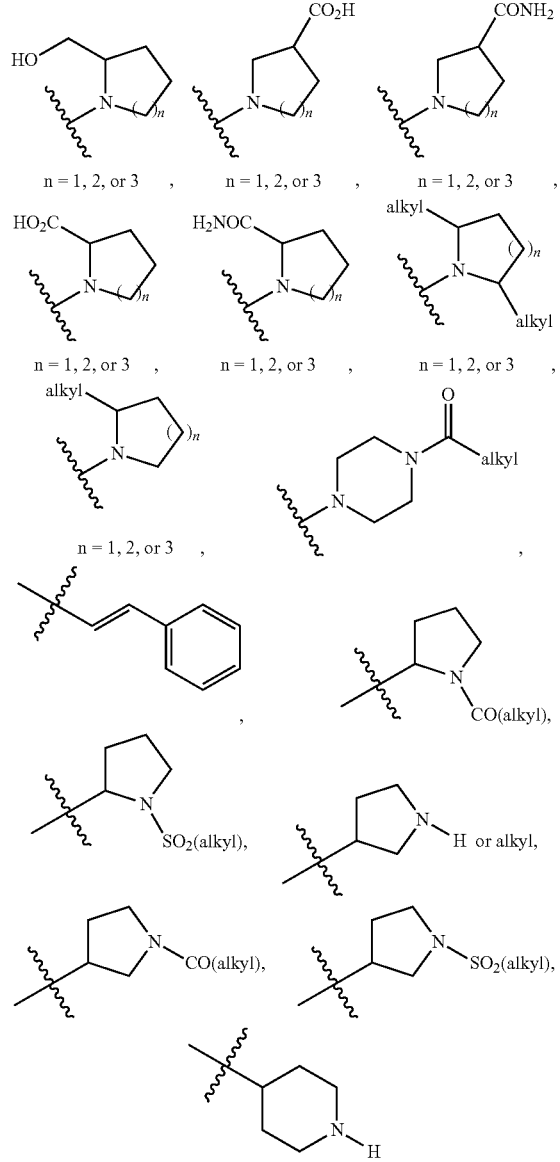

or alkyl,

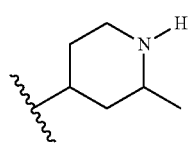 [SMILES: *C1CCNC(C)C1]

or alkyl or aryl or heteroaryl,

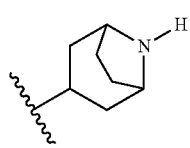 [SMILES: *C1CC2CCC(C1)N2]

or alkyl or aryl or heteroaryl,

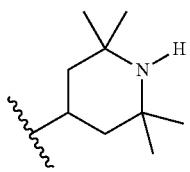 [SMILES: *C1CC(C)(C)NC(C)(C)C1]

or alkyl or aryl or heteroaryl, or a pharmaceutically acceptable salt, an isomer, a tautomer, or a prodrug thereof, and wherein the compound of Formula (I) is administered in an amount that is effective in reducing viral load of said virus in said subject. In one embodiment, V is monosubstituted phenyl. In one embodiment, X is a C-attached, a substituted or an unsubstituted, 5, 6, or 7 membered heterocycle. In another embodiment, $R_4$ and $R_7$ are hydrogen.

In other embodiments of the treatment methods of the invention, the compound administered is clemizole:

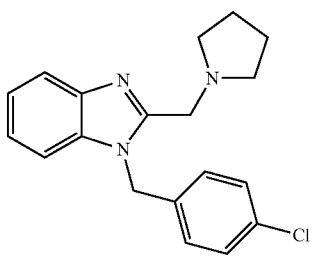 [SMILES: Clc1ccc(Cn2c(CN3CCCC3)nc3ccccc32)cc1]

or the HCl or another pharmaceutically acceptable salt thereof.

In other embodiments of the treatment methods of the invention, the compound is:

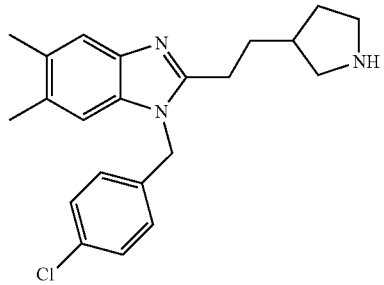 [SMILES: Cc1cc2nc(CCC3CCNC3)n(Cc3ccc(Cl)cc3)c2cc1C]

or the HCl or another pharmaceutically acceptable salt thereof.

In other embodiments of the treatment methods of the invention, the compound is:

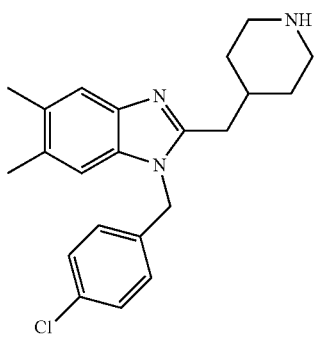 [SMILES: Cc1cc2nc(CC3CCNCC3)n(Cc3ccc(Cl)cc3)c2cc1C]

or the HCl or another pharmaceutically acceptable salt thereof.

In other embodiments of the treatment methods of the invention, the compound is:

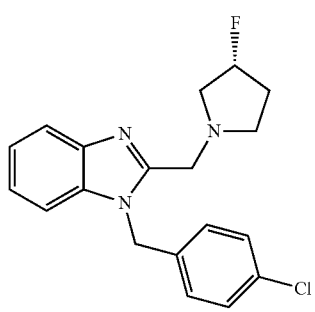 [SMILES: F[C@@H]1CCN(Cc2nc3ccccc3n2Cc2ccc(Cl)cc2)C1]

or the HCl or another pharmaceutically acceptable salt thereof, and in other embodiments of the treatment methods of the invention, the compound is:

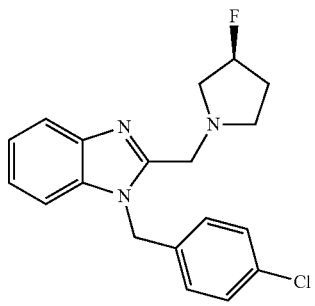

or the HCl or another pharmaceutically acceptable salt thereof.

In other embodiments of the treatment methods of the invention, the compound is:

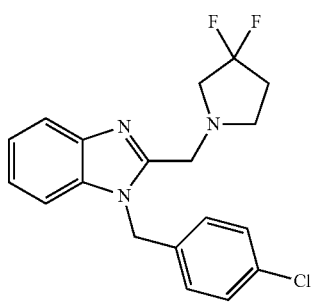 [SMILES: FC1(F)CCN(Cc2nc3ccccc3n2Cc2ccc(Cl)cc2)C1]

or the HCl or another pharmaceutically acceptable salt thereof.

In some embodiments of the treatment methods of the invention, clemizole (e.g., clemizole hydrochloride) or another clemizole analog that has similar activity to clemizole (a "Clemizole Like Analog", which refers to an analog that has an $EC_{50}$ of less than about 25 micromolar in the genotype 2a infectious clone assay described herein but has an $EC_{50}$ of greater than about 25 micromolar in the genotype 1b replicon assay described herein) is administered to an HCV patient in a daily dose of at least about 200 mg, i.e., about 100 mg BID. Typically, this about 100 mg BID administration schedule, when used with these agents, will be used in treatment regimens in which at least one additional drug is also administered to the patient, i.e., treatment regimens in which clemizole is co-administered with (i) ribavirin; (ii) interferon; (iii) ribavirin (e.g., using weight-based dosing or dosing at 15 mg/kg/day) and interferon (e.g., alpha 2a or alpha 2b, and pegylated versions of the same); or (iv) one or more of the compounds described herein which demonstrate activity in combination with clemizole that reflects additivity or minor, moderate, or strong synergy as measured by the MacSynergy II program.

Other clemizole analogs described herein have an $EC_{50}$ of less than about 25 micromolar in both the genotypes 1b replicon assay and the 2a infectious clone assay described herein ("1b Active Analogs"), may also be used at these doses, either in single-agent therapy or in the combination therapies just described. In any of these embodiments and with respect to clemizole and any clemizole analog of the invention, the patient can be a previously untreated ("naïve") patient, a patient that has not responded to a prior treatment, such as standard of care ("SOC") therapy, a post-transplant patient, or a patient co-infected with another virus. Combination therapy (e.g., administration of clemizole or any clemizole analog in combination with ribavirin and interferon alpha) can be initiated at the beginning of a course of treatment or follow pre-treatment with ribavirin, or with clemizole, or with both.

In other embodiments of the invention, however, the daily dose of clemizole or any clemizole analog for treating HCV infection is higher than about 200 mg; exemplary administration schedules include: 100 mg TID; 200 mg BID; 200 mg TID; 300 mg BID; 300 mg TID; 400 mg BID; 400 mg TID; 500 mg BID; and 500 mg TID. In other embodiments exemplary administration schedules include: about 100 mg TID; about 200 mg BID; about 200 mg TID; about 300 mg BID; about 300 mg TID; about 400 mg BID; about 400 mg TID; about 500 mg BID; and about 500 mg TID. For the more difficult to treat genotype, i.e., genotype 1, more frequent dosing or higher daily doses than that provided by about 100 mg po BID or about 200 mg po BID are preferred if clemizole or a Clemizole Like Analog is administered as single agent therapy. In all of the various embodiments, however, the clemizole hydrochloride (or other pharmaceutically acceptable salt or form of clemizole) or any clemizole analog can be administered in combination with another drug, including, but not limited to, (i) ribavirin (e.g., using fixed or weight-based dosing or dosing at 15 mg/kg/day); (ii) interferon; (iii) ribavirin (e.g., using fixed or weight-based dosing or dosing at 15 mg/kg/day) and interferon (e.g., alpha 2a or alpha 2b, and pegylated versions of the same, and for other interferons as described herein, but not limited to, albuferon); or (iv) one or more of the compounds described herein which demonstrate activity in combination with clemizole (or the selected clemizole analog) that reflects additivity or minor, moderate, or strong synergy as measured by the MacSynergy program. In any of these embodiments, the patient can be a previously untreated ("naïve") patient, a patient that has not responded to a prior treatment, such as standard of care ("SOC") therapy, a post-transplant patient, or a patient co-infected with another virus. Combination therapy (e.g., administration of clemizole or a clemizole analog in combination with ribavirin and interferon alpha, or with other direct-acting specific antivirals) can be initiated at the beginning of a course of treatment or follow pre-treatment with ribavirin, or with clemizole, or with both.

In other embodiments of the methods of the invention, the clemizole analog administered has one of the following formulae or a pharmaceutically acceptable salt thereof:

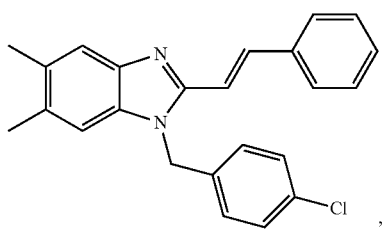

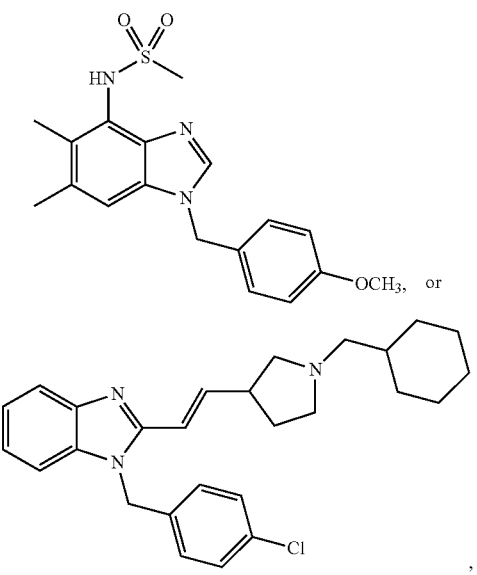

In yet other embodiments of the treatment methods of the invention, the clemizole analog administered has a structure of one of the following formulae or a pharmaceutically acceptable salt thereof:

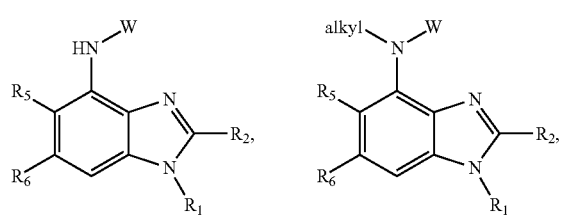

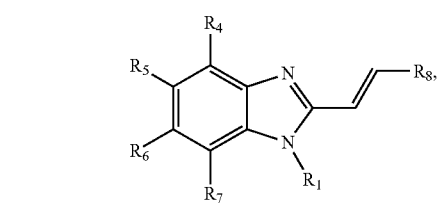

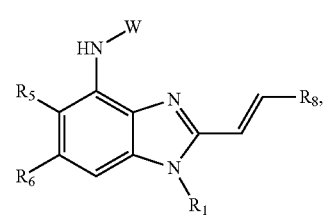

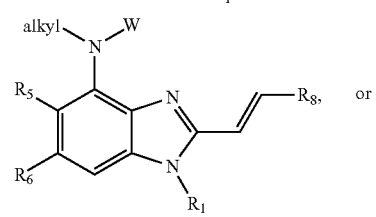

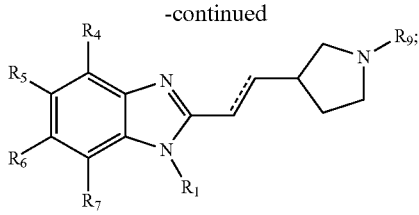

wherein R₁-R₇ are as described as in any aspect or embodiment above; R₈ is alkyl, aryl or heteroaryl, R₉ is alkyl, cycloalkyl, aryl or heteroaryl, and W is alkyl, —C(O)aryl, —C(O)alkyl, —SO₂aryl, —SO₂alkyl, —SO₂NH₂, —SO₂NH-alkyl, —C(O)NH₂ or —C(O)NH-alkyl, provided that the compounds are not

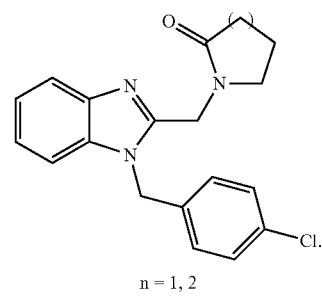

n = 1, 2

In other embodiments, the compounds of formula III, III-A, III-B, III-C, III-D, III-E, or IV, or their pharmaceutically acceptable salts, disclosed hereinbelow (or a composition (e.g., pharmaceutical) including the compound or consisting essentially of the compound), are administered according to the treatment methods of the present invention.

Also provided are methods of treating or prophylactically treating a subject who has been or is likely to be infected with a virus of the Flaviviridae family, comprising administering a clemizole, clemizole analog, or an isostere thereof, or their respective pharmaceutically acceptable salts, isomers, tautomers or prodrugs, in combination with one or more additional therapeutic agent(s), including, without limitation, an HCV NS3 protease inhibitor, an HCV NS5B RNA-dependent RNA polymerase inhibitor, a thiazolide, including but not limited to a sustained release thiazolide, a nucleoside analog, an interferon-alpha, a pegylated interferon, ribavirin, levovirin, viramidine, a TLR7 agonist, a TLR9 agonist, a cyclophilin inhibitor, an alpha-glucosidase inhibitor, an NS5A inhibitor, and an NS3 helicase inhibitor (or a composition (e.g., pharmaceutical) including the compound and the therapeutic agent(s) or consisting essentially of the compound and the therapeutic agent(s)).

In another aspect of the invention, a compound (or a composition (e.g., pharmaceutical) including the compound or consisting essentially of the compound) of Formula I-a, or a pharmaceutically acceptable salt, isomer, tautomer or prodrug thereof, is provided:

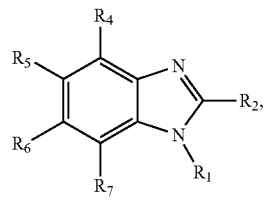

Formula I-a wherein R₁ is selected from the group consisting of:

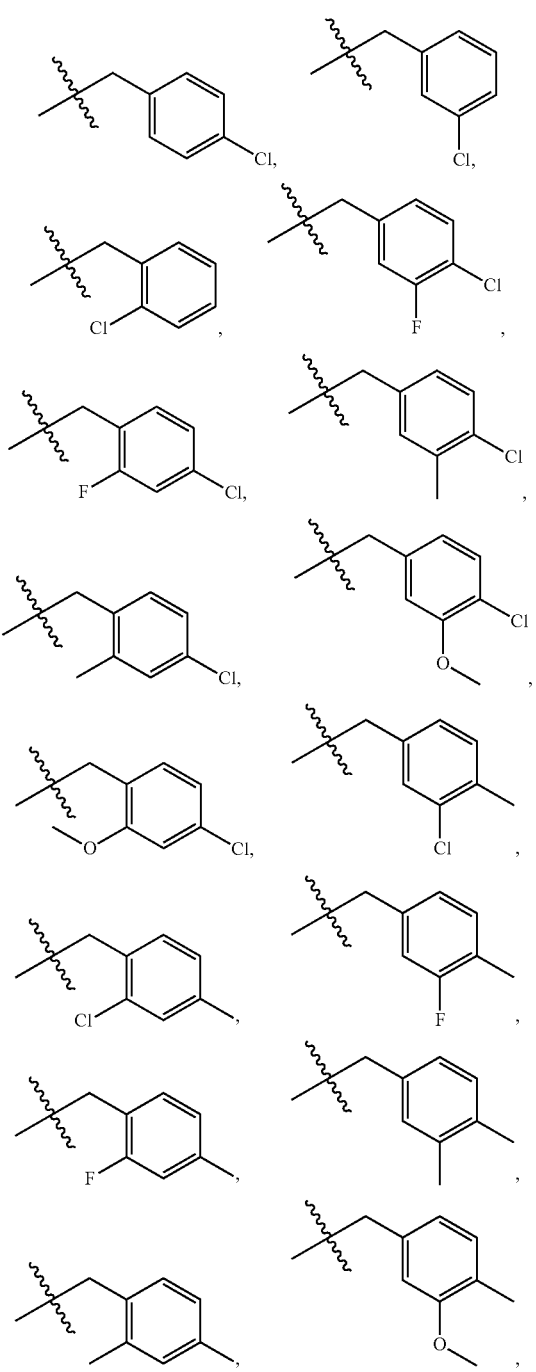

-continued

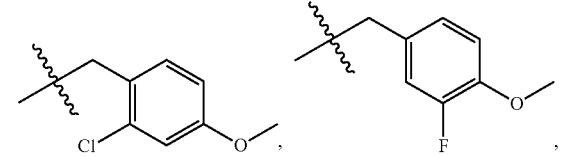

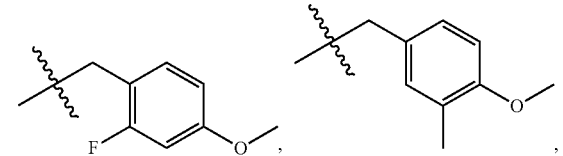

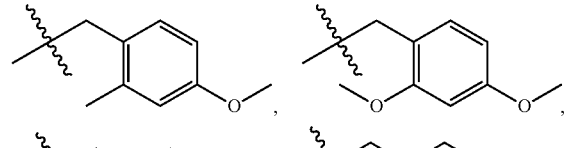

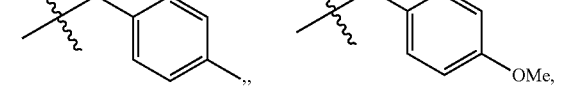

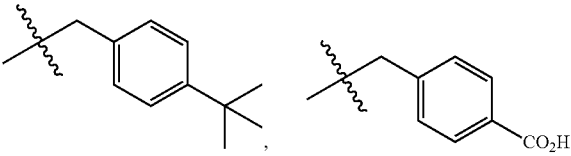

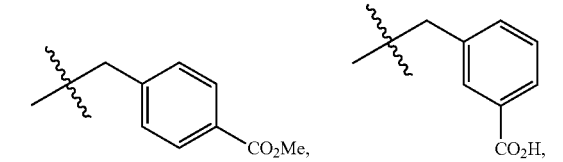

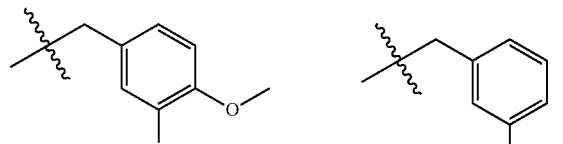

wherein R$_2$ is selected from the group consisting of: —(CH$_2$)$_n$—X, wherein n is 1 or 2, and X is selected from the group consisting of: aryl,

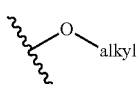

or cycloalkyl or aryl or heteroaryl or heterocyclo

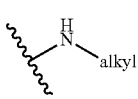

or cycloalkyl or aryl or heteroaryl or heterocyclo, —N-attached substituted heterocyclo, —N-attached halogen-substituted heterocyclo,

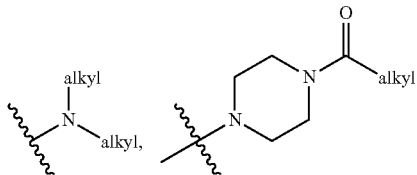

or aryl or heteroaryl or cycloalkyl,

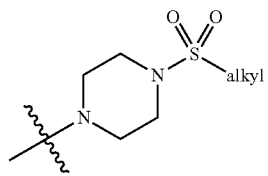

or aryl or heteroaryl or cycloalkyl,

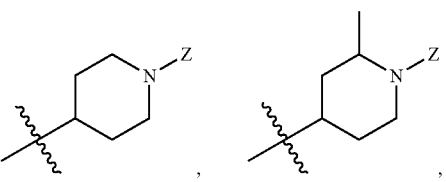

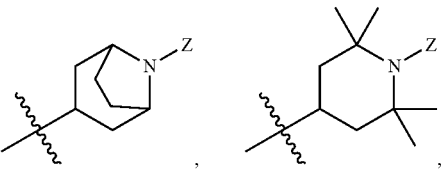

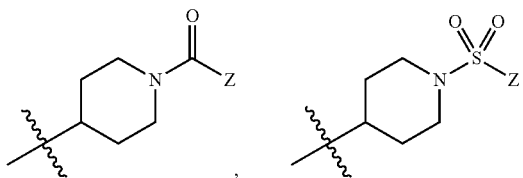

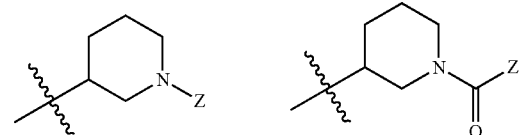

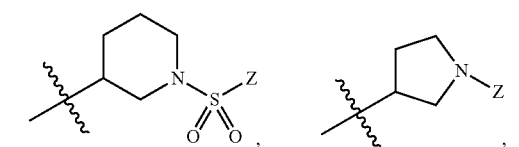

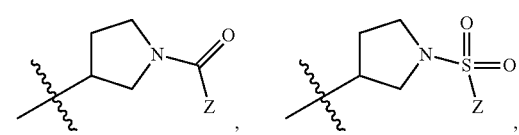

-continued

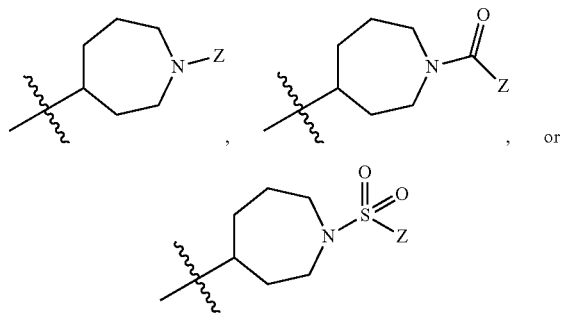

where Z is selected from H, alkyl, aryl, heteroaryl, or cycloalkyl; each of $R_4$-$R_7$ is independently selected from the group consisting of: —H, —Cl, —F, —CH$_3$, —OCH$_3$, —NH$_2$,

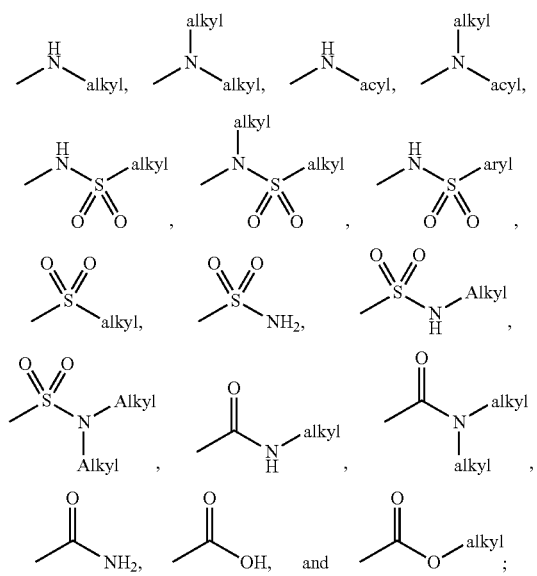

or, optionally, $R_5$ and $R_6$ are joined together with a bond to form a ring, provided that the compounds are not

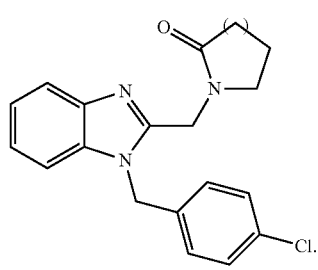

n = 1, 2

In one embodiment, the present invention provides compounds (or a composition (e.g., pharmaceutical) including the compound or consisting essentially of the compound) of Formula I-a

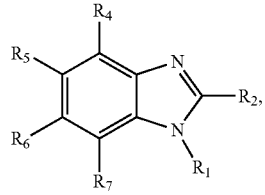

Formula I-a wherein $R_1$ is selected from the group consisting of:

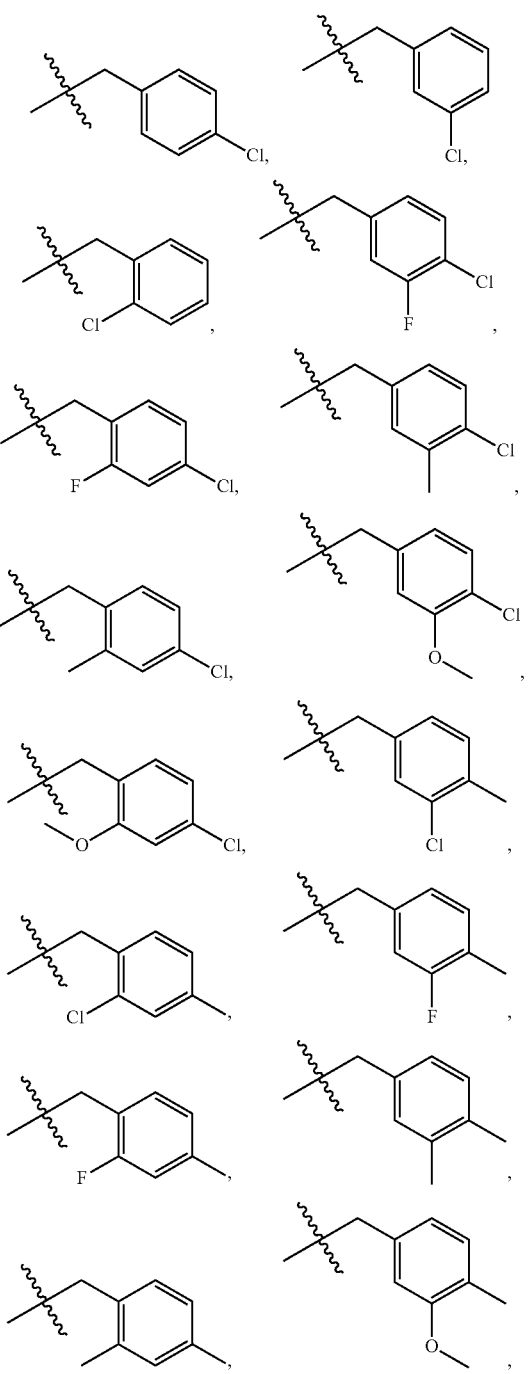

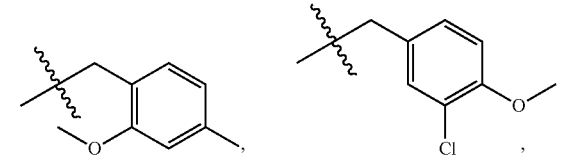
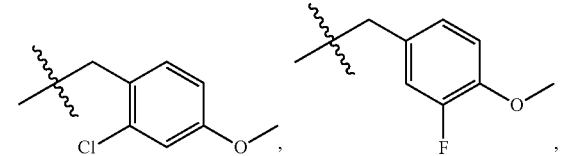
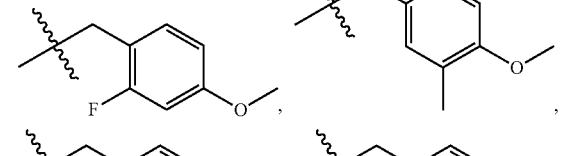
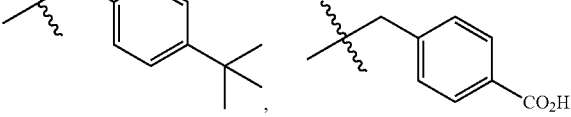
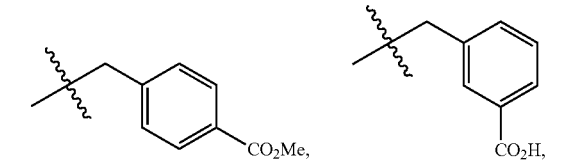
R₂ is —(CH₂)$_n$—X;
n is 1 or 2;
and X is selected from the group consisting of:
or alkyl or aryl or heteroaryl,
or alkyl or aryl or heteroaryl,
or alkyl or aryl or heteroaryl,
or alkyl or aryl or heteroaryl,
or alkyl,
or alkyl or aryl or heteroaryl, -continued

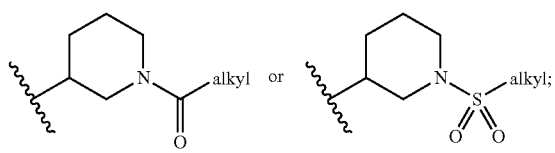

each of R₄-R₇ is independently selected from the group consisting of: —H, —Cl, —F, —CH₃, —OCH₃, —NH₂,

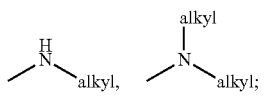

or a pharmaceutically acceptable salt, an isomer, a tautomer, or a prodrug thereof. In one embodiment, R₁ is benzyl substituted on the phenyl ring with a halogen atom. In one embodiment, X is a C-attached, a substituted or an unsubstituted, 5, 6, or 7 membered heterocycle containing at least one nitrogen atom. In one embodiment, R₄ and R₇ are hydrogen.

In another aspect of the invention, a compound (or a composition (e.g., pharmaceutical) including the compound or consisting essentially of the compound) of Formula I-b, or a pharmaceutically acceptable salt, isomer, tautomer or prodrug thereof, is provided:

Formula I-b

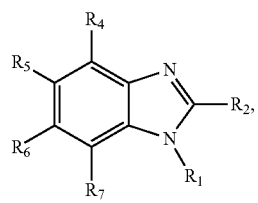

wherein R₁ is selected from the group consisting of:

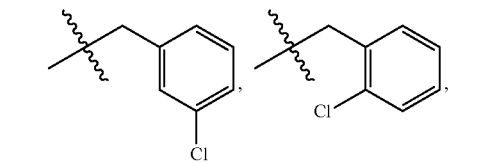

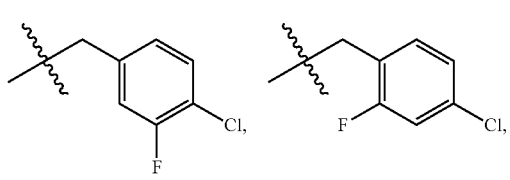

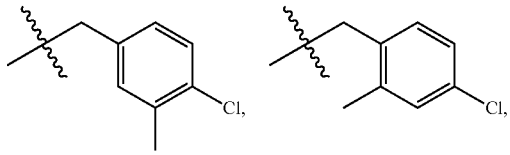

-continued

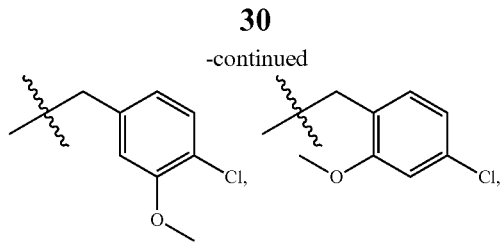

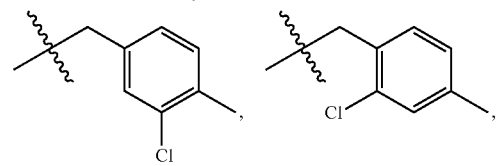

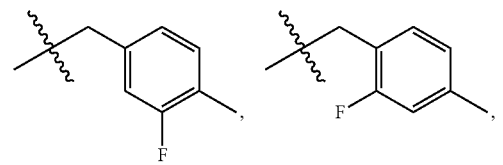

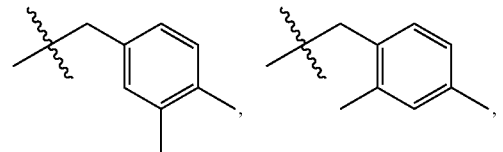

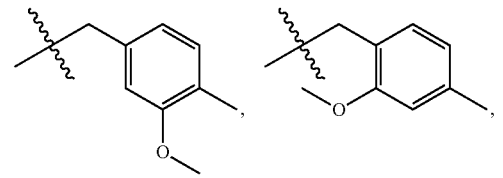

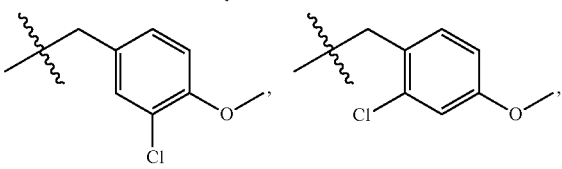

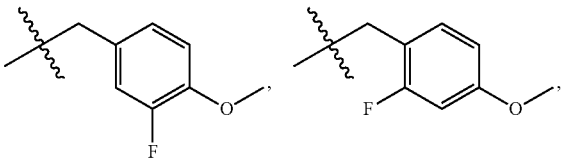

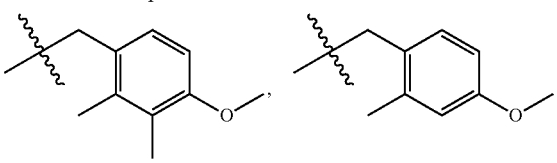

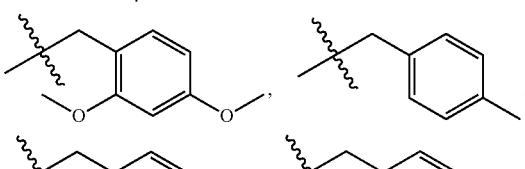

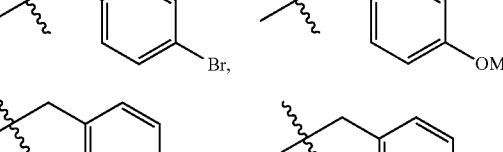

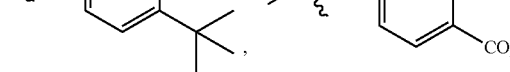

-continued

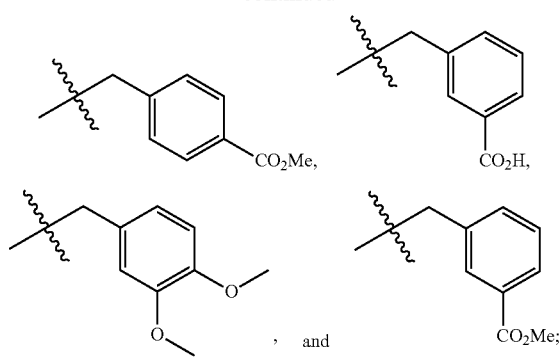

wherein R$_2$ is selected from the group consisting of —(CH$_2$)$_n$—X, wherein n is 1 or 2, and X is selected from the group consisting of: aryl, N-attached substituted heterocyclo, N-attached halogen-substituted heterocyclo,

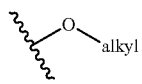

or cycloalkyl or aryl or heteroaryl or heterocyclo,

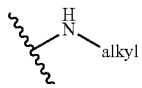

or cycloalkyl or aryl or heteroaryl or heterocyclo,

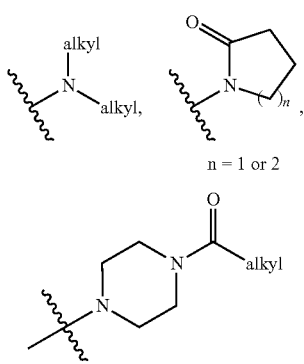

or aryl or heteroaryl or cycloalkyl,

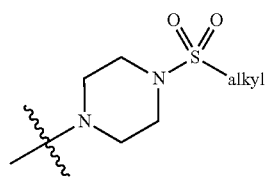

or aryl or heteroaryl or cycloalkyl,

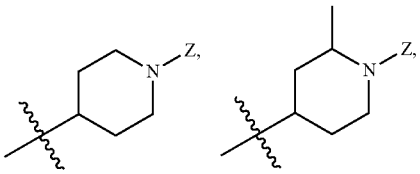
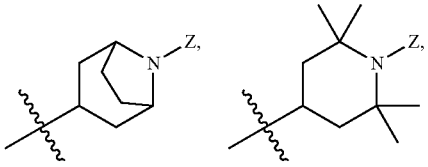
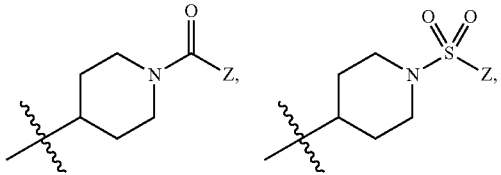
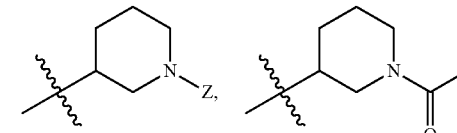
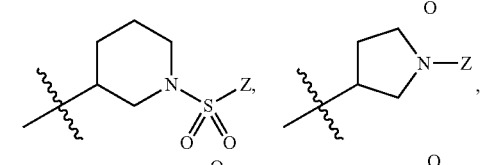
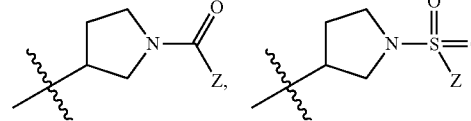
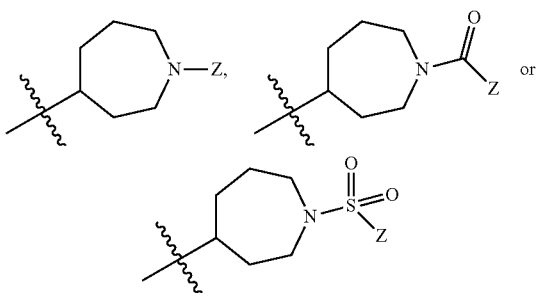

where Z is H, alkyl, aryl, heteroaryl, or cycloalkyl; provided that X is not —NMe$_2$; each of R$_4$-R$_7$ is independently selected from the group consisting of: —H, —Cl, —Br, —I, —F, —CH$_3$, —OCH$_3$, —NH$_2$,

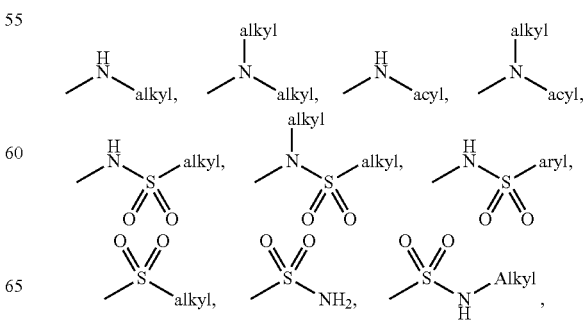

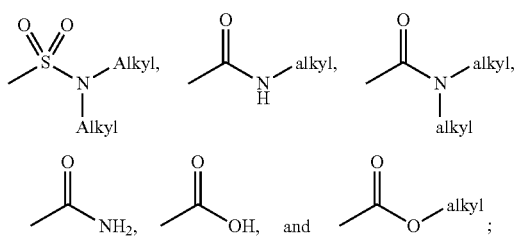

or, optionally, R$_5$ and R$_6$ are joined together with a bond to form a ring. In some embodiments, R$_1$ is 4-chlorobenzyl and R$_4$ and R$_7$ are hydrogen, provided that X is not

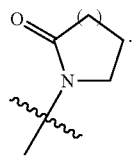

In another aspect of the invention, a compound (or a composition (e.g., pharmaceutical) including the compound or consisting essentially of the compound) of Formula I-d, or a pharmaceutically acceptable salt, isomer, tautomer or prodrug thereof is provided:

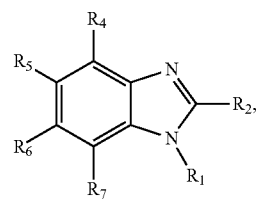

Formula I-d wherein R$_1$ is selected from the group consisting of:

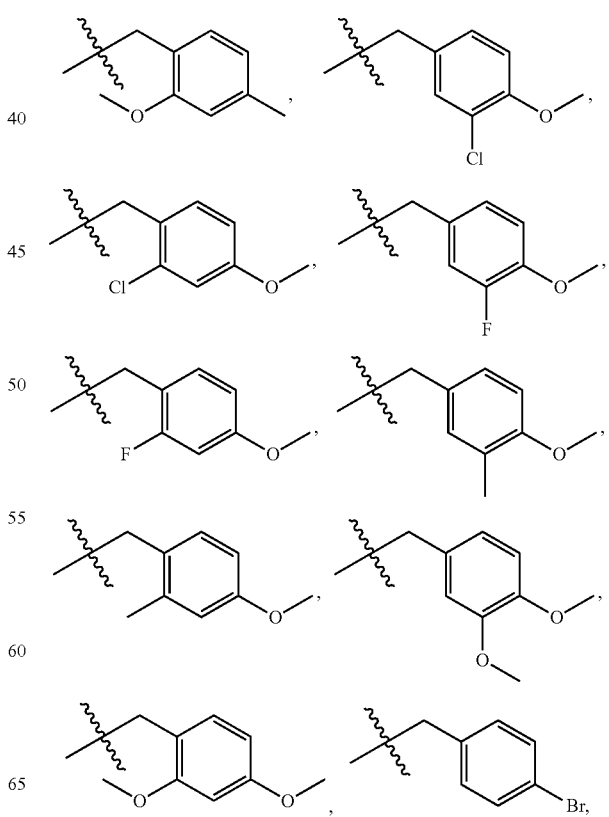

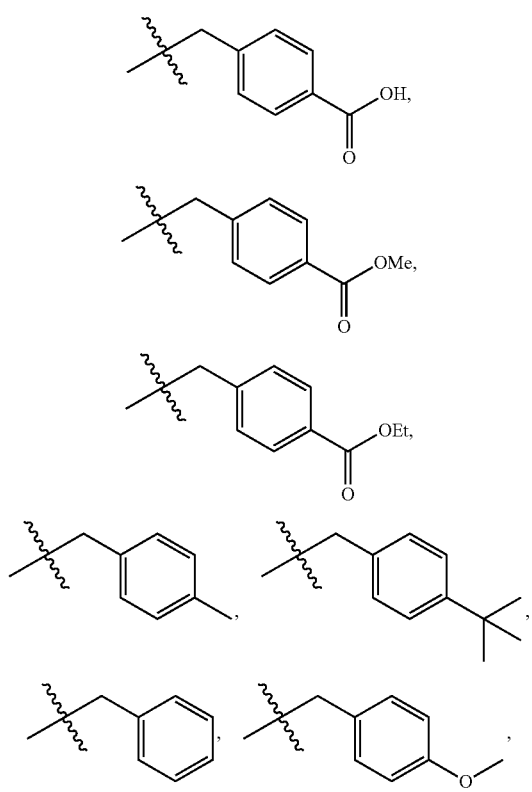
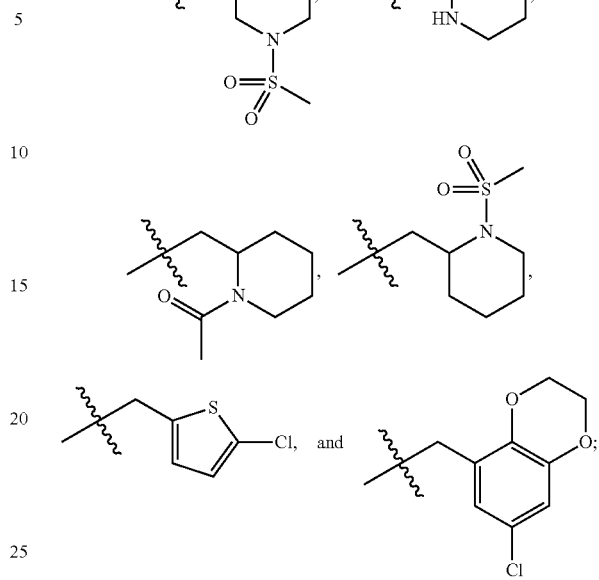
$R_2$ is $-(CHR_{10})_n-X$, n is 1 or 2, and wherein X is selected from the group consisting of: -aryl, $-CH(CH_3)OH$, N-attached substituted heterocyclo, N-attached halogen-substituted heterocyclo,
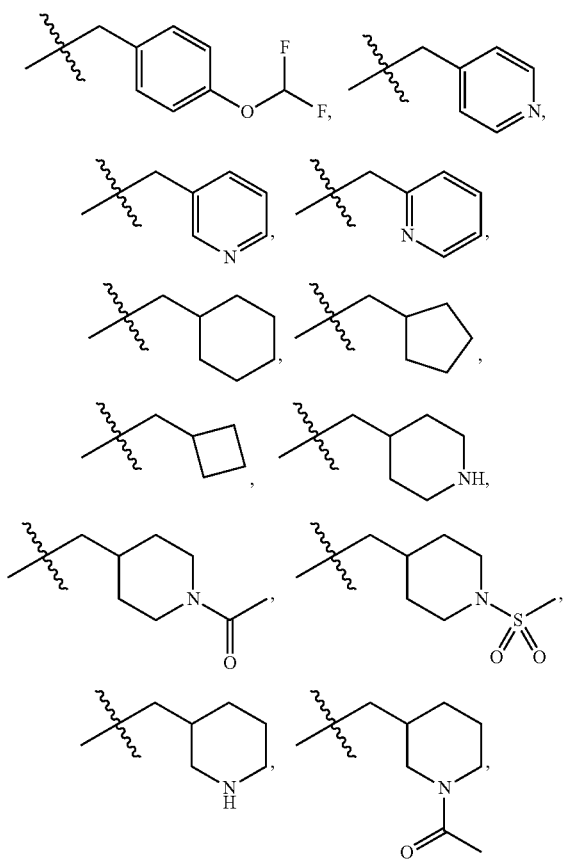
or cycloalkyl or aryl or heteroaryl or heterocyclo,
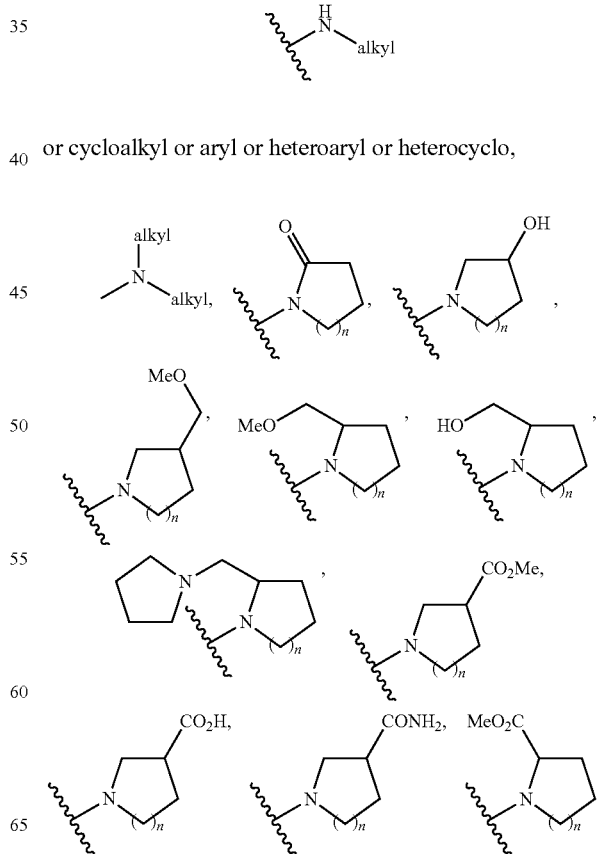

-continued
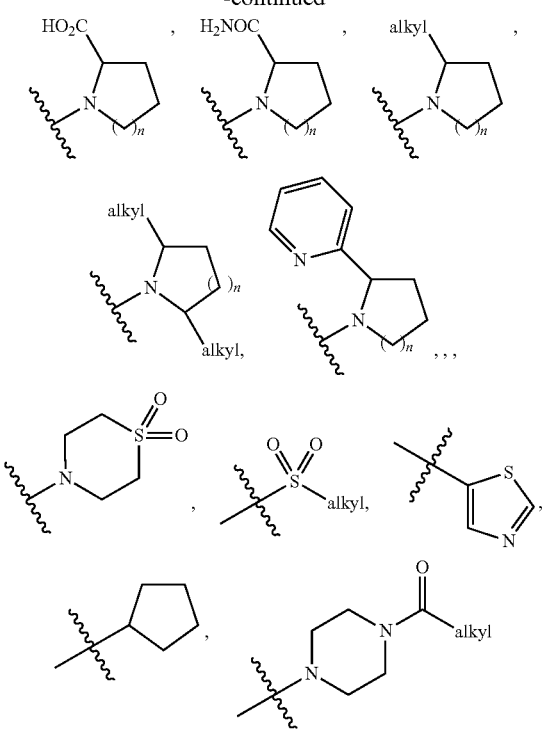
n = 1, 2, or 3
or aryl or heteroaryl or cycloalkyl,
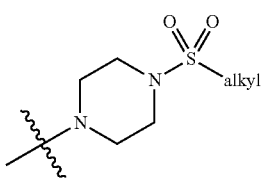
or aryl or heteroaryl or cycloalkyl,
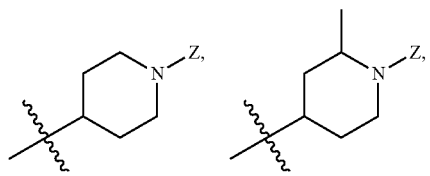
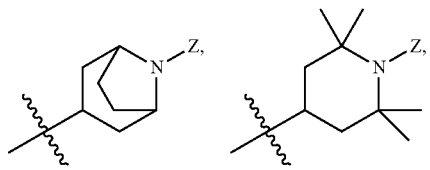
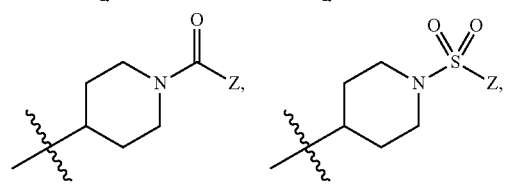
-continued
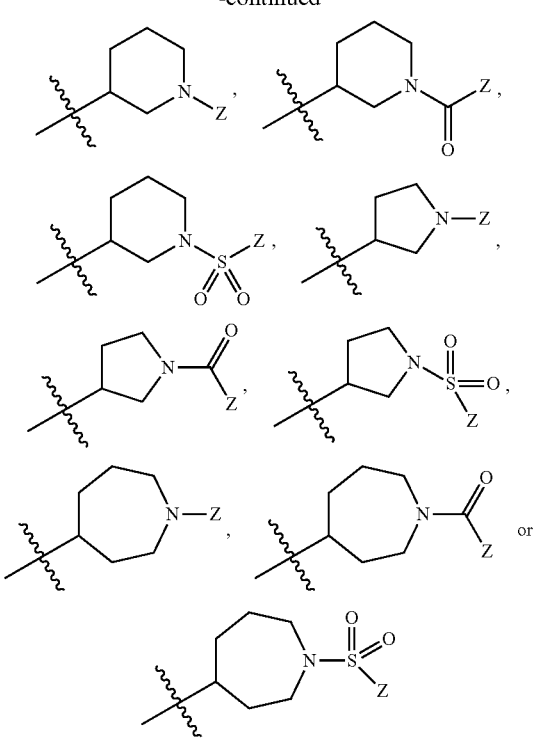
where Z is H, alkyl, aryl, heteroaryl, or cycloalkyl; each of $R_4$-$R_7$ is independently selected from the group consisting of: —H, —Cl, —F, —CH$_3$, —OCH$_3$, —NH$_2$,
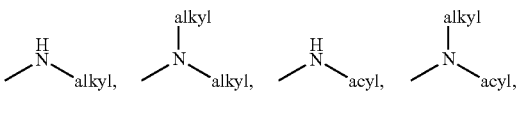
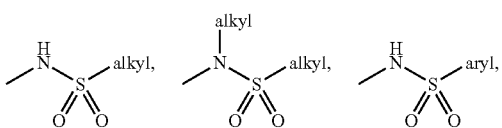
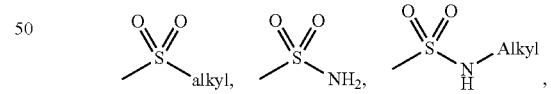
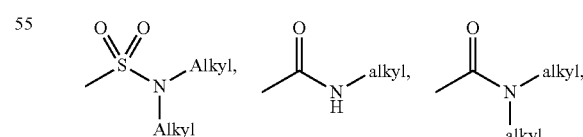
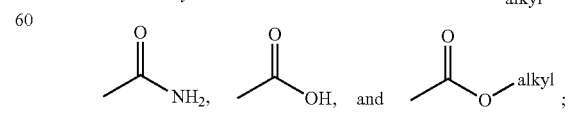
or, optionally, $R_5$ and $R_6$ are joined together with a bond to form a ring; provided that the compound is not

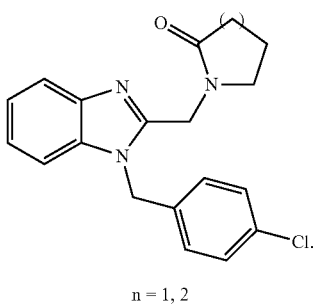
n = 1, 2
In some embodiments of the compound of Formula I-d, R₁ is 4-chlorobenzyl and R₄ and R₇ are hydrogen.
In one embodiment, the compound (or a composition (e.g., pharmaceutical) including the compound or consisting essentially of the compound) provided is of Formula I-d:
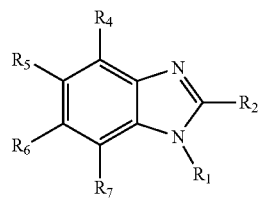
Formula I-d
wherein R₁ is selected from the group consisting of:
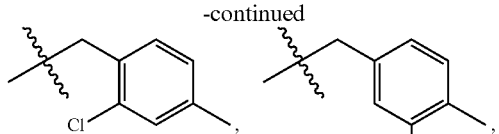
-continued
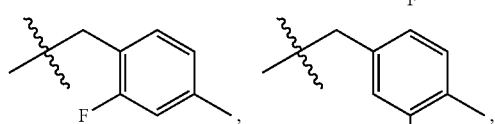
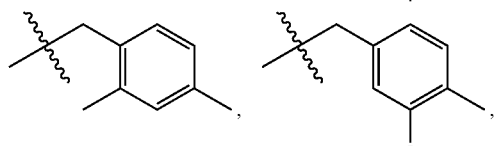
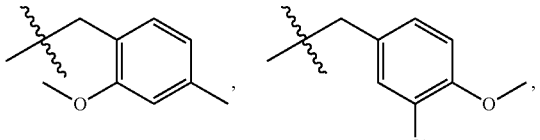
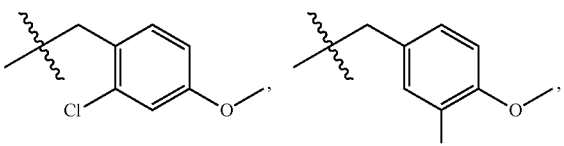
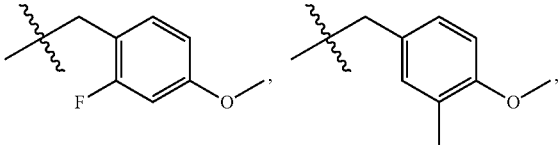
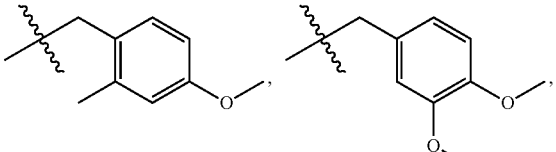
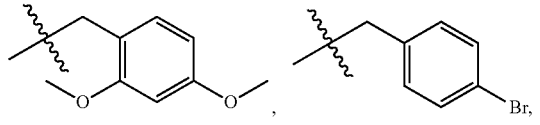
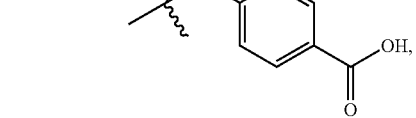
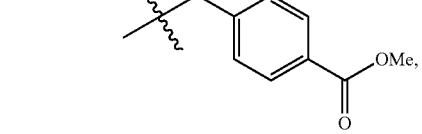
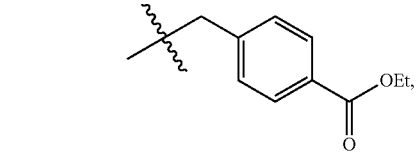

-continued
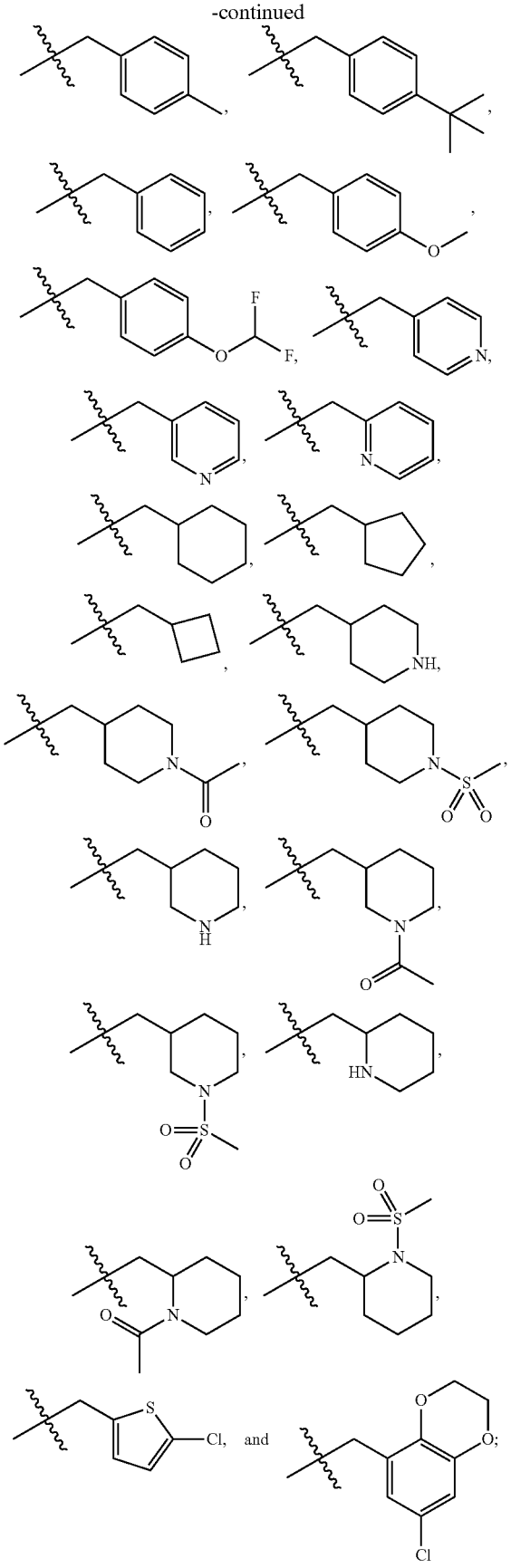
$R_2$ is —$(CHR_{10})_n$—X;
n is 1 or 2;
X is selected from the group consisting of:
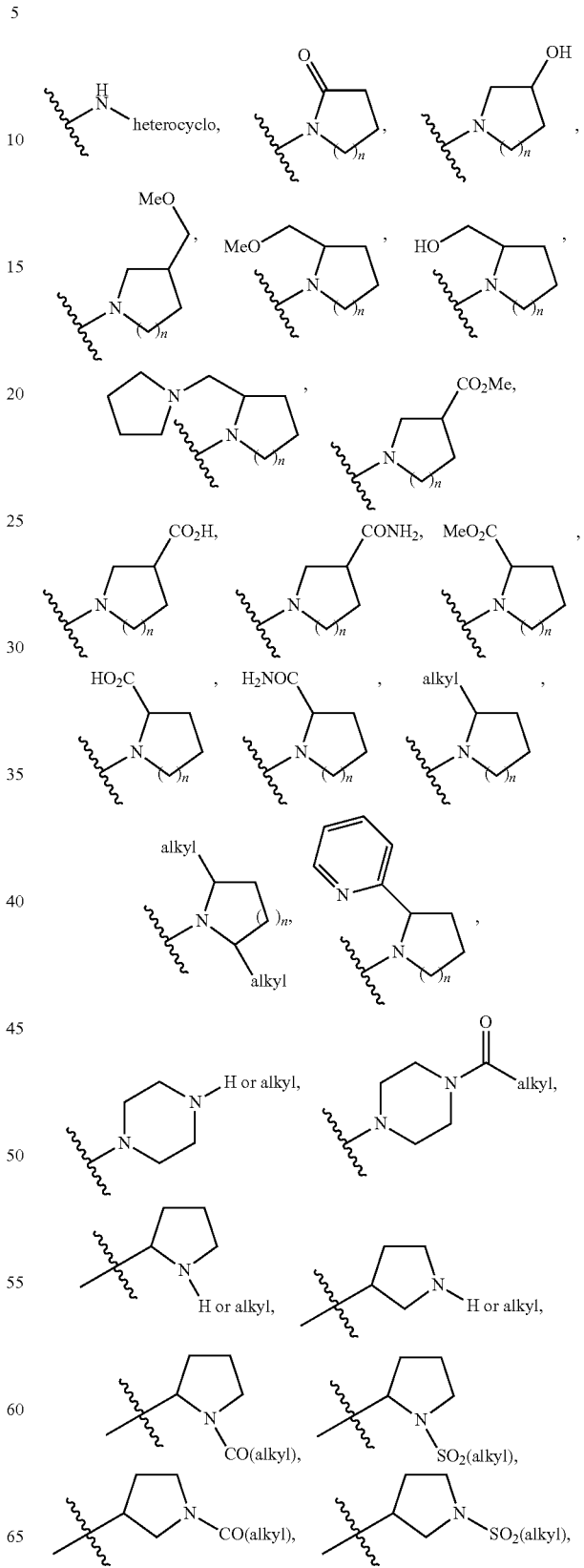

-continued

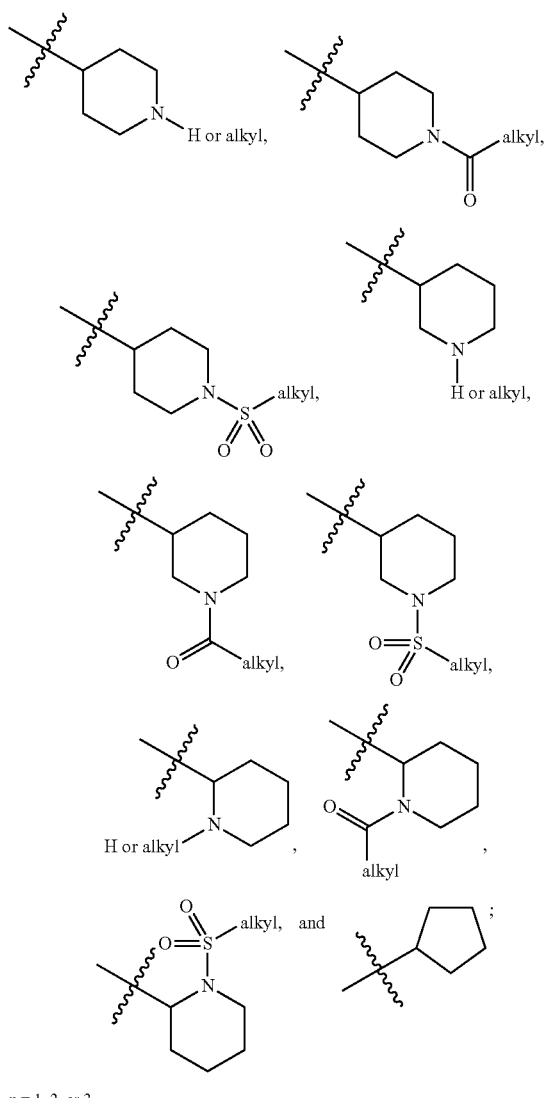

n = 1, 2, or 3 each of $R_4$-$R_7$ is independently selected from the group consisting of: —H, —Cl, —F, —CH$_3$, —OCH$_3$, —NH$_2$,

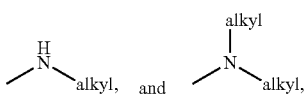

$R_{10}$ is hydrogen or alkyl;
or a pharmaceutically acceptable salt, an isomer, a tautomer, or a prodrug thereof. In one embodiment, $R_1$ is monosubstituted phenyl. In one embodiment, X is a C-attached, a substituted or an unsubstituted, 5, 6, or 7 membered heterocycle containing at least one nitrogen atom. In one embodiment, $R_4$ and $R_7$ are hydrogen.

In other embodiments, the compound (or a composition (e.g., pharmaceutical) including the compound or consisting essentially of the compound) has a structure of Formula XXXX:

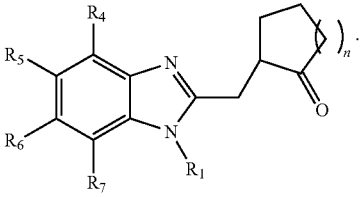

Formula XXXX provided that the compound is not

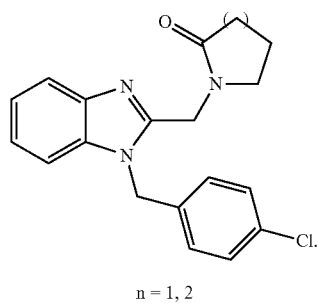

n = 1, 2

In another aspect of the invention, a compound (or a composition (e.g., pharmaceutical) including the compound or consisting essentially of the compound) of Formula I having a structure of Formula XXXXI, or a pharmaceutically acceptable salt, isomer, tautomer or prodrug thereof, is provided:

Formula XXXXI wherein $R_1$ is selected from the group consisting of: —H or

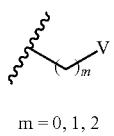

m = 0, 1, 2 wherein V is selected from alkyl, cycloalkyl, heterocyclo, aryl or heteroaryl, and n is 0, 1 or 2;
each of $R_4$-$R_7$ is independently selected from the group consisting of: —Br, —I, —Cl, —F, —CH$_3$, —CN, —OH, —OCH$_3$, —NO$_2$, —NH$_2$,

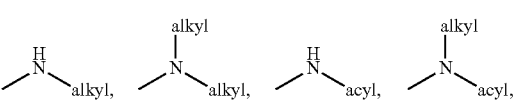

-continued

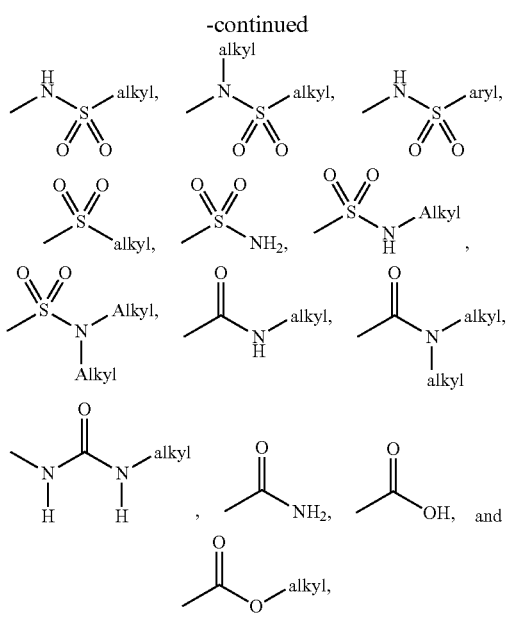

or, optionally, R$_4$ and R$_5$, R$_5$ and R$_6$, or R$_6$ and R$_7$ are joined together with a bond to form a 5, 6, or 7-membered ring; or, optionally, R$_4$ and R$_5$, R$_5$ and R$_6$, or R$_6$ and R$_7$ are joined together to form a 1,2-(methylenedioxy)benzene ring system; at least one of R$_4$-R$_7$ is not hydrogen. In some embodiments, n is 1 and R$_5$ is —S(O)$_2$alkyl, —S(O)$_2$NH$_2$, or —S(O)$_2$NH (alkyl). In another embodiment, R$_1$ is benzyl monosubstituted on the phenyl ring. In another embodiment, R$_1$ is 4-chlorobenzyl. In another embodiment, R$_7$ is hydrogen. In another embodiment, R$_4$ and R$_7$ are hydrogen.

In another aspect of the invention, a compound (or a composition (e.g., pharmaceutical) including the compound or consisting essentially of the compound) of Formula I having a structure of Formula XXXV (in two types, A and B), or a pharmaceutically acceptable salt, isomer, tautomer or prodrug thereof, is provided:

Formula XXXV-A

Formula XXXV-B wherein R$_1$ is selected from the group consisting of: —H and m = 0, 1, 2 wherein V is selected from alkyl, cycloalkyl, heterocyclo, aryl or heteroaryl;

each of R$_4$-R$_7$ is independently selected from the group consisting of: —H, —I, —Br, —Cl, —F, —CH$_3$, —CN, —OH, —OCH$_3$, —NO$_2$, —NH$_2$, or, optionally, R$_4$ and R$_5$, R$_5$ and R$_6$, or R$_6$ and R$_7$ are joined together with a bond to form a 5, 6, or 7-membered ring; or, optionally, R$_4$ and R$_5$, R$_5$ and R$_6$, or R$_6$ and R$_7$ are joined together to form a 1,2-(methylenedioxy)benzene ring system; R$_8$ is alkyl, aryl or heteroaryl, and when R$_5$ and R$_6$ are both methyl, and R$_4$ and R$_7$ are hydrogen, then R$_8$ is not phenyl. In some of the embodiments of the compound of Formula XXXV-A and Formula XXXV-B, heteroaryl is 2-pyridyl, 3-pyridyl or 4-pyridyl. In other embodiments of the compound of Formula XXXV, R$_4$ is selected from the group consisting of: —NH$_2$,

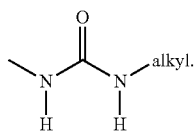

In another aspect of the invention, a compound (or a composition (e.g., pharmaceutical) including the compound or consisting essentially of the compound) of Formula I having a structure of Formula I-e, or a pharmaceutically acceptable salt, isomer, tautomer or prodrug thereof, is provided:

Formula I-e

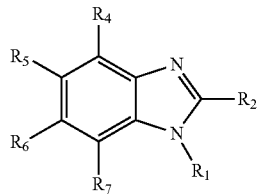

wherein $R_1$ is selected from the group consisting of: —H and

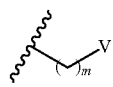

m = 0, 1, 2 wherein V is selected from alkyl, cycloalkyl, heterocyclo, aryl or heteroaryl;

$R_2$ is selected from the group consisting of: —H,

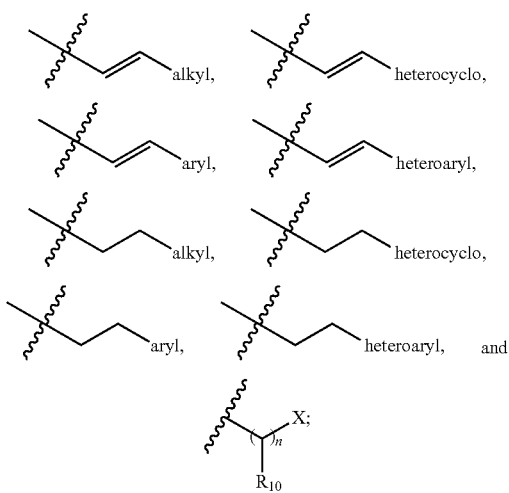

n = 0, 1, 2, 3, 4 wherein X is selected from the group consisting of: —N(alkyl)$_2$, N-attached substituted heterocyclo, N-attached halogen-substituted heterocyclo, CONH(alkyl), COHC(aryl), -alkyl, cycloalkyl, alkenyl,

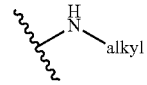

or cycloalkyl or aryl or heteroaryl or heterocyclo,

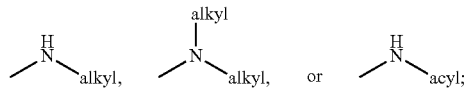

or cycloalkyl or aryl or heteroaryl or heterocyclo, -aryl, heteroaryl, —C-attached heterocyclo where heterocyclo contains at least 1 nitrogen, —O-Linker-C-attached heterocyclo where heterocyclo contains at least 1 nitrogen and —N-Linker-C-attached heterocyclo where heterocyclo contains at least 1 nitrogen, where Linker is a substituted or an unsubstituted $C_1$-$C_6$ alkylene, heteroalkylene, alkenylene, or heteroalkenylene, where in X is not —NMe$_2$; $R_4$ is selected from the group consisting of:

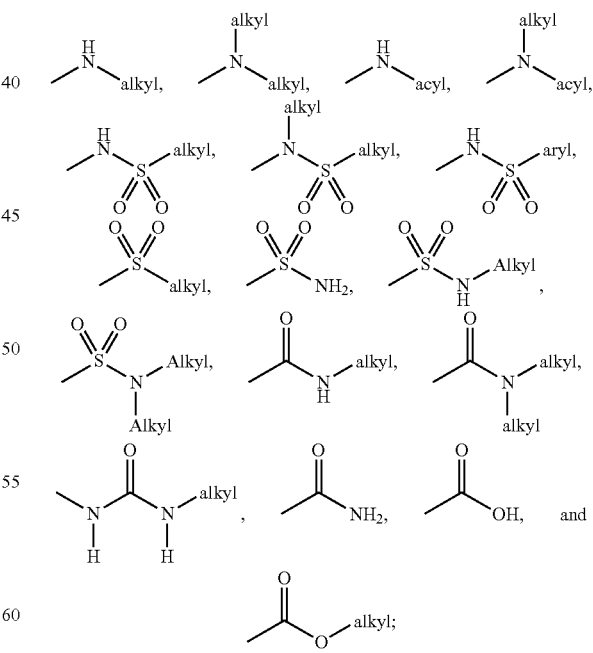

each of $R_5$-$R_7$ is independently selected from the group consisting of: —H, —I, —Br, —Cl, —F, —CH$_3$, —CN, —OH, —OCH$_3$, —NO$_2$, —NH$_2$, or, optionally, $R_4$ and $R_5$, $R_5$ and $R_6$, or $R_6$ and $R_7$ are joined together with a bond to form a 5, 6, or 7-membered ring; or, optionally, $R_4$ and $R_5$, $R_5$ and $R_6$, or $R_6$ and $R_7$ are joined together to form a 1,2-(methylenedioxy)benzene ring system;

$R_{10}$ is hydrogen or alkyl; and wherein when $R_4$ is

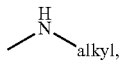

at least one of $R_5$-$R_7$ is not hydrogen. In one embodiment, $R_1$ is a benzyl monosubstituted on the phenyl ring. In another embodiment, $R_1$ is 4-chlorobenzyl. In another embodiment, $R_7$ is hydrogen. In another embodiment, $R_4$ and $R_7$ are hydrogen.

In another aspect of the invention, a compound (or a composition (e.g., pharmaceutical) including the compound or consisting essentially of the compound) of Formula I having a structure of Formula I-f, or a pharmaceutically acceptable salt, isomer, tautomer or prodrug thereof, is provided:

Formula I-f

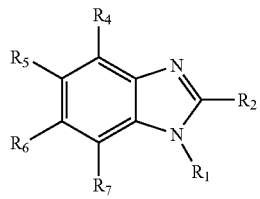

wherein $R_1$ is selected from the group consisting of: —H and

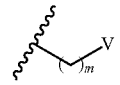

m = 0, 1, 2 wherein V is selected from cycloalkyl or heterocyclo, and m is 0, 1 or 2; $R_2$ is selected from the group consisting of: —H,

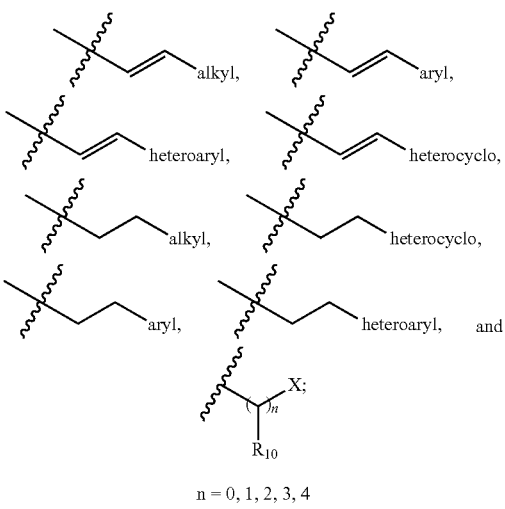

n = 0, 1, 2, 3, 4 wherein X is selected from the group consisting of: N-attached substituted heterocyclo, N-attached halogen-substituted heterocyclo,

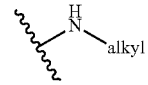

or cycloalkyl or aryl or heteroaryl or heterocyclo, —N(alkyl)$_2$, —CONH(alkyl), —COHC(aryl), -alkyl, -cycloalkyl, -alkenyl,

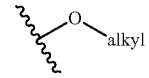

or cycloalkyl or aryl or heteroaryl or heterocyclo, -aryl, -heteroaryl, —C-attached heterocyclo where heterocyclo contains at least 1 nitrogen, —O-Linker-C-attached heterocyclo where heterocyclo contains at least 1 nitrogen and —N-Linker-C-attached heterocyclo where heterocyclo contains at least 1 nitrogen, where Linker is a substituted or an unsubstituted $C_1$-$C_6$ alkylene, heteroalkylene, alkenylene, or heteroalkenylene; each of $R_4$-$R_7$ is independently selected from the group consisting of: —H, —I, —Br, —Cl, —F, —CH$_3$, —CN, —OH, —OCH$_3$, —NO$_2$, —NH$_2$,

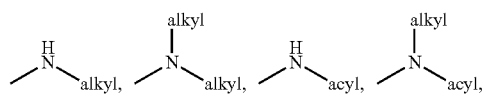

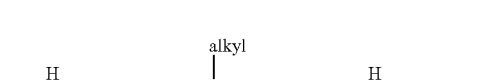

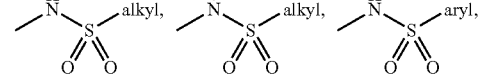

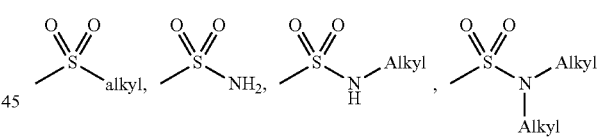

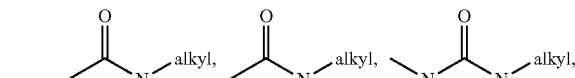

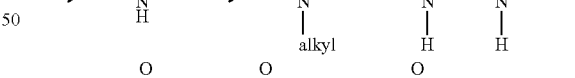

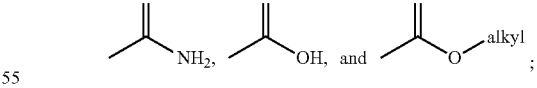

or, optionally, $R_4$ and $R_5$, $R_5$ and $R_6$, or $R_6$ and $R_7$ are joined together with a bond to form a 5, 6, or 7-membered ring; or, optionally, $R_4$ and $R_5$, $R_5$ and $R_6$, or $R_6$ and $R_7$ are joined together to form a 1,2-(methylenedioxy)benzene ring system; and $R_{10}$ is hydrogen or alkyl.

In another aspect of the invention, a compound (or a composition (e.g., pharmaceutical) including the compound or consisting essentially of the compound) of Formula I having a structure of Formula XXXXI, or a pharmaceutically acceptable salt, isomer, tautomer or prodrug thereof, is provided:

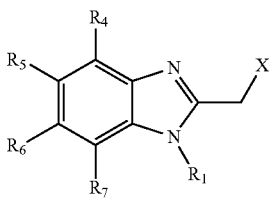

Formula XXXXI wherein X is selected from the group consisting of: alkyl, cycloalkyl, heteroaryl,

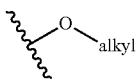

or cycloalkyl or aryl or heteroaryl or heterocyclo; $R_1$ is selected from the group consisting of: —H and

m = 0, 1, 2 wherein V is selected from alkyl, cycloalkyl, heterocyclo, aryl or heteroaryl; each of $R_4$-$R_7$ is independently selected from the group consisting of: —H, —Br, —Cl, —F, —$CH_3$, —CN, —OH, —$OCH_3$, —$NO_2$, —$NH_2$,

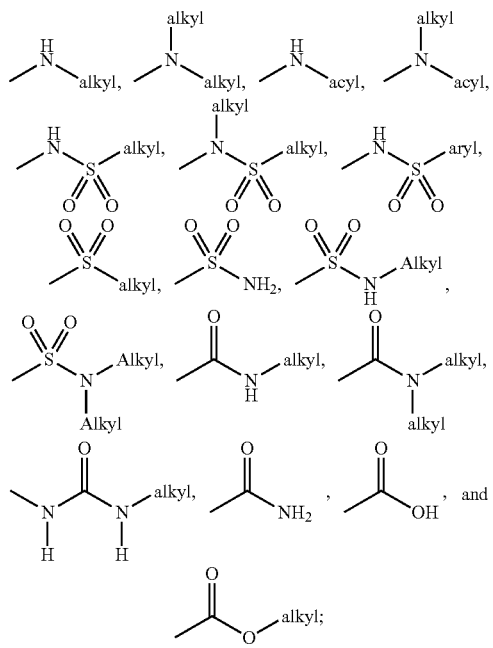

or, optionally, $R_4$ and $R_5$, $R_5$ and $R_6$, or $R_6$ and $R_7$ are joined together with a bond to form a 5, 6, or 7-membered ring; or, optionally, $R_4$ and $R_5$, $R_5$ and $R_6$, or $R_6$ and $R_7$ are joined together to form a 1,2-(methylenedioxy)benzene ring system; and wherein at least one of $R_4$-$R_7$ is other than hydrogen. In another embodiment, $R_1$ is benzyl monosubstituted on the phenyl ring. In another embodiment, $R_1$ is 4-chlorobenzyl. In another embodiment, $R_7$ is hydrogen. In another embodiment, $R_4$ and $R_7$ are hydrogen.

In another aspect, the present invention provides a compound (or a composition (e.g., pharmaceutical) including the compound or consisting essentially of the compound) of Formula III

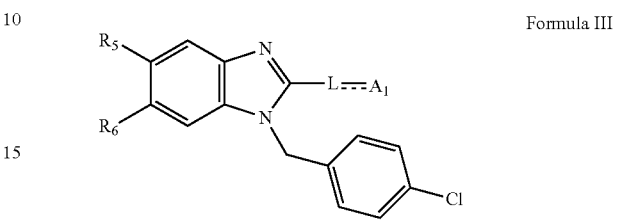

Formula III or a pharmaceutically acceptable salt, an isomer, a tautomer, or a prodrug thereof wherein L is a substituted or an unsubstituted $C_1$-$C_6$ alkylene, $C_1$-$C_6$ heteroalkylene, $C_2$-$C_6$ alkenylene, $C_2$-$C_6$ heteroalkenylene, or methyne;

$A_1$ is a substituted or an unsubstituted, 5, 6, or 7-membered heterocyclo containing at least one nitrogen atom wherein the heterocyclo is attached to L via a carbon atom or a nitrogen atom;

—NH—$C_1$-$C_6$ alkyl, —NH—$C_3$-$C_8$ cylcoalkyl, —NH-aryl, NH-heterocyclo, —O—$C_1$-$C_6$ alkyl, —O—$C_3$-$C_8$ cylcoalkyl, —O-aryl, or —O-heterocyclo;

or a substituted or an unsubstituted 5 or 6-membered cycloalkyl;

═════ denotes a single or a double bond, $R_5$ is hydrogen, a substituted or an unsubstituted $C_1$-$C_4$ alkyl, a substituted or an unsubstituted aryl or heteroaryl, or $NR_{33}R_{34}$;

$R_6$ is hydrogen or a substituted or an unsubstituted $C_1$-$C_4$ alkyl or $NR_{33}R_{34}$; and $R_{33}$ and $R_{34}$ are independently hydrogen, $C_1$-$C_6$ alkyl, a substituted or an unsubstituted $C_3$-$C_8$ cycloalkyl, or $R_{33}$ and $R_{34}$ together with the nitrogen atom to which they are attached form a 5-9 membered non aromatic heterocycle;

provided that the compound is not clemizole,

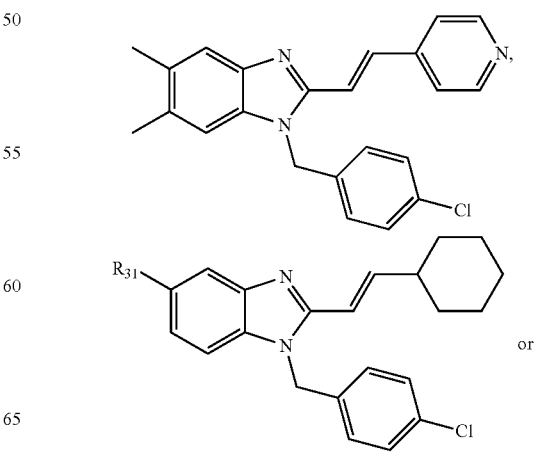

or

-continued

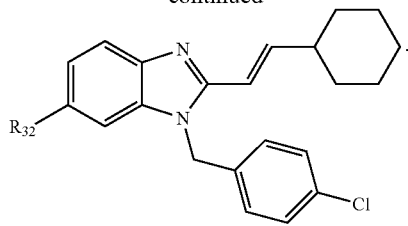

In one embodiment, the present invention provides compounds of Formula III wherein L is a substituted or an unsubstituted, 5, 6, or 7-membered heterocyclo containing at least one nitrogen atom wherein the heterocyclo is attached to L via a carbon atom. In another embodiment, L is an N-attached substituted, 5, 6, or 7 membered heterocyclo. In another embodiment, L is a substituted or an unsubstituted 5 or 6-membered heteroaryl containing at least one nitrogen atom. In another embodiment, L is an N-attached 5, 6, or 7 membered halogen-substituted heterocyclo group.

In one embodiment, the present invention provides compounds of Formula III wherein L is a substituted or an unsubstituted $C_1$-$C_6$ alkylene, $C_1$-$C_6$ heteroalkylene, $C_2$-$C_6$ alkenylene, $C_2$-$C_6$ heteroalkenylene, or methyne group;

$A_1$ is a substituted or an unsubstituted, 5 or 6 membered, non aromatic heterocycle containing at least one basic nitrogen atom wherein the heterocycle is attached to L via a carbon atom, a substituted or an unsubstituted 6 membered heteroaryl containing at least one basic nitrogen atom,

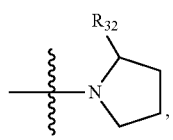

or a substituted or an unsubstituted 6 membered cycloalkyl;

$R_5$ is hydrogen, substituted or unsubstituted $C_1$-$C_4$ alkyl, substituted or unsubstituted aryl or heteroaryl, or $NR_{33}R_{34}$;

$R_6$ is hydrogen or substituted or unsubstituted $C_1$-$C_4$ alkyl;

$R_{32}$ is hydrogen, methyl, or hydroxymethyl; and $R_{33}$ and $R_{34}$ are independently hydrogen, $C_1$-$C_6$ alkyl, a substituted or an unsubstituted $C_3$-$C_8$ cycloalkyl, or together with the nitrogen atom to which they are attached form a 5-9 membered non aromatic heterocycle.

In another embodiment, the present invention provides compounds (or a composition (e.g., pharmaceutical) including the compound or consisting essentially of the compound) of Formula III-A

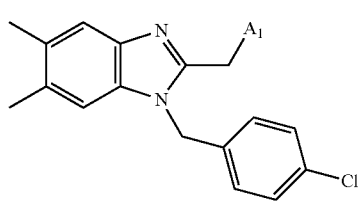

Formula III-A wherein $A_1$ is

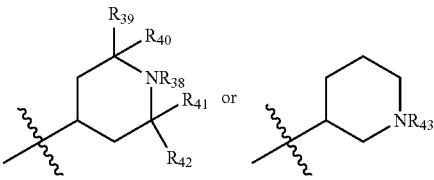

$R_{38}$ is hydrogen, an unsubstituted $C_1$-$C_3$ alkyl, $C_1$-$C_3$ alkyl substituted with a substituted or an unsubstituted $C_3$-$C_8$ cycloalkyl or phenyl group, or a substituted or an unsubstituted $C_3$-$C_8$ cycloalkyl;

$R_{39}$, $R_{40}$, $R_{11}$, and $R_{42}$ are independently hydrogen, a substituted or an unsubstituted $C_1$-$C_3$ alkyl, or $R_{40}$ and $R_{41}$ together with the carbon atoms they are attached to form a cyclic moiety; and $R_{43}$ is hydrogen, an unsubstituted $C_1$-$C_3$ alkyl, or $C_1$-$C_3$ alkyl substituted with a substituted or an unsubstituted $C_3$-$C_8$ cycloalkyl or phenyl group.

In another embodiment, the present invention provides compounds (or a composition (e.g., pharmaceutical) including the compound or consisting essentially of the compound) of formula III-B Formula III-B

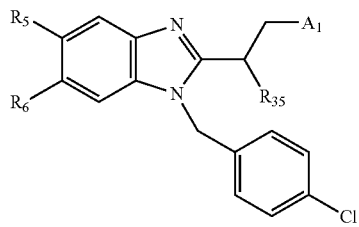

wherein, $R_{49}$ is hydrogen, a unsubstituted $C_1$-$C_3$ alkyl, $C_1$-$C_3$ alkyl substituted with a substituted or an unsubstituted $C_3$-$C_8$ cycloalkyl or phenyl group; and $R_{39}$, $R_{40}$, $R_{41}$, and $R_{42}$ are independently hydrogen, a substituted or an unsubstituted $C_1$-$C_3$ alkyl, or $R_{40}$ and $R_{41}$ together with the carbon atoms they are attached to form a cyclic moiety.

In another embodiment, the present invention provides compounds (or a composition (e.g., pharmaceutical) including the compound or consisting essentially of the compound) of Formula III-C Formula III-C wherein $R_5$ is substituted or unsubstituted $C_1$-$C_3$ alkyl or 5 membered heteroaryl group;

$R_6$ is hydrogen or a substituted or an unsubstituted $C_1$-$C_3$ alkyl;

$R_{35}$ is hydrogen or a substituted or an unsubstituted $C_1$-$C_3$ alkyl;

$A_1$ is a substituted or an unsubstituted pyridyl or

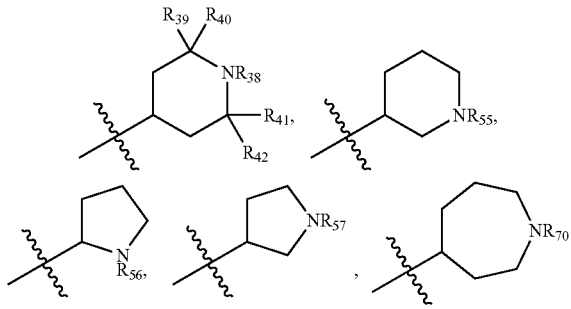

wherein each nonaromatic heterocycle is further optionally substituted on the ring, other than the substituent on the nitrogen atom, with one or more substituents;

$R_{39}$, $R_{40}$, $R_{41}$, and $R_{42}$ are independently hydrogen, a substituted or an unsubstituted $C_1$-$C_3$ alkyl, or $R_{40}$ and $R_{41}$ together with the carbon atoms they are attached to form a cyclic moiety; and $R_{38}$, $R_{55}$, $R_{56}$, $R_{57}$, and $R_{70}$ independently are hydrogen, a substituted or an unsubstituted $C_1$-$C_3$ alkyl or $C_3$-$C_8$ cycloalkyl, aryl, heteroaryl, or $R_{58}$—$SO_2$—; and $R_{58}$ is a substituted or an unsubstituted $C_1$-$C_3$ alkyl.

In another embodiment, the present invention provides compounds (or a composition (e.g., pharmaceutical) including the compound or consisting essentially of the compound) of Formula III-D Formula III-D

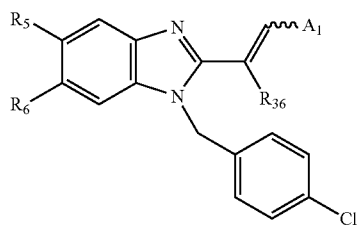

wherein $R_{36}$ is a substituted or an unsubstituted $C_1$-$C_3$ alkyl and $A_1$ is a substituted or an unsubstituted pyridyl or

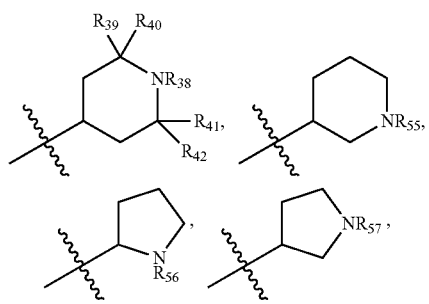

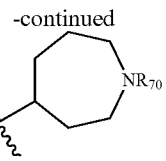

wherein each nonaromatic heterocycle is further optionally substituted on the ring, other than the substituent on the nitrogen atom, with one or more substituents;

the wiggly line denotes an E or Z stereochemistry around the double bond to which the wiggly line is attached;

$R_{39}$, $R_{40}$, $R_{41}$, and $R_{42}$ are independently hydrogen, a substituted or an unsubstituted $C_1$-$C_3$ alkyl, or $R_{40}$ and $R_{41}$ together with the carbon atoms they are attached to form a cyclic moiety;

$R_{38}$, $R_{55}$, $R_{56}$, $R_{57}$, and $R_{70}$ independently are hydrogen, a substituted or an unsubstituted $C_1$-$C_3$ alkyl or $C_3$-$C_8$ cycloalkyl, aryl, heteroaryl, or $R_{58}$—$SO_2$—; and $R_{58}$ is a substituted or an unsubstituted $C_1$-$C_3$ alkyl.

In another embodiment, the present invention provides compounds (or a composition (e.g., pharmaceutical) including the compound or consisting essentially of the compound) of Formula III-E Formula III-E

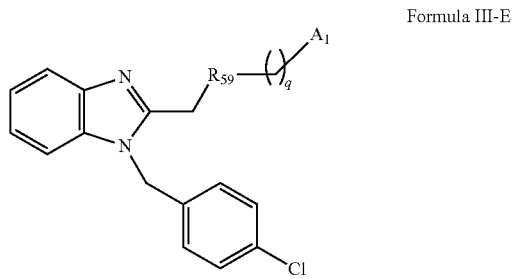

wherein $R_{59}$ is —O—, or —$NR_{60}$;

$R_{60}$ is hydrogen or a substituted or an unsubstituted $C_1$-$C_3$ alkyl; q is 0, 1, or 2;

$A_1$ is a substituted or av unsubstituted pyridyl or

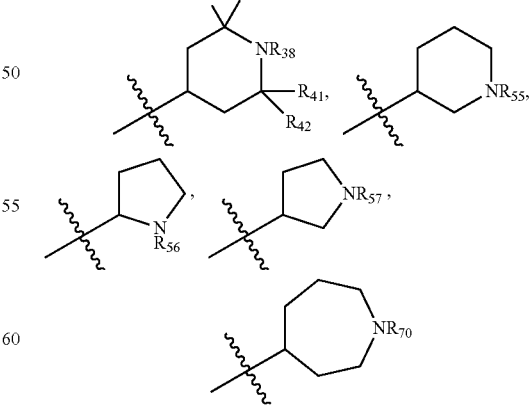

wherein each nonaromatic heterocycle is further optionally substituted on the ring, other than the substituent on the nitrogen atom, with one or more substituents;

$R_{39}$, $R_{40}$, $R_{41}$, and $R_{42}$ are independently hydrogen, a substituted or an unsubstituted $C_1$-$C_3$ alkyl, or $R_{40}$ and $R_{41}$ together with the carbon atoms they are attached to form a cyclic moiety;

$R_{38}$, $R_{55}$, $R_{56}$, $R_{57}$, and $R_{70}$ independently are hydrogen, a substituted or an unsubstituted $C_1$-$C_3$ alkyl or $C_3$-$C_8$ cycloalkyl, aryl, heteroaryl, or $R_{58}$—$SO_2$—;

$R_{58}$ is a substituted or an unsubstituted $C_1$-$C_3$ alkyl.

In another embodiment, the present invention provides compounds (or a composition (e.g., pharmaceutical) including the compound or consisting essentially of the compound) of Formula III-C, III-D, and III-E wherein $A_1$ is a 5 or 6 membered nonaromatic heterocycle.

In another embodiment, the present invention provides compounds (or a composition (e.g., pharmaceutical) including the compound or consisting essentially of the compound) of Formula IV Formula IV

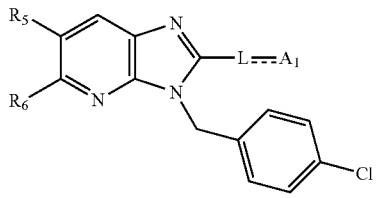

wherein L is a substituted or an unsubstituted $C_1$-$C_6$ alkylene, $C_1$-$C_6$ heteroalkylene, $C_2$-$C_6$ alkenylene, or $C_2$-$C_6$ heteroalkenylene;

$A_1$ is a substituted or an unsubstituted, 5 or 6 membered, non aromatic heterocycle containing at least one basic nitrogen atom wherein the heterocycle is attached to L via a carbon atom, a substituted or an unsubstituted 6 membered heteroaryl containing at least one basic nitrogen atom,

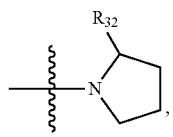

or a substituted or an unsubstituted 6 membered cycloalkyl;
------ denotes a single or double bond, $R_5$ is hydrogen, a substituted or an unsubstituted $C_1$-$C_4$ alkyl, a substituted or an unsubstituted aryl or heteroaryl, or $NR_{33}R_{34}$;

$R_6$ is hydrogen, a substituted or an unsubstituted $C_1$-$C_4$ alkyl, or $NR_{33}R_{34}$;

$R_{32}$ is hydrogen, methyl, or hydroxymethyl; and $R_{33}$ and $R_{34}$ are independently hydrogen, $C_1$-$C_6$ alkyl, a substituted or an unsubstituted $C_3$-$C_8$ cycloalkyl;
or a pharmaceutically acceptable salt thereof.

In another embodiment, the present invention provides compounds of Formula IV wherein L is $C_1$-$C_3$ alkylene and $R_5$ is hydrogen.

In other embodiments, the clemizole analogs of formula III, III-A, III-B, III-C, III-D, III-E, and IV are useful, according to the present invention, in the treatments methods and the pharmaceutical compositions of the present invention.

In another aspect of the invention, a pharmaceutical composition is provided comprising, or consisting essentially of, a compound of any one of Formulae I-XXXXI, or a pharmaceutically acceptable salt, isomer, tautomer or prodrug thereof. In one embodiment, the compound is of formula III, III-A, III-B, III-E, or IV or a pharmaceutically acceptable salt, isomer, tautomer or prodrug thereof.

In another aspect of the invention, a pharmaceutical composition is provided, comprising, or consisting essentially of, a compound of any one of Formulae I-XXXXI, or a pharmaceutically acceptable salt, isomer, tautomer or prodrug thereof, and further comprising one or more additional anti-HCV therapeutic agents selected from the group consisting of: an HCV NS3 protease inhibitor, an HCV NS5B RNA-dependent RNA polymerase inhibitor, a thiazolide, a sustained release thiazolide, a nucleoside analog, an interferon-alpha, a pegylated interferon, ribavirin, levovirin, viramidine, a TLR7 agonist, a TLR9 agonist, a cyclophilin inhibitor, an alpha-glucosidase inhibitor, an NS5A inhibitor, and an NS3 helicase inhibitor. In one embodiment, the compound formulated with one or more additional anti-HCV therapeutic agents is of formula III, III-A, III-B, III-E, or IV or a pharmaceutically acceptable salt, isomer, tautomer or prodrug thereof.

In another aspect of the invention, a pharmaceutical composition is provided, comprising, or consisting essentially of, a compound of any one of Formulae I-XXXXI, including, without limitation, the compound of formula III, III-A, III-B, or IV, or a pharmaceutically acceptable salt, isomer, tautomer or prodrug thereof, and at least one additional anti-HCV therapeutic agent selected from the group consisting of: an HCV NS3 protease inhibitor, an HCV NS5B RNA-dependent RNA polymerase inhibitor, a thiazolide, a sustained release thiazolide, a nucleoside analog, an interferon-alpha, a pegylated interferon, ribavirin, levovirin, viramidine, a TLR7 agonist, a TLR9 agonist, a cyclophilin inhibitor, an alpha-glucosidase inhibitor, an NS5A inhibitor, and an NS3 helicase inhibitor. In one embodiment, the compound of Formula I has the structure:

Formula I

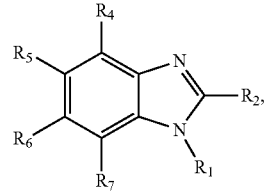

wherein $R_1$ is selected from the group consisting of: —H and

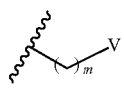

$m = 0, 1, 2$;

wherein V is selected from alkyl, cycloalkyl, heterocyclo, aryl or heteroaryl; $R_2$ is selected from the group consisting of: —H and

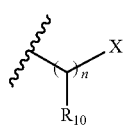

n = 0, 1, 2, 3, 4;

wherein X is selected from the group consisting of: —N(alkyl)$_2$, -alkyl, cycloalkyl, alkenyl, N-attached substituted heterocyclo, N-attached halogen-substituted heterocyclo,

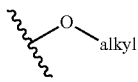

or cycloalkyl or aryl or heteroaryl or heterocyclo,

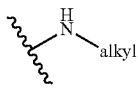

or cycloalkyl or aryl or heteroaryl or heterocyclo, -aryl, heteroaryl, —C-attached heterocyclo where heterocyclo contains at least 1 nitrogen, —O-Linker-C-attached heterocyclo where heterocyclo contains at least 1 nitrogen and —N-Linker-C-attached heterocyclo where heterocyclo contains at least 1 nitrogen, where Linker is a substituted or an unsubstituted $C_1$-$C_6$ or $C_2$-$C_6$ alkylene, heteroalkylene, alkenylene, or heteroalkenylene group; each of $R_4$-$R_7$ is independently selected from the group consisting of: —H, —Br, —Cl, —F, —CH$_3$, —CN, —OH, —OCH$_3$, —NO$_2$, —NH$_2$,

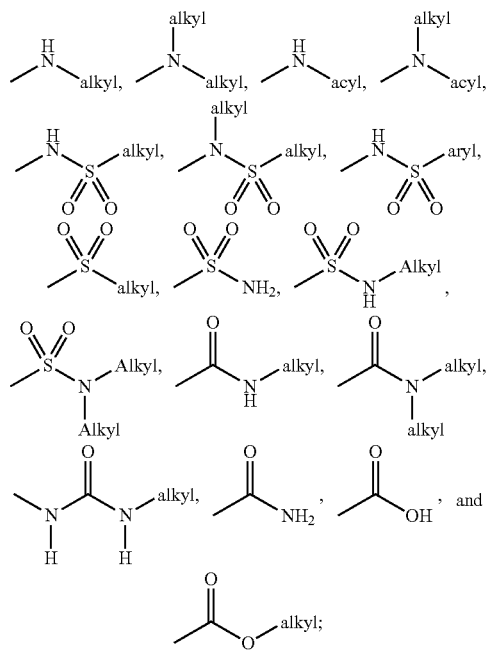

or, optionally, $R_4$ and $R_5$, $R_5$ and $R_6$, or $R_6$ and $R_7$ are joined together with a bond to form a 5, 6, or 7-membered ring; or, optionally, $R_4$ and $R_5$, $R_5$ and $R_6$, or $R_6$ and $R_7$ are joined together to form a 1,2-(methylenedioxy)benzene ring system; and $R_{10}$ is hydrogen or alkyl.

In various embodiments, the methods, compounds and pharmaceutical formulations of the present invention exclude compounds of formula

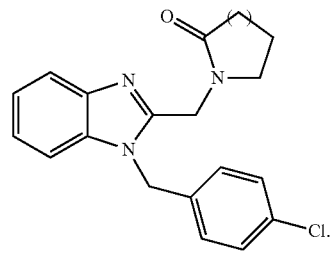

n = 1, 2

DETAILED DESCRIPTION

Before the present invention is described in greater detail, it is to be understood that this invention is not limited to particular embodiments described, and the embodiment of the invention as such may, of course, vary. It is also to be understood that the terminology used herein is for the purpose of describing particular embodiments only, and is not intended to be limiting, because the scope of the present disclosure will be limited only by the appended claims. Unless defined otherwise, all technical and scientific terms used herein have the same meaning as commonly understood by one of ordinary skill in the art to which this invention belongs. All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible. Embodiments of the present disclosure will employ, unless otherwise indicated, techniques of synthetic organic chemistry, biochemistry, biology, molecular biology, recombinant DNA techniques, pharmacology, and the like, which are within the skill of the art. Such techniques are explained fully in the literature. The examples herein are put forth so as to provide those of ordinary skill in the art with an illustrative disclosure and description of how to perform the methods and use the compounds disclosed and claimed herein. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also contemplated that, where multi-step processes are described in the present disclosure that steps can be executed in different sequence where this is logically possible. As used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

A. Definitions

In describing and claiming the disclosed subject matter, the following terminology will be used in accordance with the definitions set forth below.

By "Flaviviridae virus" is meant any virus of the Flaviviridae family, including those viruses that infect humans and non-human animals. The polynucleotide and polypeptides sequences encoding these viruses are well known in the art, and may be found at NCBI's GenBank database, e.g., as Genbank Accession numbers NC_004102, AB031663, D11355, D11168, AJ238800, NC_001809, NC_001437, NC_004355 NC_004119, NC_003996, NC_003690, NC_003687, NC_003675, NC_003676, NC_003218, NC_001563, NC_000943, NC_003679, NC_003678, NC_003677, NC_002657, NC_002032, and NC_001461, the contents of which database entries are incorporated by references herein in their entirety.

As used herein, the terms "treatment", "treating", and "treat" are defined as acting upon a disease, disorder, or condition with an agent to reduce or ameliorate the pharmacologic and/or physiologic effects of the disease, disorder, or condition and/or its symptoms. "Treatment," as used herein, covers any treatment of a disease in a host (e.g., a mammal, typically a human or non-human animal of veterinary interest), and includes: (a) reducing the risk of occurrence of the disease in a subject determined to be predisposed to the disease but not yet diagnosed as infected with the disease (b) impeding the development of the disease, and (c) relieving the disease, i.e., causing regression of the disease and/or relieving one or more disease symptoms. "Treatment" is also meant to encompass delivery of an inhibiting agent to provide a pharmacologic effect, even in the absence of a disease or condition. For example, "treatment" encompasses delivery of a disease or pathogen inhibiting agent that provides for enhanced or desirable effects in the subject (e.g., reduction of pathogen load, reduction of disease symptoms, and the like.).

As used herein, the terms "prophylactically treat" and "prophylactically treating" refer completely or partially preventing a disease or symptom thereof and/or may be therapeutic in terms of a partial or complete cure for a disease and/or adverse effect attributable to the disease.

As used herein, the term "host," "subject," "patient," or "organism" includes humans and mammals (e.g., mice, rats, pigs, cats, dogs, and horses). Typical hosts to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living host" refers to a host noted above or another organism that is alive. The term "living host" refers to the entire host or organism and not just a part excised (e.g., a liver or other organ) from the living host.

The terms "isolated compound" and "purified compound" mean a compound which has been substantially separated from, or enriched relative to, other compounds with which it occurs in nature. Isolated compounds are usually at least about 80%, at least 90% pure, at least 98% pure, or at least about 99% pure, by weight. The present disclosure is meant to include diastereomers as well as their racemic and resolved, enantiomerically pure forms and pharmaceutically acceptable salts thereof.

The term "unit dosage form," as used herein, refers to physically discrete units suitable as unitary dosages for human and/or animal subjects, each unit containing a predetermined quantity of a compound (e.g., an anti-viral compound, as described herein) calculated in an amount sufficient to produce the desired effect in association with a pharmaceutically acceptable diluent, carrier or vehicle. The specifications for unit dosage forms depend on the particular compound employed, the route and frequency of administration, and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

As used herein, a "pharmaceutical composition" and a "pharmaceutical formulation" are meant to encompass a composition suitable for administration to a subject, such as a mammal, especially a human. In general a "pharmaceutical composition" or "pharmaceutical formulation" is sterile, and preferably free of contaminants that are capable of eliciting an undesirable response within the subject (e.g., the compound (s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

The terms "therapeutically effective amount" and "an effective amount" are used interchangeably herein and refer to that amount of an agent (which may be referred to as a compound, an inhibitory agent, and/or a drug) being administered that is sufficient to effect the intended application including but not limited to disease treatment. For example, an effective amount of an inhibiting agent will relieve to some extent one or more of the symptoms of the disease, i.e., infection, being treated, and/or that amount that will prevent, to some extent, one or more of the symptoms of the disease, i.e., infection, that the host being treated has or is at risk of developing. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. inhibiting viral replication in a target cell, and inhibiting NS4B binding to viral RNA. The specific dose will vary depending on the particular compounds chosen, the dosing regimen to be followed, whether it is administered in combination with other compounds, timing of administration, the tissue to which it is administered, and the physical delivery system in which it is carried.

A heterocycle or heteroaryl containing at least one basic nitrogen atom refers to a heterocycle or heteroaryl moiety including a nitrogen atom with a pKa of about 5 to about 13. Nonlimiting examples of heterocycles or heteroaryls containing at least one basic nitrogen atom include substituted and unsubstituted piperidine, pyrrolidine, and pyridine.

"Pharmaceutically acceptable salt" refers to those salts (organic or inorganic) that retain the biological effectiveness and optionally other properties of the free bases. Pharmaceutically acceptable salts can be obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

In the event that embodiments of the disclosed agents form salts, these salts are within the scope of the present disclosure. Reference to an agent of any of the formulas herein is understood to include reference to salts thereof, unless otherwise indicated. The term "salt(s)", as employed herein, denotes acidic and/or basic salts formed with inorganic and/or organic acids and bases. In addition, when an agent contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of an agent may be formed, for example, by reacting the agent with an amount of acid or base, such as an equivalent amount, in a medium such as one in which the salt precipitates or in an aqueous medium followed by lyophilization.

Embodiments of the agents that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, malates (salts formed with malic acid), maleates (formed with maleic acid), ethanesulfonates (formed with ethanesulfonic acid), methanesulfonates (formed with methanesulfonic acid), 2-naphthalenesulfonates, nicotinates, nitrates, oxalates, pectinates, persulfates, 3-phenylpropionates, phosphates (formed with phosphoric acid), picrates, pivalates, propionates, salicylates, succinates, sulfates (such as those formed with sulfuric acid), sulfonates (such as those mentioned herein including those formed with p-toluenesulfonic acid), tartrates, thiocyanates, toluenesulfonates such as tosylates, undecanoates, and the like.

Embodiments of the agents that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Solvates of the agents of the disclosure are also contemplated herein.

To the extent that the disclosed active compounds, and salts thereof, may exist in their tautomeric form, all such tautomeric forms are contemplated herein as part of the present disclosure.

All stereoisomers of the agents, such as those that may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The term "prodrug" refers to an inactive precursor of an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N.J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of β-Lactam antibiotics, Pharm. Biotech. 11:345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur.

J. Drug Metab. Pharmacokinet, 15(2): 143-53; Balimane and Sinko (1999). Involvement of multiple transporters in the oral absorption of nucleoside analogues, Adv. Drug Delivery Rev., 39(1-3):183-209; Browne (1997). Fosphenyloin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. Drug Metab, 1(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4):265-87.

The term "administration" refers to introducing an agent of the present disclosure into a host. One preferred route of administration of the agents is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

The term "aliphatic group" refers to a saturated or unsaturated linear or branched hydrocarbon group and encompasses alkyl, alkenyl, and alkynyl groups, for example.

The terms "alk" or "alkyl" refers to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, n-octyl, dodecyl, octadecyl, amyl, 2-ethylhexyl, and the like. An alkyl group is optionally substituted, unless stated otherwise, with one or more groups, selected from aryl (optionally substituted), heteroaryl, heterocyclo (optionally substituted), carbocyclo (optionally substituted), halo, hydroxy, protected hydroxy, alkoxy (e.g., $C_1$ to $C_7$) (optionally substituted), acyl (e.g., $C_1$ to $C_7$), aryloxy (e.g., $C_1$ to $C_7$) (optionally substituted), alkylester (optionally substituted), arylester (optionally substituted), alkanoyl (optionally substituted), aroyl (optionally substituted), carboxy, protected carboxy, cyano, nitro, amino, substituted amino, (monosubstituted)amino, (disubstituted)amino, protected amino, amido, lactam, urea, urethane, sulfonyl, and the like.

The term "alkenyl" refers to straight or branched chain hydrocarbon groups having 2 to 12 carbon atoms, preferably 2 to 4 carbon atoms, and at least one double carbon to carbon bond (either cis or trans), such as ethenyl. An alkenyl group is optionally substituted, unless stated otherwise, with one or more groups, selected from aryl (including substituted aryl), heteroaryl, heterocyclo (including substituted heterocyclo), carbocyclo (including substituted carbocyclo), halo, hydroxy, alkoxy (optionally substituted), aryloxy (optionally substituted), alkylester (optionally substituted), arylester (optionally substituted), alkanoyl (optionally substituted), aroyl (optionally substituted), cyano, nitro, amino, substituted amino, amido, lactam, urea, urethane, sulfonyl, and the like.

The term, "alkenylene" refers to straight or branched chain divalent hydrocarbon groups having 2 to 12 carbon atoms, preferably 2 to 6 carbon atoms, and at least one double carbon to carbon bond (either cis or trans), such as ethenyl. For example, "$C_2$-$C_6$ alkenylene" is meant to include —CH=CH—, —C(Me)=CH—, —CH=CHCH$_2$—, —CH=CH(CH$_2$)$_2$—, —CH=CH(CH$_2$)$_3$—, —CH=CH(CH$_2$)$_4$—, and the like. An alkenylene group may be substituted and "substituted alkenylene" refers to an alkenylene group having from 1 to 5 and, in some embodiments, 1 to 3 or 1 to 2 substituents selected from aryl (optionally substituted), heteroaryl, heterocyclo (optionally substituted), carbocyclo (optionally substituted), halo, hydroxy, protected hydroxy, alkoxy (e.g., $C_1$ to $C_7$) (optionally substituted), acyl (e.g., $C_1$ to $C_7$), aryloxy (e.g., $C_1$ to $C_7$) (optionally substituted), alkylester (optionally substituted), arylester (optionally substituted), alkanoyl (optionally substituted), aroyl (optionally substituted), carboxy, protected carboxy, cyano, nitro, amino, substituted amino, (monosubstituted)amino, (disubstituted) amino, protected amino, amido, lactam, urea, urethane, sulfonyl, and the like, and includes alkenylene groups where geminal hydrogens are substituted with =O moiety.

The term "alkylene" refers to divalent saturated aliphatic hydrocarbon groups having from 1 to 12 carbon atoms and, in some embodiments, from 1 to 6 carbon atoms. The alkylene groups include branched and straight chain hydrocarbon groups. For example, "$C_1$-$C_6$ alkylene" is meant to include methylene, ethylene, propylene, butylene, 2-methylpropylene, pentylene, hexylene, and the like. "Substituted alkylene" refers to an alkylene group having from 1 to 5 and, in some embodiments, 1 to 3 or 1 to 2 substituents selected from aryl (optionally substituted), heteroaryl, heterocyclo (optionally substituted), carbocyclo (optionally substituted), halo, hydroxy, protected hydroxy, alkoxy (e.g., $C_1$ to $C_7$) (optionally substituted), acyl (e.g., $C_1$ to $C_7$), aryloxy (e.g., $C_1$ to $C_7$) (optionally substituted), alkylester (optionally substituted), arylester (optionally substituted), alkanoyl (optionally substituted), aroyl (optionally substituted), carboxy, protected carboxy, cyano, nitro, amino, substituted amino, (monosubstituted)amino, (disubstituted)amino, protected amino, amido, lactam, urea, urethane, sulfonyl, and the like, and includes alkylene groups where geminal hydrogens are substituted with =O moiety.

The term "alkynyl" refers to straight or branched chain hydrocarbon groups having 2 to 12 carbon atoms, preferably 2 to 4 carbon atoms, and at least one triple carbon to carbon bond, such as ethynyl. An alkynyl group is optionally substituted, unless stated otherwise, with one or more groups, selected from aryl (including substituted aryl), heteroaryl, heterocyclo (including substituted heterocyclo), carbocyclo (including substituted carbocyclo), halo, hydroxy, alkoxy (optionally substituted), aryloxy (optionally substituted), alkylester (optionally substituted), arylester (optionally substituted), alkanoyl (optionally substituted), aroyl (optionally substituted), cyano, nitro, amino, substituted amino, amido, lactam, urea, urethane, sulfonyl, and the like.

The term "alkoxy" refers to an alkyl group linked to oxygen thus: R—O—. In this function, R represents the alkyl group. An example is the methoxy group $CH_3O$—.

"Organic groups" may be functionalized or otherwise comprise additional functionalities associated with the organic group, such as carboxyl, amino, hydroxyl, and the like, which may be protected or unprotected. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, and the like. Thus, "alkyl group" includes ethers, esters, haloalkyls, nitroalkyls, carboxyalkyls, hydroxyalkyls, sulfoalkyls, and the like.

"Cyano" refers to a —CN radical.

The terms "halo" and "halogen" refer to the fluoro, chloro, bromo or iodo groups. There can be one or more halogen groups, which can be the same or different. In an embodiment, each halogen can be substituted by one of the other halogens.

The term "haloalkyl" refers to an alkyl group as defined above that is substituted by one or more halogen atoms. The halogen atoms may be the same or different. The term "dihaloalkyl" refers to an alkyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the alkyl group has been replaced by a fluoro group.

The term "cycloalkyl" refers to a mono-, bi-, or tricyclic saturated ring that is fully saturated or partially unsaturated. Examples of such a group includes cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like. A cycloalkyl group is optionally substituted, unless stated otherwise, with one or more groups, selected from aryl (including substituted aryl), heterocyclo (including substituted heterocyclo), carbocyclo (including substituted carbocyclo), halo, hydroxy, protected hydroxy, alkoxy (e.g., $C_1$ to $C_7$) (optionally substituted), acyl (e.g., $C_1$ to $C_7$), aryloxy (e.g., $C_1$ to $C_7$) (optionally substituted), alkylester (optionally substituted), arylester (optionally substituted), alkanoyl (optionally substituted), aroyl (optionally substituted), carboxy, protected carboxy, cyano, nitro, amino, substituted amino, (monosubstituted)amino, (disubstituted)amino, protected amino, amido, lactam, urea, urethane, sulfonyl, and the like.

The term "(cycloalkyl)alkyl" refers to the above-defined cycloalkyl group substituted by an above defined alkyl group. Examples of such a group include (cyclohexyl)methyl, 3-(cyclopropyl)-n-propyl, 5-(cyclopentyl)hexyl, 6-(adamantyl)hexyl, and the like. A (cycloalkyl)alkyl group is optionally substituted, unless stated otherwise, with one or more groups, selected from alkyl (including substituted alkyl), aryl (including substituted aryl), heterocyclo (including substituted heterocyclo), carbocyclo (including substituted carbocyclo), halo, hydroxy, protected hydroxy, alkoxy (e.g., $C_1$ to $C_7$) (optionally substituted), acyl (e.g., $C_1$ to $C_7$), aryloxy (e.g., $C_1$ to $C_7$) (optionally substituted), alkylester (optionally substituted), arylester (optionally substituted), alkanoyl (optionally substituted), aroyl (optionally substituted), carboxy, protected carboxy, cyano, nitro, amino, substituted amino, (monosubstituted)amino, (disubstituted)amino, protected amino, amido, lactam, urea, urethane, sulfonyl, and the like.

The term "substituted phenyl" refers to a phenyl group substituted with one or more moieties, and in some instances one, two, or three moieties, chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl)amino, N-(phenylsulfonyl)amino or phenyl, substituted or unsubstituted, such that, for example, a biphenyl or naphthyl group results.

Examples of the term "substituted phenyl" include a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2, 3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(isopropyl)phenyl, 2, 3, or 4-ethylphenyl, 2, 3 or 4-(n-propyl) phenyl and the like; a mono or di(alkoxy)phenyl group, for example, 2,6-dimethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono- or di(hydroxymethyl)phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like.

The term "(substituted phenyl)alkyl" refers to one of the above substituted phenyl groups attached to one of the above-described alkyl groups. The (substituted phenyl)alkyl is connected to another moiety, i.e a compound having a clemizole scaffold, through the alkyl portion of the (substituted phenyl) alkyl. Examples of (substituted phenyl)alkyl include such groups as 2-phenyl-1-chloroethyl, 2-(4'-methoxyphenyl) ethyl, 4-(2',6'-dihydroxy phenyl)$_n$-hexyl, 2-(5'-cyano-3'-methoxyphenyl)$_n$-pentyl, 3-(2',6'-dimethylphenyl)$_n$-propyl, 4-chloro-3-aminobenzyl, 6-(4'-methoxyphenyl)-3-carboxy (n-hexyl), 5-(4'-aminomethylphenyl)-3-(aminomethyl)$_n$-pentyl, 5-phenyl-3-oxo-n-pent-1-yl, (4-hydroxynapth-2-yl) methyl and the like.

The terms "ar" or "aryl" refer to aromatic homocyclic (i.e., hydrocarbon) mono-, bi- or tricyclic ring-containing groups preferably having 6 to 12 members such as phenyl, naphthyl and biphenyl. An aryl group is optionally substituted, unless stated otherwise, with one or more groups, selected from alkyl (optionally substituted alkyl), alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and the like. Optionally, adjacent substituents, together with the atoms to which they are bonded, form a 3- to 7-member ring.

The term "heteroaryl" refers to optionally substituted five-membered or six-membered rings that have 1 to 4 heteroatoms, such as oxygen, sulfur and/or nitrogen atoms, either alone or in conjunction with, additional nitrogen, sulfur or oxygen ring atoms. Furthermore, the above optionally substituted five-membered or six-membered rings can optionally be fused to an aromatic 5-membered or 6-membered ring system. For example, the rings can be optionally fused to an aromatic 5-membered or 6-membered ring system such as a benzene, pyridine or a triazole system.

The following ring systems are non-limiting examples of the heterocyclic (whether substituted or unsubstituted) radicals denoted by the term "heteroaryl": thienyl, furyl, pyrrolyl, imidazolyl, pyrazolyl, oxazolyl, isoxazolyl, thiazolyl, isothiazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

A heteroaryl group is optionally substituted, unless stated otherwise, with one or more groups, selected from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl (optionally, substituted), cycloalkyl (optionally substituted), (cycloalkyl)alkyl (optionally substituted), phenyl (optionally substituted), phenylalkyl (optionally substituted phenylalkyl). Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $C_4$ alkoxy group, similarly, "lower alkylthio" means a $C_1$ to $C_4$ alkylthio group.

The terms "heterocycle", "heterocyclic", "heterocyclic group" or "heterocyclo" refer to fully saturated or partially unsaturated or completely unsaturated, including aromatic ("heteroaryl") or nonaromatic cyclic groups (for example, 3- to 13-member monocyclic, 1-5 to 17-member bicyclic, or 10- to 20-member tricyclic ring systems, preferably containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. An N-attached heterocyclo is a heterocyclo moiety where the heterocyclo moiety is attached to a compound, e.g., a compound of Formula I through a nitrogen that forms part of the heterocyclo ring. Non-limiting examples of N-attached heterocyclo include but are not limited to

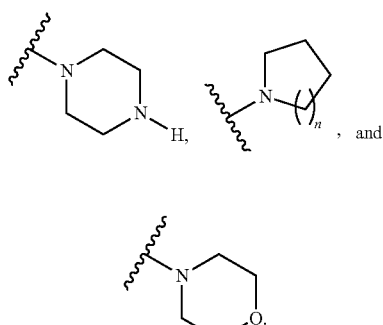

n = 1, 2 or 3

A C-attached heterocyclo is a heterocyclo moiety wherein the heterocyclo moiety is attached to a compound, e.g., a compound of formula II-a, b, or c through a carbon that forms part of the heterocyclo ring. Non-limiting examples include

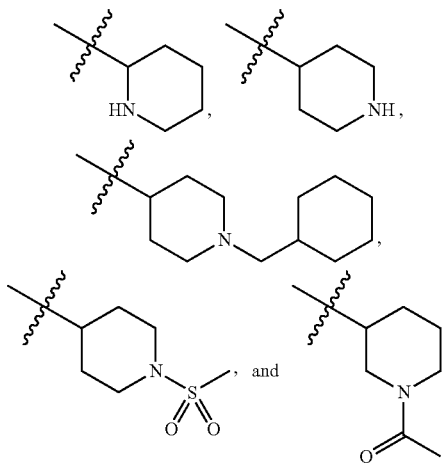

The rings of multi-ring heterocycles may be fused, bridged and/or joined through one or more Spiro unions.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranly, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl, or furo[2,3-b]pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo[3.2.1]octane), azaspiroalkyls (such as 1,4 dioxa-8-azaspiro[4.5]decane), imidazopyridinyl (such as imidazo[1,5-a]pyridin-3-yl), triazolopyridinyl (such as 1,2,4-triazolo[4,3-a]pyridin-3-yl), and hexahydroimidazopyridinyl (such as 1,5,6,7,8,8a-hexahydroimidazo[1,5-a]pyridin-3-yl), and the like.

Exemplary tricyclic heterocyclic groups include carbazolyl, benzidolyl, phenanthrolinyl, acridinyl, phenanthridinyl, xanthenyl and the like.

A heterocyclo group is optionally substituted, unless stated otherwise, with one or more groups, selected from alkyl (including substituted alkyl), alkenyl, oxo, aryl (including substituted aryl), heterocyclo (including substituted heterocyclo), carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, and the like., where optionally one or more pair of substituents together with the atoms to which they are bonded form a 3- to 7-member ring.

The term "alkanoyl" refers to an alkyl group (which may be optionally substituted as described above) linked to a carbonyl group (i.e. —C(O)-alkyl). Similarly, the term "aroyl" refers to an aryl group (which may be optionally substituted as described above) linked to a carbonyl group (i.e., —C(O)-aryl).

The term "(monosubstituted)amino" refers to an amino group with one substituent chosen from the group consisting of phenyl, substituted phenyl, alkyl (including substituted alkyl), $C_1$ to $C_4$ acyl, $C_2$ to $C_7$ alkenyl (including $C_2$ to $C_7$ substituted alkenyl), $C_2$ to $C_7$ alkynyl, $C_7$ to $C_{16}$ alkylaryl (including $C_7$ to $C_{16}$ substituted alkylaryl), and heteroaryl group. The (monosubstituted) amino can additionally have an amino-protecting group as encompassed by the term "protected (monosubstituted)amino." The term "(disubstituted) amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term, "heteroalkenylene" refers to straight or branched chain divalent hydrocarbon groups having 3 to 12 carbon atoms, and, in some embodiments, 3 to 4 carbon atoms, and at least one double carbon to carbon bond (either cis or trans), such as ethenyl, which include from 1 to 4, and, in some embodiments, from 1 to 2 —O—, —NR$^x$—, or —S— moieties, where R$^x$ is hydrogen, alkyl (optionally substituted) or alkanoyl (optionally substituted), where the —O—, —NR$^x$—, or —S— moiety is preferably not attached to a carbon to carbon double bond. For example, "$C_3$-$C_6$ heteroalkenylene" is meant to include —CH=CH—CH$_2$—O—, —CH=CH—CH$_2$—NH—, -(Me)C=CH—CH$_2$—O—, -(Me)C=CH—CH$_2$—NH—, —CH=CH—(CH$_2$)$_2$—O—, —CH=CH—(CH$_2$)$_2$—NH—, —CH=CH—(CH$_2$)$_3$—O—, —CH=CH—(CH$_2$)$_3$—NH—, —CH=CH—(CH$_2$)$_4$—O—, —CH=CH—(CH$_2$)$_4$—NH—. A "substituted heteroalkenylene" refers to an heteroalkenylene group having from 1 to 5 and, in some embodiments, 1 to 3 or 1 to 2 substituents selected from aryl (optionally substituted), heterocyclo (optionally substituted), carbocyclo (optionally substituted), halo, hydroxy, protected hydroxy, alkoxy (e.g., $C_1$ to $C_7$) (optionally substituted), acyl (e.g., $C_1$ to $C_7$), aryloxy (e.g., $C_1$ to $C_7$) (optionally substituted), alkylester (optionally substituted), arylester (optionally substituted), alkanoyl (optionally substituted), aroyl (optionally substituted), carboxy, protected carboxy, cyano, nitro, amino, substituted amino, (monosubstituted)amino, (disubstituted)amino, protected amino, amido, lactam, urea, urethane, sulfonyl, and the like, and includes alkylene groups where geminal hydrogens are substituted with =O moiety.

The term "heteroalkylene" refers to divalent saturated aliphatic hydrocarbon groups having from 1 to 12 carbon atoms and, in some embodiments, from 1 to 6 carbon atoms, which include from 1 to 4, and, in some embodiments, from 1 to 2 —O—, —NR$^x$—, or —S— moieties, where R$^x$ is hydrogen, alkyl (optionally substituted) or alkanoyl (optionally substituted). The heteroalkylene groups include branched and straight chain heteroalkylene groups. For example, "$C_1$-$C_6$ heteroalkylene" is meant to include methylene-O—, methylene-NH—, ethylene-O—, ethylene-NH—, propylene-O—, propylene-NH—, butylene-O—, butylene-NH—, pentylene-O— and pentylene-NH—, and hexylene-O— and hexylene-NH, and the like. "Substituted heteroalkylene" refers to an alkylene group having from 1 to 5 and, in some embodiments, 1 to 3 or 1 to 2 substituents selected from aryl (optionally substituted), heterocyclo (optionally substituted), carbocyclo (optionally substituted), halo, hydroxy, protected hydroxy, alkoxy (e.g., $C_1$ to $C_7$) (optionally substituted), acyl (e.g., $C_1$ to $C_7$), aryloxy (e.g., $C_1$ to $C_7$) (optionally substituted), alkylester (optionally substituted), arylester (optionally substituted), alkanoyl (optionally substituted), aroyl (optionally substituted), carboxy, protected carboxy, cyano, nitro, amino, substituted amino, (monosubstituted)amino, (disubstituted) amino, protected amino, amido, lactam, urea, urethane, sulfonyl, and the like, and includes heteroalkylene groups where geminal hydrogens are substituted with =O moiety.

The term "heteroaryl(alkyl)" refers to an alkyl group as defined above, substituted at any position by a heteroaryl group, as above defined.

"Isosteres" are different atoms, molecules, or ions that have different molecular formulae but have similar or identical outer shell electron arrangements and also have similar properties (e.g., pharmacological properties (e.g., pharmacokinetic and pharmacodynamic)).

The term "methyne" refers to the trivalent hydrocarbon radical =CR$^y$—. For an unsubstituted methyne, R$^y$ is hydrogen. For a substituted methyne, R$^y$ is alkyl (optionally substituted).

"Moiety" refers to a specific segment or functional group of a molecule. Chemical moieties are often recognized chemical entities embedded in or appended to a molecule.

"Nitro" refers to the —NO$_2$ radical.

"Oxa" refers to the —O— radical.

"Oxo" refers to the =O radical.

"Sulfonyl" refers to the groups: —S(O$_2$)—H, —S(O$_2$)-(alkyl), —S(O$_2$)-(cycloalkyl), —S(O$_2$)-(amino), —S(O$_2$)-(aryl), —S(O$_2$)-(heteroaryl), and —S(O$_2$)-(heterocycloalkyl).

"Sulfonamidyl" or "sulfonamido" refers to a —S(O)$_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —S(O)$_2$—NRR radical may be taken together with the nitrogen to which it is attached to form a 4-, 5-, 6-, or 7-membered ring (—S(O$_2$)-heterocycloalkyl). In some embodiments, it is a $C_1$-$C_{10}$ sulfonamido, wherein each R in sulfonamido contains 1 carbon, 2 carbons, 3 carbons, or 4 carbons total. A sulfonamido group is optionally substituted by one or more of the substituents described herein for alkyl, cycloalkyl, aryl, heteroaryl respectively. A "sulfone" refers to a —S(O$_2$)-(alkyl), —S(O$_2$)-(aryl), —S(O$_2$)-(heteroaryl), or —S(O$_2$)-(heterocycloalkyl) (when the sulfone group is attached to a carbon atom in the heterocycloalkyl). A sulfonamido group is optionally substituted by one or more of the substituents described herein for alkyl, cycloalkyl, aryl, and heteroaryl.

The terms "solvent," "organic solvent," and "inert solvent" each mean a solvent inert under the conditions of the reaction being described. Non-limiting examples include benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like.

The term "protecting group" refers to chemical moieties that block some or all reactive moieties of a compound and prevent such moieties from participating in certain chemical reactions until the protective group is removed, for example, those moieties listed and described in T. W. Greene, P. G. M. Wuts, Protective Groups in Organic Synthesis, 3rd ed. John Wiley & Sons (1999). Where different protecting groups are employed, that each (different) protective group may be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid moieties may be blocked with base labile groups such as, without limitation, methyl, or ethyl, and hydroxy reactive moieties may be blocked with base labile groups such as acetyl in the presence of amines blocked with acid labile groups such as tert-butyl carbamate or with carbamates that are both acid and base stable but hydrolytically removable.

In an embodiment, the term "ring" can refer to a chemical moiety having a ring structure comprising 3 to 10 carbon atoms in which one or more carbon atoms may be optionally substituted with a heteroatom, such as N, O, or S. A ring may or may not be aromatic and thus may be completely unsaturated, completely saturated, or partially unsaturated; and a ring may refer to a ring within a fused system or an unfused ring. Unless stated otherwise, the definition of "ring" does not modify other definitions of rings provided herein.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional composition components or method steps. Such additional composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

B. Methods, Compounds, and Compositions of the Invention(s)

Aspects and embodiments of the present invention(s) include methods and compositions for treatment (including prophylactic treatment) of infection by a virus that encodes NS4B. Such a virus includes any virus of the Flaviviridae family encompassing e.g., flaviviruses, pestiviruses and hepatitis C viruses. Other NS4B encoding viruses include yellow fever virus (YFV); Dengue virus, including Dengue types 1-4; Japanese Encephalitis virus; Murray Valley Encephalitis virus; St. Louis Encephalitis virus; West Nile virus; tick-borne encephalitis virus; Kunjin virus; Central European encephalitis virus; Russian spring-summer encephalitis virus; Powassan virus; Kyasanur Forest disease virus; Omsk hemorrhagic fever virus; and their respective genotypes as well as subgenotypes. The subject methods and compositions are particularly useful for treating or prophylactically treating HCV, including one or more genotypes 1, 2, 3, 4, 5, 6, and the like, as well as subtypes of any HCV genotype (e.g., 1a, 1b, 2a, 2b, 3a, and the like.).

In one embodiment, the method of treating such viral infection comprises administering to a subject infected with a virus from the Flaviviridae family, an effective amount of clemizole or clemizole analog, or a pharmaceutically acceptable salt, an isomer, a tautomer or a prodrug thereof.

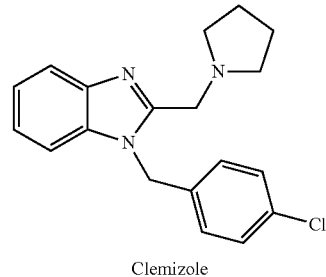 [SMILES: Clc1ccc(Cn2c(CN3CCCC3)nc3ccccc32)cc1]

Clemizole

In one aspect, the subject method is effective in reducing viral load in the infected subject by e.g., at least about 5%, 10%, 15%, 20%, 25%, 30%, 35%, 40%, 45%, 50%, 60%, 70%, 80%, 90%, 95% or even higher as compared to the level of viral load present in the subject prior to such treatment. Without being bound by any particular theory, the reduction in viral load can be effected, in whole or in part, by reducing binding of NS4B polypeptide to the viral genome. In the case of HCV, a decrease in viral load upon administering clemizole or clemizole analog can be attributable to, at least in part, a decrease in binding of NS4B polypeptide to HCV negative strand RNA, e.g., at a site on the 3'UTR.

The subject treatment methods can also employ prodrugs of clemizole, clemizole analogs or isosteres thereof. Exemplary prodrugs can be activated by liver enzymes (e.g., cyclic-1,3-propanyl esters substituted with groups that promote an oxidative cleavage reaction by CYP3A, and the like.). These modifications can render clemizole inactive or less active until it reaches the liver (see, Current Opinion in Investigational Drugs 2006 Vol 7 No 2, 109-117; *J. Med. Chem.* 2008, 51, 2328-2345; and Nucleosides, Nucleotides, and Nucleic Acids, 24 (5-7):375-381, (2005) each of which is incorporated herein by reference for the corresponding discussion).

In one embodiment, a clemizole analog provided by the present invention is a compound of Formula I-A, shown below. The structure of clemizole is shown beside Formula I-A.

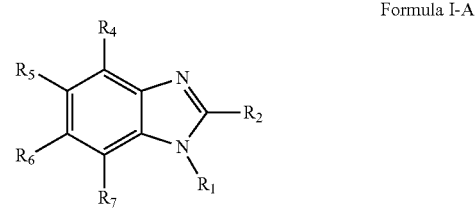

Formula I-A

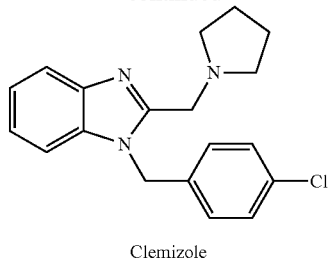

Clemizole

In one embodiment, $R_1$ is —H or

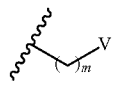

m = 0, 1, 2 wherein V is selected from alkyl, cycloalkyl, heterocyclo, aryl, or heteroaryl.

In another embodiment, $R_1$ is

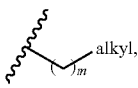

m = 0, 1, 2 wherein the alkyl moiety is unsubstituted or substituted. The alkyl moiety forming part (m=1 or 2) or all (m=0) of $R_1$, can be branched or unbranched. The alkyl moiety of $R_1$ includes, but is not limited to, methyl, ethyl, n-propyl, iso-propyl, n-butyl, iso-butyl, tert-butyl, n-pentyl, iso-pentyl, n-hexyl, septyl, heptyl, nonyl, and decyl.

In yet another embodiment, $R_1$ is

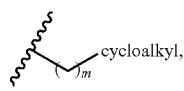

n = 0, 1, 2 wherein the cycloalkyl moiety is unsubstituted or substituted. The cycloalkyl moiety forming part (m=1 or 2) or all (m=0) of $R_1$, includes, but is not limited to, cyclopropyl, cyclobutyl, cyclopentyl and cyclohexyl. Non-limiting exemplary $R_1$ include the following formulae:

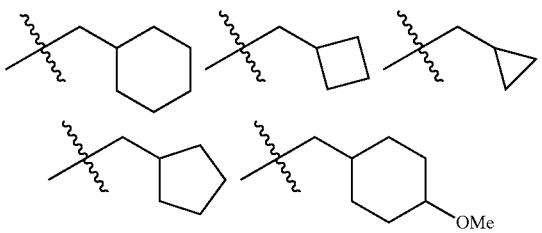

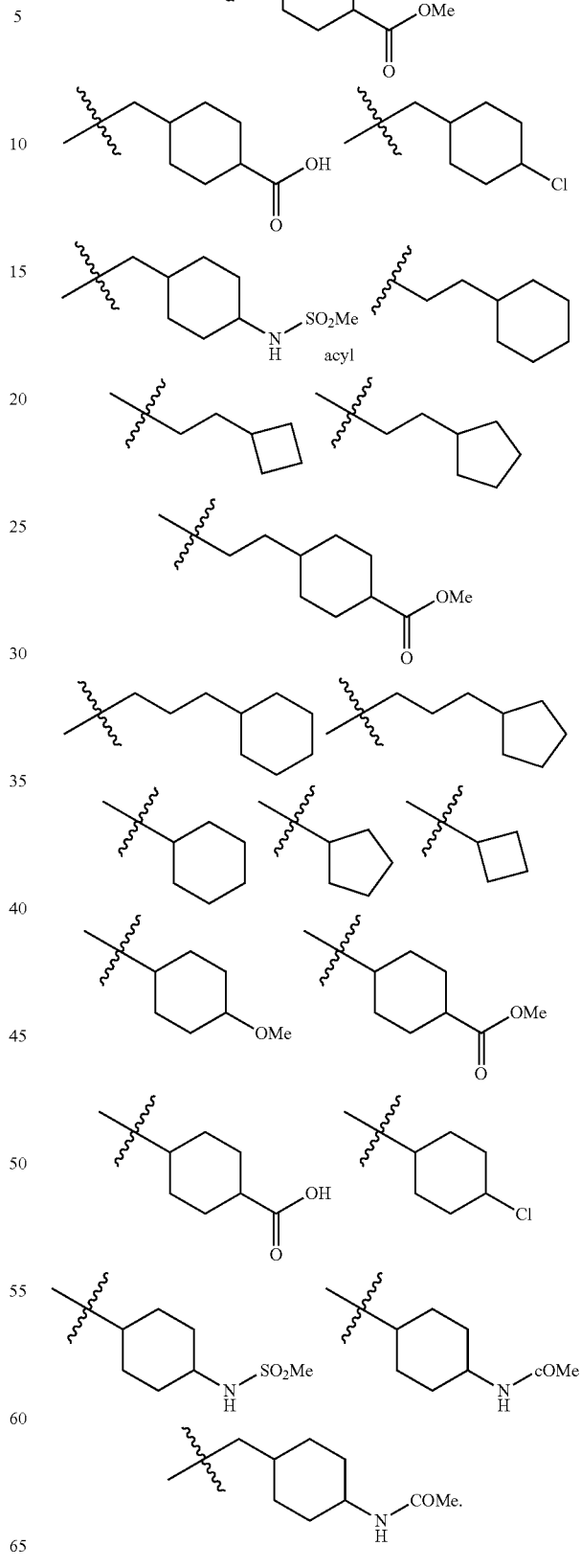

The invention further provides $R_1$ having the formula:
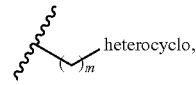
m = 0, 1, 2
wherein the heterocyclo moiety is unsubstituted or substituted. The heterocyclo moiety forming part (m=1 or 2) or all (m=0) of $R_1$, includes, but is not limited to, azetidinyl, pyrrolidinyl, morpholinyl, piperidinyl, or piperazinyl. Non-limiting exemplary $R_1$ include the following formulae:
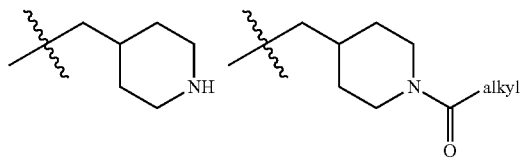
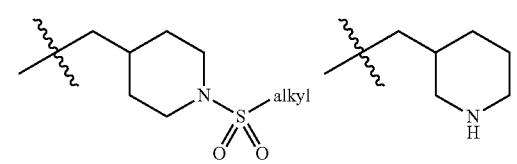
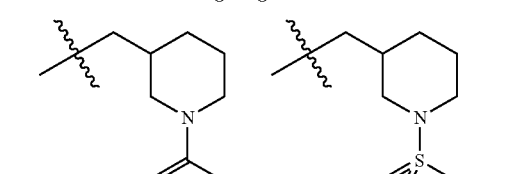
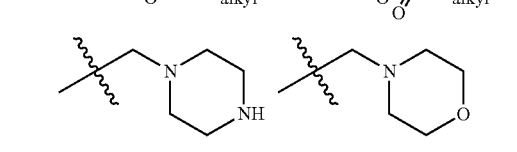
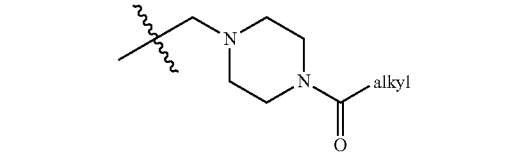
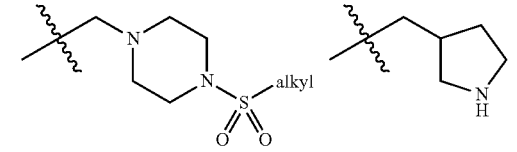
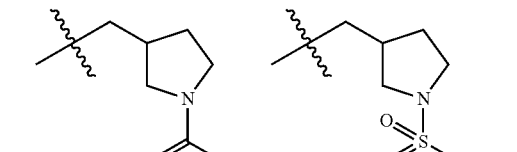
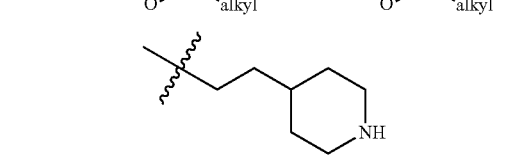
-continued
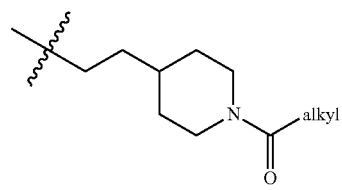
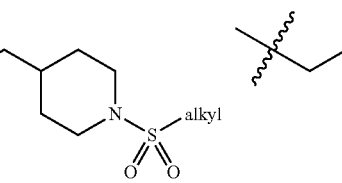
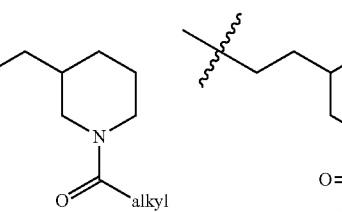
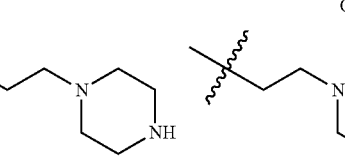
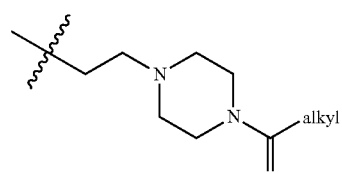
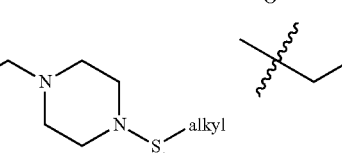
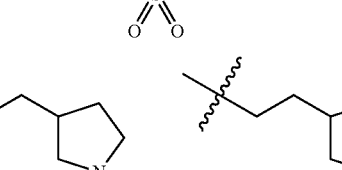
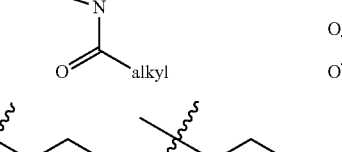
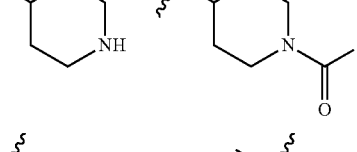
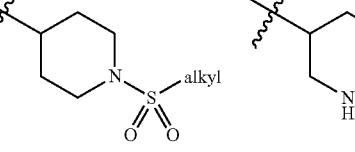

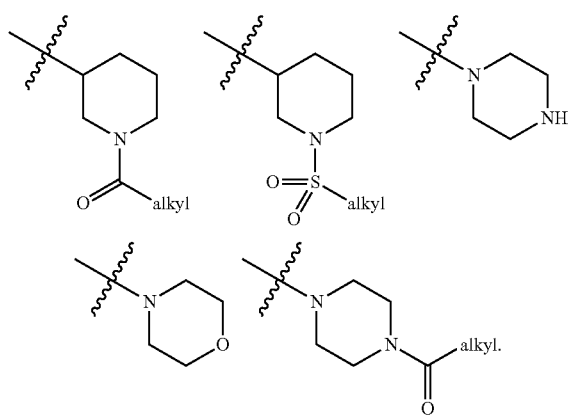

In the above formulae, alkyl includes, but is not limited to, methyl, ethyl, n-propyl, iso-propyl, n-butyl, iso-butyl, tert-butyl, n-pentyl, iso-pentyl, n-hexyl, septyl, heptyl, nonyl, and decyl.

In yet other embodiments, $R_1$ is

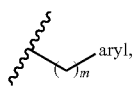

m = 0, 1, 2 wherein the aryl moiety is unsubstituted or substituted. The aryl moiety forming part (m=1 or 2) or all (m=0) of $R_1$, includes, but is not limited to, phenyl, naphthyl and fluorenyl. Non-limiting exemplary $R_1$ include the following formulae:

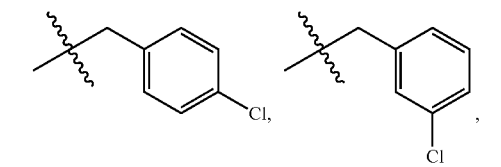
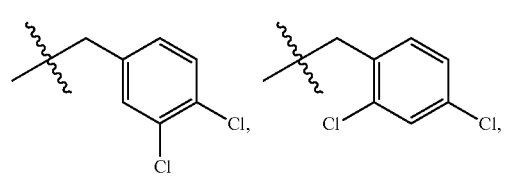
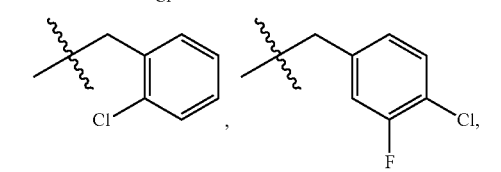
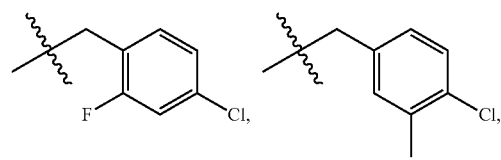
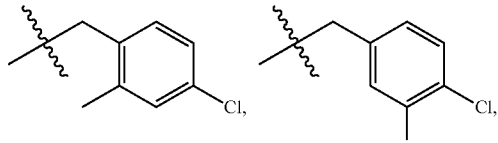
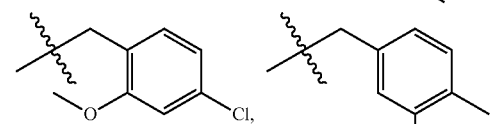
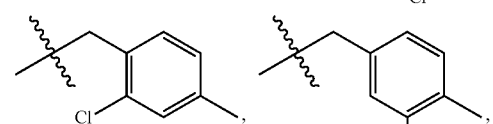
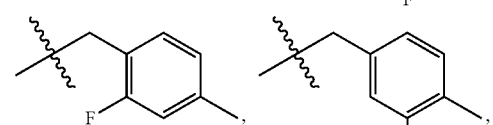
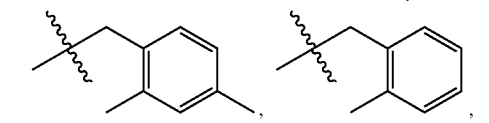
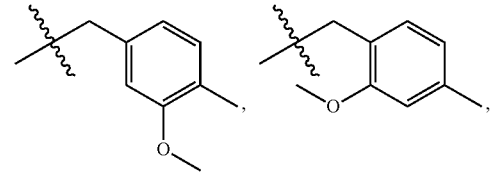
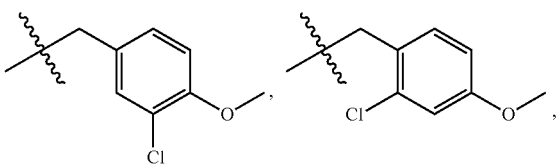
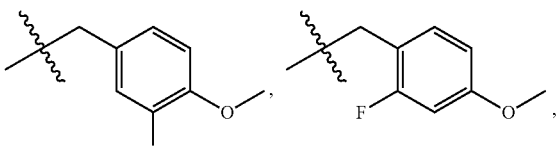
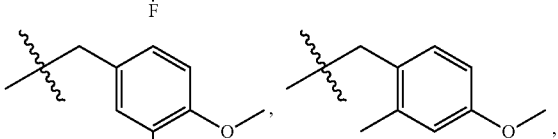
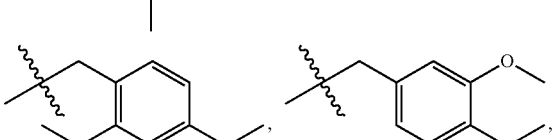
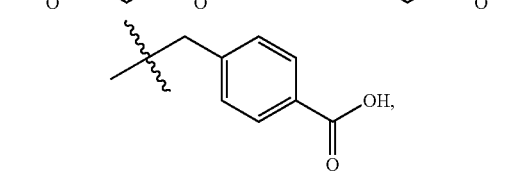

-continued

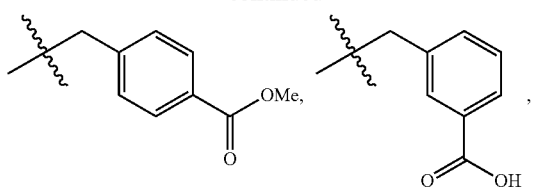
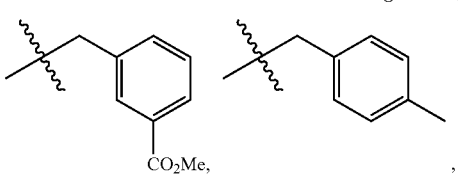
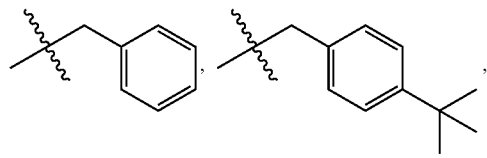
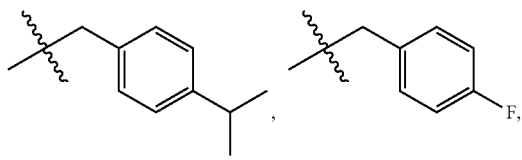
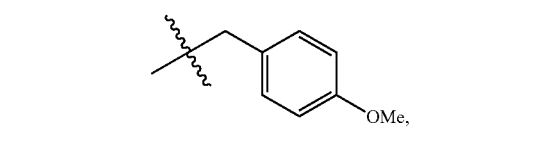
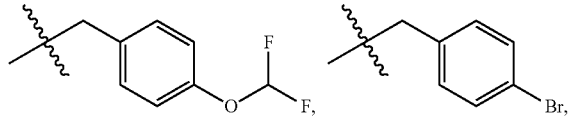
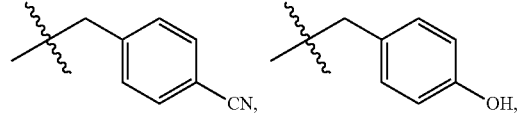
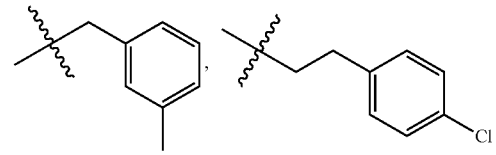
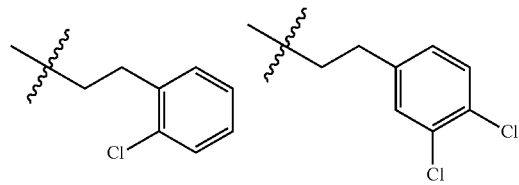
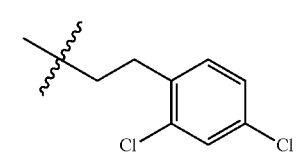
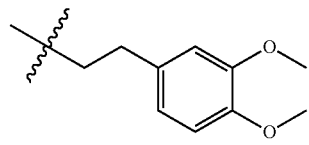

-continued

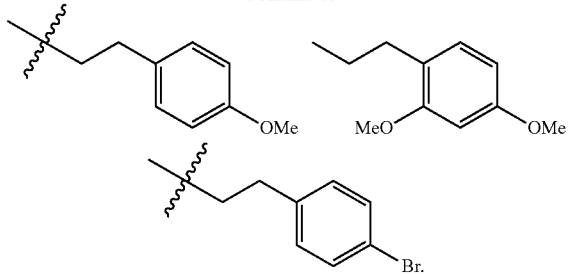

Additionally, $R_1$ can be

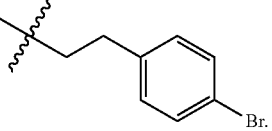

m = 0, 1, 2 wherein the heteroaryl moiety is unsubstituted or substituted. In some embodiments, the heteroaryl moiety is a monocyclic 5 membered heteroaryl. Monocyclic heteroaryl includes, but is not limited to, pyrrolyl, imidazolyl, thiazolyl, and pyrazolyl. Additional non-limiting monocyclic 5-membered heteroaryl moieties include the following formulae:

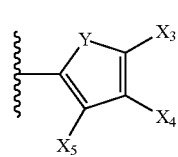
Group E

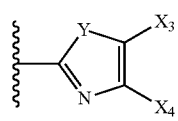
Group D

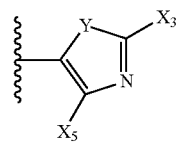
Group F

For compounds of Group D, E, and F, Y is selected from the group consisting of: —O, —S, —NH, —N-alkyl, and —N-acyl; $X_3$ is selected from the group consisting of: —H, —$CH_3$, —Cl, —F, $CF_3$ and —$OCH_3$; and $X_4$ and $X_5$ are, when present, independently selected from the group consisting of: H and $CH_3$.

Alternatively, when $R_1$ is

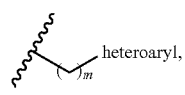

m = 0, 1, 2 heteroaryl may be a six membered heteroaryl moiety. The six membered heteroaryl moiety includes but is not limited to 2-pyridyl, 3-pyridyl, 4-pyridyl, pyrimidinyl, pyridizinyl, pyrazinyl, or triazinyl.

Non limiting examples of $R_1$ include the following formulae:

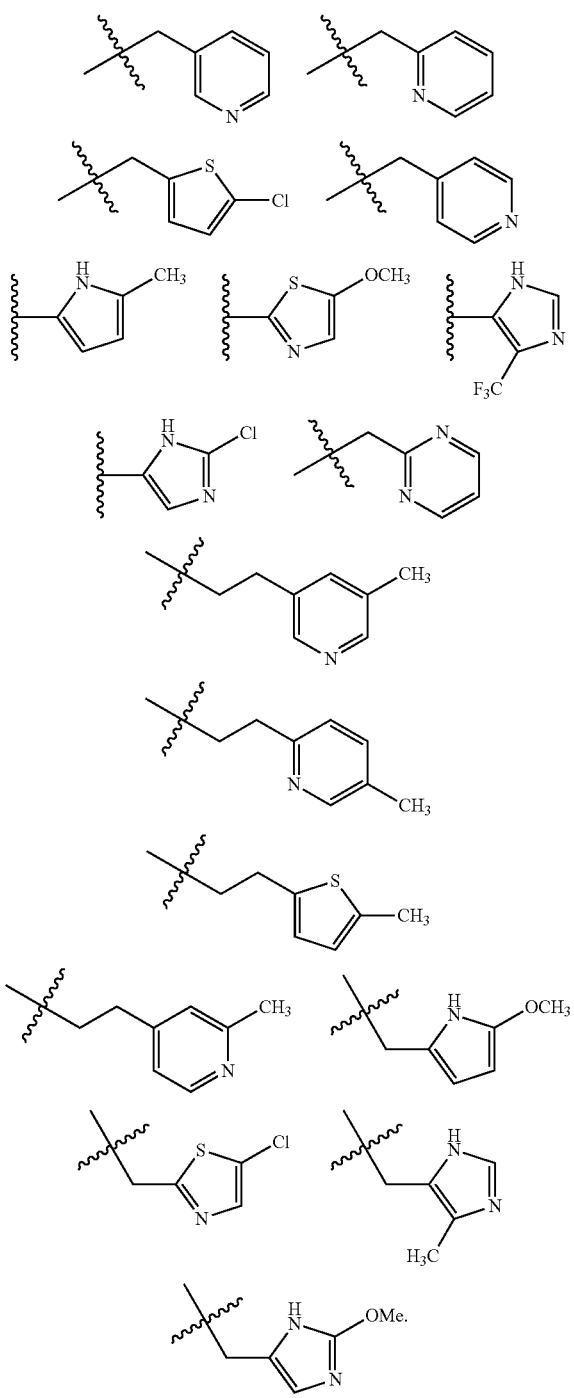

The alkyl, cycloalkyl, heterocyclo, aryl or heteroaryl moiety of $R_1$ may be substituted by one or more substituents selected from the group consisting of alkyl, aryl, heterocyclo, carbocyclo, halo, hydroxy, protected hydroxy, alkoxy, acyl, aryloxy, alkylester, arylester, alkanoyl, aroyl, carboxy, protected carboxy, cyano, nitro, amino, substituted amino, (monosubstituted)amino, (disubstituted)amino, protected amino, amido, lactam, urea, urethane, and sulfonyl.

$R_2$ is

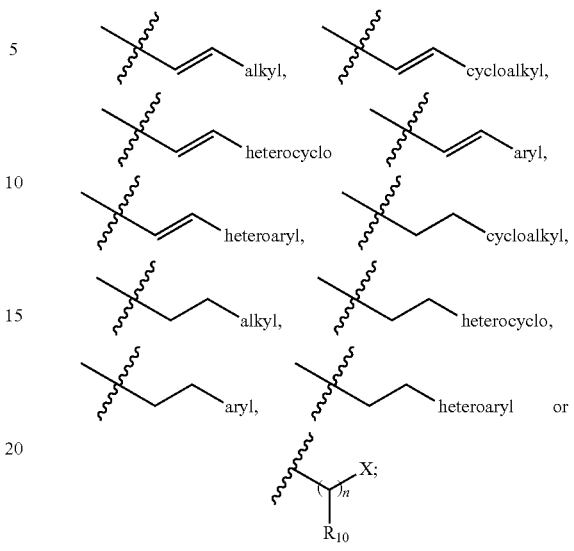

$n = 0, 1, 2, 3, 4$ wherein X is selected from the group consisting of:

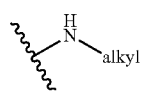

or cycloalkyl or aryl or heteroaryl or heterocyclo, —N(alkyl)$_2$, CONH(alkyl), COHC(aryl), -alkyl, -cycloalkyl, -alkenyl,

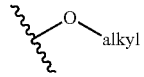

or cycloalkyl or aryl or heteroaryl or heterocyclo-heteroaryl, —C attached heterocyclo where heterocyclo contains at least 1 nitrogen, —O-Linker-C-attached heterocyclo where heterocyclo contains at least 1 nitrogen and —N-Linker-C-attached heterocyclo where heterocyclo contains at least 1 nitrogen, where Linker is substituted or unsubstituted $C_1$-$C_6$ alkylene, heteroalkylene, alkenylene, or heteroalkenylene; $R_{10}$ is hydrogen or alkyl (including, but not limited to, methyl, ethyl, n-propyl, iso-propyl, n-butyl, iso-butyl, tert-butyl, n-pentyl, iso-pentyl, n-hexyl, septyl, heptyl, nonyl, and decyl).

In some embodiments, $R_2$ is —SH, —S-alkyl or alkyl, where alkyl includes, but is not limited to, methyl, ethyl, n-propyl, iso-propyl, n-butyl, iso-butyl, tert-butyl, n-pentyl, iso-pentyl, n-hexyl, septyl, heptyl, nonyl, and decyl. In other embodiments, $R_2$ is -alkenyl (including, but not limited to, vinyl, allyl, 3-buten-1yl, 2-buten-1yl, methallyl, 3-methyl-2-buten-1-yl, 4-penten-1-yl, 3-penten-1-yl, 5-hexen-1-yl, and 4-methyl-3-penten-1-yl) When $R_2$ is —S-alkyl, alkyl, or alkenyl, the alkyl or alkenyl moiety is substituted by one or more substituents selected from the group consisting of alkyl, aryl, heterocyclo, carbocyclo, halo, hydroxy, protected hydroxy, alkoxy, acyl, aryloxy, alkylester, arylester, alkanoyl, aroyl, carboxy, protected carboxy, cyano, nitro, amino, substituted amino, (monosubstituted)amino, (disubstituted)amino, protected amino, amido, lactam, urea, urethane, and sulfonyl.

Some exemplary S-alkyl R₂ include, but are not limited to:

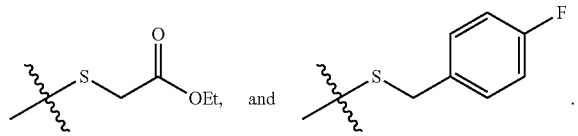 [SMILES: *SCC(=O)OCC ; "and" ; *SCc1ccc(F)cc1 ; "."]

Alternatively, R₂ is heteroaryl, —CH₂CH₂CH₂NHCO (aryl), —CH₂CH₂CH₂NHCO(heteroaryl),

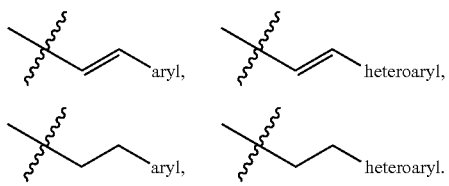

The aryl moiety forming part of R₂ is unsubstituted or substituted. The aryl moiety includes, but is not limited to, phenyl, naphthyl and fluorenyl. The heteroaryl moiety forming part or all of R₂ is unsubstituted or substituted. In some embodiments, heteroaryl moiety forming part or all of R₂ is a monocylic 5 membered heteroaryl. Monocyclic heteroaryl includes, but is not limited to, pyrrolyl, imidazolyl, thiazolyl, and pyrazolyl. Additional non-limiting monocyclic 5 membered heteroaryl moieties include the following formulae:

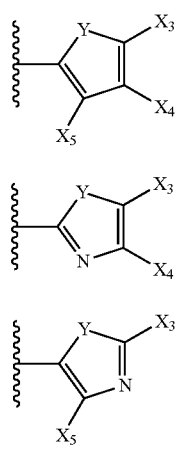

Group E

Group D

Group F

For compounds of Group D, E, and F, Y is selected from the group consisting of: —O, —S, —NH, —N-alkyl, and —N-acyl; X₃ is selected from the group consisting of: —H, —CH₃, —Cl, —F, —Br, —I, CF₃ and —OCH₃; and X₄ and X₅ are, when present, independently selected from the group consisting of: H and CH₃.

Additionally the invention provides compounds wherein when R₂ is heteroaryl, —CH₂CH₂CH₂NHCO(heteroaryl),

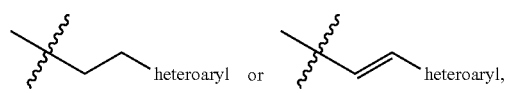

the heteroaryl moiety may be a six membered hetereoaryl moiety. The six membered heteroaryl moiety includes, but is not limited to, 2-pyridyl, 3-pyridyl, 4-pyridyl, pyridazinyl, pyrimidinyl, pyrazinyl, or triazinyl.

When R₂ is heteroaryl, —CH₂CH₂CH₂NHCO(aryl), —CH₂CH₂CH₂NHCO(heteroaryl),

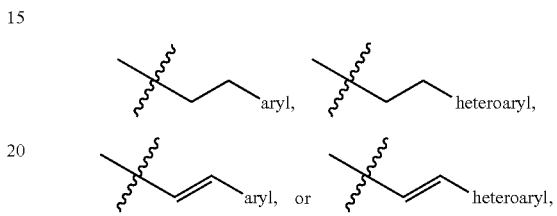

the aryl or heteroaryl moiety may be substituted with one or more substituents selected from the group consisting of alkyl, aryl, heterocyclo, carbocyclo, halo, hydroxy, protected hydroxy, alkoxy, acyl, aryloxy, alkylester, arylester, alkanoyl, aroyl, carboxy, protected carboxy, cyano, nitro, amino, substituted amino, (monosubstituted)amino, (disubstituted) amino, protected amino, amido, lactam, urea, urethane, and sulfonyl.

Some non-limiting exemplary R₂ include the following:

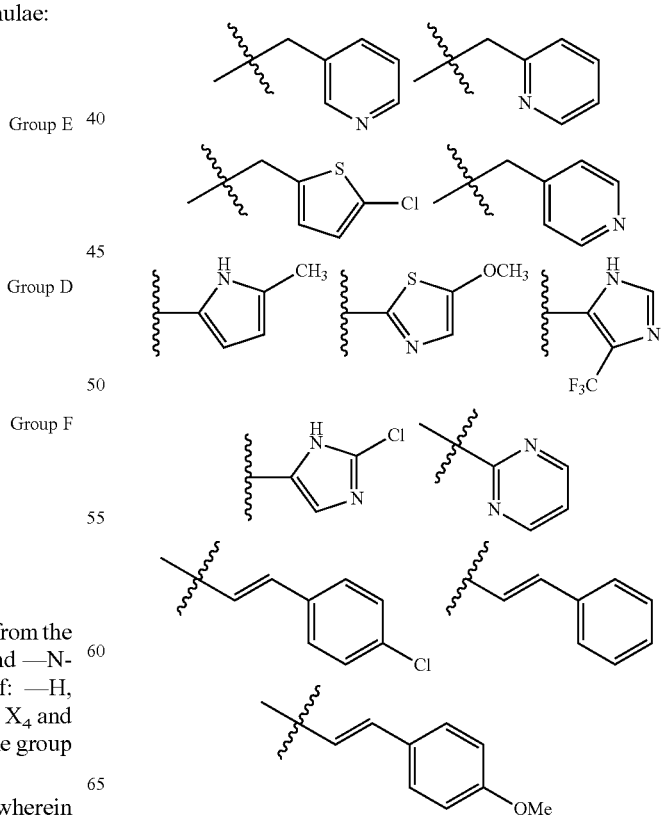

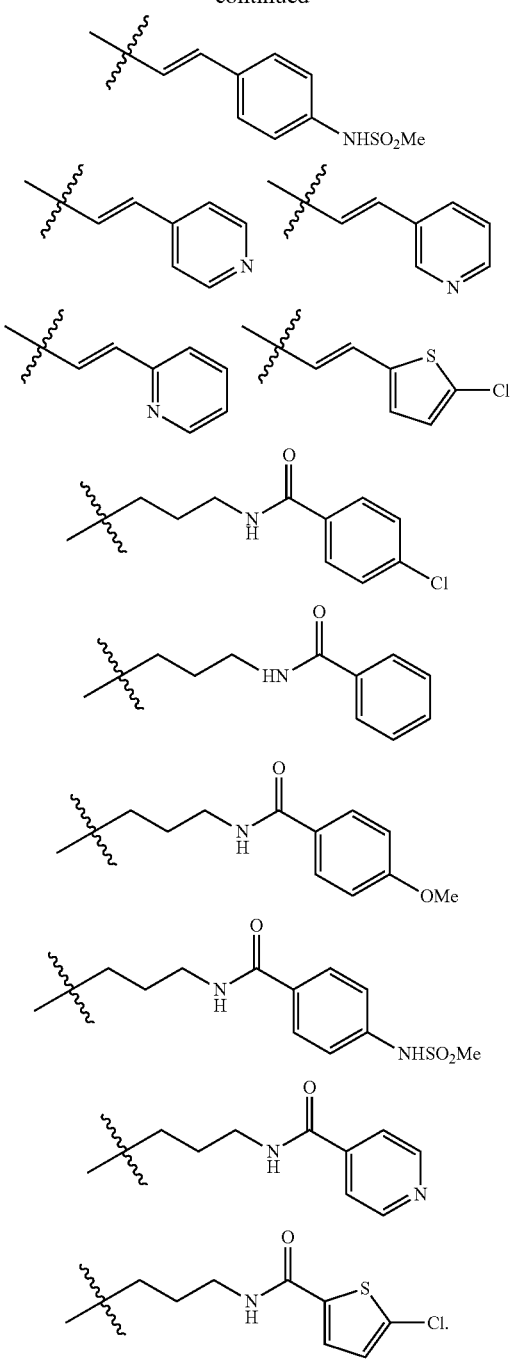

The invention also provides for compounds wherein $R_2$ is

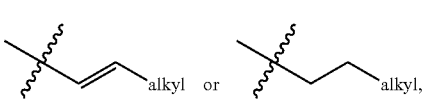

wherein alkyl is unsubstituted or substituted. Alkyl is branched or unbranched and includes, but is not limited to, methyl, ethyl, n-propyl, iso-propyl, n-butyl, iso-butyl, tert-butyl, n-pentyl, iso-pentyl, n-hexyl, septyl, heptyl, nonyl, and decyl). In other embodiments of the invention, $R_2$ may also be

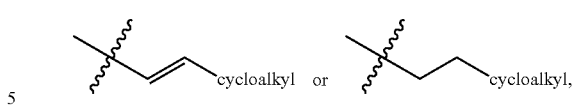

wherein cycloalkyl is unsubstituted or substituted. The cycloalkyl is a 3, 4, 5, 6, 7, or 8 membered ring and includes, but is not limited to, cyclopropyl, cyclobutyl, cyclopentyl and cyclohexyl. Exemplary examples include, but are not limited to,

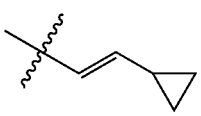 [SMILES: */C=C/C1CC1]

and the fully saturated counterpart moiety.

Additionally, $R_2$ may be

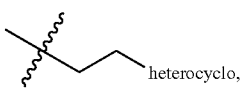

or the alkenyl counterpart moiety, wherein heterocyclo is unsubstituted or substituted. The heterocyclo includes, but is not limited to, azetidinyl, pyrrolidinyl, morpholinyl, piperidinyl, or piperazinyl.

In yet other embodiments, $R_2$ is

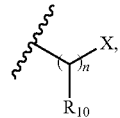

n = 0, 1, 2, 3, 4 where X is selected from alkyl, aryl,

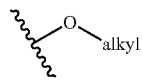

or cycloalkyl or aryl or heteroaryl or heterocyclo —NH-acyl, —NHSO$_2$-aryl, —CO$_2$Et,

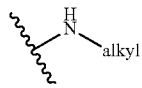

or cycloalkyl or aryl or heteroaryl or heterocyclo, —N(alkyl)$_2$, and heterocyclo. $R_{10}$ is hydrogen or alkyl (including but not limited to methyl, ethyl, n-propyl, iso-propyl, n-butyl, iso-butyl, tert-butyl, n-pentyl, iso-pentyl, n-hexyl, septyl, heptyl, nonyl, and decyl). For example, $R_{10}$ is hydrogen, methyl, or ethyl. In some embodiments when $R_2$ is

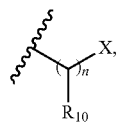

n = 0, 1, 2, 3, 4 and X is alkyl,

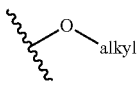

or cycloalkyl or aryl or heteroaryl or heterocyclo NH-acyl (wherein acyl is C(O)alkyl),

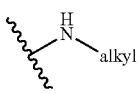

or cycloalkyl or aryl or heteroaryl or heterocyclo, or —N(alkyl)$_2$, the alkyl moiety is unsubstituted or substituted. The alkyl moiety forming part of X includes but is not limited to ethyl, n-propyl, n-butyl, tert-butyl, n-pentyl, iso-pentyl, n-hexyl, septyl, heptyl, nonyl, and decyl.

In other embodiments when R$_2$ is

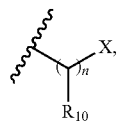

n = 0, 1, 2, 3, 4 and X is cycloalkyl or —O-cycloalkyl, the cycloalkyl moiety is unsubstituted or substituted. The cycloalkyl is a 3, 4, 5, 6, 7, or 8 membered ring and includes, but is not limited to, cyclopropyl, cyclobutyl, cyclopentyl and cyclohexyl. Exemplary R$_2$ includes, but is not limited to, —CH$_2$-cyclopentyl, —CH$_2$—O-cyclohexyl, and —O-cyclobutyl.

Additionally, R$_2$ is

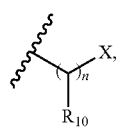

n = 0, 1, 2, 3, 4 and X is aryl, —NH-acyl (where acyl is C(O)aryl), or —NHSO$_2$-aryl. R$_{10}$ is hydrogen or alkyl (including, but not limited to, methyl, ethyl, n-propyl, iso-propyl, n-butyl, iso-butyl, tert-butyl, n-pentyl, iso-pentyl, n-hexyl, septyl, heptyl, nonyl, and decyl). In some embodiments, R$_{10}$ is hydrogen, methyl, or ethyl. The aryl moiety forming part of X is naphthyl or fluorenyl, any of which phenyl, naphthyl or fluorenyl are unsubstituted or substituted. In further embodiments, R$_2$ is

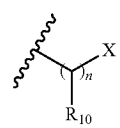

n = 0, 1, 2, 3, 4, and X is heterocyclo or —O-heterocyclo, wherein the heterocyclo moiety is unsubstituted or substituted. The heterocyclo moiety forming X, includes, but is not limited to, azetidinyl, morpholinyl, or piperazinyl. R$_{10}$ is hydrogen or alkyl (including, but not limited to, methyl, ethyl, n-propyl, iso-propyl, n-butyl, iso-butyl, tert-butyl, n-pentyl, iso-pentyl, n-hexyl, septyl, heptyl, nonyl, and decyl). For example, R$_{10}$ is hydrogen, methyl, or ethyl. Non-limiting embodiments include —CH(CH$_3$) piperidinyl, —CH$_2$pyrrolidinyl, and

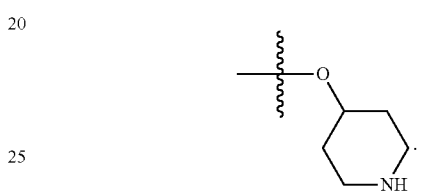

The alkyl, aryl, heteroaryl and heterocyclo moiety forming all or part of X may be substituted by one or more substituents which is selected from the group consisting of: alkyl, aryl, heterocyclo, carbocyclo, halo, hydroxy, protected hydroxy, alkoxy, acyl, aryloxy, alkylester, arylester, alkanoyl, aroyl, carboxy, protected carboxy, cyano, nitro, amino, substituted amino, (monosubstituted)amino, (disubstituted)amino, protected amino, amido, lactam, urea, urethane, and sulfonyl. Additionally, the alkyl and heterocyclo moiety forming all or part of X may be substituted by an oxo group.

In some embodiments, R$_2$ is —X, —CH$_2$—X or —CH$_2$CH$_2$—X, wherein X is selected from the group consisting of:

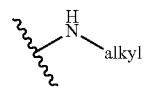

or cycloalkyl or aryl or heteroaryl or heterocyclo,

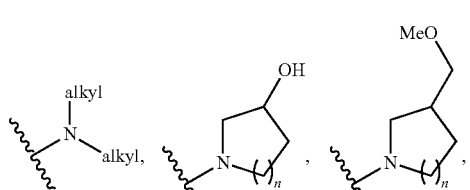

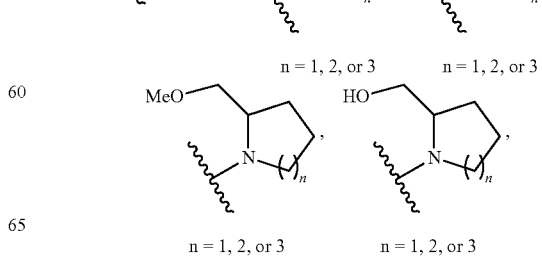

91

-continued

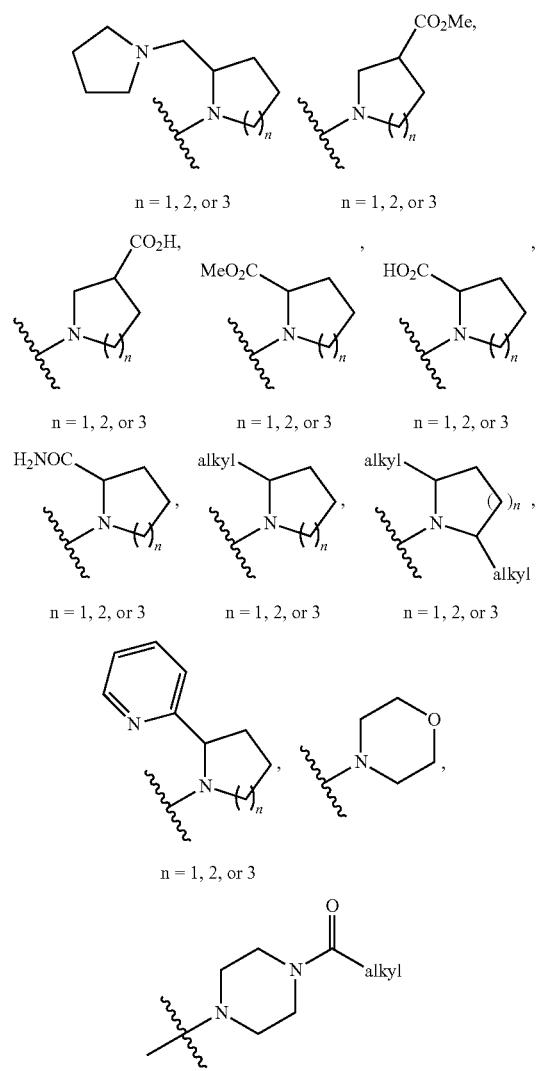

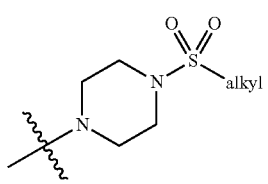

or aryl or heteroaryl or cycloalkyl,

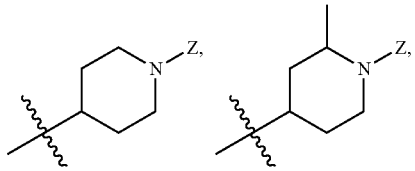

or aryl or heteroaryl or cycloalkyl,

92

-continued

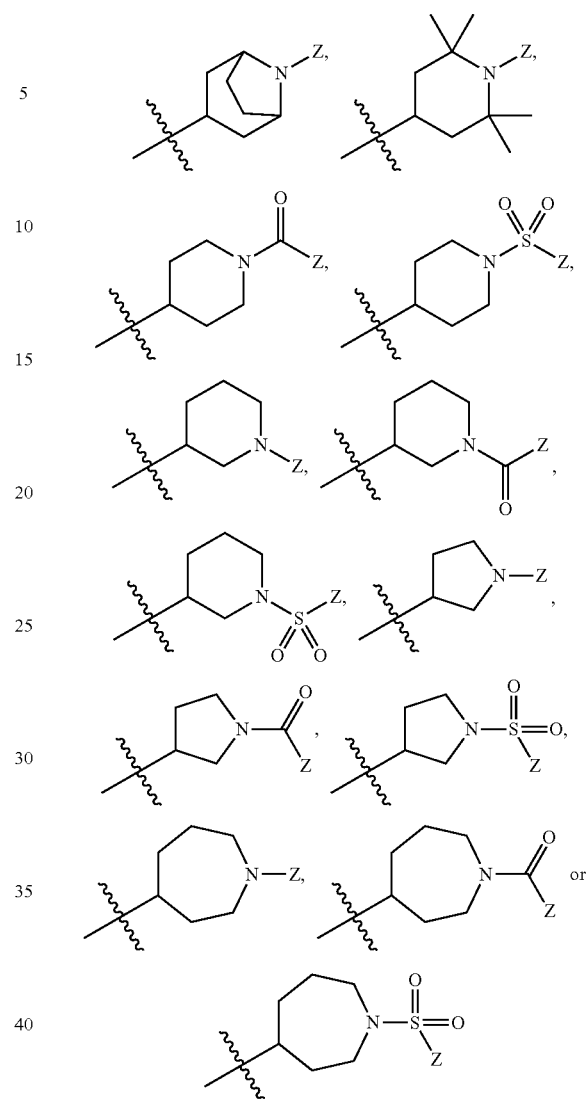

Other examples of $R_2$ moieties are listed in Table 1b.

In various embodiments of compounds having a clemizole scaffold or an isostere scaffold as described above, each of $R_4$-$R_7$, and $R_3$, if present, is independently selected from the group consisting of: —H, —Cl, —F, —CH$_3$, —OCH$_3$, —OH, —NH$_2$, —NO$_2$,

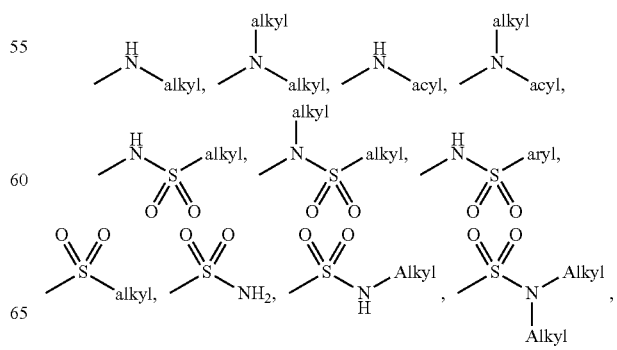

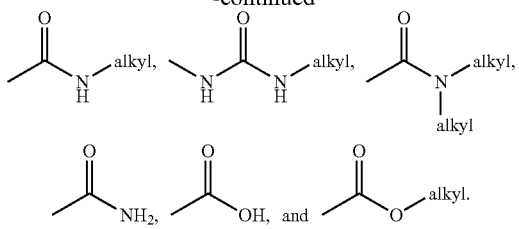

In the moieties that form part of $R_3$-$R_7$, the alkyl and aryl moieties are unsubstituted or substituted. The alkyl moieties that form part of $R_3$-$R_7$ include, but are not limited to, methyl, ethyl, n-propyl, iso-propyl, n-butyl, iso-butyl, tert-butyl, n-pentyl, iso-pentyl, n-hexyl, septyl, heptyl, nonyl, and decyl. The aryl moieties that form part of $R_3$-$R_7$ include, but are not limited to, phenyl, naphthyl and fluorenyl. The alkyl and aryl moieties that form part of $R_3$-$R_7$ may be substituted by one or more substituents which is selected from the group consisting of alkyl, aryl, heterocyclo, carbocyclo, halo, hydroxy, protected hydroxy, alkoxy, acyl, aryloxy, alkylester, arylester, alkanoyl, aroyl, carboxy, protected carboxy, cyano, nitro, amino, substituted amino, (monosubstituted)amino, (disubstituted)amino, protected amino, amido, lactam, urea, urethane, and sulfonyl.

In one embodiment, at least one of $R_4$-$R_7$ is a hydrogen. In other embodiments, $R_3$ is hydrogen. In further embodiments, at least two of $R_4$-$R_7$ is a hydrogen. Alternatively, at least two of $R_4$-$R_7$ are hydrogen, and the remaining $R_4$-$R_7$ groups (and $R_3$, if present) are independently selected from the group consisting of: —I, —Br, —Cl, —F, —CH$_3$, and —OCH$_3$. In yet other embodiments, $R_5$ and $R_6$ are substituted, and the substituted moiety is, for each substituted position, independently selected from the group consisting of: —I, —Br, —Cl, —F, —CH$_3$, and —OCH$_3$, while $R_4$ and $R_7$ (and $R_3$ if present) are hydrogen.

In some other embodiments, $R_4$ and $R_5$, $R_5$ and $R_6$, or $R_6$ and $R_7$ are joined together with a bond to form a ring; or, optionally, $R_4$ and $R_5$, $R_5$ and $R_6$, or $R_6$ and $R_7$ are joined together to form a 1,2-(methylenedioxy)benzene ring system, such as

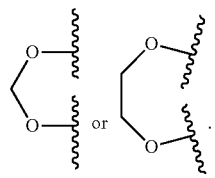

In one embodiment, the ring is composed of a structure selected from the group consisting of:

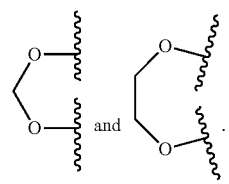

In a further embodiment, $R_5$ and $R_6$ are connected by one of the rings having a structure selected from the group consisting of:

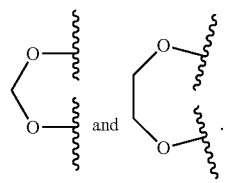

In some of the embodiments of the invention, a compound of Formula I having a structure of Formula I-I is provided wherein $R_2$ and $R_4$-$R_7$ are defined as in any one of the aspects or embodiments of Formula I above:

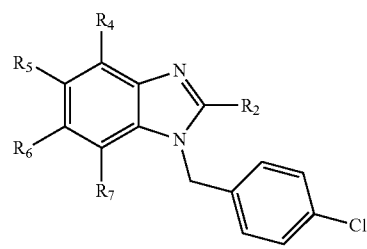

Formula I-I

In various embodiments of the invention, a compound of Formula I having a structure of Formula XXXV-A and Formula XXXV-B is provided:

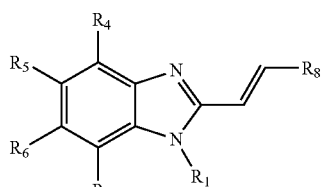

Formula XXXV-A

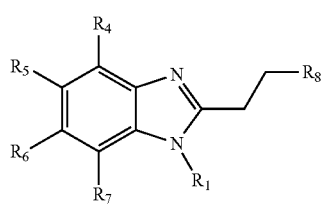

Formula XXXV-B wherein $R_8$ is aryl, cycloalkyl, heterocyclo, heteroaryl or alkyl. The $R_8$ groups aryl, cycloalkyl, heterocyclo, heteroaryl or alkyl are described above in the discussion of the $R_2$ groups corresponding to the groups aryl, cycloalkyl, heterocyclo, heteroaryl or alkyl. In some embodiments when $R_5$ and $R_6$ are both methyl, and $R_4$ and $R_7$ are hydrogen, then $R_8$ is not phenyl. In other embodiments, $R_2$ heteroaryl is 2-pyridyl, 3-pyridyl or 4-pyridyl. Additionally, the invention provides compounds of Formula XXXV-A and Formula XXXV-B, wherein $R_4$ is selected from the group consisting of: —NH$_2$,

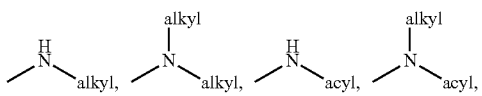

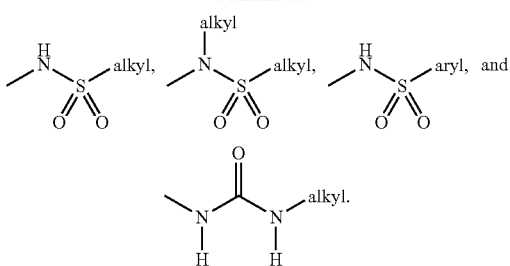

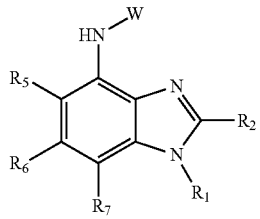

Formula XXXVI-A

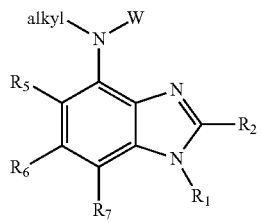

Formula XXXVI-B

Other compounds of Formula XXXV-A and Formula XXXV-B are provided wherein the compounds have a structure of one of the following formulae:

Formula XXXV-C

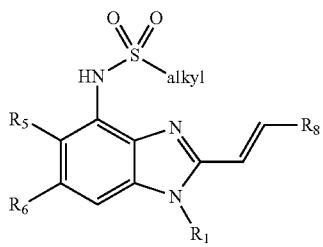

wherein W is H, alkyl, —C(O)aryl, —C(O)alkyl, —SO$_2$aryl, —SO$_2$alkyl, or —C(O)NHR wherein alkyl and aryl are as defined above for

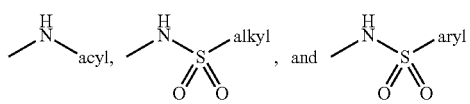

of $R_3$-$R_7$. In some embodiments, the compound of Formula XXXVI is a compound wherein when W is —SO$_2$alkyl, alkyl is ethyl, propyl, butyl, pentyl, hexyl, septyl, nonyl, or decyl. In other embodiments of compounds of Formula XXXVI-A and Formula XXXVI-B, when $R_4$— is,

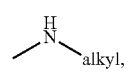

at least one of $R_5$-$R_7$ is other than hydrogen.

The invention provides additional compounds of Formula XXXVII:

Formula XXXV-D

Formula XXXVII

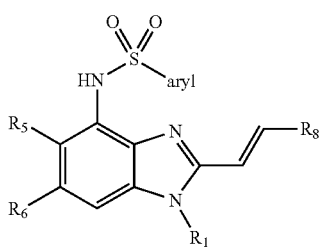

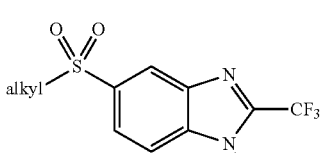

Formula XXXV-E

Formula XXXV-F wherein alkyl is defined as above for

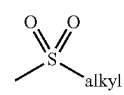

(bottom row)

The invention also provides compounds of Formula I having a structure of Formula XXXVI-A or Formula XXXVI-B:

of $R_4$-$R_7$. In some embodiments, the compound of Formula XXXVIII is not: a compound wherein alkyl is methyl and $R_1$ is unsubstituted benzyl.

In some embodiments of the invention, the compound of Formula XXXIX is a compound where when $R_4$, $R_5$, $R_6$, and $R_7$ are all hydrogen, then $R_1$ is not para-bromo benzyl. In some embodiments of the compound of Formula XXXVIII, $R_4$ and $R_7$ are hydrogen. In other embodiments, $R_4$ is —I, —Br, —Cl, —F, —CH$_3$, —OCH$_3$, —OH, —NH$_2$, —NO$_2$,

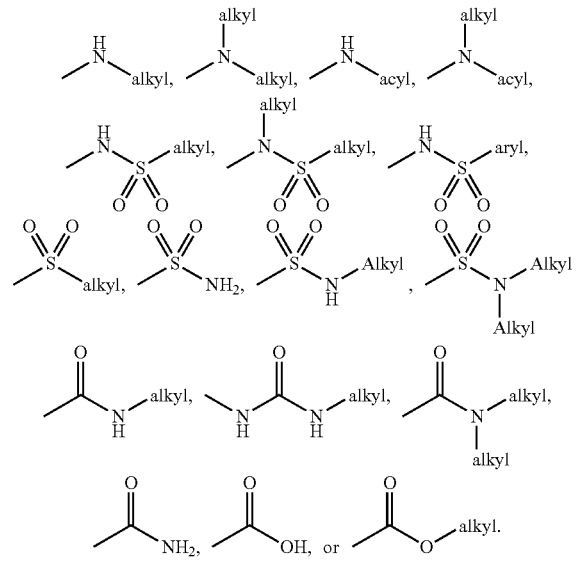

The invention provides yet other compounds of Formula I having a structure of Formula XXXIX:

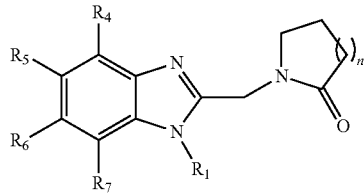

Formula XXXIX wherein n is 1 or 2, and at least one of $R_4$-$R_7$ is not hydrogen. In another embodiment, $R_1$ is benzyl monosubstituted on the phenyl ring. In another embodiment, $R_1$ is 4-chlorobenzyl. In another embodiment, $R_7$ is hydrogen. In another embodiment, $R_4$ and $R_7$ are hydrogen.

Alternatively, the invention provides compounds of Formula I having a structure of Formula XXXX:

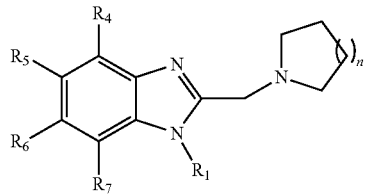

Formula XXXX wherein n is 1 or 2. In some embodiments of the invention, at least one of $R_4$-$R_7$ is not hydrogen. In other embodiments of the invention, when n is 1 and $R_4$ and $R_7$ are hydrogen, then $R_5$ and $R_6$ are not both ethoxy. In yet other embodiments of the invention, a compound of Formula XXXX is the compound wherein n is 1 and $R_5$ is —S(O)$_2$alkyl, —S(O)$_2$NH$_2$, or —S(O)$_2$NH(alkyl). In another embodiment, $R_1$ is benzyl monosubstituted on the phenyl ring. In another embodiment, $R_1$ is 4-chlorobenzyl. In another embodiment, $R_7$ is hydrogen. In another embodiment, $R_4$ and $R_7$ are hydrogen.

The invention provides yet other compounds of Formula I having a structure of Formula XXXXI:

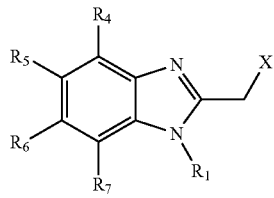

Formula XXXXI wherein X is selected from the group consisting of: -alkyl, -cycloalkyl, -heteroaryl, —O(CH$_2$)$_d$CH$_3$, or

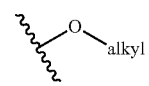

or cycloalkyl or aryl or heteroaryl or heterocyclo;

d is 1, 2, or 3;

$R_1$ is selected from the group consisting of: —H and

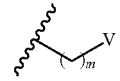

m = 0, 1, 2 wherein V is selected from alkyl, cycloalkyl, heterocyclo, aryl or heteroaryl, and m is 0, 1 or 2;

each of $R_4$-$R_7$ is independently selected from the group consisting of: —H, —I, —Br, —Cl, —F, —CH$_3$, —CN, —OH, —OCH$_3$, —NO$_2$, —NH$_2$,

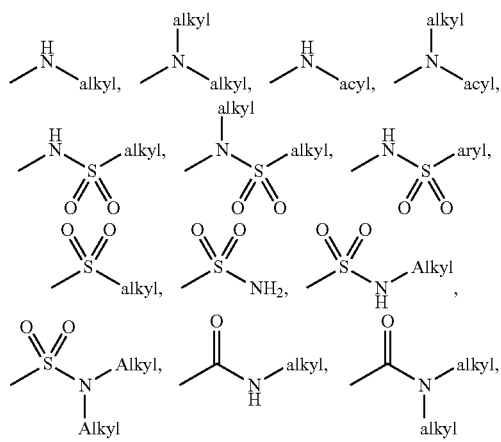

-continued

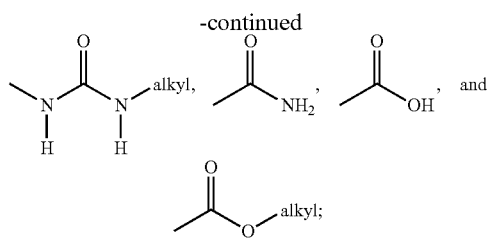

or, optionally, $R_4$ and $R_5$, $R_5$ and $R_6$, or $R_6$ and $R_7$ are joined together with a bond to form a 5, 6, or 7-membered ring; or, optionally, $R_4$ and $R_5$, $R_5$ and $R_6$, or $R_6$ and $R_7$ are joined together to form a 1,2-(methylenedioxy)benzene ring system; and wherein at least one of $R_4$-$R_7$ is other than hydrogen. In another embodiment, $R_1$ is benzyl monosubstituted on the phenyl ring. In another embodiment, $R_1$ is 4-chlorobenzyl. In another embodiment, $R_7$ is hydrogen. In another embodiment, $R_4$ and $R_7$ are hydrogen.

In still other embodiments of the invention, for compounds of Formula I and Formulae II-XXXIV, $R_1$ is —H or

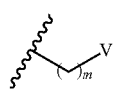

m = 0, 1, 2 wherein V is selected from alkyl, cycloalkyl, heterocyclo, aryl or heteroaryl; $R_2$ is —H,

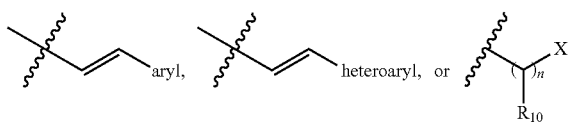

n = 0, 1, 2, 3, 4;

X is selected from the group consisting of: —N-attached substituted heterocyclo, —N-attached halogen-substituted heterocyclo,

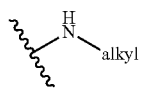

or cycloalkyl or aryl or heteroaryl or heterocyclo, —N(alkyl)$_2$, CONH(alkyl), COHC(aryl), -alkyl, cycloalkyl, alkenyl,

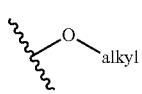

or cycloalkyl or aryl or heteroaryl or heterocyclo, -aryl, heteroaryl, —C-attached heterocyclo where heterocyclo contains at least 1 nitrogen, —O-Linker-C-attached heterocyclo where heterocyclo contains at least 1 nitrogen and —N-Linker-C-attached heterocyclo where heterocyclo contains at least 1 nitrogen, where Linker is substituted or unsubstituted $C_1$-$C_6$ alkylene, heteroalkylene, alkenylene, or heteroalkenylene; $R_{10}$ is hydrogen or alkyl, and each of $R_4$-$R_7$ is independently selected from the group consisting of: —H, —I, —Br, —Cl, —F, —CH$_3$, —OCH$_3$, —OH, —NH$_2$, —NO$_2$,

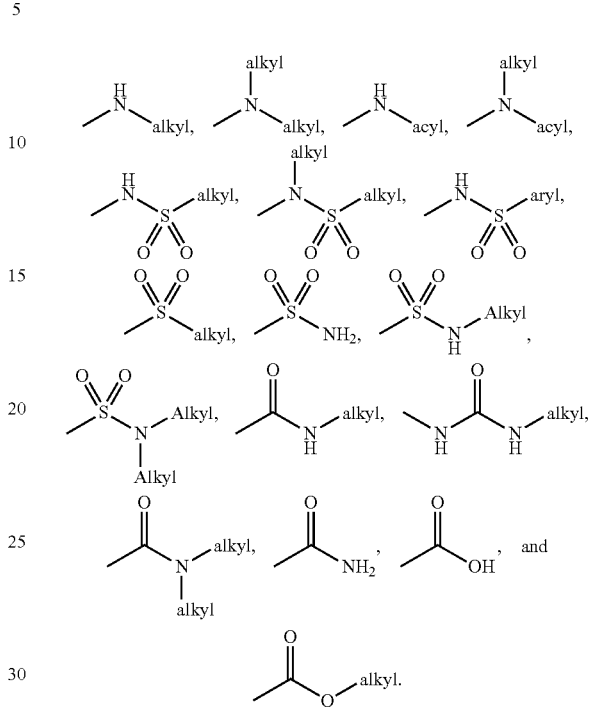

In other embodiments of the invention, for compounds of Formula I and Formulae II-XXXIV, $R_1$ is —H or

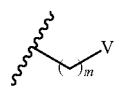

m = 0, 1, 2 wherein V is selected from alkyl, cycloalkyl, heterocyclo, aryl or heteroaryl; $R_2$ is —H,

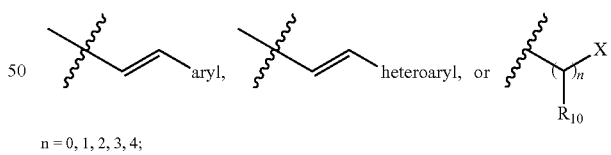

n = 0, 1, 2, 3, 4;

X is selected from the group consisting of: —N(alkyl)$_2$, —CONH(alkyl), —COHC(aryl), -alkyl, -cycloalkyl, -alkenyl,

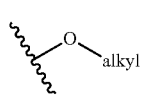

or cycloalkyl or aryl or heteroaryl or heterocyclo, -aryl, -heteroaryl,

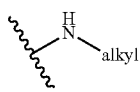

or cycloalkyl or aryl or heteroaryl or heterocyclo, —C-attached heterocyclo where heterocyclo contains at least 1 nitrogen, —O-Linker-C-attached heterocyclo where heterocyclo contains at least 1 nitrogen and —N-Linker-C-attached heterocyclo where heterocyclo contains at least 1 nitrogen, where Linker is a substituted or an unsubstituted $C_1$-$C_6$ alkylene, heteroalkylene, alkenylene, or heteroalkenylene; $R_{10}$ is hydrogen or alkyl, and n is 0, 1, 2, 3, or 4; $R_7$ is H; and $R_4$, $R_5$, $R_6$, and $R_3$ (if present) are each independently selected from the group consisting of: —H, —I, —Br, —Cl, —F, —CH$_3$, —OCH$_3$, —OH, —NH$_2$, —NO$_2$,

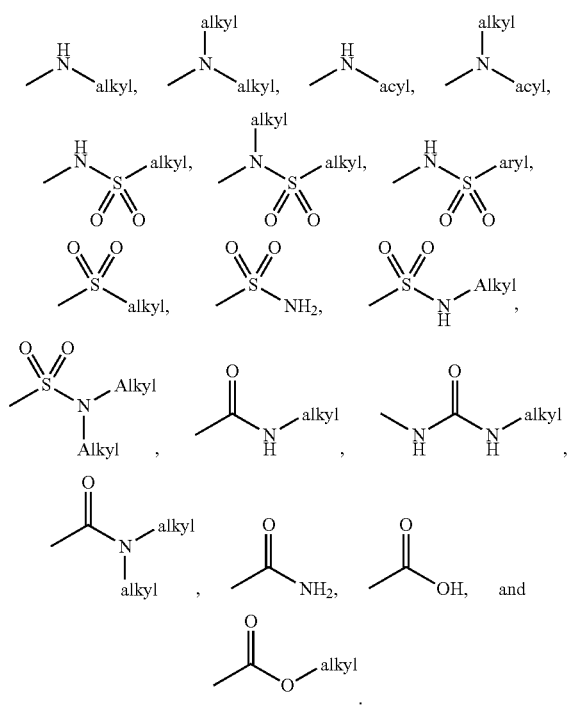

For compounds of Formula I and Formulae II-XXXIV, $R_1$ can be —H or

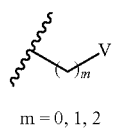

m = 0, 1, 2 wherein V is selected from alkyl, cycloalkyl, heterocyclo, aryl or heteroaryl, and m is 0, 1 or 2; $R_2$ can be —H,

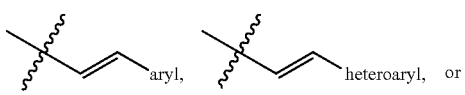

-continued

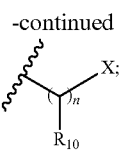

n = 0, 1, 2, 3, 4

X is selected from the group consisting of: N-attached substituted heterocyclo, N-attached halogen-substituted heterocyclo,

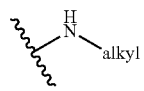

or cycloalkyl or aryl or heteroaryl or heterocyclo, —N(alkyl)$_2$, —CONH(alkyl), —COHC(aryl), -alkyl, -cycloalkyl, -alkenyl,

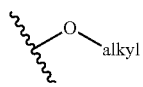

or cycloalkyl or aryl or heteroaryl or heterocyclo, aryl, -heteroaryl, —C-attached heterocyclo where heterocyclo contains at least 1 nitrogen, —O-Linker-C-attached heterocyclo where heterocyclo contains at least 1 nitrogen and —N-Linker-C-attached heterocyclo where heterocyclo contains at least 1 nitrogen, where Linker is substituted or unsubstituted substituted or unsubstituted $C_1$-$C_6$ alkylene, heteroalkylene, alkenylene, or heteroalkenylene; $R_{10}$ is hydrogen or alkyl, and n is 0, 1, 2, 3, or 4; $R_7$ is H; $R_4$ is selected from the group consisting of:

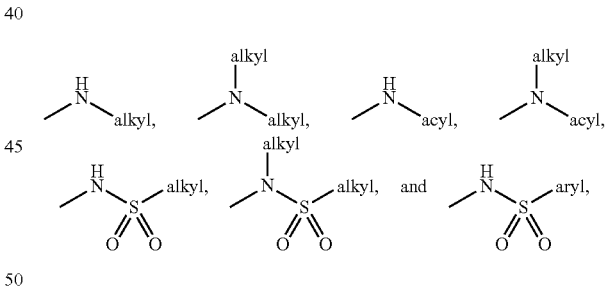

and $R_4$, $R_6$, and $R_3$ (if present) can each independently be selected from the group consisting of: —H, —I, —Br, —Cl, —F, —CH$_3$, —OCH$_3$, and —OH.

In addition, compounds of Formula I and Formulae II-XXXIV can have the following substitution pattern: $R_1$ is —H or

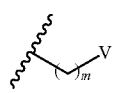

m = 0, 1, 2 wherein V is selected from alkyl, cycloalkyl, heterocyclo, aryl or heteroaryl; $R_2$ is —H,

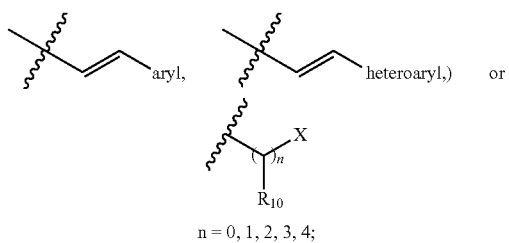

n = 0, 1, 2, 3, 4;

X is selected from the group consisting of: —N-attached substituted heterocyclo, —N-attached halogen-substituted heterocyclo,

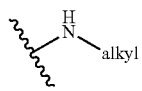

or cycloalkyl or aryl or heteroaryl or heterocyclo, —N(alkyl)$_2$, —CONH(alkyl), —COHC(aryl), -alkyl, -cycloalkyl, -alkenyl,

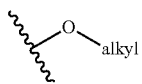

or cycloalkyl or aryl or heteroaryl or heterocyclo, -aryl, -heteroaryl, —C-attached heterocyclo where heterocyclo contains at least 1 nitrogen, —O-Linker-C-attached heterocyclo where heterocyclo contains at least 1 nitrogen and —N-Linker-C-attached heterocyclo where heterocyclo contains at least 1 nitrogen, where Linker is substituted or unsubstituted substituted or unsubstituted $C_1$-$C_6$ alkylene, heteroalkylene, alkenylene, or heteroalkenylene; $R_{10}$ is hydrogen or alkyl; $R_2$ is H; $R_5$ is selected from the group consisting of:

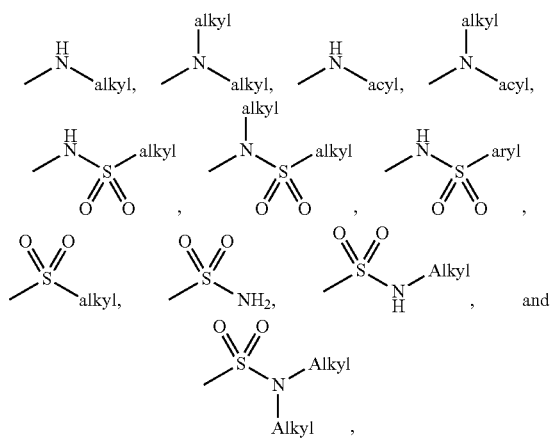

and $R_4$, $R_6$, and $R_3$ (if present) are each independently selected from the group consisting of: —H, —I, —Br, —Cl, —F, —CH$_3$, —OCH$_3$, and —OH.

Moreover, the compounds of Formula I and Formulae II-XXXIV can include the following combinations of substitutents: $R_1$ is selected from the group consisting of

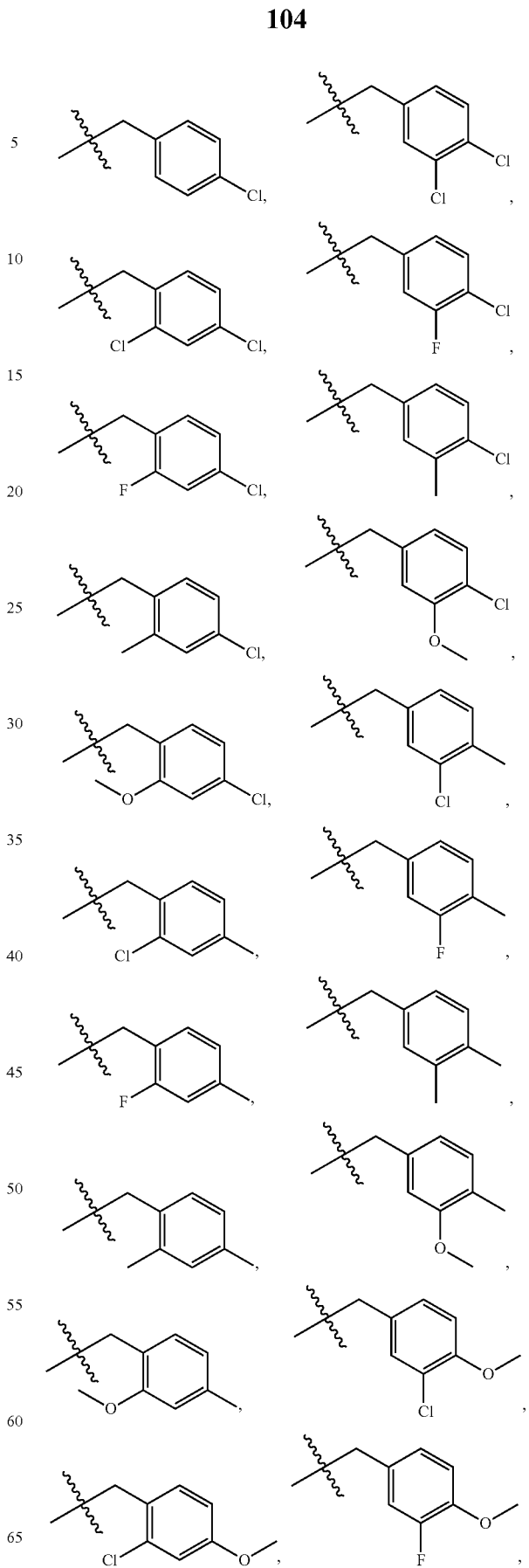

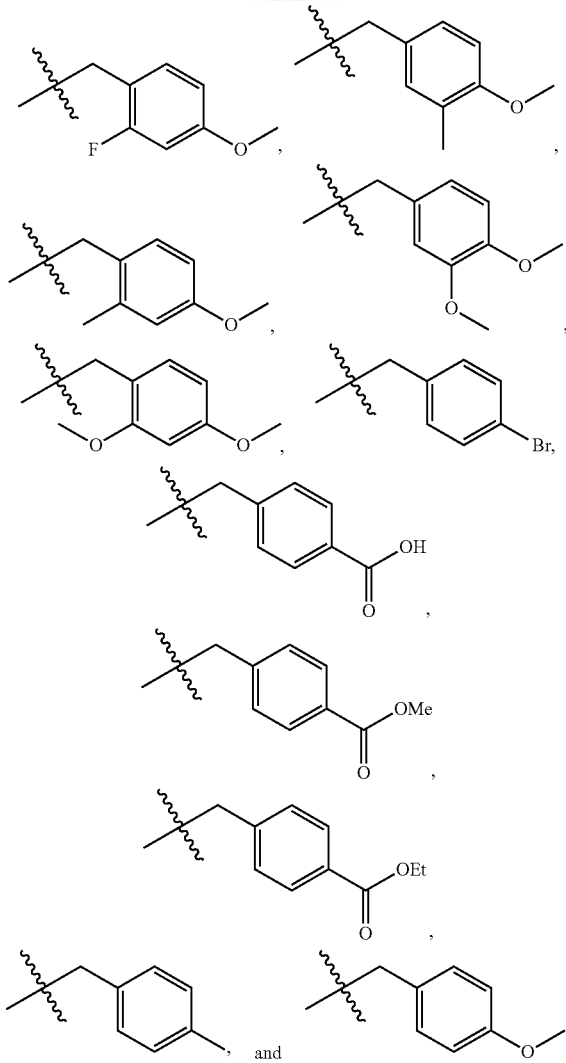

$R_2$ is selected from the group consisting of: —H, —CF$_3$, —CH$_2$CH$_3$, CH$_2$OH,

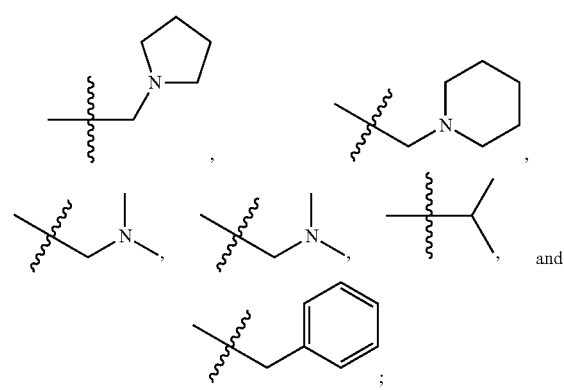

$R_3$, if present, is hydrogen; $R_4$ is selected from the group consisting of: —H and —NH$_2$; $R_5$ and $R_6$ are independently selected from the group consisting of: —H, —CH$_3$, —I, —Br, —Cl, —F, —OCH$_3$, —NH$_2$,

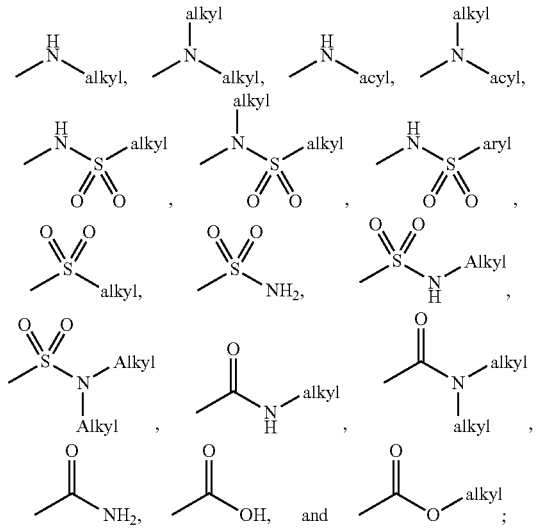

and $R_7$ is —H. In certain embodiments within these embodiments, $R_1$ is benzyl monosubstituted on the phenyl ring. In another embodiment, $R_1$ is 4-chlorobenzyl. In another embodiment, $R_7$ is hydrogen. In another embodiment, $R_4$ and $R_7$ are hydrogen.

Formula I

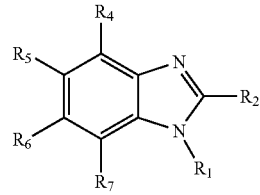

Some non-limiting illustrative compounds of the present invention having a structure of Formula I include those in which $R_1$ is any $R_1$ moiety described in Table 1a, in combination with any $R_2$ moiety described in Table 1b, and any $R_4$, $R_5$, $R_6$, and $R_7$ as described in Table 1c. A compound of Formula I includes any combination of $R_1$, $R_2$, $R_4$, $R_5$, $R_6$, and $R_7$.

In another aspect, the present invention provides a compound of Formula III

Formula III

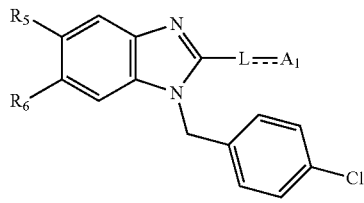

or a pharmaceutically acceptable salt, an isomer, a tautomer, or a prodrug thereof thereof wherein L is a substituted or an unsubstituted C$_1$-C$_6$ alkylene, C$_1$-C$_6$ heteroalkylene, C$_2$-C$_6$ alkenylene, C$_2$-C$_6$ heteroalkenylene, or methyne;

$A_1$ is
a substituted or an unsubstituted, 5, 6, or 7-membered heterocyclo containing at least one nitrogen atom wherein the heterocyclo is attached to L via a carbon atom or a nitrogen atom;
—NH—$C_1$-$C_6$ alkyl, —NH—$C_3$-$C_8$ cyloalkyl, —NH-aryl, NH-heterocyclo, —O—$C_1$-$C_6$ alkyl, —O—$C_3$-$C_8$ cyloalkyl, —O-aryl, or —O-heterocyclo;
or a substituted or an unsubstituted 5 or 6-membered cycloalkyl;
----- denotes a single or a double bond, $R_5$ is hydrogen, a substituted or an unsubstituted $C_1$-$C_4$ alkyl, a substituted or an unsubstituted aryl or heteroaryl, or $NR_{33}R_{34}$;

$R_6$ is hydrogen or a substituted or an unsubstituted $C_1$-$C_4$ alkyl or $NR_{33}R_{34}$;

$R_{32}$ is hydrogen or a substituted or an unsubstituted $C_1$-$C_6$ alkyl; and $R_{33}$ and $R_{34}$ are independently hydrogen, $C_1$-$C_6$ alkyl, a substituted or an unsubstituted $C_3$-$C_8$ cycloalkyl, or together with the nitrogen atom to which they are attached form a 5-9 membered non aromatic heterocycle;
provided that the compound is not clemizole,

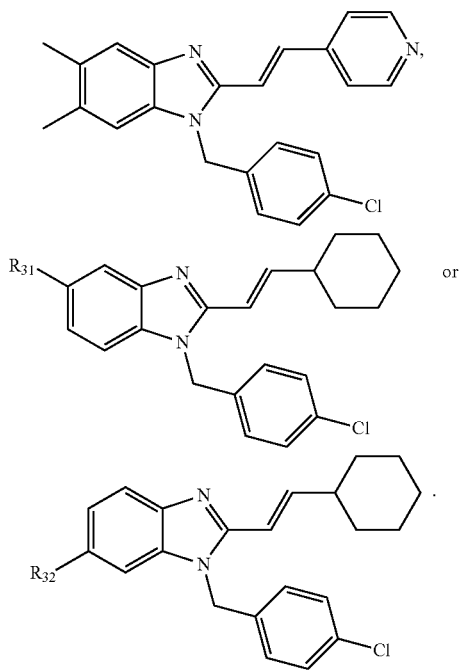

Therefore, the L-$A_1$ moiety represents, according to the present invention, certain embodiments of $R_2$.

In one embodiment, the present invention provides compounds of Formula III wherein L is a substituted or an unsubstituted, 5, 6, or 7-membered heterocyclo containing at least one nitrogen atom wherein the heterocyclo is attached to L via a carbon atom. In another embodiment, L is an N-attached substituted, 5, 6, or 7 membered heterocyclo. In another embodiment, L is a substituted or unsubstituted 5 or 6-membered heteroaryl containing at least one nitrogen atom. In another embodiment, L is an N-attached 5, 6, or 7 membered halogen-substituted heterocyclo group.

In another embodiment, the present invention provides compounds of Formula III wherein L is a substituted or an unsubstituted $C_1$-$C_6$ alkylene, $C_1$-$C_6$ heteroalkylene, $C_2$-$C_6$ alkenylene, $C_2$-$C_6$ heteroalkenylene, or methyne group;

$A_1$ is a substituted or an unsubstituted, 5 or 6 membered, non aromatic heterocycle containing at least one basic nitrogen atom wherein the heterocycle is attached to L via a carbon atom, a substituted or an unsubstituted 6 membered heteroaryl containing at least one basic nitrogen atom,

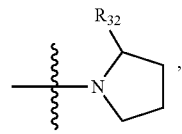

or a substituted or an unsubstituted 6 membered cycloalkyl;

$R_5$ is hydrogen, a substituted or an unsubstituted $C_1$-$C_4$ alkyl, a substituted or an unsubstituted aryl or heteroaryl, or $NR_{33}R_{34}$;

$R_6$ is hydrogen or a substituted or an unsubstituted $C_1$-$C_4$ alkyl;

$R_{32}$ is hydrogen, methyl, or hydroxymethyl; and $R_{33}$ and $R_{34}$ are independently hydrogen, $C_1$-$C_6$ alkyl, a substituted or an unsubstituted $C_3$-$C_8$ cycloalkyl, or together with the nitrogen atom to which they are attached form a 5-9 membered non aromatic heterocycle.

In another embodiment, the present invention provides compounds of Formula III-A Formula III-A

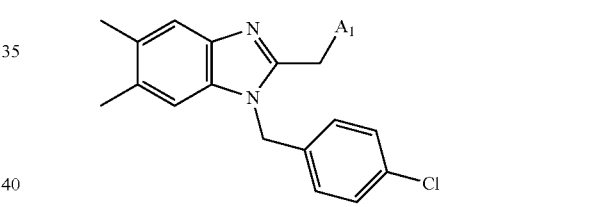

wherein $A_1$ is

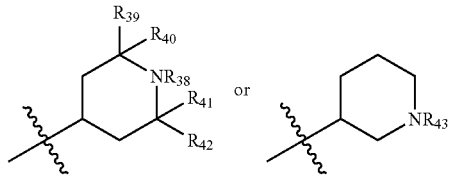

$R_{38}$ is hydrogen, an unsubstituted $C_1$-$C_3$ alkyl, $C_1$-$C_3$ alkyl substituted with a substituted or an unsubstituted $C_3$-$C_8$ cycloalkyl or phenyl group, or a substituted or an unsubstituted $C_3$-$C_8$ cycloalkyl;

$R_{39}$, $R_{40}$, $R_{41}$, and $R_{42}$ are independently hydrogen, a substituted or an unsubstituted $C_1$-$C_3$ alkyl, or $R_{40}$ and $R_{41}$ together with the carbon atoms they are attached to form a cyclic moiety; and $R_{43}$ is hydrogen, an unsubstituted $C_1$-$C_3$ alkyl, or $C_1$-$C_3$ alkyl substituted with a substituted or an unsubstituted $C_3$-$C_8$ cycloalkyl or phenyl group.

In another embodiment, the present invention provides compounds of formula III-B

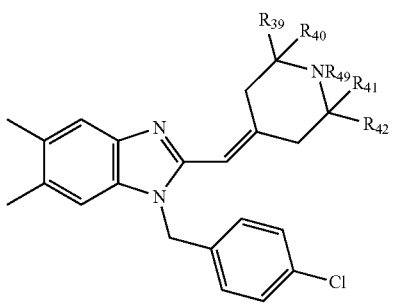

Formula III-B wherein, $R_{49}$ is hydrogen, a unsubstituted $C_1$-$C_3$ alkyl, $C_1$-$C_3$ alkyl substituted with a substituted or an unsubstituted $C_3$-$C_8$ cycloalkyl or phenyl group; and $R_{39}$, $R_{40}$, $R_{41}$, and $R_{42}$ are independently hydrogen, a substituted or an unsubstituted $C_1$-$C_3$ alkyl, or $R_{40}$ and $R_{41}$ together with the carbon atoms they are attached to form a cyclic moiety.

In another embodiment, the present invention provides compounds of Formula III-C

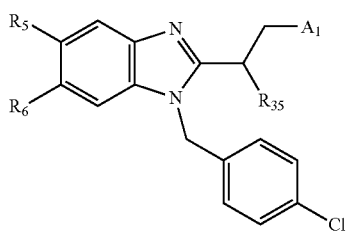

Formula III-C wherein $R_5$ is a substituted or an unsubstituted $C_1$-$C_3$ alkyl or 5 membered heteroaryl group;

$R_6$ is hydrogen or a substituted or an unsubstituted $C_1$-$C_3$ alkyl;

$R_{35}$ is hydrogen or a substituted or an unsubstituted $C_1$-$C_3$ alkyl;

$A_1$ is a substituted or an unsubstituted pyridyl or

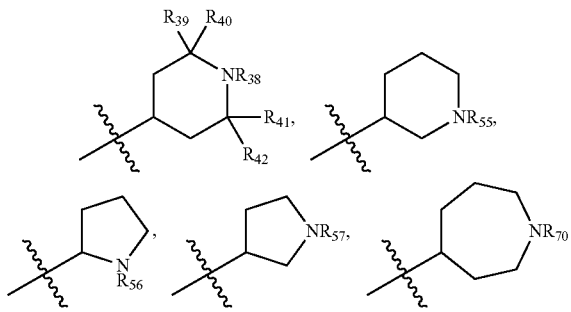

wherein each nonaromatic heterocycle is optionally substituted on the ring, other than the substituent on the nitrogen atom, with one or more substituents;

$R_{39}$, $R_{40}$, $R_{41}$, and $R_{42}$ are independently hydrogen, a substituted or an unsubstituted $C_1$-$C_3$ alkyl, or $R_{40}$ and $R_{41}$ together with the carbon atoms they are attached to form a cyclic moiety; and $R_{38}$, $R_{55}$, $R_{56}$, $R_{57}$, and $R_{70}$ independently are hydrogen, a substituted or an unsubstituted $C_1$-$C_3$ alkyl or $C_3$-$C_8$ cycloalkyl, aryl, heteroaryl, or $R_{58}$—$SO_2$—;

$R_{58}$ is a substituted or an unsubstituted $C_1$-$C_3$ alkyl.

In the embodiments where $R_{40}$ and $R_{41}$ together with the carbon atoms they are attached to form a cyclic moiety, A1 is at least a bicyclic ring. Within these embodiments, in some embodiments, $R_{40}$ and $R_{41}$ together form a —$(CH_2)_f$— chain wherein f is 2 or 3. In another embodiment, $R_{38}$, $R_{55}$, $R_{56}$, $R_{57}$, and $R_{70}$ are substituted or unsubstituted —$CH_2$-aryl or —$CH_2$-heteroaryl.

In another embodiment, the present invention provides compounds of Formula III of Formula III-D

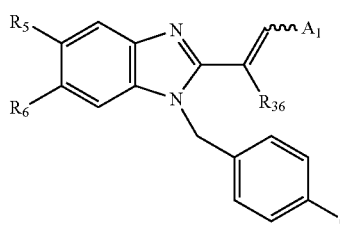

Formula III-D wherein $R_{36}$ is substituted or unsubstituted $C_1$-$C_3$ alkyl and $A_1$ is a substituted or an unsubstituted pyridyl or

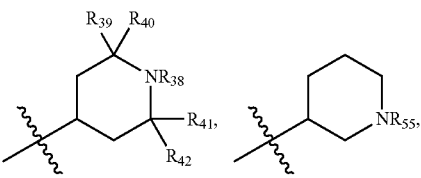

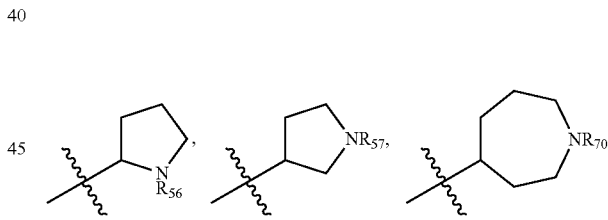

wherein each nonaromatic heterocycle is further optionally substituted on the ring, other than the substituent on the nitrogen atom, with one or more substituents;

the wiggly line denotes an E or Z stereochemistry around the double bond to which the wiggly line is attached;

$R_{39}$, $R_{40}$, $R_{41}$, and $R_{42}$ are independently hydrogen, a substituted or an unsubstituted $C_1$-$C_3$ alkyl, or $R_{40}$ and $R_{41}$ together with the carbon atoms they are attached to form a cyclic moiety;

$R_{38}$, $R_{55}$, $R_{56}$, $R_{57}$, and $R_{70}$ independently are hydrogen, a substituted or an unsubstituted $C_1$-$C_3$ alkyl or $C_3$-$C_8$ cycloalkyl, aryl, heteroaryl, or $R_{58}$—$SO_2^-$, $R_{58}$ is a substituted or an unsubstituted $C_1$-$C_3$ alkyl.

In one embodiment, the double bond attached to $A_1$ and $R_{36}$ has "E" stereochemistry. In one embodiment, the double bond attached to A1 and $R_{36}$ has "Z" stereochemistry. In another embodiment, $R_{38}$, $R_{55}$, $R_{56}$, $R_{57}$, and $R_{70}$ are a substituted or an unsubstituted —$CH_2$-aryl or —$CH_2$-heteroaryl, In another embodiment, the present invention provides compounds of Formula III-E

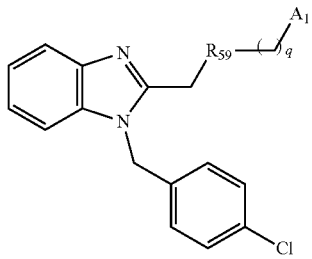

Formula III-E $R_{59}$ is —O—, or —$NR_{60}$;

$R_{60}$ is hydrogen or a substituted or an unsubstituted $C_1$-$C_3$ alkyl;

q is 0, 1, or 2;

$A_1$ is a substituted or an unsubstituted pyridyl or

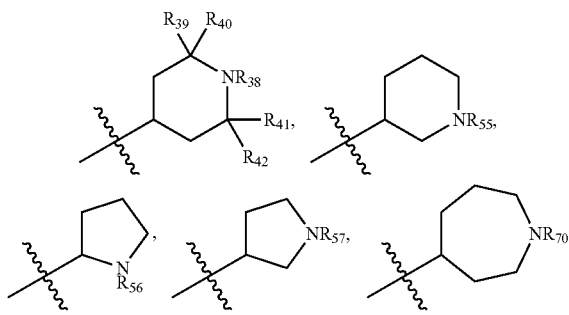

wherein each nonaromatic heterocycle is further optionally substituted on the ring, other than the substituent on the nitrogen atom, with one or more substituents;

$R_{39}$, $R_{40}$, $R_{41}$, and $R_{42}$ are independently hydrogen, a substituted or an unsubstituted $C_1$-$C_3$ alkyl, or $R_{40}$ and $R_{41}$ together with the carbon atoms they are attached to form a cyclic moiety;

$R_{38}$, $R_{55}$, $R_{56}$, $R_{57}$, and $R_{70}$ independently are hydrogen, a substituted or an unsubstituted $C_1$-$C_3$ alkyl or $C_3$-$C_8$ cycloalkyl, aryl, heteroaryl, or $R_{58}$—$SO_2$—;

$R_{58}$ is a substituted or an unsubstituted $C_1$-$C_3$ alkyl.

In one embodiment, $R_{38}$, $R_{55}$, $R_{56}$, $R_{57}$, and $R_{70}$ are a substituted or an unsubstituted —$CH_2$-aryl or —$CH_2$-heteroaryl.

In another embodiment, the present invention provides compounds of Formula III-C, III-D, and III-E wherein $A_1$ is a 5 or 6 membered nonaromatic heterocycle.

In another embodiment, the present invention provides compounds of Formula IV wherein L is $C_1$-$C_3$ alkylene and $R_{30}$ is hydrogen. In another embodiment, the present invention provides compounds of formula III wherein L is —$CH_2$—, —$CH_2$—$CH_2$—, —$CH(Me)$-$CH_2$—, —$CH_2$—$CH_2$—$CH_2$—, —$CH_2$—$CH_2$—$CH_2$—$CH_2$—. In another embodiment, the present invention provides compounds of formula III wherein L is —CH=CH— or —$CH(Me)$=CH—. In another embodiment, L is —$CH_2$—O—, —$CH_2$—NH—, —$CH_2$—NH—$CH_2$—, —$CH_2$—O—$CH_2$—.

In another embodiment, $R_{38}$, $R_{55}$, $R_{56}$, $R_{57}$, and $R_{70}$ are hydrogen. In another embodiment, $R_{38}$, $R_{49}$, $R_{55}$, $R_{56}$, $R_{57}$, and $R_{70}$ are $C_1$-$C_3$ alkyl substituted with a substituted or an unsubstituted aryl or $C_3$-$C_8$ cycloalkyl group.

In another embodiment, the present invention provides compounds of Formula IV

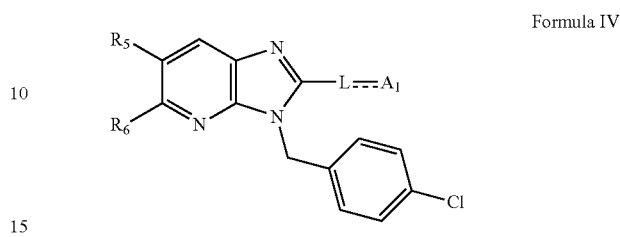

Formula IV wherein L is a substituted or an unsubstituted $C_1$-$C_6$ alkylene, $C_1$-$C_6$ heteroalkylene, $C_2$-$C_6$ alkenylene, or $C_2$-$C_6$ heteroalkenylene;

$A_1$ is a substituted or an unsubstituted, 5 or 6 membered, non aromatic heterocycle containing at least one basic nitrogen atom wherein the heterocycle is attached to L via a carbon atom, a substituted or unsubstituted 6 membered heteroaryl containing at least one basic nitrogen atom,

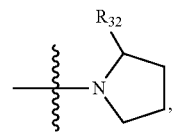

or a substituted or an unsubstituted 6 membered cycloalkyl;

----- denotes a single or double bond, $R_5$ is hydrogen, a substituted or an unsubstituted $C_1$-$C_4$ alkyl, a substituted or an unsubstituted aryl or heteroaryl, or $NR_{33}R_{34}$;

$R_6$ is hydrogen, a substituted or an unsubstituted $C_1$-$C_4$ alkyl, or $NR_{33}R_{34}$;

$R_{32}$ is hydrogen, methyl, or hydroxymethyl; and $R_{33}$ and $R_{34}$ are independently hydrogen, $C_1$-$C_6$ alkyl, a substituted or an unsubstituted $C_3$-$C_8$ cycloalkyl;

or a pharmaceutically acceptable salt thereof.

In another embodiment, the present invention provides compounds of Formula IV wherein L is $C_1$-$C_3$ alkylene and $R_5$ is hydrogen.

In other embodiments, the present invention provides compounds that are disclosed in summary and detail wherein, $R_5$ and $R_6$ are a substituted or an unsubstituted $C_1$-$C_6$ alkyl. In other embodiments, $R_5$ and $R_6$ are a substituted or an unsubstituted $C_1$-$C_3$ alkyl. In other embodiments, $R_5$ and $R_6$ are independently methyl, ethyl, propyl, isopropyl, butyl, 2-butyl, or tertiary butyl. In other embodiments, $R_5$ and $R_6$ are hydrogen.

TABLE 1a

| $R_1$ moieties of the compound of Formula I include, but are not limited to, the following: Illustrative $R_1$ moieties | |
|---|---|
| hydrogen | R1-1 |
| Methyl | R1-2 |
| ethyl | R1-3 |

TABLE 1a-continued
R1 moieties of the compound of Formula I include, but are not limited to, the following:
Illustrative R1 moieties
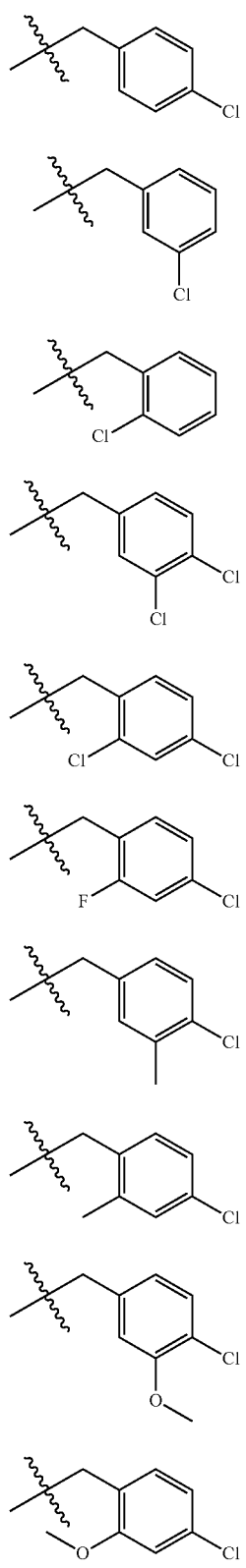
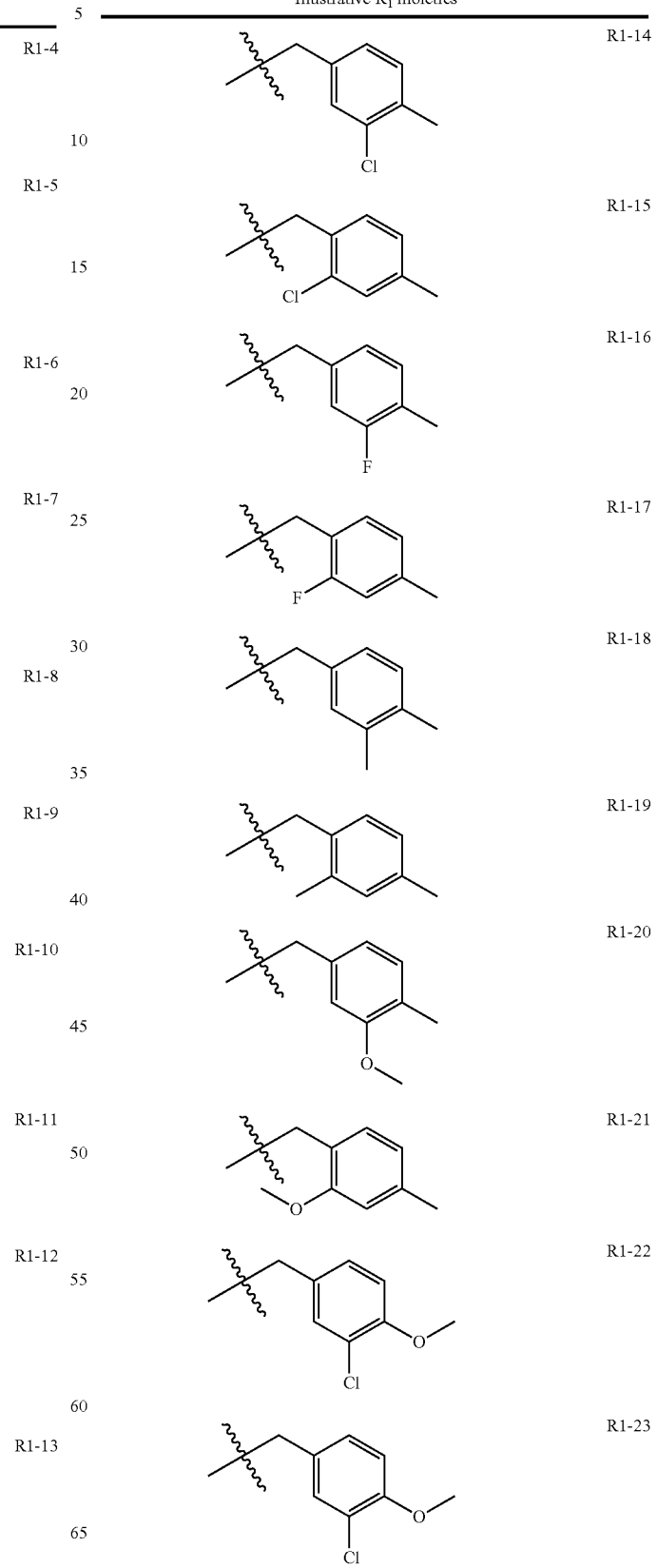

TABLE 1a-continued
R1 moieties of the compound of Formula I include, but are not limited to, the following:
Illustrative R1 moieties
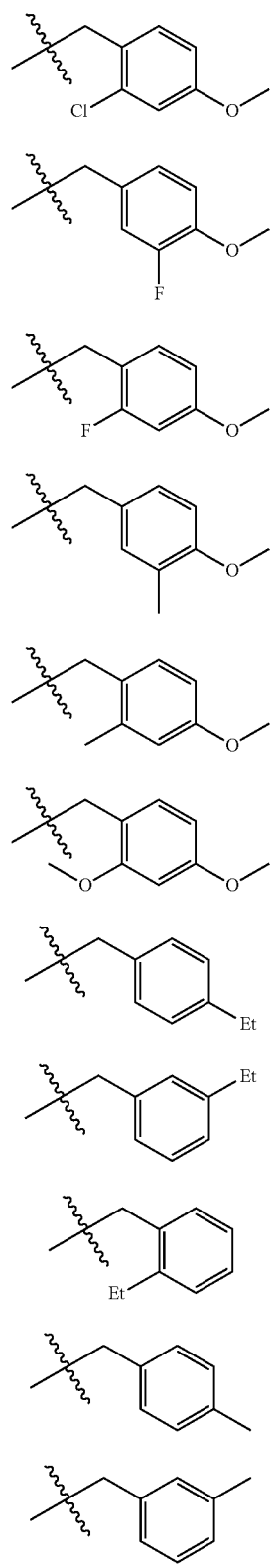
R1-24
R1-25
R1-26
R1-27
R1-28
R1-29
R1-30
R1-31
R1-32
R1-33
R1-34
TABLE 1a-continued
R1 moieties of the compound of Formula I include, but are not limited to, the following:
Illustrative R1 moieties
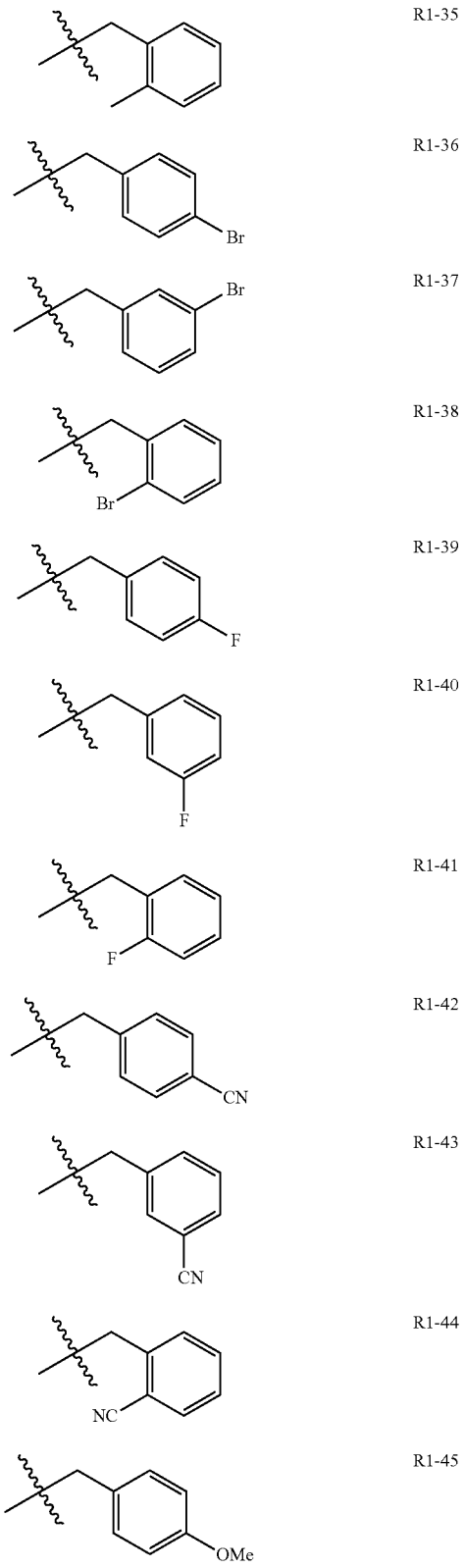
R1-35
R1-36
R1-37
R1-38
R1-39
R1-40
R1-41
R1-42
R1-43
R1-44
R1-45

TABLE 1a-continued
R₁ moieties of the compound of Formula I include, but are not limited to, the following:
Illustrative R₁ moieties
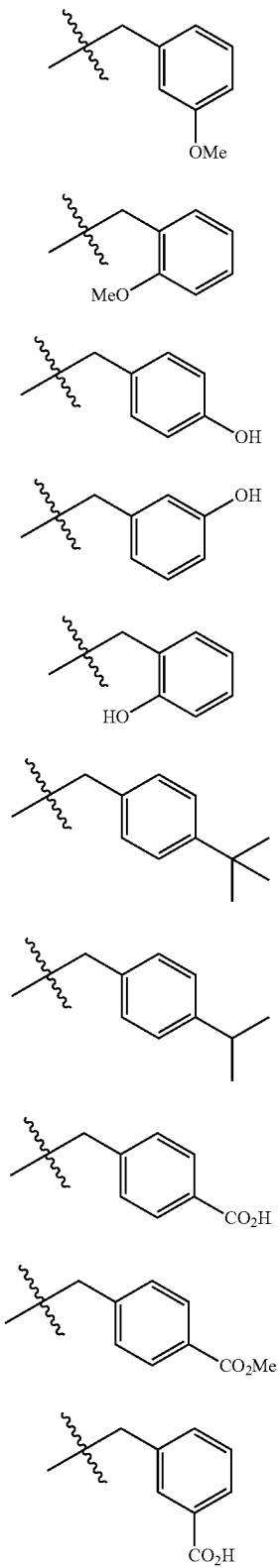
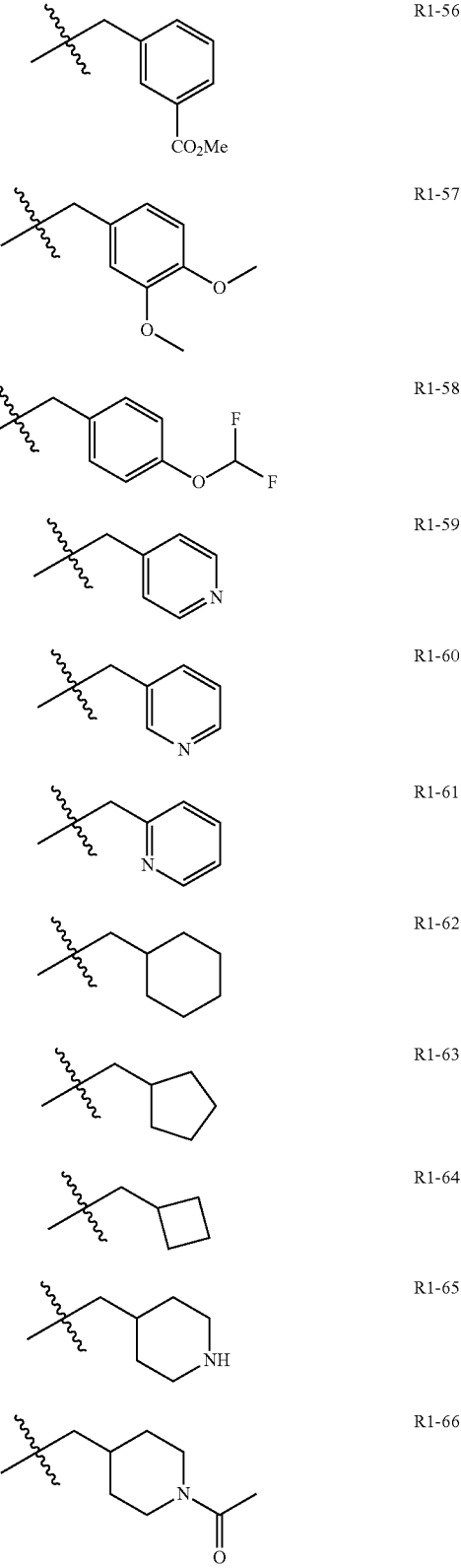

TABLE 1a-continued
R₁ moieties of the compound of Formula I include, but are not limited to, the following:
Illustrative R₁ moieties
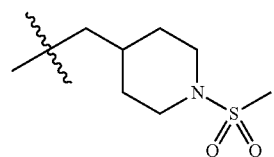 [SMILES: *CC1CCN(S(C)(=O)=O)CC1] R1-67
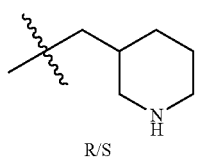 [SMILES: *CC1CCCNC1] R1-68
R/S
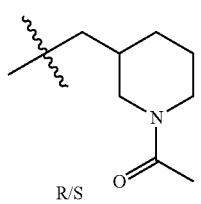 [SMILES: *CC1CCCN(C(C)=O)C1] R1-69
R/S
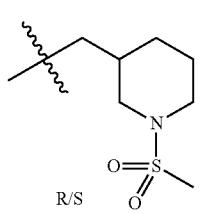 [SMILES: *CC1CCCN(S(C)(=O)=O)C1] R1-70
R/S
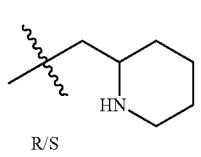 [SMILES: *CC1CCCCN1] R1-71
R/S
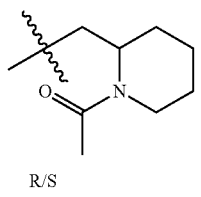 [SMILES: *CC1CCCCN1C(C)=O] R1-72
R/S
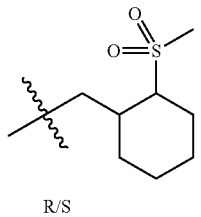 [SMILES: *CC1CCCCC1S(C)(=O)=O] R1-73
R/S
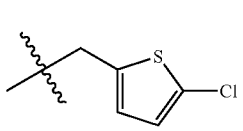 [SMILES: *Cc1ccc(Cl)s1] R1-74
TABLE 1a-continued
R₁ moieties of the compound of Formula I include, but are not limited to, the following:
Illustrative R₁ moieties
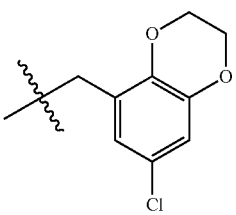 [SMILES: *Cc1cc(Cl)cc2c1OCCO2] R1-75
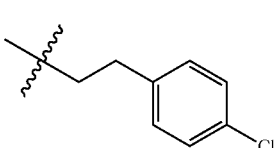 R1-76
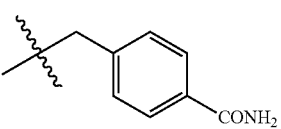 R1-77
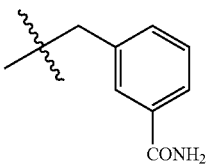 [SMILES: *Cc1cccc(C(N)=O)c1] R1-78
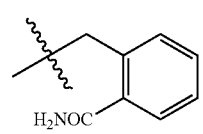 R1-79
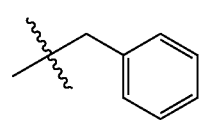 R1-80
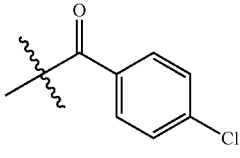 [SMILES: *C(=O)c1ccc(Cl)cc1] R1-81
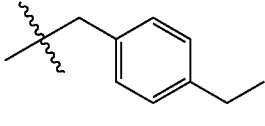 [SMILES: *Cc1ccc(CC)cc1] R1-82
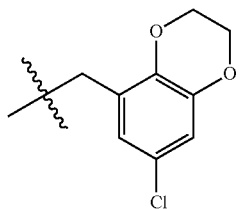 [SMILES: *Cc1cc(Cl)cc2c1OCCO2] R1-83

TABLE 1a-continued

R₁ moieties of the compound of Formula I include, but are not limited to, the following:
Illustrative R₁ moieties

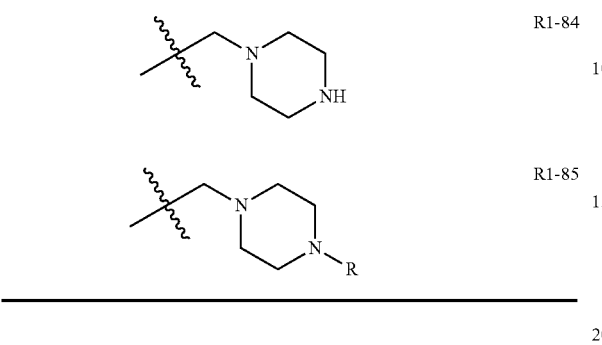

R1-84

R1-85

TABLE 1b

R₂ moieties of the compounds of Formula I include, but are not limited to, the following:
Exemplary R₂

| | |
|---|---|
| —CH₂NH₂ | R2-1 |
| —CH₂NMe₂ | R2-2 |
| —CH₂NEt₂ | R2-3 |
| —CH₂N(nPr)₂ | R2-4 |
| —CH₂N(iPr)₂ | R2-5 |

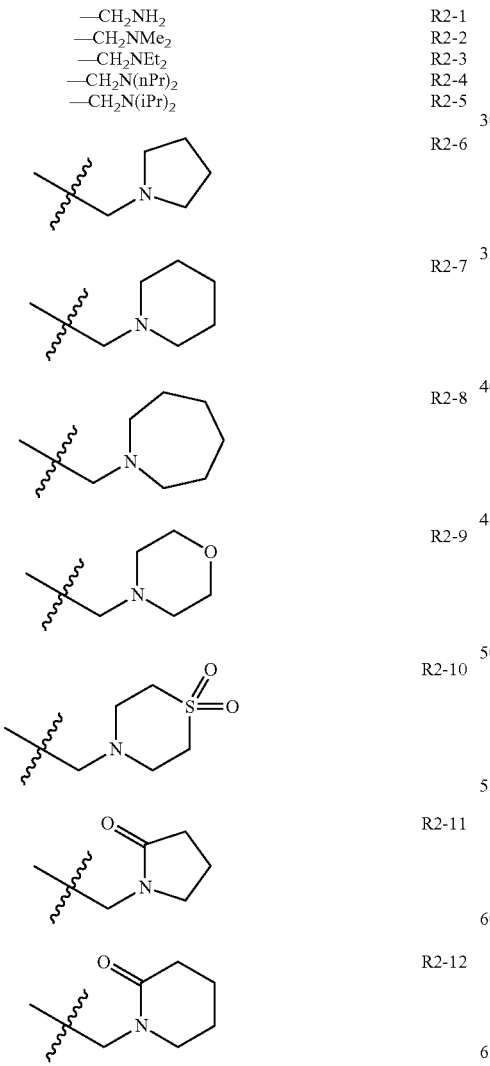

TABLE 1b-continued

R₂ moieties of the compounds of Formula I include, but are not limited to, the following:
Exemplary R₂

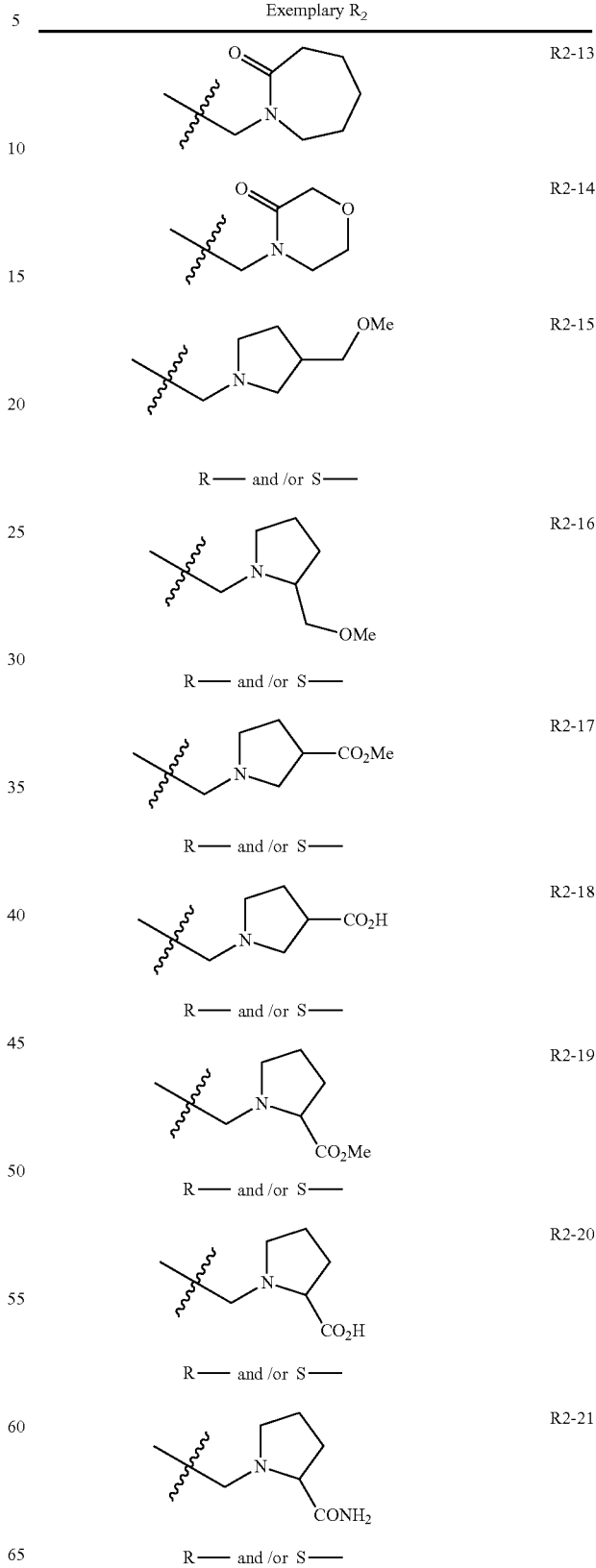

TABLE 1b-continued

R$_2$ moieties of the compounds of Formula I include, but are not limited to, the following:
Exemplary R$_2$

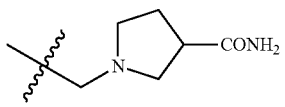 R2-22

R— and /or S—

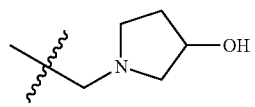 R2-23

R— and /or S—

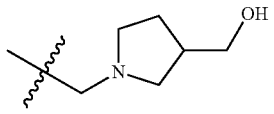 R2-24

R— and /or S—

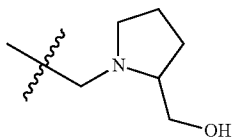 R2-25

R— and /or S—

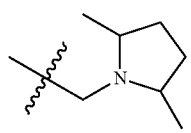 R2-26

R— and /or S—

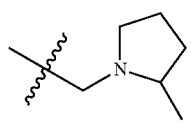 R2-27

R— and /or S—

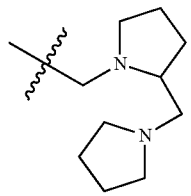 R2-28

R— and /or S—

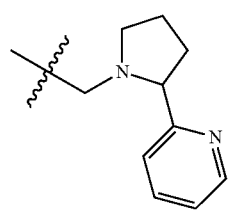 R2-29

R— and /or S—

TABLE 1b-continued

R$_2$ moieties of the compounds of Formula I include, but are not limited to, the following:
Exemplary R$_2$

| | |
|---|---|
| —CH$_2$OH | R2-30 |
| —CH(CH$_3$)OH | R2-31 |
| H | R2-32 |

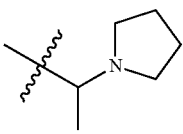 R2-33

R— and /or S—

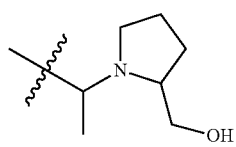 R2-34

(R, R), (S, S), (R, S), (S, R)

| | |
|---|---|
| —CF$_3$ | R2-35 |
| —CH$_3$ | R2-36 |
| —CH$_2$CH$_3$ | R2-37 |
| —CH(CH$_3$)$_2$ | R2-38 |
| —CH$_2$CH(CH$_3$)$_2$ | R2-39 |
| —C$_4$H$_9$ | R2-40 |
| —C$_5$H$_{11}$ | R2-41 |
| —CH$_2$Ph | R2-42 |

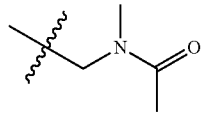 [SMILES: *CN(C)C(C)=O] R2-43

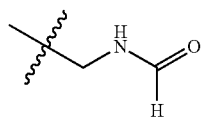 [SMILES: *CNC=O] R2-44

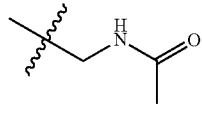 [SMILES: *CNC(C)=O] R2-45

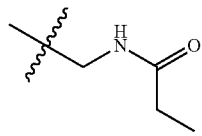 [SMILES: *CNC(=O)CC] R2-46

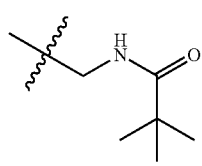 [SMILES: *CNC(=O)C(C)(C)C] R2-47

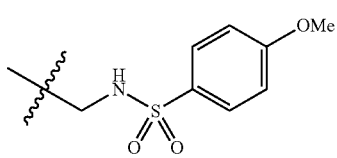 [SMILES: *CNS(=O)(=O)c1ccc(OC)cc1] R2-48

TABLE 1b-continued

R₂ moieties of the compounds of Formula I include, but are not limited to, the following:
Exemplary R₂

| | |
|---|---|
| [structure: -(CH₂)₃-NH-C(O)-CH₂-Ph] | R2-49 |
| —SH | R2-50 |
| [structure: -CH₂-C(O)-OEt] | R2-51 |
| [structure: -S-CH₂-C(O)-OEt] | R2-52 |
| [structure: -S-CH₂-C₆H₄-F (para)] | R2-53 |
| —NH₂ | R2-54 |
| [structure: -S(O)₂-propyl] | R2-55 |
| [structure: -CH=CH-Ph (trans)] | R2-56 |
| [structure: thiazol-5-yl] | R2-57 |
| [structure: 2-oxo-1,2-dihydropyridin-3-yl] | R2-58 |
| [structure: 6-oxo-1,6-dihydropyridin-3-yl] | R2-59 |
| [structure: (1-methylpyrrolidin-2-yl)methyl] | R2-60 |

TABLE 1b-continued

R₂ moieties of the compounds of Formula I include, but are not limited to, the following:
Exemplary R₂

| | |
|---|---|
| [structure: (1-methylpyrrolidin-3-yl)methyl] R/S | R2-61 |
| [structure: (1-acetylpyrrolidin-2-yl)methyl] R/S | R2-62 |
| [structure: (1-methylsulfonylpyrrolidin-2-yl)methyl] R/S | R2-63 |
| [structure: (1-acetylpyrrolidin-3-yl)methyl] R/S | R2-64 |
| [structure: (1-methylsulfonylpyrrolidin-3-yl)methyl] R/S | R2-65 |
| [structure: (1-methylpiperidin-4-yl)methyl] | R2-66 |
| [structure: (1-acetylpiperidin-4-yl)methyl] | R2-67 |
| [structure: (1-methylsulfonylpiperidin-4-yl)methyl] | R2-68 |
| [structure: (1-methylpiperidin-3-yl)methyl] R/S | R2-69 |

TABLE 1b-continued
R₂ moieties of the compounds of Formula I include, but are not limited to, the following:
Exemplary R₂
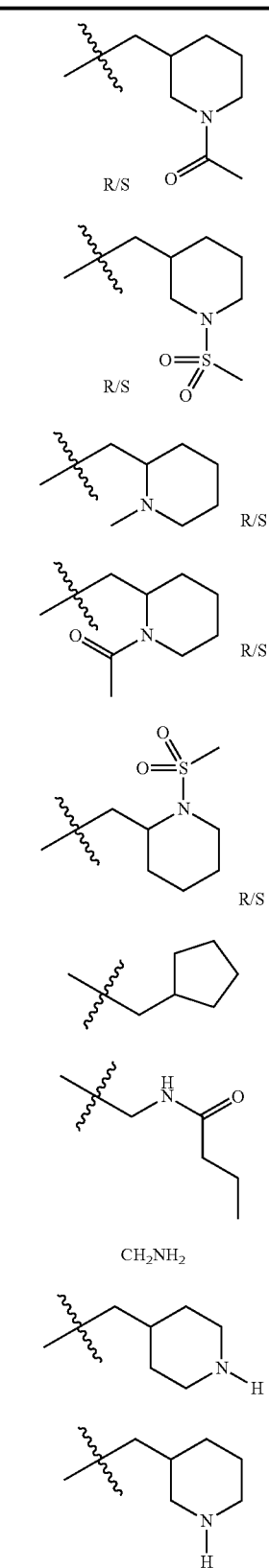
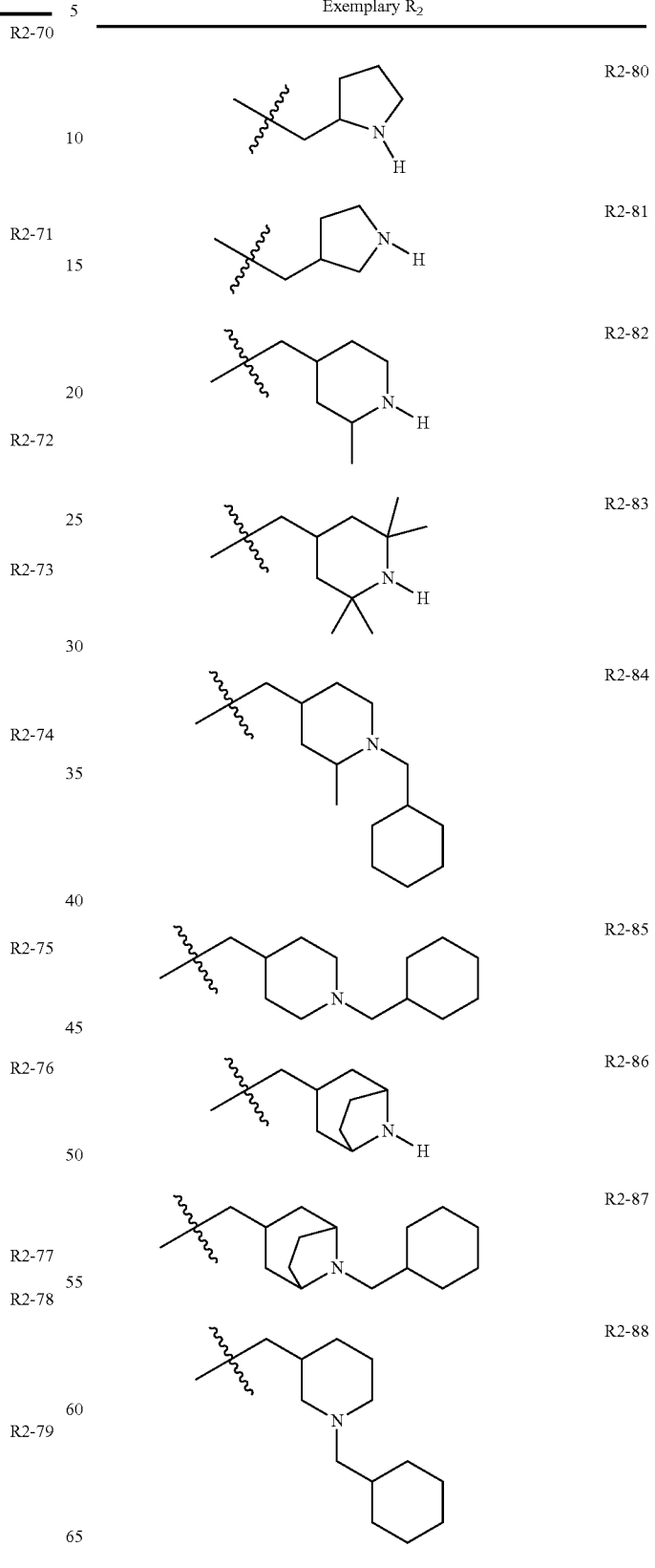

TABLE 1b-continued
R₂ moieties of the compounds of Formula I include, but are not limited to, the following:
Exemplary R₂
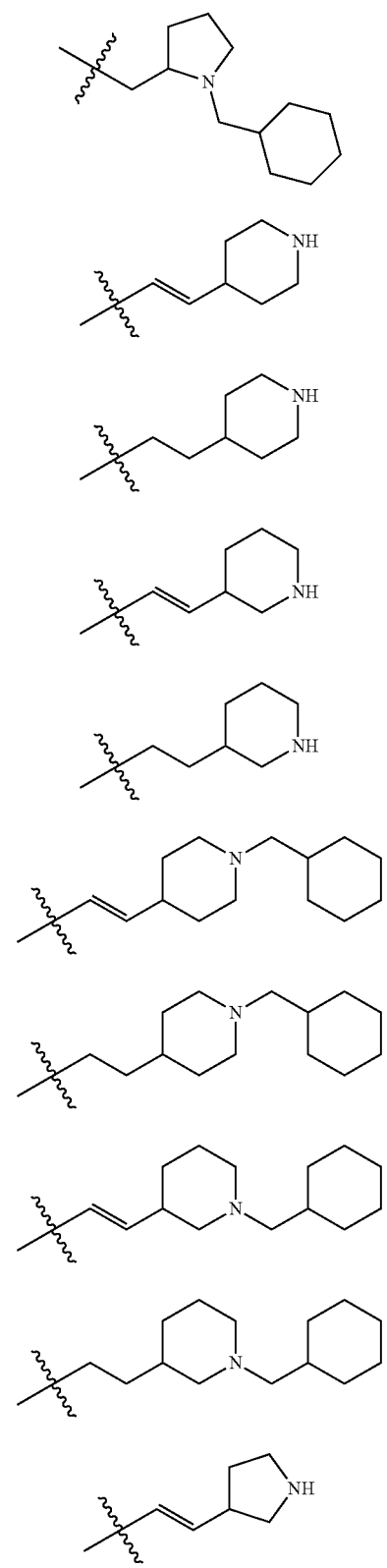
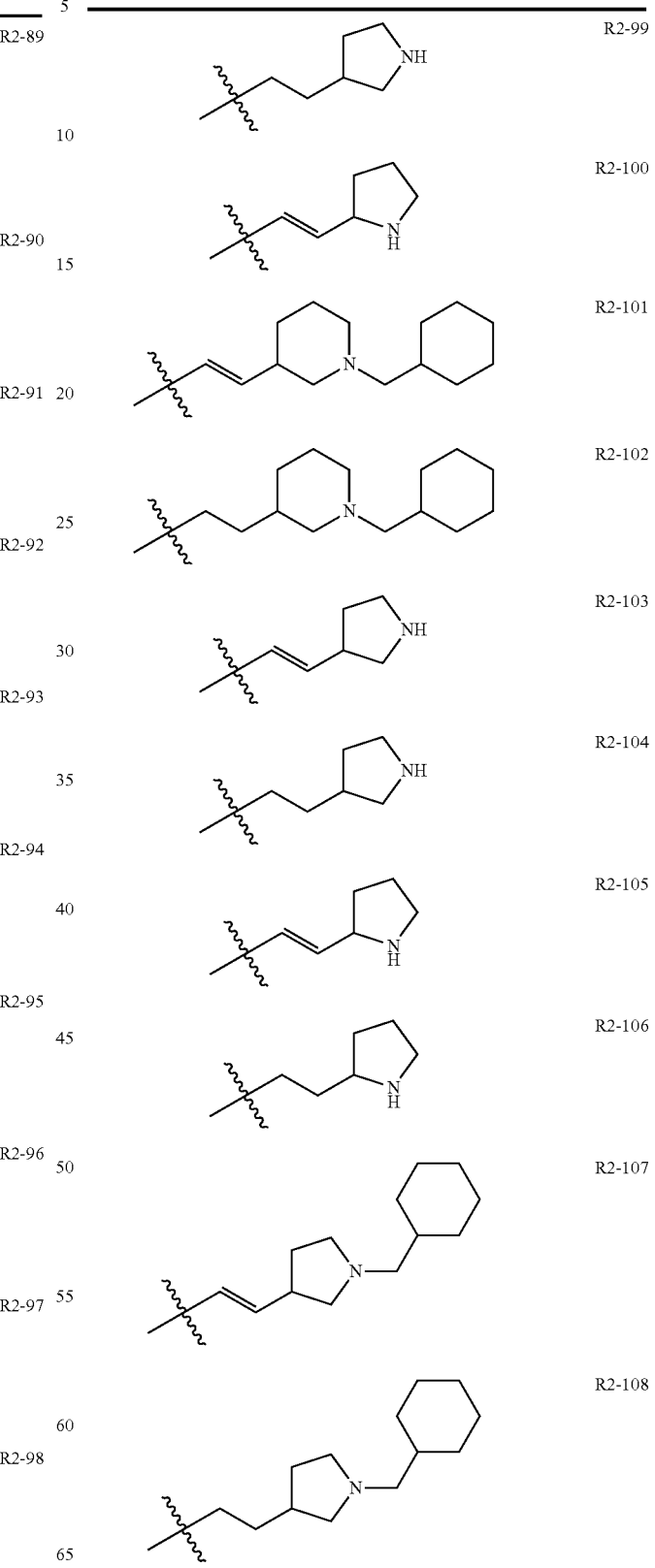

131

TABLE 1b-continued

R$_2$ moieties of the compounds of Formula I include, but are not limited to, the following:
Exemplary R$_2$

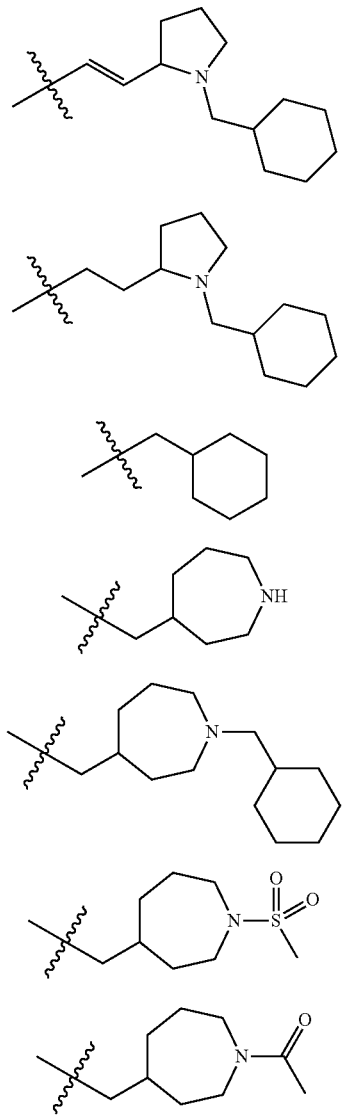

R2-109

R2-110

R2-111

R2-112

R2-113

R2-114

R2-115

132

TABLE 1b-continued

R$_2$ moieties of the compounds of Formula I include, but are not limited to, the following:
Exemplary R$_2$

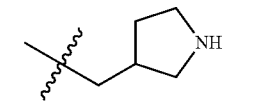

R2-116

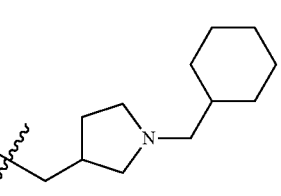

R2-117

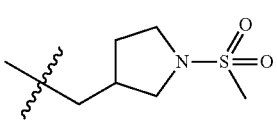 [SMILES: *CC1CCN(S(C)(=O)=O)C1]

R2-118

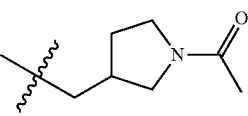 [SMILES: *CC1CCN(C(C)=O)C1]

R2-119

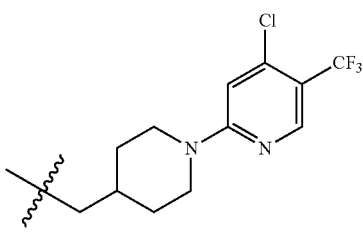 [SMILES: *CC1CCN(c2cc(Cl)c(C(F)(F)F)cn2)CC1]

R2-120

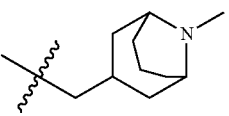 [SMILES: *CC1CC2CCCC(C1)N2C]

R2-121

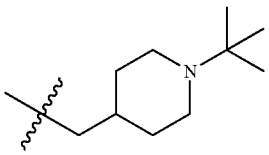 [SMILES: *CC1CCN(C(C)(C)C)CC1]

R2-122

TABLE 1c

R$_4$, moieties of the compounds of Formula I include, but are not limited to, the following:
Illustrative R$_3$, R$_4$, R$_5$, R$_6$, and R$_7$ Moieties

| R4-1 | R4-2 | R4-3 | R4-4 | R4-5 |
| hydrogen | methyl | ethyl | chloro | fluoro |
| R4-6 | R4-7 | R4-8 | R4-9 | R4-10 |
| bromo | hydroxy | —OMe | —NO$_2$ | —NH$_2$ |
| R4-11 | R4-12 | R4-13 | R4-14 | R4-15 |
| —NHCOCH$_3$ | —NHCOCH(CH$_3$)$_2$ | —NHCOCF$_3$ | —NHCOPh | —NHCONHC$_4$H$_9$ |
| R4-16 | R4-17 | R4-18 | R4-19 | R4-20 |

TABLE 1c-continued

R4, moieties of the compounds of Formula I include, but are not limited to, the following:
Illustrative $R_3$, $R_4$, $R_5$, $R_6$, and $R_7$ Moieties

| | | | | |
|---|---|---|---|---|
| —N(Et)$_2$ | —NHSO$_2$Me | —NHSO$_2$CF$_3$ | 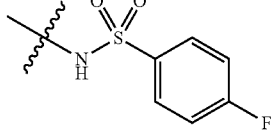 | 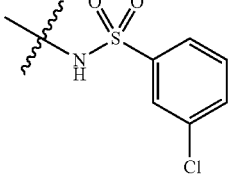 |
| R4-21 | R4-22 | R4-23 | R4-24 | R4-25 |
| —SO$_2$Me | —CN | $R_4$ and $R_5$ are —OCH$_2$O— | $R_5$ and $R_6$ are —OCH$_2$O— | $R_6$ and $R_7$ are —OCH$_2$O— |
| R4-26 | R4-27 | R4-28 | R4-29 | R4-30 |
| $R_4$ and $R_5$ are —OCH$_2$CH$_2$O— | $R_5$ and $R_6$ are —OCH$_2$CH$_2$O— | $R_6$ and $R_7$ are —OCH$_2$CH$_2$O— | —CO$_2$H | —CF$_3$ |
| R4-31 | R4-32 | R4-33 | R4-34 | R4-35 |
| —OEt | —SO$_2$NH$_2$ | —SO$_2$NHMe | SO$_2$NMe$_2$ | NHC(O)Me |
| R4-36 | R4-37 | R4-38 | R4-39 | R4-40 |
| —NHC(O)Ph | —NMeC(O)Et | —NMeC(O)Ph | —C(O)NHMe | —C(O)NEt$_2$ |
| R4-41 | R4-42 | R4-43 | R4-41 | R4-42 |
| —C(O)NH$_2$ | —NHC(O)NHMe | —CO$_2$Me | —C(O)NH$_2$ | —NHC(O)NHMe |

Additional non-limiting illustrative compounds of the present invention have a structure of any of Formulae II-XXXIX include those in which $R_1$ is any $R_1$ moiety described in Table 1a in combination with any $R_2$ moiety described in Table 1b, and any $R_3$, $R_4$, $R_5$, $R_6$, and $R_7$ as described in Table 1c. Thus, a compound of any of Formulae II-XXXIX can include any combination of $R_1$, $R_2$, $R_3$, $R_4$, $R_5$, $R_6$, and $R_7$.

Certain 1b Active Analogs of the invention include without limitation the following compounds:

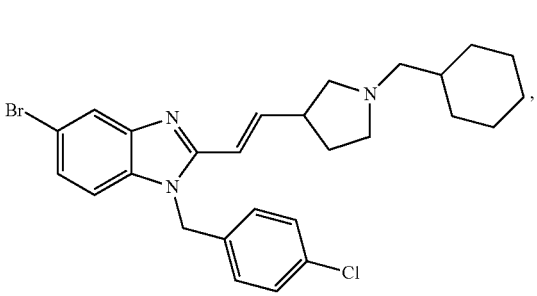

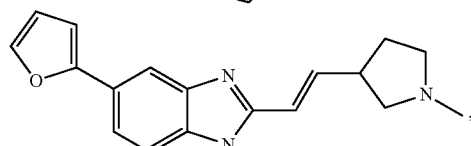

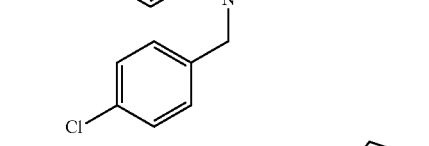

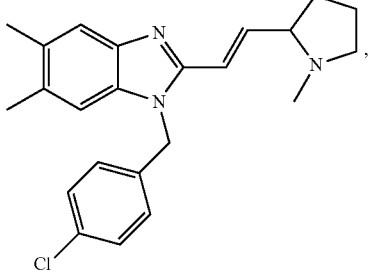

-continued

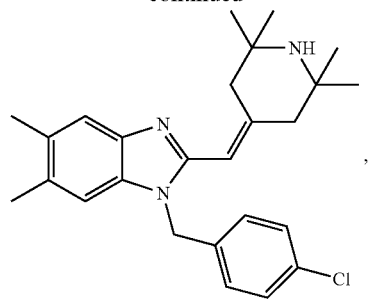

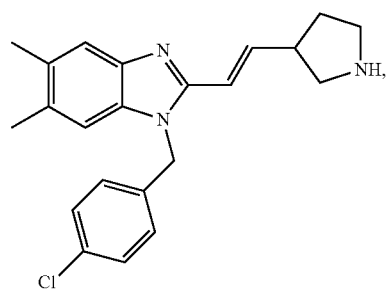

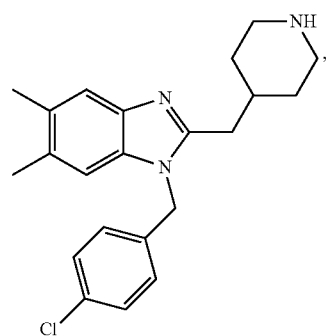

135
-continued
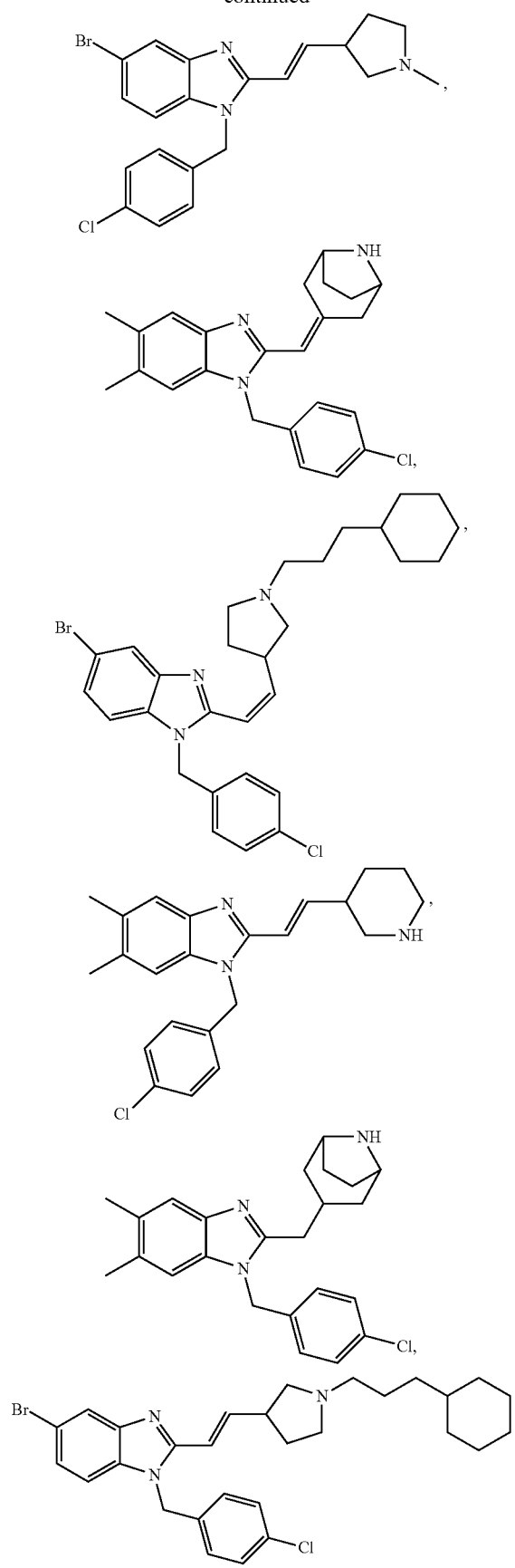
136
-continued
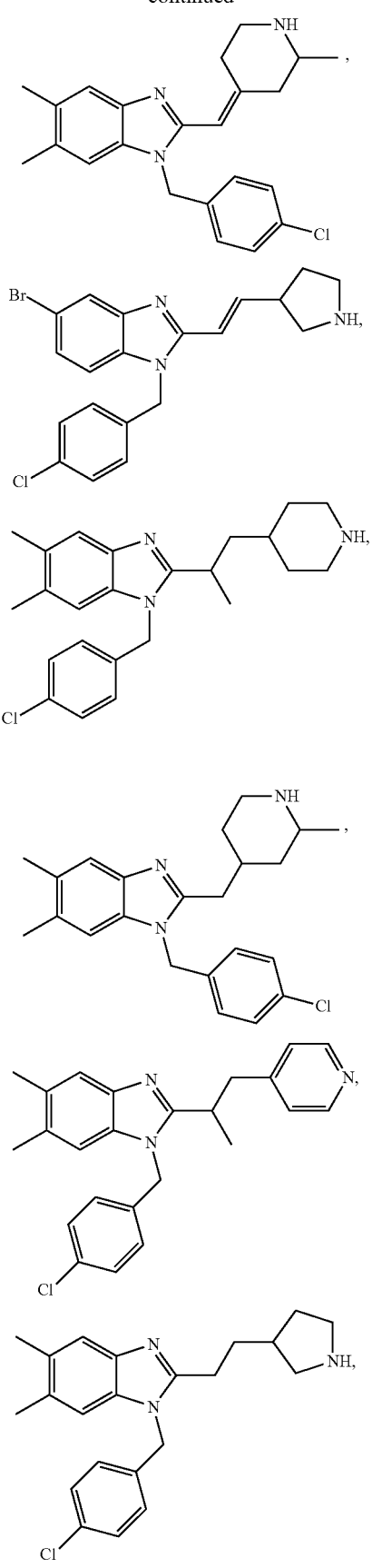

137
-continued
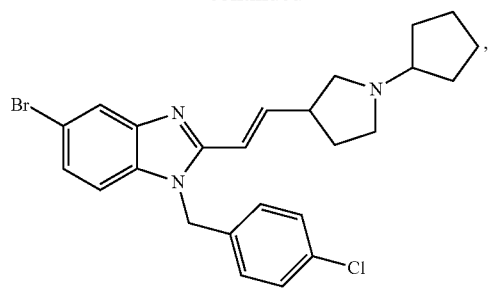
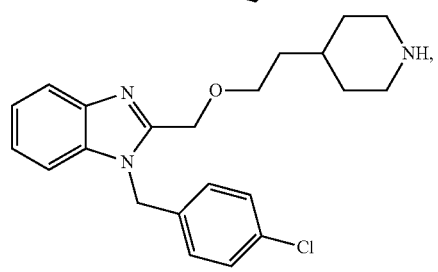
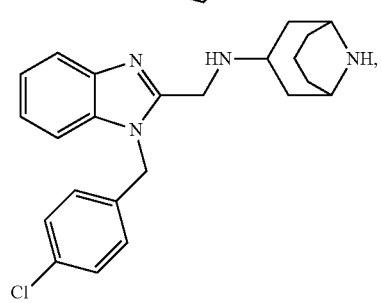
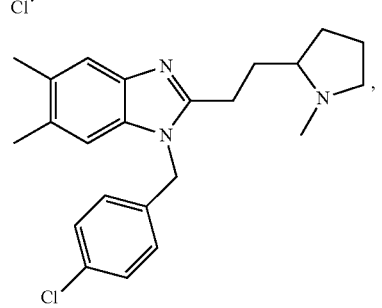
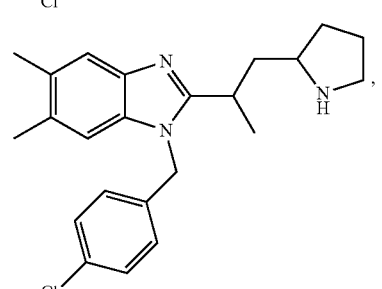
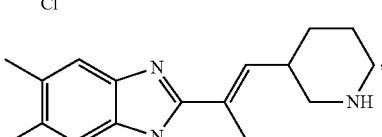
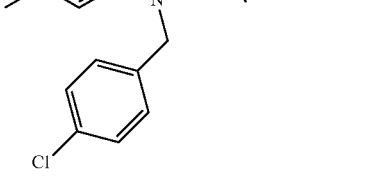
138
-continued
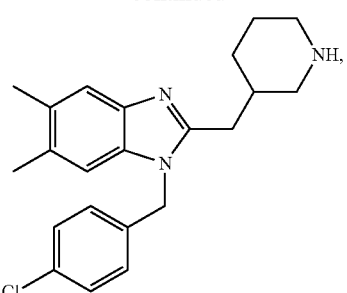
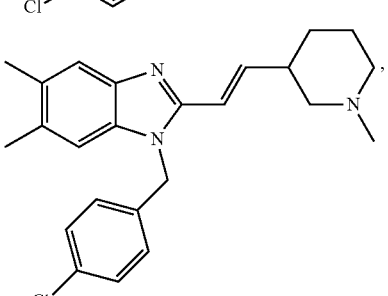
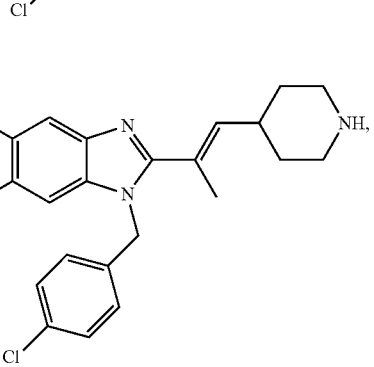
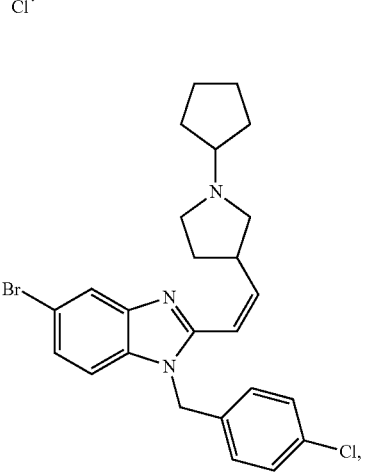
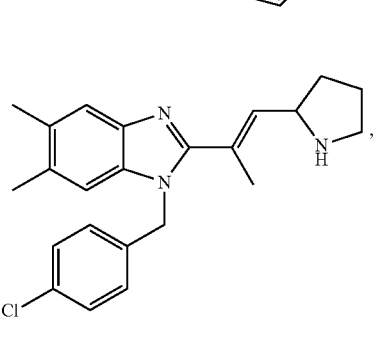

139 -continued
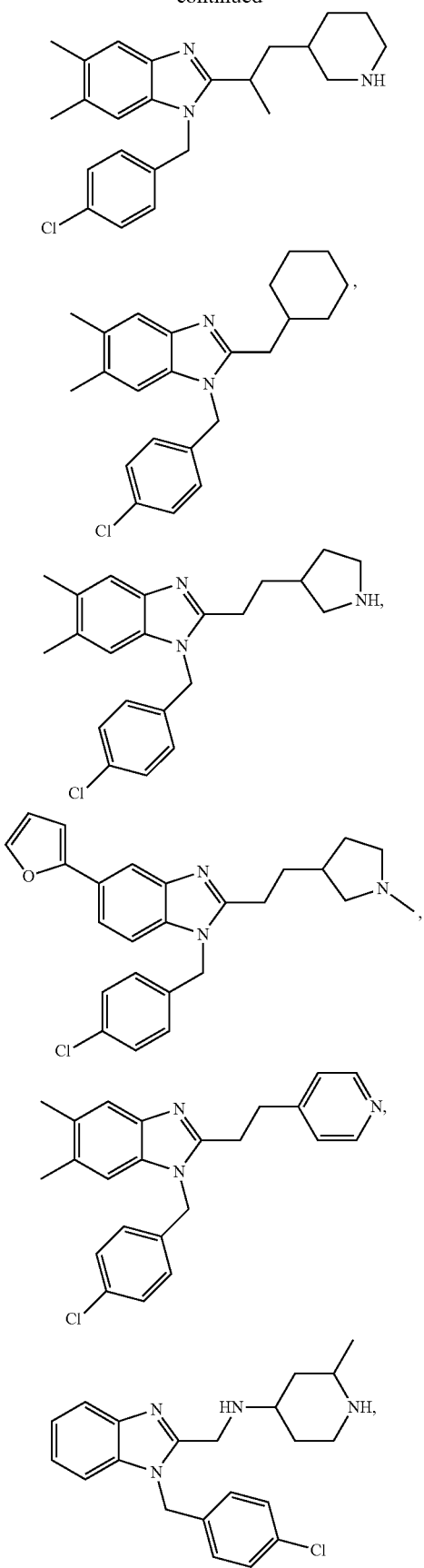
140 -continued
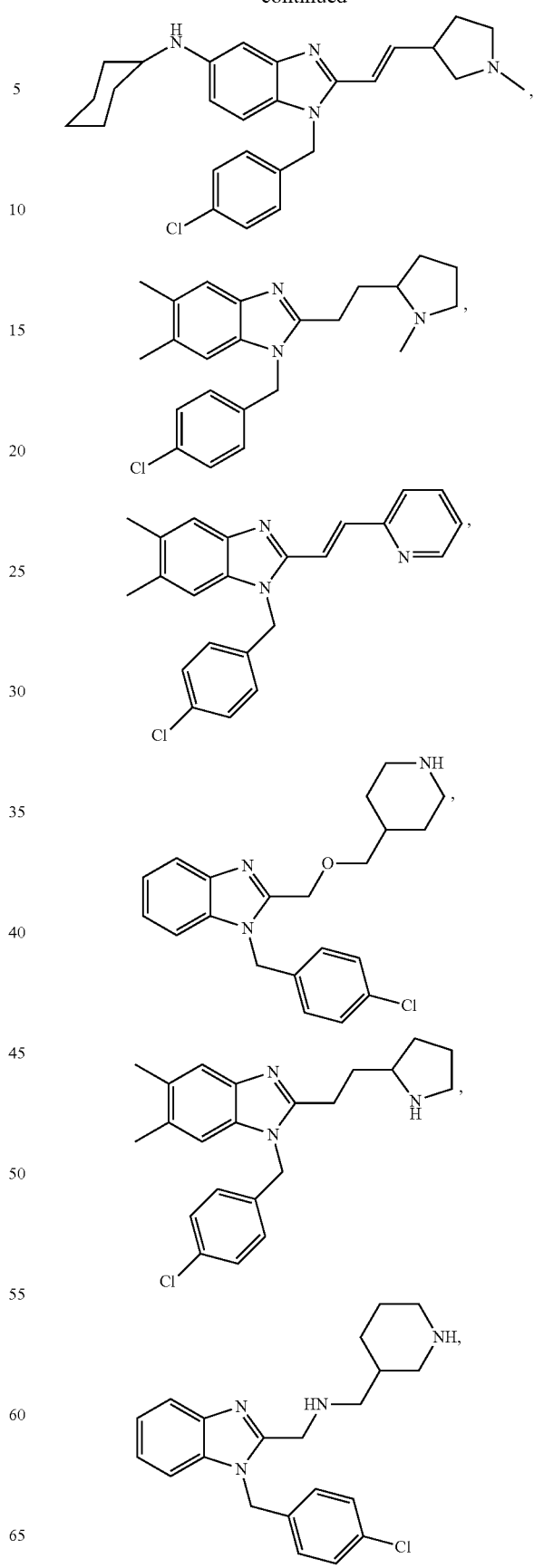

-continued
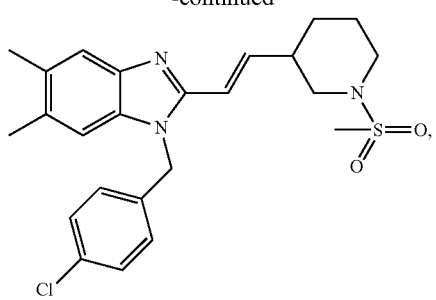
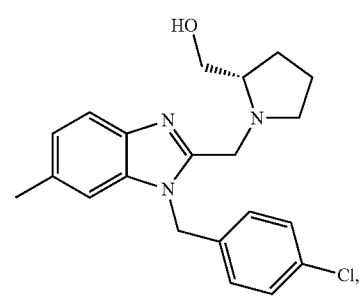
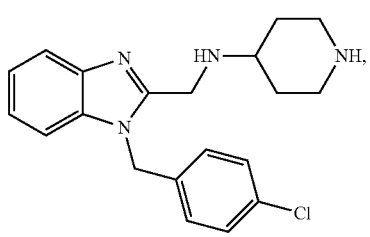
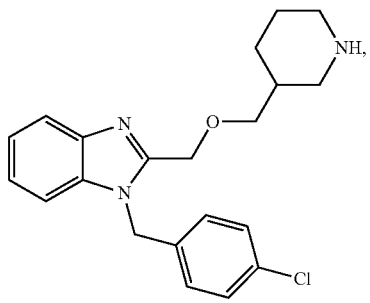
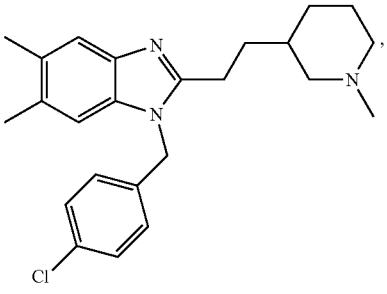
and pharmaceutically acceptable salts thereof.
Other compounds of the invention include without limitation the following compounds:
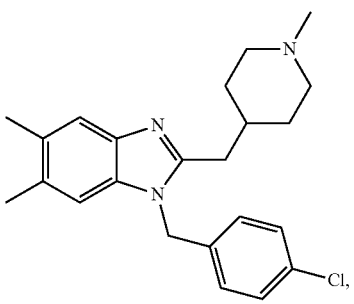
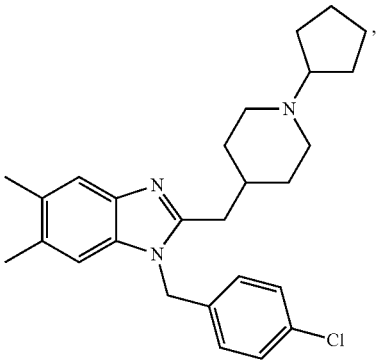
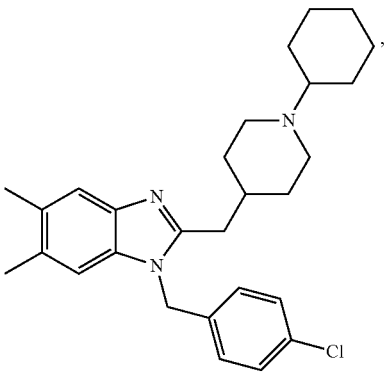
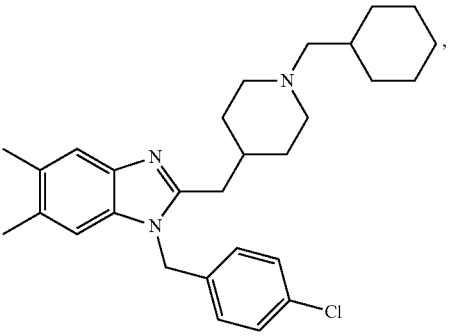

143
-continued
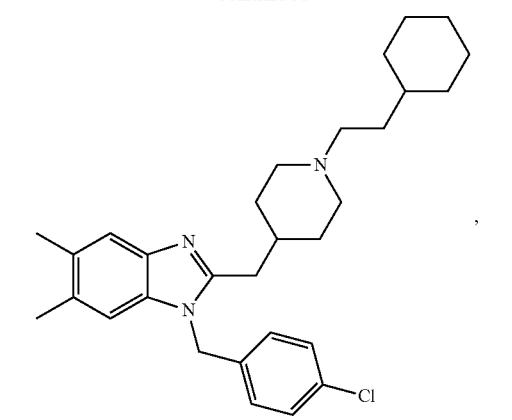
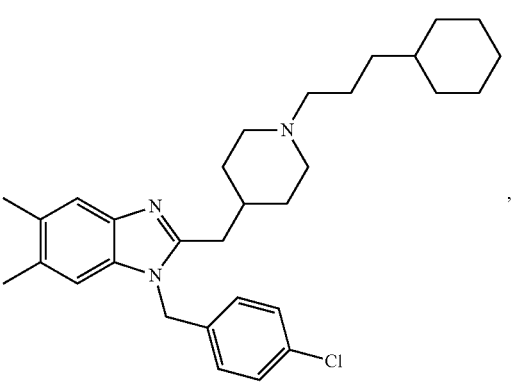
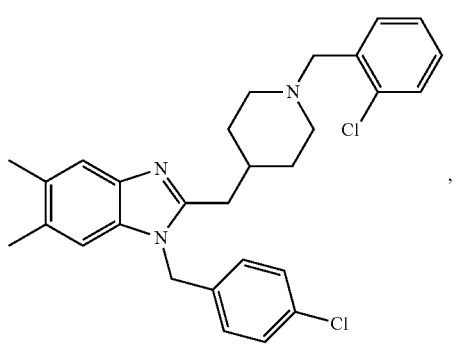
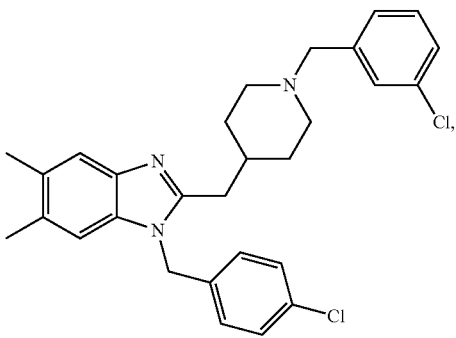
144
-continued
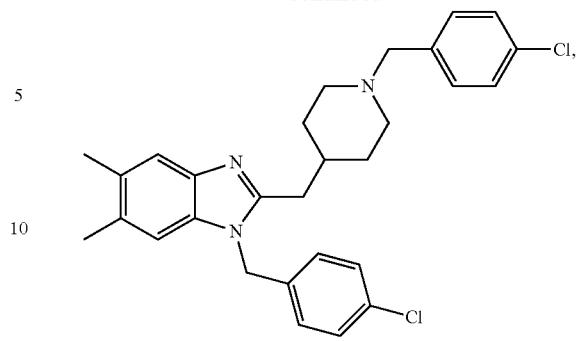
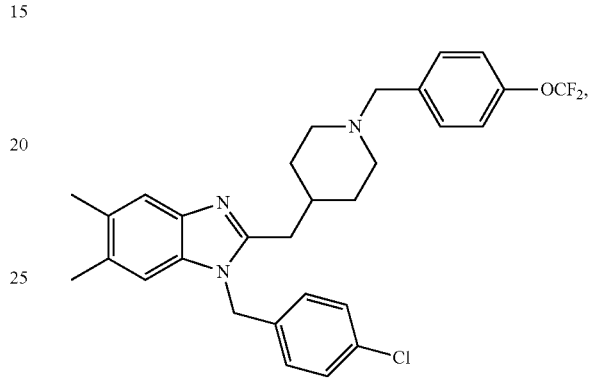
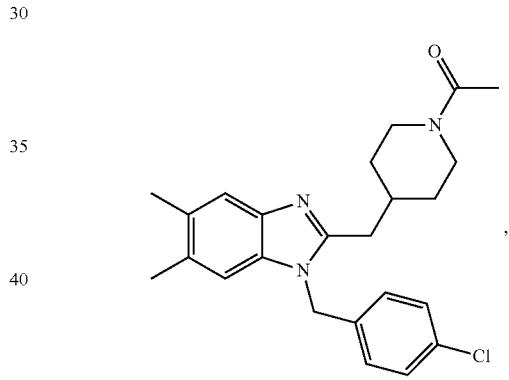
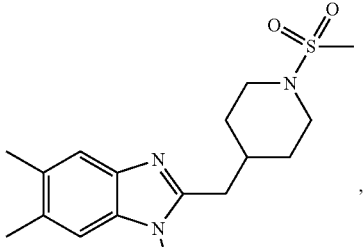
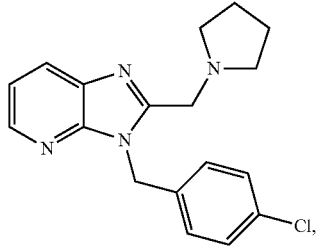

145
-continued
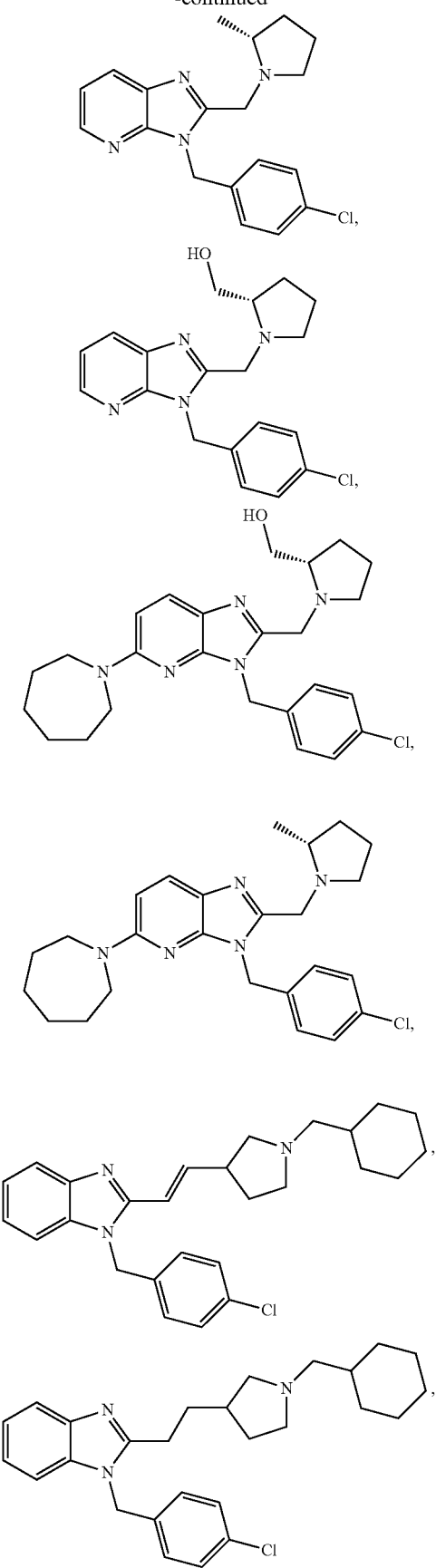
146
-continued
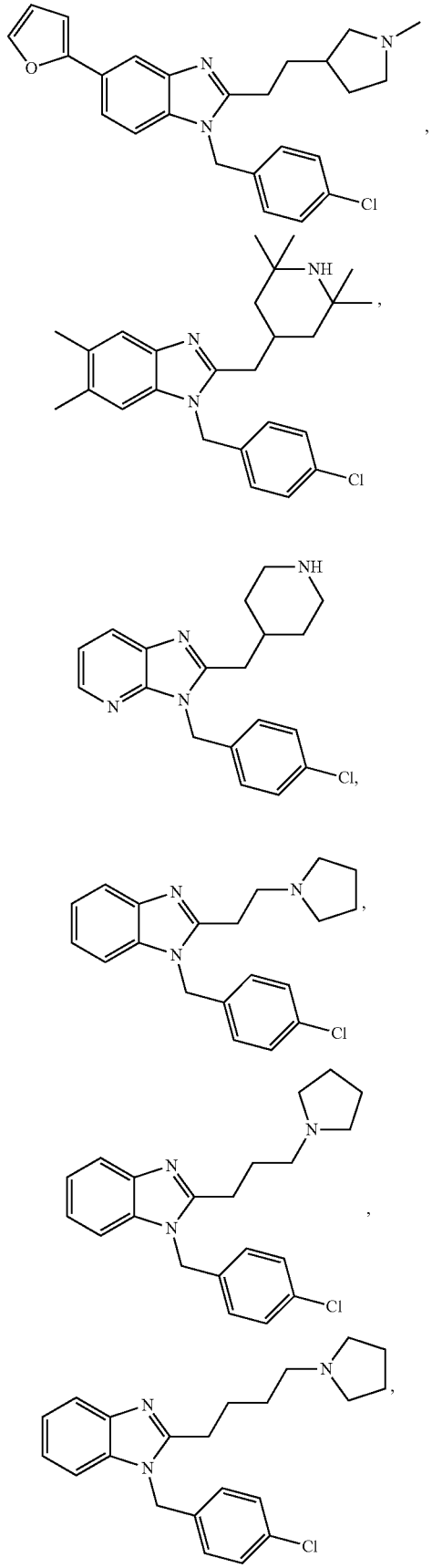

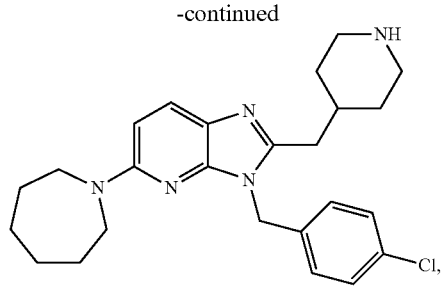
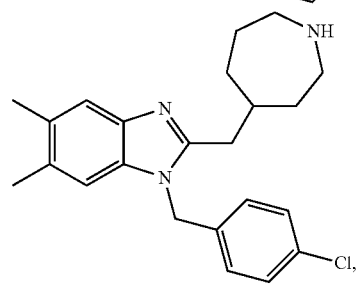
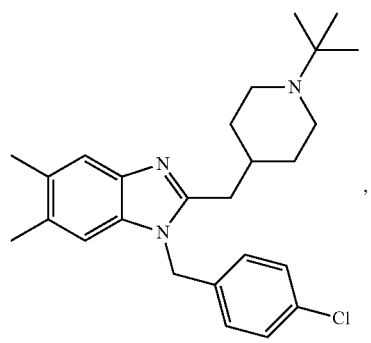
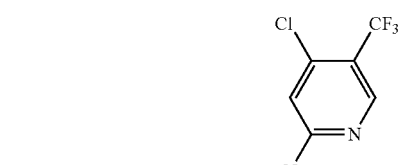
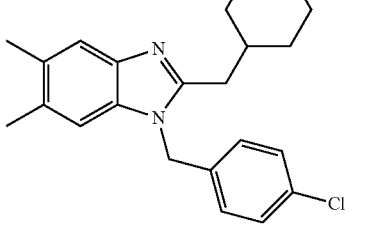
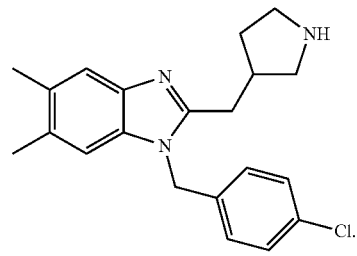
and
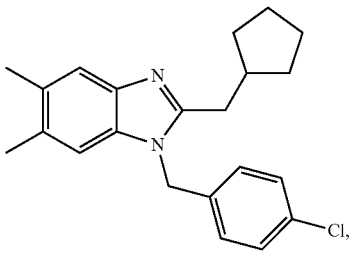
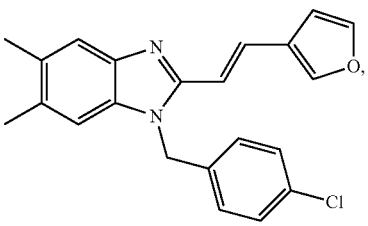
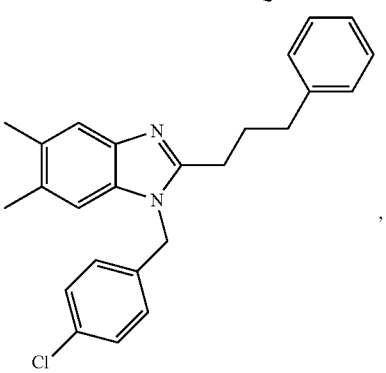
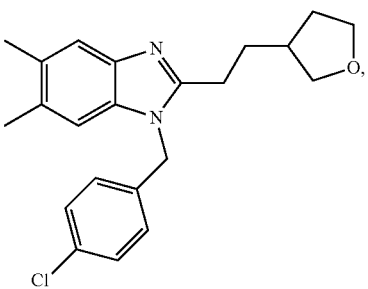
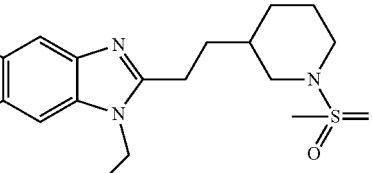
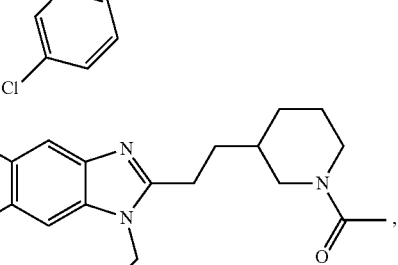
Clemizole Like Analogs of the invention include without limitation the following compounds:

149
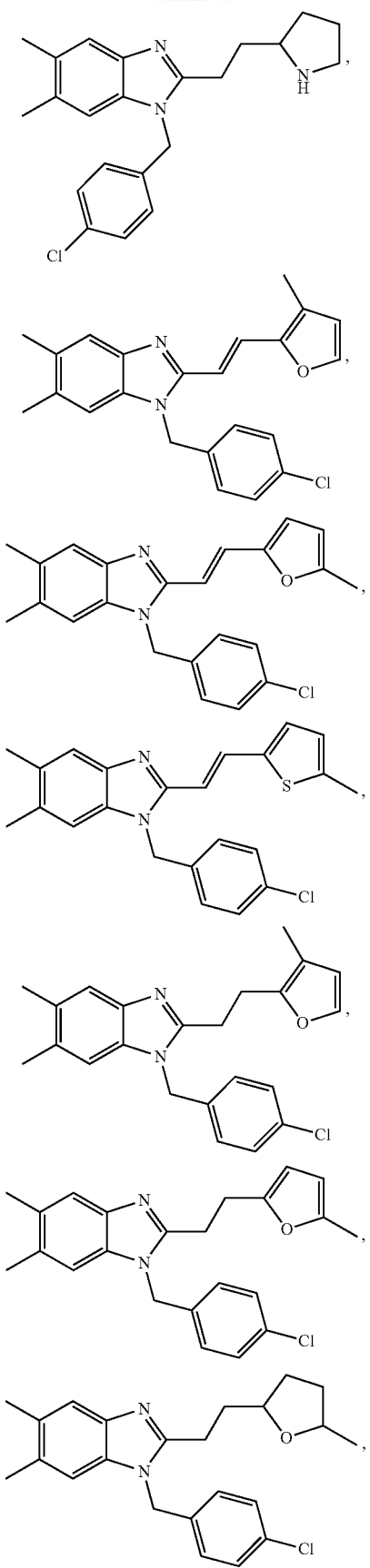
150
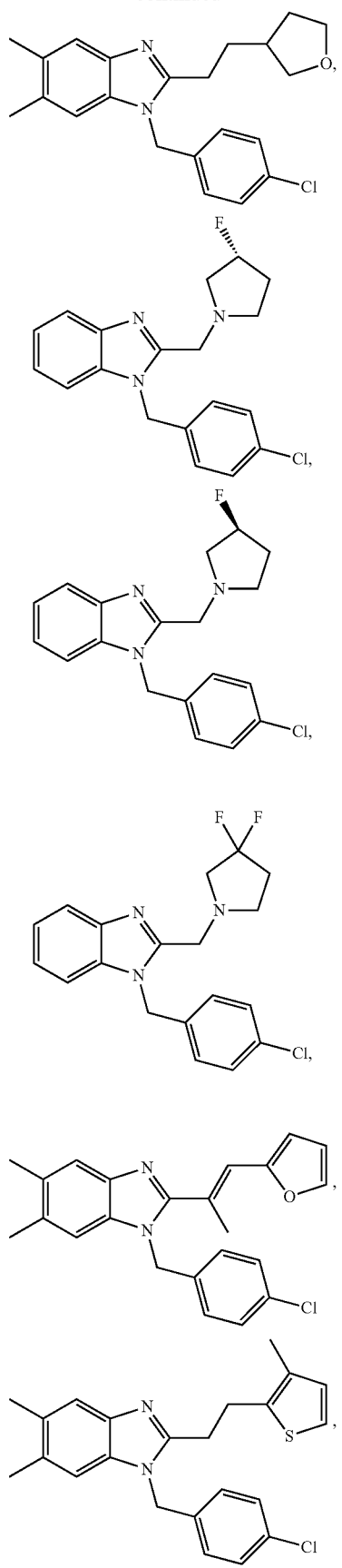

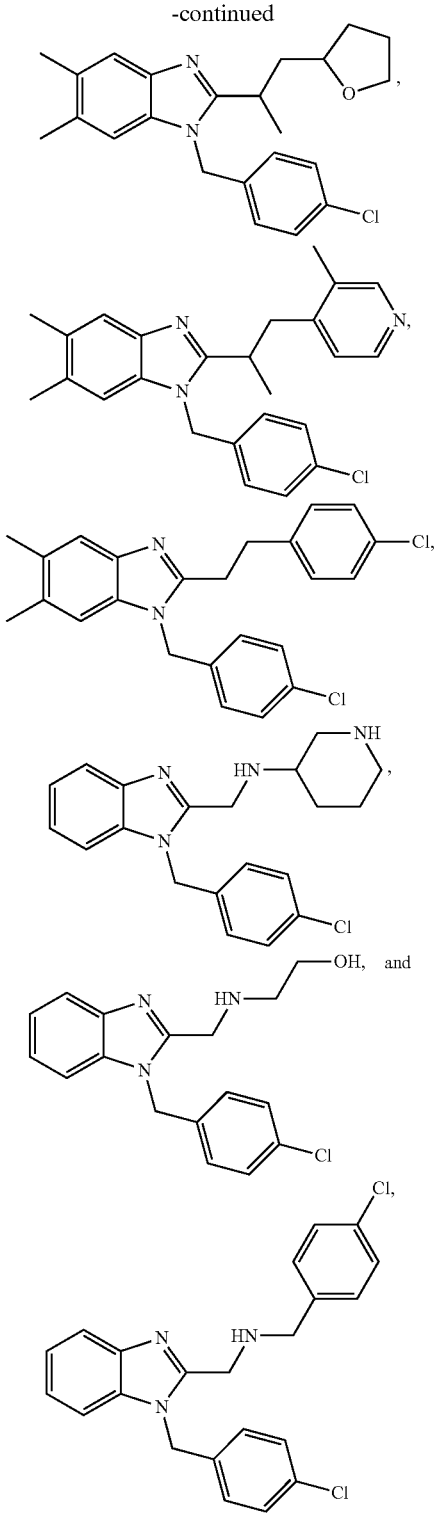

Embodiments of the present invention include prodrugs of clemizole, clemizole analogs, and compounds having a clemizole scaffold, and their isosteres. The compounds provided herein as viral inhibiting agents (compounds and inhibiting agents are interchangeable as is appropriate for the particular usage herein) are generally capable of inhibiting viral replication in vitro and/or in vivo. For example a compound of the present invention when contacted with an HCV-infected cell (e.g., an HCV-infected liver cell), reduces the amount of infectious HCV viral particles produced by the HCV-infected cell by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or at least about 95% or even higher, compared to the number of infectious HCV viral particles produced by the cell not contacted with the inhibiting agent.

A wide variety of methods are available to assess whether a compound can reduce viral load in vitro and/or in vivo. In vitro assay typically determines the number of viral particles present in the culture medium, wherein an in vivo assay typically measures the viral titer present in a bodily fluid of an infected subject. Bodily fluids suitable for viral titer measurement include but are not limited to blood, serum, plasma, saliva, semen, spinal fluid, urine, sweat, and cerebral spinal fluid. Commonly employed methods for detecting viral load in vitro or in vivo include quantitative polymerase chain reaction (PCR) and branched DNA (bDNA) test. Numerous quantitative assays for measuring the viral load (titer) of HCV RNA have been developed. Many such assays are available commercially, including a quantitative reverse transcription PCR(RT-PCR) (Amplicor HCV Monitor™, Roche Molecular Systems, New Jersey); and a branched DNA (deoxyribonucleic acid) signal amplification assay (Quantiplex™ HCV RNA Assay (bDNA), Chiron Corp., Emeryville, Calif.). See, e.g., Gretch et al. (1995) *Ann. Intern. Med.* 123:321-329. Also of interest is a nucleic acid test (NAT) sold by Chiron Corporation under the trade name Procleix®, which NAT simultaneously tests for the presence of HIV-1 and HCV. See, e.g., Vargo et al. (2002) *Transfusion* 42:876-885.

The compounds provided herein can also be characterized by their ability to inhibit binding of NS4B polypeptide to the 3'UTR of HCV negative strand RNA by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or at least about 95% or higher, compared to the binding of NS4B polypeptide to the 3'UTR of HCV negative strand RNA in the absence of the compound.

In some embodiments, the inhibiting agents of the present invention inhibit binding of NS4B polypeptide to the 3'UTR of HCV negative strand RNA with a 50% inhibitory concentration ($IC_{50}$) of about 100 µM to 50 µM, about 50 µM to 25 µM, about 25 µM to 10 µM, about 10 µM to 5 µM, about 5 µM to 1 µM, about 1 µM to 500 nM, about 500 nM to 400 nM, about 400 nM to 300 nM, about 300 nM to 250 nM, about 250 nM to 200 nM, about 200 nM to 150 nM, about 150 nM to 100 nM, about 100 nM to 50 nM, about 50 nM to 30 nM, about 30 nM to 25 nM, about 25 nM to 20 nM, about 20 nM to 15 nM, about 15 nM to 10 nM, about 10 nM to 5 nM, less than about 5 nM, less than about 1 nM, less than about 0.1 nM, or less than about 0.01 nM.

In other embodiments, the inhibiting agents of the present invention lack substantial cross-reactivity with HERG $K^+$ channel. Drug-induced cardiac arrhythmia, such as QT prolongation, is a serious safety concern in the discovery, development and use of new medications. Drug-induced QT interval prolongation is an active field of research and has been reviewed (Pearlstein et al. *J. Med. Chem.* (2003), 46(11): 2017-2022; Fermini et al., *Annual Reports in Medicinal Chemistry* (2004), 39:323; http://www.qtdrugs.org). A common cause of QT prolongation is the inhibition of the cardiac HERG $K^+$ channel by a drug. Drugs from widely different chemical classes and therapeutic utility have been shown to block HERG activity. Many medications known to be HERG channel inhibitors interact with the channel at concentrations similar to the desired therapeutic concentration. One strategy to prevent the occurrence of drug-induced QT interval prolongation is to select drug candidates that show a reduced affinity for the HERG K$^+$ channel. This property can be characterized by an in vitro assay utilizing HEK293 or CHO cells stably transfected with the hERG gene and utilizing a patch-clamp technique to determine Ikr current. Accordingly, some preferred inhibiting agents of the present invention exhibit reduced affinity for or lack substantial cross-reactivity with the HERG K$^+$ channel. In one aspect, an exemplary inhibiting agent of the present invention has a HERG IC$_{50}$ of greater than about 100 nM. In another aspect, the inhibiting agent described herein has a HERG IC$_{50}$ of greater than about 500 nM, 1,000 nM, 5,000 nM, 1 µM, 5 µM, 10 µM, 50 µM, 100 µM or even higher. For instance, to mitigate hERG channel inhibition, the following illustrative compounds of the invention are shown. In these compounds, the basicity of the tertiary amine of clemizole-like compounds is attenuated by steric or electronic modifications or the tertiary amine is absent.

1

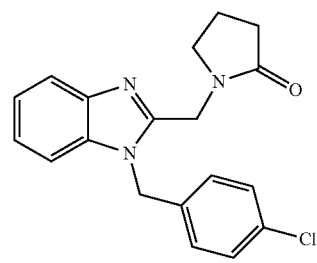

2

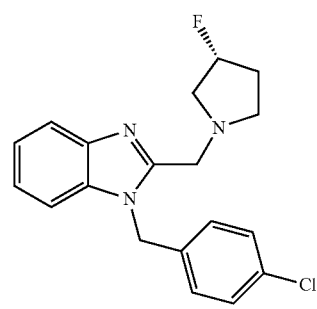

3

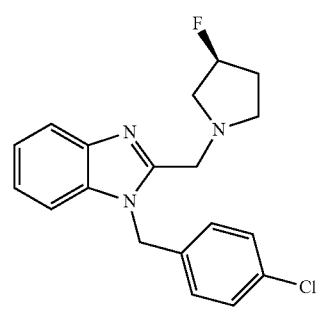

4

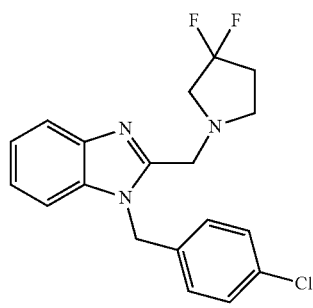

5

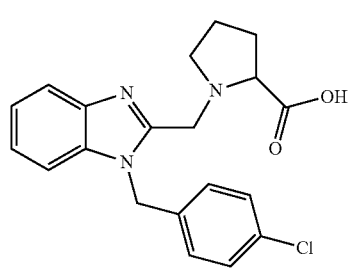

6

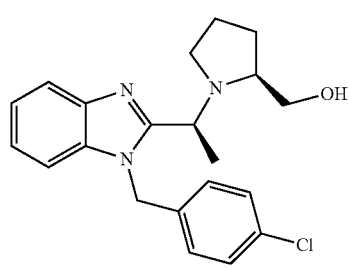

7

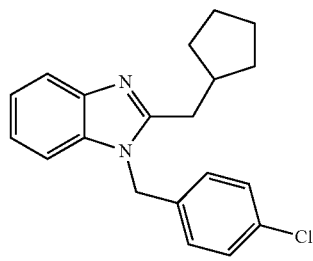

8

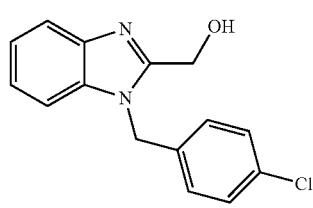

9

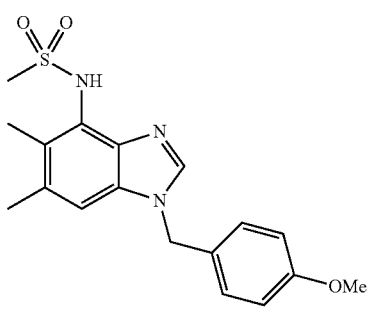

-continued

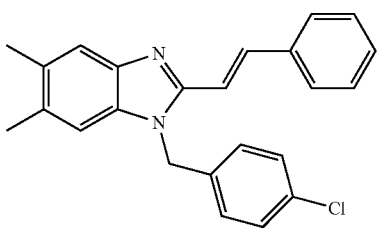

Methods of Synthesis

In general, the inhibiting agents provided herein including clemizole, clemizole analogs, isosteres thereof can be made according to organic synthesis techniques known to those skilled in this art and/or according to the synthesis schemes provided herein. Where desired, synthesis of the subject compound begins with commercially available chemicals and/or from compounds described in the chemical literature. "Commercially available chemicals" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Il.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.). In addition, Methods known to one of ordinary skill in the art may be identified through various reference books and databases. Suitable reference books and treatise that detail the synthesis of reactants useful in the preparation of the inhibiting agents described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R.V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes. Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures can also be used.

When desired, the (R)- and (S)-isomers of the compounds of the present invention, if present, may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts.

Many of the optionally substituted starting compounds and other reactants are commercially available, e.g., from Aldrich Chemical Company (Milwaukee, Wis.) or can be readily prepared by those skilled in the art using commonly employed synthetic methodology.

The compounds of the invention can be synthesized by an appropriate combination of known synthetic methods in the art and the instant disclosure. The discussion below is offered to illustrate certain of the diverse methods available for use in making the compounds of the invention and is not intended to limit the scope of reactions or reaction sequences that can be used in preparing the compounds of the present invention.

Scheme 1: A general method is illustrated for introducing amine side chains at the 2-position of benzimidazole.

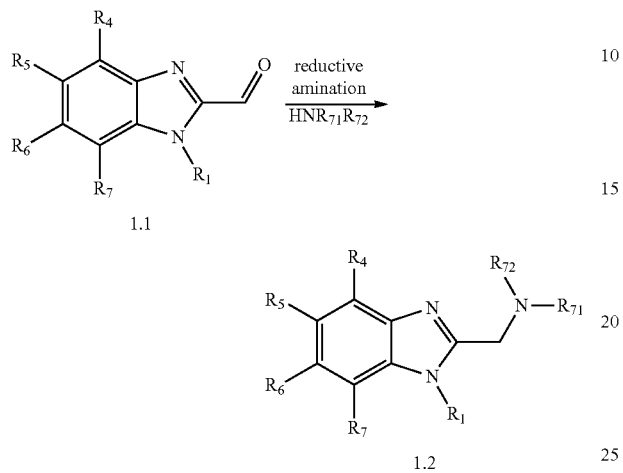

Compounds of structure 1.2 can be synthesized by treating an appropriately substituted benzimidazole-carbaldehyde 1.1 with a primary or secondary amine and $NaBH(OAc)_3$. Compounds 1.2.1, containing an X group which is an N-attached heterocycle is also synthesized similarly. As shown above, $R_{72}$ and $R_{71}$ can be alkyl, hydrogen, or the like, or together with the nitrogen atom to which they are attached may form a heterocyle.

Scheme 2: A general method is illustrated for cyclization to a benzimidazole ring system.

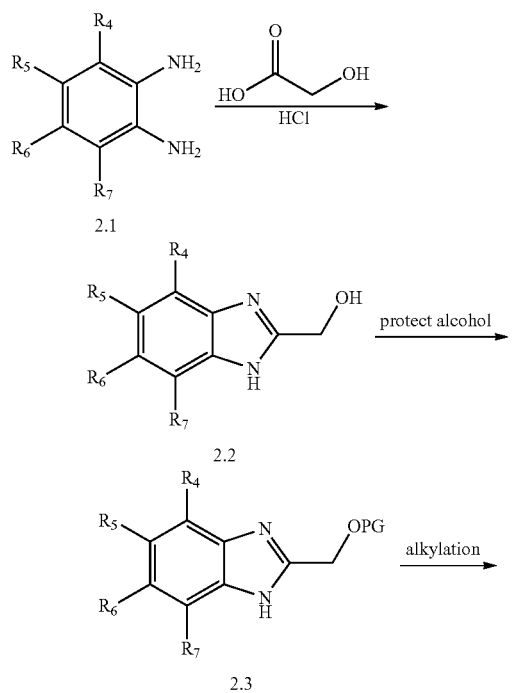

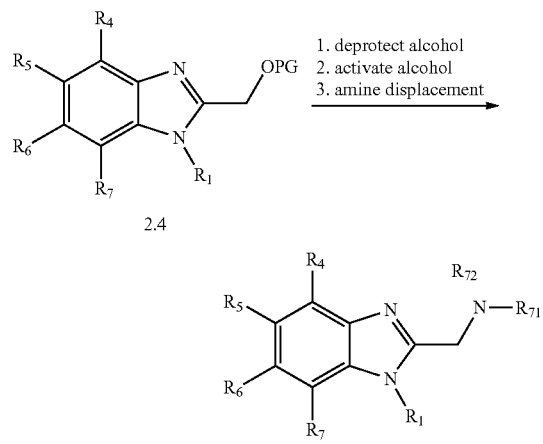

Compounds of general structure 2.5 can be synthesized by treating substituted 1,2-phenylenediamine 2.1 with 4 N HCl and glycolic acid at 110° C. (Roth, T. et al. *J. Med. Chem.* 1997, 40 (26), 4199) to provide 2.2. Alcohol 2.2 is then protected with an appropriate protecting group followed by alkylation of the benzimidazole to provide 2.4. The alcohol is then deprotected, activated, and displaced with an appropriate primary or secondary amine to provide final compound 2.5. Compounds where $R_{72}R_{71}N$— forms a heterocycle are also synthesized similarly. As shown above, $R_{72}$ and $R_{71}$ can be alkyl, hydrogen, or the like, or together with the nitrogen atom to which they are attached may form a heterocyle.

Scheme 3: A general method is illustrated for benzimidazole nitration.

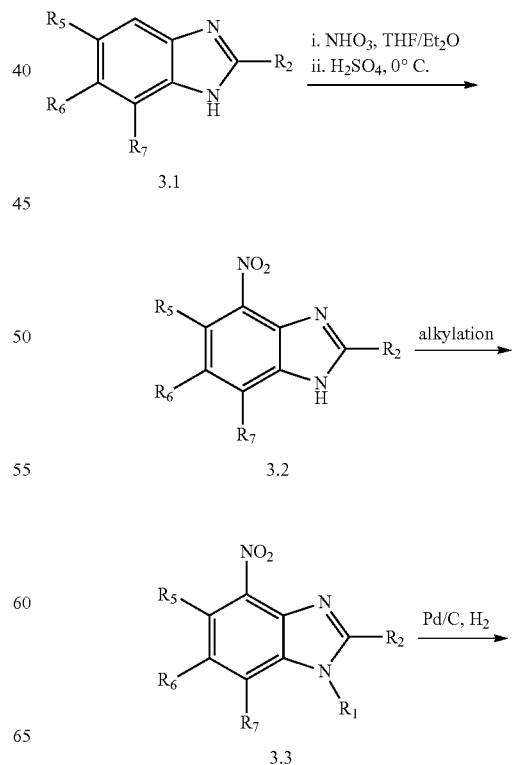

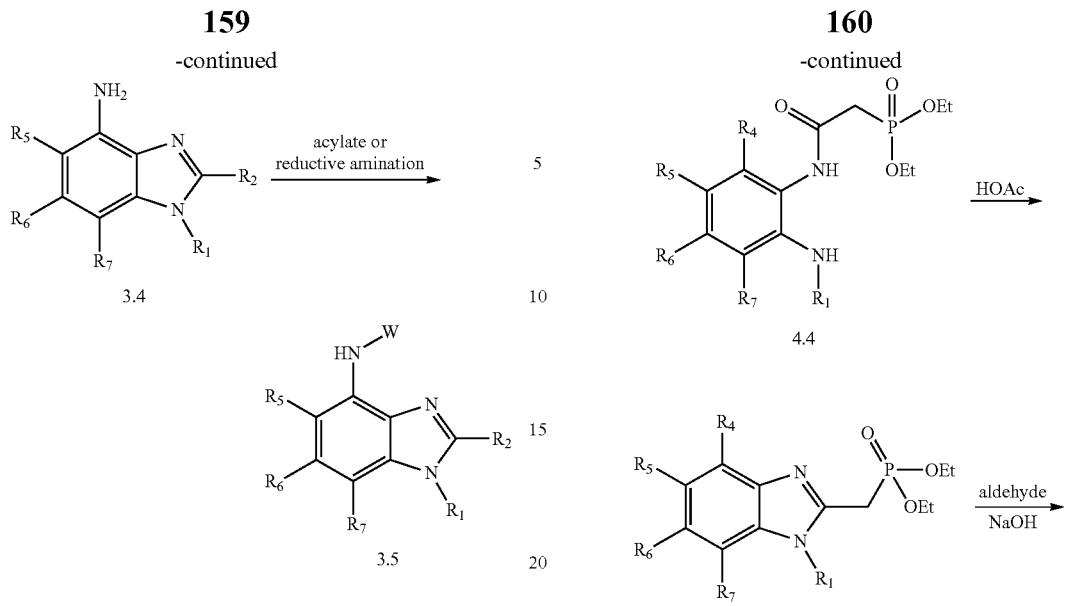

Compounds of general structure 3.5 can be obtained by treating substituted benzimidazole 3.1 with 70% nitric acid to provide the nitric acid salt of 3.1. Addition of concentrated sulfuric acid then provides 3.2 (Zhang, P. et al, *Tet. Lett.* 2007, 48, 8659). Alkylation with an alkyl halide, followed by hydrogenation over palladium-on-carbon provides 3.4. The resulting aromatic amine can then be acylated or alkylated to provide compound 3.5. Compound 3.4 may be converted to sulfonamides, for example, by reacting with appropriate sulfonyl halides. As used here, W—NH— is an embodiment of $R_4$.

Scheme 4: A general method is illustrated for coupling of aldehydes to diethylmethylphosphonate.

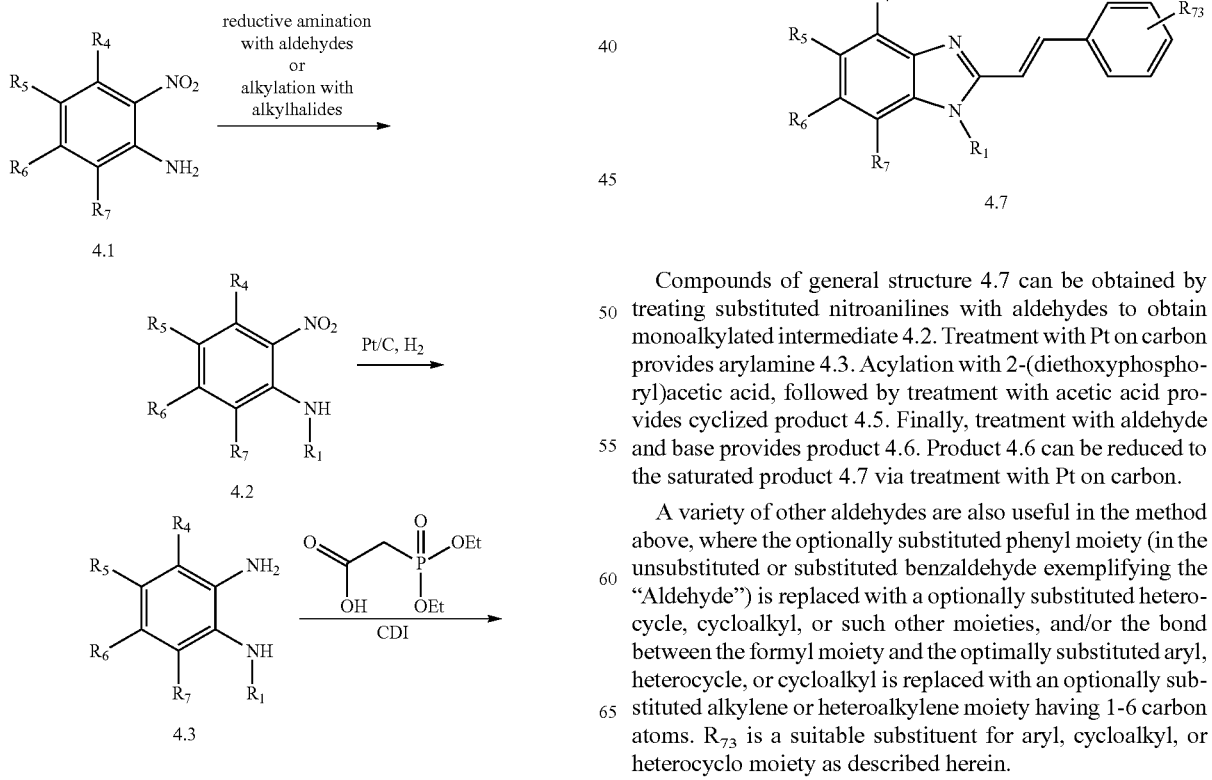

Compounds of general structure 4.7 can be obtained by treating substituted nitroanilines with aldehydes to obtain monoalkylated intermediate 4.2. Treatment with Pt on carbon provides arylamine 4.3. Acylation with 2-(diethoxyphosphoryl)acetic acid, followed by treatment with acetic acid provides cyclized product 4.5. Finally, treatment with aldehyde and base provides product 4.6. Product 4.6 can be reduced to the saturated product 4.7 via treatment with Pt on carbon.

A variety of other aldehydes are also useful in the method above, where the optionally substituted phenyl moiety (in the unsubstituted or substituted benzaldehyde exemplifying the "Aldehyde") is replaced with a optionally substituted heterocycle, cycloalkyl, or such other moieties, and/or the bond between the formyl moiety and the optimally substituted aryl, heterocycle, or cycloalkyl is replaced with an optionally substituted alkylene or heteroalkylene moiety having 1-6 carbon atoms. $R_{73}$ is a suitable substituent for aryl, cycloalkyl, or heterocyclo moiety as described herein.

Scheme 4.1: A general method is illustrated for coupling of ketones to diethylmethylphosphonate.

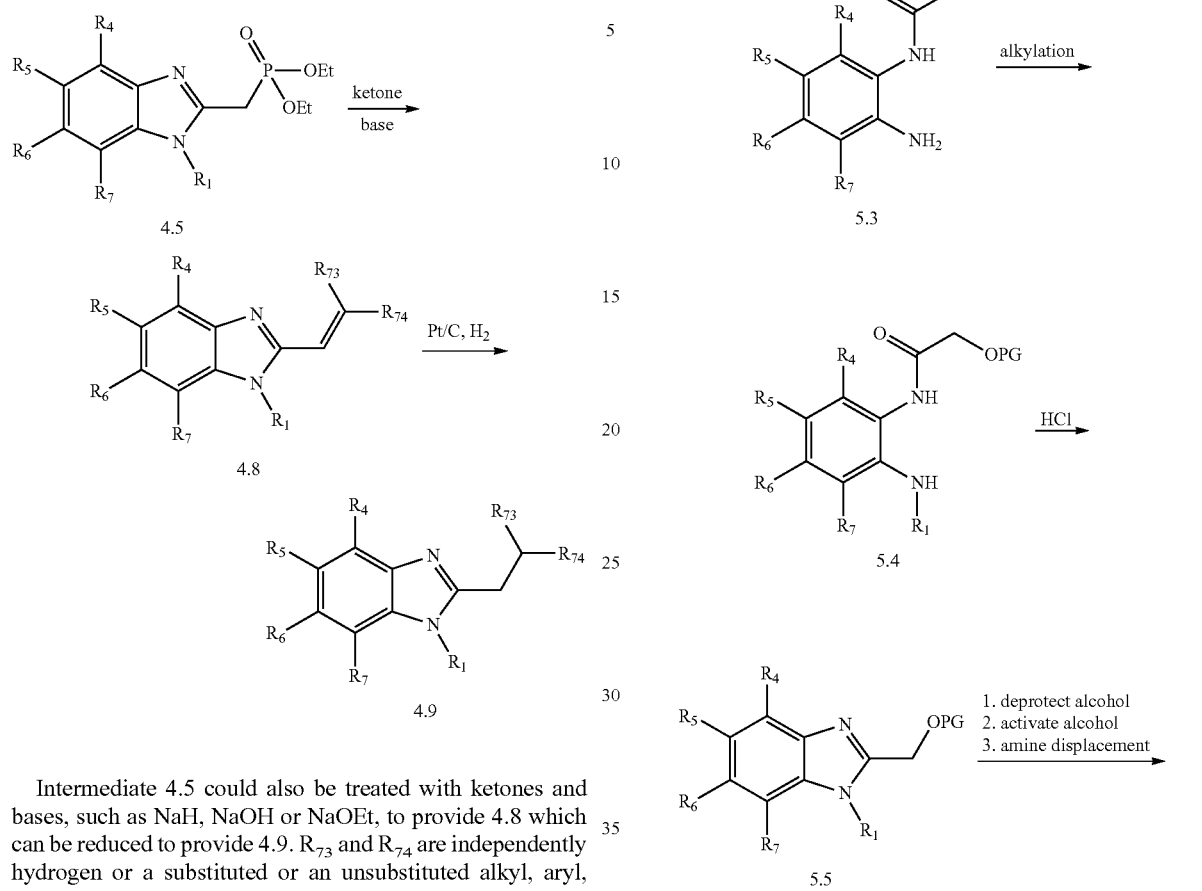

Intermediate 4.5 could also be treated with ketones and bases, such as NaH, NaOH or NaOEt, to provide 4.8 which can be reduced to provide 4.9. $R_{73}$ and $R_{74}$ are independently hydrogen or a substituted or an unsubstituted alkyl, aryl, heterocycle, and the like, or $R_{73}$ and $R_{74}$ together with the carbon atom they are attached form a cycloalkyl or heterocyclo group.

Scheme 5: A general method is illustrated for the synthesis of unsymmetrically substituted benzimidazoles analogs.

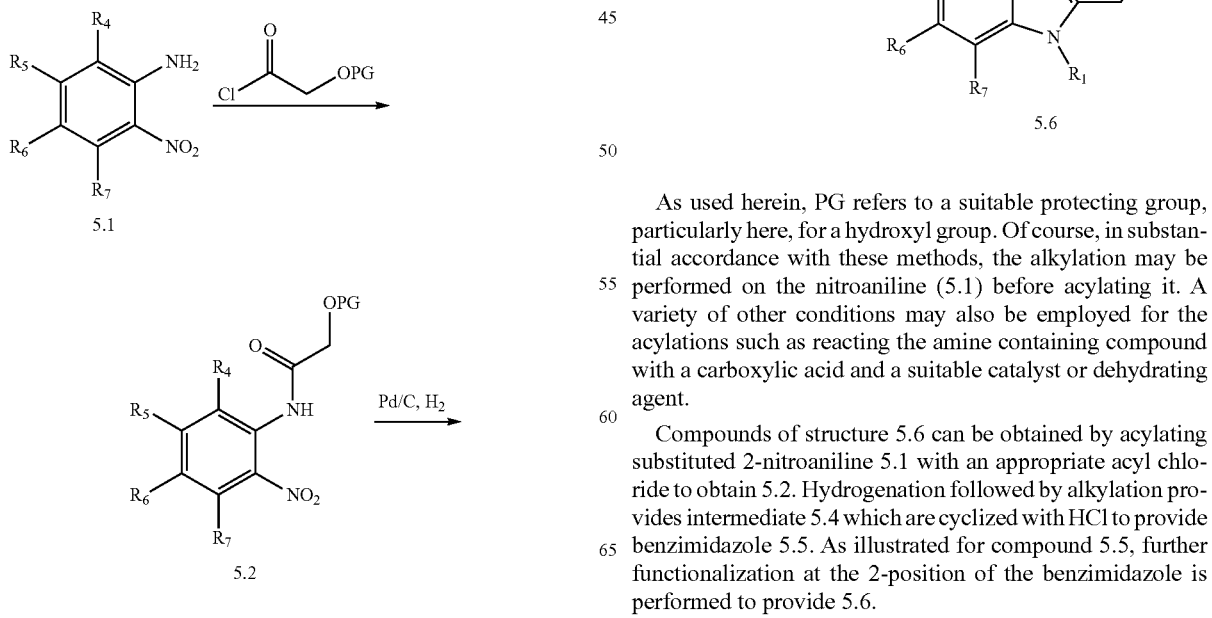

As used herein, PG refers to a suitable protecting group, particularly here, for a hydroxyl group. Of course, in substantial accordance with these methods, the alkylation may be performed on the nitroaniline (5.1) before acylating it. A variety of other conditions may also be employed for the acylations such as reacting the amine containing compound with a carboxylic acid and a suitable catalyst or dehydrating agent.

Compounds of structure 5.6 can be obtained by acylating substituted 2-nitroaniline 5.1 with an appropriate acyl chloride to obtain 5.2. Hydrogenation followed by alkylation provides intermediate 5.4 which are cyclized with HCl to provide benzimidazole 5.5. As illustrated for compound 5.5, further functionalization at the 2-position of the benzimidazole is performed to provide 5.6.

Scheme 6: A general method is illustrated for the synthesis of benzimidazole analogs with ether linkages:

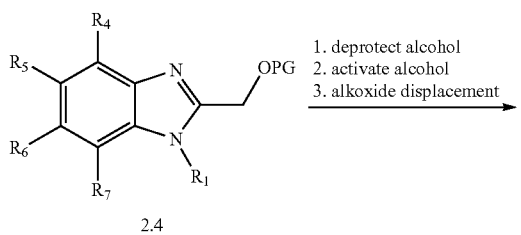

2.4

1. deprotect alcohol
2. activate alcohol
3. alkoxide displacement

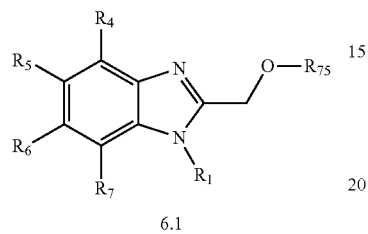

6.1

Compounds of general structure 6.1 are synthesized similarly to compounds 2.5 except for replacing primary or secondary amines with alkoxides to provide final compound 6.1. —CH$_2$—O—R$_{75}$ constitutes various R$_2$ moieties useful in the compounds and methods of the present invention.

The scheme described below (see, Schering A G U.S. Pat. No. 3,470,194, incorporated herein by reference) is an alternative synthesis scheme for making clemizole or clemizole analogs. It starts with commercially available 2-nitroaniline 2.11 followed by reductive alkylation to provide 2.12. Reduction with Raney nickel followed by treatment with chloroacetic acid provides the benzimidazole methyl chloride 2.14. Treatment with pyrrolidine then provides clemizole 2.15. In Synthetic Method 2.2, o-phenylene diamine 2.16 is treated with chloroacetic acid to provide intermediate 2.17. Alkylation with pyrrolidine gives intermediate 2.18. Deprotonation with NaH followed by treatment with p-chlorobenzylchloride provides clemizole 2.15.

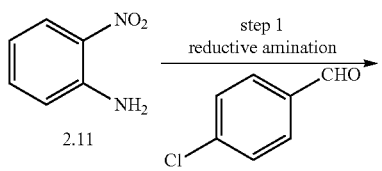

2.11 step 1
reductive amination

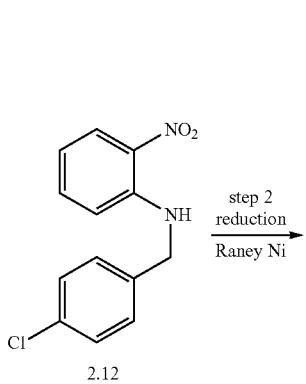

2.12 step 2
reduction
Raney Ni

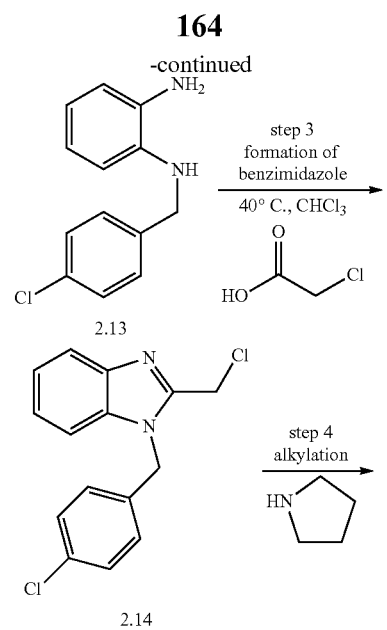

2.13 step 3
formation of
benzimidazole
40° C., CHCl$_3$ 2.14 step 4
alkylation

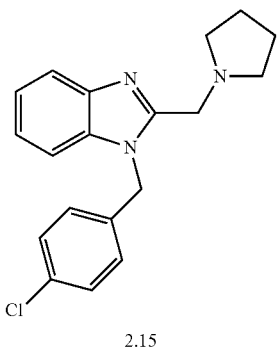

2.15

The synthesis of one or more of the inhibiting agents of the present invention may employ protecting groups and blocking groups. Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups are known in the art and include, but are not limited to, the following moieties.

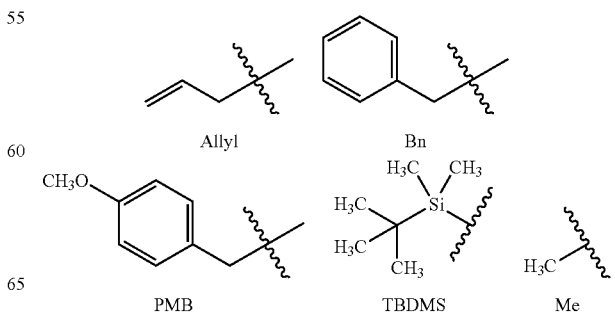

Allyl     Bn

PMB     TBDMS     Me

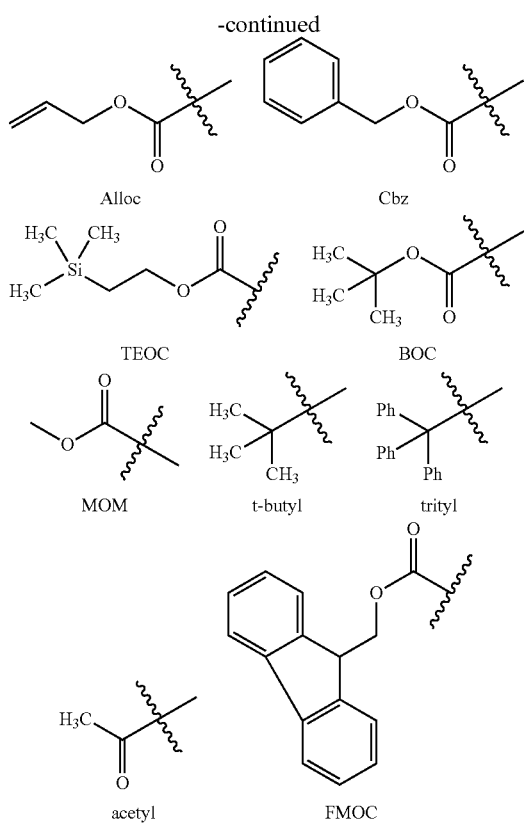

Pharmaceutical Formulations and Routes of Administration

The present invention provides pharmaceutical compositions comprising or consisting essentially of one or more inhibiting agents disclosed herein with or without pharmaceutically acceptable excipients, diluents, carriers and/or adjuvants. In some embodiment, the clemizole- or clemizole analog-containing pharmaceutical compositions are formulated to be substantially free of excipients. In other embodiments, inhibiting agents can be formulated with one or more pharmaceutically acceptable auxiliary substances.

In an embodiment, the inhibiting agent can be combined with another anti-viral agent to prepare a composition of the invention, and the composition can include one or more pharmaceutically acceptable excipients, diluents, carriers and/or adjuvants.

A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In an embodiment of the present disclosure, the inhibiting agent is administered to the host using any means capable of resulting in the desired effect (e.g., reduction in viral load, reduction in liver fibrosis, increase in liver function, and the like). Thus, the inhibiting agent can be incorporated into a variety of formulations for therapeutic administration. For example, the inhibiting agent can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the inhibiting agent may be administered in the form of its pharmaceutically acceptable salts, or a subject active agent may be used alone or in appropriate association, as well as in combination, with other pharmaceutically active compounds. The following methods and excipients are merely exemplary and are in no way limiting.

For oral preparations, the inhibiting agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Embodiments of the inhibiting agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Embodiments of the inhibiting agent can be utilized in aerosol formulation to be administered via inhalation. Embodiments of the inhibiting agent agent can be formulated into pressurized acceptable propellants such as dichlorodifluoromethane, propane, nitrogen and the like.

Furthermore, embodiments of the inhibiting agent can be made into suppositories by mixing with a variety of bases such as emulsifying bases or water-soluble bases. Embodiments of the inhibiting agent can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more inhibiting agents. Similarly, unit dosage forms for injection or intravenous administration may comprise the inhibiting agent in a composition as a solution in sterile water, normal saline or another pharmaceutically acceptable carrier.

Embodiments of the inhibiting agent can be formulated in an injectable composition in accordance with the invention. Typically, injectable compositions are prepared as liquid solutions or suspensions; solid forms suitable for solution in, or suspension in, liquid vehicles prior to injection may also be prepared. The preparation may also be emulsified or the active ingredient (inhibiting agent) encapsulated in liposome vehicles in accordance with the invention.

In an embodiment, the inhibiting agent is formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of the inhibiting agent can be accomplished using any of a variety of refillable, pump systems. Pumps provide consistent, controlled release over time. In some embodiments, the inhibiting agent is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, and the like.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their more consistent controlled release and relatively small size (see, e.g., PCT published application no. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent is delivered using an implantable drug delivery system, e.g., a system that is programmable to provide for administration of the agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present disclosure is the Synchromed infusion pump (Medtronic).

Suitable excipient vehicles for the inhibiting agent are, for example, water, saline, dextrose, glycerol, ethanol, or the like, and combinations thereof. In addition, if desired, the vehicle may contain minor amounts of auxiliary substances such as wetting or emulsifying agents of pH buffering agents. Methods of preparing such dosage forms are known, or will be apparent upon consideration of this disclosure, to those skilled in the art. See, e.g., *Remington's Pharmaceutical Sciences, Mack Publishing Company, Easton, Pa.,* 17th edition, 1985. The composition or formulation to be administered will, in any event, contain a quantity of the inhibiting agent adequate to achieve the desired state in the subject being treated.

Compositions of the present invention include those that comprise a sustained-release or controlled release matrix. In addition, embodiments of the present invention can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho) esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix. Similarly, the sustained release formulations of embodiments of the invention can help maintain viral-inhibiting concentrations over a longer time interval.

In another embodiment, the pharmaceutical composition of the present disclosure (as well as combination compositions) is delivered in a controlled release system. For example, the inhibiting agent may be administered using intravenous infusion, an implantable osmotic pump, a transdermal patch, liposomes, or other modes of administration. In one embodiment, a pump may be used (Sefton (1987). *CRC Crit, Ref. Biomed. Eng.* 14:201; Buchwald et al. (1980). *Surgery* 88:507; Saudek et al. (1989). *N. Engl. J. Med.* 321:574). In another embodiment, polymeric materials are used. In yet another embodiment a controlled release system is placed in proximity of the therapeutic target, e.g., the liver, thus requiring a fraction of the systemic dose. Other controlled release systems are discussed in the review by Langer (1990). *Science* 249:1527-1533.

In another embodiment, the compositions of the present invention (as well as combination compositions separately or together) include those formed by impregnation of an inhibiting agent described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

The inhibiting agents disclosed herein can be formulated in a pharmaceutical composition comprising an effective amount of the inhibiting agent for its intended use. For example, clemizole or clemizole analog of the present invention can be formulated in a unit dose of about 10 mg to about 500 mg for treating viral infections, especially infections by a virus of the Flaviviridae family. In some embodiments, clemizole or clemizole analog of the present invention is formulated in a unit dose of about 25 mg to about 250 mg, of about 25 mg to about 100 mg, or of about 50 mg to about 100 mg. In particular, clemizole can be formulated in 25 mg, 50 mg, 75 mg, 100 mg, 125 mg, 150 mg or 200 mg unit dose form. In one embodiment, the unit dose form is a tablet; in another, the unit dose form is a capsule. The tablet can be formulated as immediate release dose form or as sustained release form. In yet another embodiment, the unit dose form is a liquid.

Uses of the Compounds and Pharmaceutical Compositions of the Present Invention(s)

The subject compounds and pharmaceutical compositions thereof are particularly useful for treating infection by a virus of the Flaviviridae family. The treatment methods typically comprise administering to a subject infected with such virus a therapeutically effective amount of an inhibiting agent in one or more doses, alone or in combination with other agents. For subjects already infected with a virus of the Flaviviridae family such as Hepatitis Virus C, the method of the present invention is generally effective in reducing the viral load over a period of a few days, a few weeks or a few months.

The present invention also provides methods of prophylactically treating an infection by a virus of the Flaviviridae family of viruses comprising administering an effective amount of an inhibiting agent described herein to a subject in need thereof. Prophylactic treatment of infection by a virus of the Flaviviridae family (including, but not limited to, HCV) is particularly important for patients who will be undergoing liver transplantation for HCV-associated end stage liver disease (ESLD). It has been reported that the new graft is nearly certain to be infected with HCV if viremia is present at the time of transplantation. Prophylactic treatment with clemizole or clemizole analogs or the isosterers thereof can be performed to reduce or eliminate HCV viral load prior to liver transplantation, and can help prevent the recurrence of HCV after transplantation. The administeration of clemizole, clemizole analogs, or isosterers of the present invention may also be used for patients who cannot tolerate full doses of standard of care therapy (pegylated interferon and ribavirin). Where desired, for pre-transplant patients with ESLD, or post-transplant patients with HCV recurrence, either clemizole or clemizole analog monotherapy, or clemizole/clemizole analog in combination with regular or reduced doses of pegylated interferon and ribavirin, can be used to treat these patients. Similarly, clemizole or clemizole analogs in combination with nitazoxanide (or another thiazolide, or sustained formulations of either of these) can be used to treat these patients, as can clemizole plus nitazoxanide (or another thiazolide, or sustained formulations of either of these) plus standard of care medications, at reduced or regular doses, as tolerated. Clemizole, administered via any of the above embodiments, can also be administered as suppressive (e.g., maintenance) or consolidation therapy, such after effective suppression of HCV by regimens containing clemizole or other agents.

The inhibiting agent of the present invention and pharmaceutical composition comprising the same can be administered to a subject in one or more doses. In an embodiment, the inhibiting agent can be administered in an amount of about 100 mg to 1000 mg per dose, e.g., about 100 mg to 200 mg, about 200 mg to 250 mg, about 250 mg to 500 mg, about 500 mg to 750 mg, or about 750 mg to 1000 mg per dose. In one embodiment, the agent is clemizole hydrochloride, the unit dose is 100 mg, and two unit doses are administered orally BID (a 200 mg daily dose). In another embodiment, the agent is clemizole hydrochloride, the unit dose is about 100 mg, and one unit dose is administered orally in the morning and another in the evening for a total of about 200 mg daily dose. In other embodiments, the agent is clemizole hydrochloride, which is administered orally, the unit dose is about 100 mg, and the administration schedule is either about 100 mg TID, about 200 mg BID, about 200 mg TID, about 300 mg BID, about 300 mg TID, about 400 mg BID, about 400 mg TID, about 500 mg BID, or about 500 mg TID. In another embodiment, the agent is clemizole hydrochloride, the unit dose is 100 mg, and one unit dose is administered orally in the morning and another in the evening for a total of 200 mg daily dose. In other embodiments, the agent is clemizole hydrochloride, which is administered orally, the unit dose is 100 mg, and the administration schedule is either 100 mg TID, 200 mg BID, 200 mg TID, 300 mg BID, 300 mg TID, 400 mg BID, 400 mg TID, 500 mg BID, or 500 mg TID.

In an embodiment, the agent is a clemizole analog, and the amount of the inhibiting agent per dose is determined on a per body weight basis. For example, in an embodiment, the inhibiting agent can be administered in an amount of about 0.5 mg/kg to 100 mg/kg, e.g., about 0.5 mg/kg to 1 mg/kg, about 1 mg/kg to 10 mg/kg, about 10 mg/kg to 25 mg/kg, about 25 mg/kg to 50 mg/kg per dose, about 50 mg/kg to 100 mg/kg.

Those of skill will readily appreciate that dose levels can vary as a function of the specific inhibiting agent administered, the severity of the symptoms, and the susceptibility of the subject to side effects. Preferred dosages for a given compound are readily determinable by those of skill in the art by a variety of means.

In an embodiment, multiple doses of the inhibiting agent are administered. The frequency of administration of the inhibiting agent can vary depending on any of a variety of factors, e.g., severity of the symptoms, and the like. For example, in an embodiment, the inhibiting agent is administered once per month, twice per month, three times per month, every other week (qow), once per week (qw), twice per week (biw), three times per week (tiw), four times per week, five times per week, six times per week, every other day (qod), daily (qd), twice a day (BID), or three times a day (TID). As discussed above, in one embodiment, the inhibiting agent is administered continuously.

By way of illustration, efficacious dosing of clemizole can include dosing at about 500 mg po BID, about 400 mg po BID, about 300 mg po BID, about 200 mg po BID, about 100 mg po BID, 500 mg po BID, 400 mg po BID, 300 mg po BID, 200 mg po BID, or 100 mg po BID. Thus, the total daily dose can also be split among multiple doses, which allows for a lower dose at each administration with less potential for sedation while maintaining sufficient efficacy. Alternatively, a more frequent dosing schedule can be applied for sever cases, for example, TID administration or administration every 4, 6, 8, or 12 hours of a 100 mg, 200 mg, 300 mg, 400 mg or higher dose.

Clemizole was marketed in the United States as Allercur®, a product of J. B. Roerig and Company, Div., Chas. Pfizer & Co., Inc. The trade name of J. B. Roerig & Co. Division, Chas. Pfizer & Co., Inc., for clemizole tannate was Allercur oral suspension; for clemizole hydrochloride, Allercur parenteral and Allercur tablets. The 1966 PDR touted clemizole's advantage of being exceptionally well tolerated. In some embodiments, a simple and convenient dosing regimen for treating patients with an HCV infection includes any regimen previously shown effective for use of clemizole as an antipruritic. In one embodiment, a BID dosing regimen is employed. In one embodiment, the regimen is 100 mg po BID. In another embodiment, the regimen is 200 mg po BID. In another embodiment, the regimen is 300 mg po BID. In another embodiment, the regimen is 400 mg po BID. In another embodiment, the regimen is 500 mg po BID. In other embodiments, these same doses are used but the administration schedule is TID.

The duration of administration of the inhibiting agent, e.g., the period of time over which the inhibiting agent is administered, can vary, depending on any of a variety of factors, e.g., patient response, and the like. For example, the inhibiting agent can be administered over a period of time of about one day to one week, about two weeks to four weeks, about one month to two months, about two months to four months, about four months to six months, about six months to eight months, about eight months to 1 year, about 1 year to 2 years, or about 2 years to 4 years, or more.

The practice of a method of the present invention typically involves administering an effective amount of an inhibiting agent or a pharmaceutical composition comprising such inhibiting agent. The specific dose will vary depending on the particular compounds chosen, the dosing regimen to be followed, whether it is administered in combination with other compounds, timing of administration, the tissue to which it is administered, and the physical delivery system in which it is carried. In an embodiment, an effective amount of the inhibiting agent is an amount that, when administered in one or more doses to a host (e.g., human) in need thereof, reduces HCV viral load in the individual by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% or more, compared to the viral load in the individual not treated with the inhibiting agent.

Viral load can be measured by measuring the titer or level of virus in serum. These methods include, but are not limited to, a quantitative polymerase chain reaction (PCR) and a branched DNA (bDNA) test. Quantitative assays for measuring the viral load (titer) of HCV RNA have been developed. Many such assays are available commercially, including a quantitative reverse transcription PCR(RT-PCR) (Amplicor HCV Monitor™, Roche Molecular Systems, New Jersey); and a branched DNA (deoxyribonucleic acid) signal amplification assay (Quantiplex™ HCV RNA Assay (bDNA), Chiron Corp., Emeryville, Calif.). See, e.g., Gretch et al. (1995) *Ann. Intern. Med.* 123:321-329. Also of interest is a nucleic acid test (NAT) sold by Chiron Corporation under the trade name Proceix®, which NAT simultaneously tests for the presence of HIV-1 and HCV. See, e.g., Vargo et al. (2002) *Transfusion* 42:876-885.

In some embodiments, an effective amount of the inhibiting agent is an amount that, when administered in one or more doses to a host (e.g., human) in need thereof, increases liver function in the individual by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, or more, compared to the liver function in the individual not treated with the inhibiting agent.

In some embodiments, an effective amount of the inhibiting agent is an amount that, when administered in one or more doses to a host (e.g., human) in need thereof, reduces the blood levels of liver enzymes. An initial step in detecting liver damage is a simple blood test to determine the presence of certain liver enzymes in the blood. Under normal circumstances, these enzymes reside within the cells of the liver. But when the liver is injured for any reason, such as the injury that occurs as a result of HCV infection, these enzymes are spilled into the blood stream. Among the most sensitive and widely used of these liver enzymes are the aminotransferases. They include aspartate aminotransferase (AST or SGOT) and alanine aminotransferase (ALT or SGPT). These enzymes are normally contained within liver cells. If the liver is injured, the liver cells spill the enzymes into blood, raising the enzyme levels in the blood and signaling the liver damage. In one embodiment, then, an effective amount of the inhibiting agent is an amount that, when administered in one or more doses, decreases AST or ALT levels in the blood.

In some embodiments, an effective amount of the inhibiting agent is an amount that, when administered in one or more doses to a host (e.g., a human) in need thereof, reduces liver fibrosis in the host by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, or more, compared to the degree of liver fibrosis in the individual not treated with the inhibiting agent.

Liver fibrosis reduction can be determined by analyzing a liver biopsy sample. An analysis of a liver biopsy comprises assessments of two major components: necroinflammation assessed by "grade" as a measure of the severity and ongoing disease activity, and the lesions of fibrosis and parenchymal or vascular remodeling as assessed by "stage" as being reflective of long-term disease progression. See, e.g., Brunt (2000) *Hepatol.* 31:241-246; and METAVIR (1994) *Hepatology* 20:15-20. Based on analysis of the liver biopsy, a score is assigned. A number of standardized scoring systems exist which provide a quantitative assessment of the degree and severity of fibrosis. These include the METAVIR, Knodell, Scheuer, Ludwig, and Ishak scoring systems.

The METAVIR scoring system is based on an analysis of various features of a liver biopsy, including fibrosis (portal fibrosis, centrilobular fibrosis, and cirrhosis); necrosis (piecemeal and lobular necrosis, acidophilic retraction, and ballooning degeneration); inflammation (portal tract inflammation, portal lymphoid aggregates, and distribution of portal inflammation); bile duct changes; and the Knodell index (scores of periportal necrosis, lobular necrosis, portal inflammation, fibrosis, and overall disease activity). The definitions of each stage in the METAVIR system are as follows: score:

0, no fibrosis; score: 1, stellate enlargement of portal tract but without septa formation; score: 2, enlargement of portal tract with rare septa formation; score: 3, numerous septa without cirrhosis; and score: 4, cirrhosis.

Knodell's scoring system, also called the Hepatitis Activity Index, classifies specimens based on scores in four categories of histologic features: I. Periportal and/or bridging necrosis; II. Intralobular degeneration and focal necrosis; III. Portal inflammation; and IV. Fibrosis. In the Knodell staging system, scores are as follows: score: 0, no fibrosis; score: 1, mild fibrosis (fibrous portal expansion); score: 2, moderate fibrosis; score: 3, severe fibrosis (bridging fibrosis); and score: 4, cirrhosis. The higher the score, the more severe the liver tissue damage. Knodell (1981) Hepatol. 1:431.

In the Scheuer scoring system scores are as follows: score: 0, no fibrosis; score: 1, enlarged, fibrotic portal tracts; score: 2, periportal or portal-portal septa, but intact architecture; score: 3, fibrosis with architectural distortion, but no obvious cirrhosis; score: 4, probable or definite cirrhosis. Scheuer (1991) J. Hepatol. 13:372.

The Ishak scoring system is described in Ishak (1995) J. Hepatol. 22:696-699. Stage 0, No fibrosis; Stage 1, Fibrous expansion of some portal areas, with or without short fibrous septa; stage 2, Fibrous expansion of most portal areas, with or without short fibrous septa; stage 3, Fibrous expansion of most portal areas with occasional portal to portal (P-P) bridging; stage 4, Fibrous expansion of portal areas with marked bridging (P-P) as well as portal-central (P-C); stage 5, Marked bridging (P-P and/or P-C) with occasional nodules (incomplete cirrhosis); stage 6, Cirrhosis, probable or definite.

The benefit of a therapy provided by the invention can also be measured and assessed by using the Child-Pugh scoring system which comprises a multicomponent point system based upon abnormalities in serum bilirubin level, serum albumin level, prothrombin time, the presence and severity of ascites, and the presence and severity of encephalopathy. Based upon the presence and severity of abnormality of these parameters, patients may be placed in one of three categories of increasing severity of clinical disease: A, B, or C.

The subject inhibiting agents and pharmaceutical compositions containing the agents can be used in combination of one or more other therapeutic agents for treating viral infection and other diseases. For example, the inhibiting agents and pharmaceutical formulations provided herein can be employed in combination with other anti-viral agents to treat viral infection. In an embodiment, in accordance with the methods of the present invention, an inhibiting agent that is used to treat a host infected by a Flaviviridae family viral infection is used in combination with one or more other anti-HCV agents to treat HCV infection. In another embodiment, in accordance with the methods of the present invention, an inhibiting agent that prevents the binding of NS4B to the 3'-UTR of HCV RNA (also referred to herein as an "HCV NS4B antagonist") can be used in combination with one or more other anti-HCV agents to treat HCV infection.

In addition, the inhibiting agents and pharmaceutical compositions containing the agents can be used in combination with another agent (e.g., an anti-viral agent) to prophylactically treat an infection with a virus from the Flaviviridae family of viruses including but not limited to HCV. Embodiments of the method involve administering to an individual in need thereof one or more inhibiting agents that inhibit binding of an NS4B polypeptide to the 3'UTR of HCV negative strand RNA.

In some embodiments, the combination therapies described herein provided a synergistic effect. As used herein, a synergistic effect is achieved when a greater therapeutic effect results with a combination therapy than using either drug or monotherapy alone. In combination therapy with a synergistic effect, lower dosages of one or both of the drugs or therapies may be used so that the therapeutic index is increased and toxic side effects are reduced.

Current medical practice to treat HCV infection typically employs an agent monotherapy or a combination therapy. In particular, current medical practice to treat HCV infection typically employs either interferon-alpha monotherapy or combination therapy with ribavirin (such as Rebetol or Copegus) and either an interferon-alpha (such as interferon alpha 2a and 2b) or pegylated interferon alpha (such as Pegasys, marketed by Roche, or PEG-Intron, marketed by Schering Plough). In accordance with the methods of the present disclosure, an inhibiting compound can be used in combination with these standard therapies to treat HCV infection.

A number of HCV protease inhibitors are in development for the treatment of HCV infection, and in accordance with the methods of the present disclosure, co-administration of an inhibiting agent that prevents the binding of NS4B to the 3'-UTR of HCV RNA and an HCV protease inhibitor can be efficacious in the treatment of HCV. In one embodiment, an interferon alpha and/or a nucleoside analog such as ribavirin is/are also employed in this combination therapy. Suitable HCV protease inhibitors include, but are not limited to, telaprevir (VX-950, Vertex), BILN 2061 and BI12202 (Boehringer Ingelheim), boceprevir (SCH 503034, Schering Plough), ITMN191 (Roche/InterMune/Array BioPharma), MK-7009 (Merck), TMC435350 (Tibotec/Medivir), ACH-1095 and ACH-806 (Achillion/Gilead), and other inhibitors of NS3/NS4A protease, including, but not limited to, compounds in development by Presidio.

A number of HCV RNA polymerase (NS5B) inhibitors are in development for the treatment of HCV infection, and in accordance with the methods of the present disclosure, co-administration of an inhibiting agent that prevents the binding of NS4B to the 3'-UTR of HCV RNA and an HCV RNA polymerase inhibitor can be efficacious in the treatment of HCV. In one embodiment, an interferon alpha and/or a nucleoside analog such as ribavirin and/or an HCV protease inhibitor is/are also employed in this combination therapy. Suitable HCV RNA polymerase inhibitors include, but are not limited to, valopicitabine (NM283, Idenix/Novartis), HCV-796 (Wyeth/ViroPharma), R1626 (Roche), R7128 (Roche/Pharmasset), GS-9190 (Gilead), MK-0608 (Merck), PSI-6130 (Pharmasset), and PFE-868,554 (PFE).

A number of toll-like receptor (TLR) agonists are in development for the treatment of HCV infection, and in accordance with the methods of the present disclosure, co-administration of an NS4B antagonist that prevents the binding of NS4B to the 3'-UTR of HCV RNA and a TLR agonist can be efficacious in the treatment of HCV. In one embodiment, an interferon alpha and/or a nucleoside analog such as ribavirin and/ or an HCV protease inhibitor and/or an HCV RNA polymerase inhibitor is/are also employed in this combination therapy. Suitable TLR agonists include, but are not limited to, TLR7 agonists (i.e., ANA245 and ANA975 (Anadys/ Novartis)) and TLR9 agonists (i.e., Actilon (Coley) and IMO-2125 (Idera)).

A number of thiazolide derivatives are in development for the treatment of HCV infection, and in accordance with the methods of the present disclosoure, co-administration of an NS4B antagonist that prevents the binding of NS4B to the 3'-UTR of HCV RNA and a thiazolide, including, but not limited to, Nitazoxanide (Alinia, or other sustained release formulations of nitazoxanide or other thiazolides, Romark Laboratories) can be efficacious in the treatment of HCV. In an embodiment, an interferon alpha and/or a nucleoside analog such as ribavirin and/or an HCV protease inhibitor and/or an HCV RNA polymerase inhibitor and/or a TLR agonist is/are also employed in this combination therapy.

In another embodiment of the methods of the invention, co-administration of an inhibiting agent that prevents the binding of NS4B to the 3'-UTR of HCV RNA and a cyclophilin inhibitor (i.e., NIM-811 (Novartis) and DEBIO-025 (Debiopharm)) and/or an alpha-glucosidase inhibitor (i.e., Celgosivir (Migenix)) and/or one or more agents from one or more of the other classes of HCV therapeutic agents discussed herein is used to treat HCV infection. Moreover, there are several targets within NS4B, and compounds that interact with these other targets can, in accordance with the methods of the present disclosure, be used in combination with an NS4B antagonist that prevents the binding of NS4B to the 3'-UTR of HCV RNA and, optionally, one or more of the other classes of inhibiting agents mentioned herein, to treat HCV infection. Such additional NS4B targets include: the N-terminal amphipathic helix (see PCT publication WO 2002/089731, incorporated herein by reference), the NS4B GTPase (see PCT publication WO 2005/032329, incorporated herein by reference), the second amphipathic helix, the PIP2 binding activity of the first amphipathic helix in NS4B (see PCT publication WO 2009/148541, incorporated herein by reference).

Other agents that can be used in combination with inhibiting agents of the present disclosure that prevent the binding of NS4B to the 3'-UTR of HCV RNA include (i) agents targeting NS5A, including, but not limited to, A-831 (Arrow Therapeutics), AZD2836 (Astra Zeneca), and agents in development by XTL/Presidio or BMS (see PCT publications WO 2006/133326 and WO 2008/021928, incorporated herein by reference); (ii) agents targeting TBC1D$_2$O and/or NS5A's interaction with TBC1D$_2$O (see PCT publication WO 2007/018692 and U.S. patent application Ser. No. 11/844,993, incorporated herein by reference), (iii) agents targeting NS4B's GTPase activity (see PCT publication WO 2005/032329 and US patent application publication 2006/0199174, incorporated herein by reference); (iv) agents inhibiting membrane association mediated by the HCV amphipathic helices, such as those found in NS5A, NS4B, and NS5B (see PCT publication WO 2002/089731, supra), (v) agents targeting PIP2 or BAAPP domains in HCV proteins, such as those found in NS4B and NS5A (see U.S. provisional patent application 60/057,188, supra); (vi) agents targeting HCV entry, assembly, or release, including antibodies to co-receptors; (vii) agents targeting HCV NS3 helicase; (viii) siRNAs, shRNAs, antisense RNAs, or other RNA-based molecules targeting sequences in HCV; (ix) agents targeting microRNA122 or other microRNAs modulating HCV replication; (x) agents targeting PD-1, PD-L1, or PD-L2 interactions or pathway (see U.S. patent application publications 20080118511, 20070065427, 20070122378, incorporated herein by reference); (xi) agents targeting HCV amphipathic helix function, such as AH2 inhibitors; and (xii) prenylation inhibitors (e.g., U.S. Pat. Nos. 5,503,973, 5,876,920, 6,159,939, 6,627,610, 7,342,016, 5,874,442, 7,101,897, and 6,232,338, each of which are incorporated herein by reference).

In another embodiment of the present disclosure, an inhibiting agent that prevents the binding of NS4B to the 3'-UTR of HCV RNA is used in combination with one or more drugs capable of treating an HIV infection to treat a patient that is co-infected with HIV and HCV. In another embodiment of the present disclosure, an inhibiting agent that prevents the binding of NS4B to the 3'-UTR of HCV RNA is used in combination with one or more drugs capable of treating an HBV infection to treat a patient that is co-infected with HBV and HCV. In an embodiment, an inhibiting agent that prevents the binding of NS4B to the 3'-UTR of HCV RNA is used in combination with a PD-L1 inhibitor to treat a viral infection.

As mentioned above, embodiments of the present include the administration of an inhibiting agent identified herein (or by using an embodiment of the screen of the invention) in conjunction with at least one additional therapeutic agent to treat a viral infection. Suitable additional therapeutic agents include, but are not limited to, ribavirin; a nucleoside analog (e.g., levovirin, viramidine, and the like.); an NS3 inhibitor; an NS5 inhibitor; an interferon; and a side effect management agent.

In an embodiment, the at least one additional suitable therapeutic agent includes ribavirin. Ribavirin, 1-β-D-ribofuranosyl-1H-1,2,4-triazole-3-carboxamide, available from ICN Pharmaceuticals, Inc., Costa Mesa, Calif., is described in the Merck Index, compound No. 8199, Eleventh Edition. Its manufacture and formulation is described in U.S. Pat. No. 4,211,771. The disclosure also contemplates use of derivatives of ribavirin (see, e.g., U.S. Pat. No. 6,277,830).

In an embodiment, the at least one additional suitable therapeutic agent includes levovirin. Levovirin is the L-enantiomer of ribavirin, and exhibits the property of enhancing a Th1 immune response over a Th2 immune response. Levovirin is manufactured by ICN Pharmaceuticals.

In an embodiment, the at least one additional suitable therapeutic agent includes viramidine. Viramidine is a 3-carboxamidine derivative of ribavirin, and acts as a prodrug of ribavirin. It is efficiently converted to ribavirin by adenosine deaminases.

Nucleoside analogs that are suitable for use in a combination therapy include, but are not limited to, ribavirin, levovirin, viramidine, isatoribine, an L-ribofuranosyl nucleoside as disclosed in U.S. Pat. No. 5,559,101 and encompassed by Formula I of U.S. Pat. No. 5,559,101 (e.g., 1-β-L-ribofuranosyluraeil, 1-β-L-ribofuranosyl-5-fluorouracil, 1-β-L-ribofuranosylcytosine, 9-β-L-ribofuranosyladenine, 9-β-L-ribofuranosylhypoxanthine, 9-β-L-ribofuranosylguanine, 9-β-L-ribofuranosyl-6-thioguanine, 2-amino-α-L-ribofuranl[1',2': 4,5]oxazoline, $O^2,O^2$-anhydro-1-α-L-ribofuranosyluracil, 1-α-L-ribofuranosyluracil, 1-(2,3,5-tri-O-benzoyl-α-ribofuranosyl)-4-thiouracil, 1-α-L-ribofuranosylcytosine, 1-α-L-ribofuranosyl-4-thiouracil, 1-α-L-ribofuranosyl-5-fluorouracil, 2-amino-β-L-arabinofurano[1',': 4,5]oxazoline, $O^2,O^2$-anhydro-β-L-arabinofuranosyluracil, 2'-deoxy-β-L-uridine, 3'5'-Di-O-benzoyl-2'deoxy-4-thio β-L-uridine, 2'-deoxy-β-L-cytidine, 2'-deoxy-β-L-4-thiouridine, 2'-deoxy-β-L-thymidine, 2'-deoxy-β-L-5-fluorouridine, 2',3'-dideoxy-β-L-uridine, 2'-deoxy-β-L-5-fluorouridine, and 2'-deoxy-β-L-inosine); a compound as disclosed in U.S. Pat. No. 6,423,695 and encompassed by Formula I of U.S. Pat. No. 6,423,695; a compound as disclosed in U.S. Patent Publication No. 2002/0058635, and encompassed by Formula 1 of U.S. Patent Publication No. 2002/0058635; a nucleoside analog as disclosed in WO 01/90121 A2 (Idenix); a nucleoside analog as disclosed in WO 02/069903 A2 (Biocryst Pharmaceuticals Inc.); a nucleoside analog as disclosed in WO 02/057287 A2 or WO 02/057425 A2 (both Merck/Isis); and the like.

In an embodiment, the at least one additional suitable therapeutic agent can include HCV NS3 inhibitors. Suitable HCV non-structural protein-3 (NS3) inhibitors include, but are not limited to, a tri-peptide as disclosed in U.S. Pat. Nos. 6,642,204, 6,534,523, 6,420,380, 6,410,531, 6,329,417, 6,329,379, and 6,323,180 (Boehringer-Ingelheim); a compound as disclosed in U.S. Pat. No. 6,143,715 (Boehringer-Ingelheim); a macrocyclic compound as disclosed in U.S. Pat. No. 6,608,027 (Boehringer-Ingelheim); an NS3 inhibitor as disclosed in U.S. Pat. Nos. 6,617,309, 6,608,067, and 6,265,380 (Vertex Pharmaceuticals); an azapeptide compound as disclosed in U.S. Pat. No. 6,624,290 (Schering); a compound as disclosed in U.S. Pat. No. 5,990,276 (Schering); a compound as disclosed in Pause et al. (2003) *J. Biol. Chem.* 278:20374-20380; NS3 inhibitor BILN 2061 (Boehringer-Ingelheim; Lamarre et al. (2002) *Hepatology* 36:301 A; and Lamarre et al. (Oct. 26, 2003) *Nature* doi:10.1038/nature02099); NS3 inhibitor VX-950 (Vertex Pharmaceuticals; Kwong et al. (Oct. 24-28, 2003) 54$^{th}$ Ann. Meeting AASLD); NS3 inhibitor SCH$_6$ (Abib et al. (Oct. 24-28, 2003) Abstract 137. Program and Abstracts of the 54$^{th}$ Annual Meeting of the American Association for the Study of Liver Diseases (AASLD). Oct. 24-28, 2003. Boston, Mass.); any of the NS3 protease inhibitors disclosed in WO 99/07733, WO 99/07734, WO 00/09558, WO 00/09543, WO 00/59929 or WO 02/060926 (e.g., compounds 2, 3, 5, 6, 8, 10, 11, 18, 19, 29, 30, 31, 32, 33, 37, 38, 55, 59, 71, 91, 103, 104, 105, 112, 113, 114, 115, 116, 120, 122, 123, 124, 125, 126 and 127 disclosed in the table of pages 224-226 in WO 02/060926); an NS3 protease inhibitor as disclosed in any one of U.S. Patent Publication Nos. 2003019067, 20030187018, and 20030186895; and the like.

In an embodiment, the NS3 inhibitor used in a combination therapy of the invention is a member of the class of specific NS3 inhibitors, e.g., NS3 inhibitors that inhibit NS3 serine protease activity and that do not show significant inhibitory activity against other serine proteases such as human leukocyte elastase, porcine pancreatic elastase, or bovine pancreatic chymotrypsin, or cysteine proteases such as human liver cathepsin B.

In an embodiment, the at least one additional suitable therapeutic agent includes NS5B inhibitors. Suitable HCV non-structural protein-5 (NS5; RNA-dependent RNA polymerase) inhibitors include, but are not limited to, a compound as disclosed in U.S. Pat. No. 6,479,508 (Boehringer-Ingelheim); a compound as disclosed in any of International Patent Application Nos. PCT/CA02/01127, PCT/CA02/01128, and PCT/CA02/01129, all filed on Jul. 18, 2002 by Boehringer Ingelheim; a compound as disclosed in U.S. Pat. No. 6,440,985 (ViroPharma); a compound as disclosed in WO 01/47883, e.g., JTK-003 (Japan Tobacco); a dinucleotide analog as disclosed in Zhong et al. (2003) *Antimicrob. Agents Chemother.* 47:2674-2681; a benzothiadiazine compound as disclosed in Dhanak et al. (2002) *J. Biol Chem.* 277(41): 38322-7; an NS5B inhibitor as disclosed in WO 02/100846 A1 or WO 02/100851 A2 (both Shire); an NS5B inhibitor as disclosed in WO 01/85172 A1 or WO 02/098424 A1 (both Glaxo SmithKline); an NS5B inhibitor as disclosed in WO 00/06529 or WO 02/06246 A1 (both Merck); an NS5B inhibitor as disclosed in WO 03/000254 (Japan Tobacco); an NS5B inhibitor as disclosed in EP 1 256,628 A2 (Agouron); JTK-002 (Japan Tobacco); JTK-109 (Japan Tobacco); and the like.

In an embodiment, the NS5 inhibitor used in the combination therapies of the invention is a member of the class of specific NS5 inhibitors, e.g., NS5 inhibitors that inhibit NS5 RNA-dependent RNA polymerase and that lack significant inhibitory effects toward other RNA dependent RNA polymerases and toward DNA dependent RNA polymerases.

In an embodiment, the at least one additional therapeutic agent is an interferon, e.g., interferon-alpha (IFN-α). Any known IFN-α can be used in the treatment methods of the invention. The term "interferon-alpha" as used herein refers to a family of related polypeptides that inhibit viral replication and cellular proliferation and modulate immune response. The term "IFN-α" includes naturally occurring IFN-α; synthetic IFN-α; derivatized IFN-α (e.g., PEGylated IFN-α, glycosylated IFN-α, and the like); and analogs of naturally occurring or synthetic IFN-α; essentially any IFN-α that has antiviral properties, as described for naturally occurring IFN-α.

Suitable alpha interferons include, but are not limited to, naturally-occurring IFN-α (including, but not limited to, naturally occurring IFN-α 2a, IFN-α 2b); recombinant interferon alpha-2b such as Intron-A interferon available from Schering Corporation, Kenilworth, N.J.; recombinant interferon alpha-2a such as Roferon interferon available from Hoffmann-La Roche, Nutley, N.J.; recombinant interferon alpha-2C such as Berofor alpha 2 interferon available from Boehringer Ingelheim Pharmaceutical, Inc., Ridgefield, Conn.; interferon alpha-n1, a purified blend of natural alpha interferons such as Sumiferon available from Sumitomo, Japan or as Wellferon interferon alpha-n1 (INS) available from the Glaxo-Wellcome Ltd., London, Great Britain; and interferon alpha-n3a mixture of natural alpha interferons made by Interferon Sciences and available from the Purdue Frederick Co., Norwalk, Conn., under the Alferon tradename.

The term "IFN-α" also encompasses consensus IFN-α. Consensus IFN-α (also referred to as "CIFN" and "IFN-con" and "consensus interferon") encompasses, but is not limited to, the amino acid sequences designated IFN-con$_1$, IFN-con$_1$ and IFN-con$_1$ which are disclosed in U.S. Pat. Nos. 4,695,623 and 4,897,471; and consensus interferon as defined by determination of a consensus sequence of naturally occurring interferon alphas (e.g., Infergen®, InterMune, Inc., Brisbane, Calif.). IFN-con$_1$ is the consensus interferon agent in the Infergen® alfacon-1 product. The Infergen® consensus interferon product is referred to herein by its brand name (Infergen®) or by its generic name (interferon alfacon-1). DNA sequences encoding IFN-con may be synthesized as described in the aforementioned patents or other standard methods. In an embodiment, the at least one additional therapeutic agent is CIFN.

In an embodiment, fusion polypeptides comprising an IFN-α and a heterologous polypeptide can also be used in the combination therapies of the invention. Suitable IFN-α fusion polypeptides include, but are not limited to, Albuferon-alpha™ (a fusion product of human albumin and IFN-α; Human Genome Sciences; see, e.g., Osborn et al. (2002) *J. Pharmacol. Exp. Therap.* 303:540-548). Also suitable for use in the present disclosure are gene-shuffled forms of IFN-α. See e.g., Masci et al. (2003) *Curr. Oncol. Rep.* 5:108-113. Other suitable interferons include), Multiferon (Viragen), Medusa Interferon (Flamel Technology), Locteron (Octopus), and Omega Interferon (Intarcia/Boehringer Ingelheim).

The term "IFN-α" also encompasses derivatives of IFN-α that are derivatized (e.g., are chemically modified relative to the naturally occurring peptide) to alter certain properties such as serum half-life. As such, the term "IFN-α" includes glycosylated IFN-α; IFN-α derivatized with polyethylene glycol ("PEGylated IFN-α"); and the like. PEGylated IFN-α, and methods for making same, is discussed in, e.g., U.S. Pat. Nos. 5,382,657; 5,981,709; and 5,951,974. PEGylated IFN-α encompasses conjugates of PEG and any of the above-described IFN-α molecules, including, but not limited to, PEG conjugated to interferon alpha-2a (Roferon, Hoffman La-Roche, Nutley, N.J.), interferon alpha 2b (Intron, Schering-Plough, Madison, N.J.), interferon alpha-2c (Berofor Alpha, Boehringer Ingelheim, Ingelheim, Germany); and consensus interferon as defined by determination of a consensus sequence of naturally occurring interferon alphas (Infergen®, InterMune, Inc., Brisbane, Calif.).

In an embodiment, the IFN-α polypeptides can be modified with one or more polyethylene glycol moieties, i.e., PEGylated. The PEG molecule of a PEGylated IFN-α polypeptide is conjugated to one or more amino acid side chains of the IFN-α polypeptide. In an embodiment, the PEGylated IFN-α contains a PEG moiety on only one amino acid. In another embodiment, the PEGylated IFN-α contains a PEG moiety on two or more amino acids, e.g., the IFN-α contains a PEG moiety attached to two, three, four, five, six, seven, eight, nine, or ten different amino acid residues. IFN-α may be coupled directly to PEG (i.e., without a linking group) through an amino group, a sulfhydryl group, a hydroxyl group, or a carboxyl group.

To determine the optimum combination of an inhibiting agent, such as clemizole, with other anti-HCV agents, HCV replication assays and/or animal studies can be performed in the presence of various combinations of the various anti-HCV agents. Increased inhibition of replication in the presence of an additional agent (above that observed with monotherapy) is evidence for the potential benefit of the combination therapy.

For example, HCV replication assays employing a luciferase reporter-linked HCV genome in the presence of various combinations of clemizole and an NS3 protease inhibitor (SCH503034, boceprevir) demonstrated strong synergy (using Bliss Independence Theory as implemented in MacSynergy II). In such assays, luciferase activity is directly proportional to HCV RNA genome replication. In this method, Huh 7.5 cells were electroporated with a wild-type luciferase reporter-linked HCV genome, and plated replicates were cultured in the presence of the indicated concentrations of clemizole and SCH503034 (SCH) for 72 hours, followed by lysis and determination of luciferase activity, essentially as described (Nature Biotechnology 26, 1019-1027 (2008), which is incorporated herein by reference). The results can be plotted on a linear or log scale as a function of drug concentrations to generate replication inhibition curves. The inhibition curve for the NS3 inhibitor showed significantly more inhibition in the presence of increasing concentrations of clemizole. In particular, at low micromolar concentrations of SCH503034 (such as 1-5 micromolar), addition of clemizole can increase the inhibition of HCV replication in a dose-dependent manner by up to several logs. Similarly increased efficacy of combination therapy (over monotherapy) should occur in accordance with the methods of the invention when an NS4B antagonist, such as clemizole or a clemizole analog, is co-administered with other NS3 protease inhibitors, and with other anti-HCV agents that have a mechanism of action distinct from NS4B antagonists that have the same mechanism of action as clemizole. These results not only provide clear evidence for the benefit of combination therapy of clemizole and SCH503034, but also demonstrate that improved efficacy and likely decreased resistance can occur following in vivo therapy with this and similar combination therapies provided by the present disclosure. Moreover, these results demonstrate that one skilled in the art can readily perform assays to determine optimal combination therapies with the NS4B antagonists useful in embodiments of the methods of the present invention and other anti-HCV agents in view of the disclosure herein.

In addition to boceprevir (SCH503034), which exhibited strong synergy with clemizole, the following compounds exhibited additivity or synergy with clemizole: ITMN-191 (also known as RG7227)—additivity; VX-950—strong synergy; interferon—additivity; NM283—additivity; HCV796—additivity; and ribavirin—additivity. See also Example 5 below.

In an embodiment, side effect management agents can be used in the treatment methods of the invention, and these include agents that are effective in pain management; agents that ameliorate gastrointestinal discomfort; analgesics, anti-inflammatories, antipsychotics, antineurotics, anxiolytics, and hematopoietic agents. In addition, embodiments of the invention contemplate the use of any compound for palliative care of patients suffering from pain or any other side effect in the course of treatment with a subject therapy. Exemplary palliative agents include acetaminophen, ibuprofen, other NSAIDs, H2 blockers, and antacids.

The inhibiting agents and pharmaceutical compositions provided herein can be used to treat a variety of patients or hosts infected with a virus of the Flavirivirus family. The subject treatment methods may particularly benefit "treatment failure patients". Such patients include, but are not limited to, those who have failed to respond to previous therapy for HCV (referred to as "non-responders") or who initially responded to previous therapy, but in whom the therapeutic response was not maintained (referred to as "relapsers"). The previous therapy generally can include treatment with any anti-viral agent other than an inhibiting agent of the present disclosure.

Other patients that may benefit from the subject treatments are individuals who have been clinically diagnosed as infected with HCV. Such individuals include naïve individuals (e.g., individuals not previously treated for HCV). Individuals who are infected with HCV can be identified by detecting HCV RNA in their blood, and/or having an anti-HCV antibody in their serum.

In some embodiments, hosts suitable for treatments of the present invention have an HCV titer of at least about $10^5$, at least about $5 \times 10^5$, or at least about $10^6$, genome copies of HCV per milliliter of serum. The patient may be infected with any HCV genotype (genotype 1, including 1a and 1b, 2, 3, 4, 6, and the like. and subtypes (e.g., 2a, 2b, 3a, and the like.)), particularly a difficult to treat genotype such as HCV genotype 1 and particular HCV subtypes and quasispecies.

Also suitable for treatment are HCV-positive hosts (as described above) who exhibit severe fibrosis or early cirrhosis (non-decompensated, Child's-Pugh class A or less), or more advanced cirrhosis (decompensated, Child's-Pugh class B or C) due to chronic HCV infection and who are viremic despite prior anti-viral treatment, or who have a contraindication to therapy with a known anti-viral agent.

In an embodiment, HCV-positive hosts with stage 3 or 4 liver fibrosis according to the METAVIR scoring system are suitable for treatment with the methods of the present disclosure. In another embodiment, hosts suitable for treatment with embodiments of the present disclosure are patients with decompensated cirrhosis with clinical manifestations, including patients with far-advanced liver cirrhosis, including those awaiting liver transplantation. In still another embodiment, hosts suitable for treatment with embodiments of the present disclosure include patients with milder degrees of fibrosis including those with early fibrosis (stages 1 and 2 in the METAVIR, Ludwig, and Scheuer scoring systems; or stages 1, 2, or 3 in the Ishak scoring system).

In an embodiment of the present disclosure, to help optimally select patients most likely to benefit from therapy, as well as to monitor efficacy of therapy—especially in the face of potential drug resistant mutant viruses—the use of appropriate diagnostic tests provided by the present invention can be of great benefit. For example, assessing the sensitivity of the specific virus found in a given patient to the contemplated therapy can help identify the best match between candidate patient and the corresponding appropriate therapy. In the case of clemizole, clemizole analogs, compounds having a clemizole scaffold, or other inhibiting agents identified herein, this can be done by isolating the NS4B sequence from a given patient's HCV isolate and determining the efficacy of the drug's inhibition of RNA binding by the patient's NS4β isoform. This is especially important, because there currently is no efficient way of studying the drug sensitivity of a given patient's virus, because patient-derived inoculums cannot be readily cultured. The value of using such diagnostic assays to guide therapy has been extensively validated in HIV.

Combination therapy with clemizole in accordance with embodiments of the present invention includes, for example and without limitation, (1) treatment with clemizole plus nitazoxanide, (2) treatment with clemizole followed by nitazoxanide, (3) treatment with clemizole plus nitazoxanide and a NS3 protease inhibitor, (4) treatment with clemizole plus nitazoxanide plus a NS3 protease inhibitor plus a NS5B polymerase inhibitor, (5) treatment with clemizole plus a NS3 protease inhibitor plus a NS5B polymerase inhibitor, (6) treatment with clemizole plus nitazoxanide plus a NS3 protease inhibitor plus a NS4B second amphipathic helix inhibitor, (7) treatment with clemizole plus nitazoxanide plus a NS4B second amphipathic helix inhibitor, (8) treatment with clemizole plus a NS3 protease inhibitor plus a NS4B second amphipathic helix inhibitor, (9) treatment with clemizole plus ribavirin, (10) treatment with clemizole followed by nitazoxanide plus ribavirin; and (11) any other combinations of one or more agents listed above (1)-(10). In some embodiments, the one or more additional therapeutica agents are administered prior to, concurrent with, or subsequent to the treatment with clemizole, clemizole analogs or isosterers of the present invention. In various embodiments, the inhibiting agent is clemizole hydrochloride (1-p-chlorobenzyl-2-(1-pyrrolidinyl)methylbenzimidazole hydrochloride), an analog or clemizole, or a derivative thereof.

Nitazoxanide administration in accordance with the combination therapies of the invention can be, for illustration and without limitation, 500 mg po BID. Other doses, other thiazolides, or other formulations of nitazoxanide or another thiazolide, such as sustained release formulations, can also be used in the combination therapies of the invention.

The inhibiting agents and pharmaceutical compositions thereof can be administered to a subject using any available method and route suitable for drug delivery, including in vivo and ex vivo methods, as well as systemic and localized routes of administration.

Routes of administration include intranasal, intramuscular, intratracheal, subcutaneous, intradermal, topical application, intravenous, rectal, nasal, oral, and other enteral and parenteral routes of administration. Routes of administration may be combined, if desired, or adjusted depending upon the agent and/or the desired effect. An active agent can be administered in a single dose or in multiple doses.

Embodiments of the inhibiting agent can be administered to a host using available conventional methods and routes suitable for delivery of conventional drugs, including systemic or localized routes. In general, routes of administration contemplated by the disclosure include, but are not limited to, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the inhibiting agent. Where systemic delivery is desired, administration typically involves invasive or systemically absorbed topical or mucosal administration of pharmaceutical preparations.

The inhibiting agent can also be delivered to the subject by enteral administration. Enteral routes of administration include, but are not limited to, oral and rectal (e.g., using a suppository) delivery.

Methods of administration of the inhibiting agent through the skin or mucosa include, but are not limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more. In some embodiments, clemizole or clemizole analog is administered by oral, intravenous, transdermal, sublingual, intramuscular, or rectal route.

The anti-viral activity of clemizole analogs of the invention can be demonstrated in cell-based assays. For example, a clemizole analog of interest can be contacted with a mammalian cell that harbors all or part of an HCV genome; and the effect of the test agent on HCV replication is determined. Suitable cells include mammalian liver cells that are permissive for HCV replication, e.g., an immortalized human hepatocyte cell line that is permissive for HCV. For example, a suitable mammalian cell is Huh7 hepatocyte or a subclone of Huh7 hepatocyte, e.g., Huh-7.5. Suitable cell lines are described in, e.g., Blight et al. (2002) *J. Virol.* 76:13001; and Zhang et al. (2004) *J. Virol.* 78:1448. In an embodiment, the HCV genome in the cell comprises a reporter, e.g., a nucleotide sequence encoding luciferase, a fluorescent protein, or other protein that provides a detectable signal; and determining the effect, if any, of the test agent on HCV replication is achieved by detection of a signal from the reporter.

Having disclosed various aspects and embodiments of the present invention in summary and in detail, the aspects and embodiments of the present invention are illustrated and not limited by the following examples.

EXAMPLES

The following examples are put forth so as to provide those of ordinary skill in the art with a complete disclosure and description of how to make and use the present disclosure, and are not intended to limit the scope of what the inventors regard as their disclosure nor are they intended to represent that the experiments below are all or the only experiments performed. Efforts have been made to ensure accuracy with respect to numbers used (e.g., amounts, temperature, and the like.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Testing for Anti HCV Genotype 1b Activity of the Compounds of the Present Invention A suitable 1b HCV RNA replicon assay uses the Huh7 cell line, which contains an HCV 1b RNA replicon with a stable luciferase (LUC) reporter. This construct contains modifications that make the cell line more robust and provides stable LUC expression for anti-viral screening. The LUC reporter is used as an indirect measure of HCV replication. The activity of the LUC reporter is directly proportional to HCV RNA levels and positive control anti-viral compounds behave comparably using LUC endpoints.

HCV assays suitable for use in demonstrating the anti-viral activity of the compounds useful in the methods of the invention include the Luciferase Assay for HCV Replicon Reporter Cell Lines and the MTT Assay for HCV Replicon Reporter Cell Lines described in this example. The embodiments of these assays described in this example were developed by Shanghai ChemPartner Co., Ltd., a corporation of China with its principal office located at 720 Cailun Road, Building No. 3, Shanghai 201203, China.

A. Luciferase Assay for HCV Genotype 1b Replicon Reporter Cell Lines

Fresh growth medium is prepared just before use. The container used in the procedure is a 10 cm diameter culture dish. HCV replicon reporter cell lines are used. Prepare complete medium: add FBS and appropriate additives as described in "Culture Media", below. Pre-warm the medium in a 37° C. thermostat water bath. Remove the dish from a 37° C./$CO_2$ incubator. Check the cell name and complete medium and passage number marked on the dish. Aspirate the medium carefully and add 1 ml PBS to rinse the cells. Remove and discard the solution and add 1 ml of 0.25% Trypsin/0.02% EDTA. Rinse the cells with the added Trypsin/EDTA to ensure all the cells have been rinsed. Remove the Trypsin/EDTA with a vacuum pump and incubate at 37° C. for 3-5 minutes. Examine the cell morphology under an inverted microscope to confirm that a single cell suspension is clearly visible. Add 3 ml of complete medium to the dish and suspend the cell by gentle pipetting. Count the cell numbers with a hematometer. Adjust cell density to 100 k/ml by adding appropriate volume of the complete medium. Add 100 μl of cell suspension to each well of a 96-well white plate; the cell density is thus 10 k per well. Mark the plate with cell name, passage number, seeding density, date and the name of the operator. Place the 96-well assay plate in 37° C./5% $CO_2$ incubator for 24 hours.

Compounds are prepared or provided at 25 mM in 100% DMSO. This is the compound stock solution. The dilution procedure should be performed in a cell culture hood. Dispense the stock solution into the second column of a 96-well plate. Prepare 9-step (10 concentrations total), 5-fold serial dilutions by transferring 10 μl of the compound into the next well containing 40 μl of DMSO. Repeat for all compounds. Aspirate 2 μl of the above compound solution from each well and add into 198 μl complete media using a 12-channel pipetter to obtain the 10-fold concentration compound solution with 1% DMSO, mix well.

Remove the 96-well assay plate from the 37° C./5% $CO_2$ incubator, examine the cell morphology under an inverted microscope. In a cell culture hood, add 10 ml of the 10× concentration compounds solution into each well on the 96-well assay plate. All compound's dose responses are done in duplicate. The starting final concentration of the compounds is 25 μM, and DMSO final concentration 0.1%. Mark the plate with compound code(s) and concentrations. Place the 96-well assay plate into $CO_2$ incubator for 48 hours. Add 30 μl of Stead-Glo Luciferase System (Promega) reagent to each well and mix by gentle shaking on a plate shaker for 5 minutes to allow throughout cell lysis. Measure the luminescence with Envision (Perkin Elmer) with an integration time of 2 seconds. Record and analyze the data.

The cell culture media is DMEM complete: DMEM (Life Technologies #41965-039) supplemented with 10% FCS, 2 mM Glutamin (Life Technologies #25030-024), Penicillin (100 IU/ml)/Streptomycin (100 μg/ml) (Life Technologies #15140-114) and 1× nonessential amino acids (Life Technologies #11140-035). G418 ("Geneticin", Life Technologies): concentrations are given as weight per volume of the original substance. Specific activity of a typical batch is ca. 700 μg/mg as stated by the manufacturer. This value does not necessarily reflect the biological activity in a user's system. Therefore each new batch of G418 should be tested individually e.g., in an electroporation experiment using different selection conditions (0.2-1 mg/ml).

B. MTT Assay for HCV Replicon Reporter Cell Lines

The MTT assay (and the MTS assay) is a laboratory test and standard colorimetric assay (an assay which measures changes in color) for measuring the activity of enzymes that reduce MTT or MTS+PMS to formazan, giving a purple color. It can also be used to determine cytotoxicity of potential medicinal agents and other toxic materials, since those agents would result in cell toxicity and therefore metabolic dysfunction and therefore decreased performance in the assay. Yellow MTT (3-(4,5-dimethylthiazol-2-yl)-2,5-diphenyltetrazolium bromide, a tetrazole) is reduced to purple formazan in living cells. http://en.wikipedia.org/wiki/MTT_assay-cite_note-pmid6606682-0#cite_note-pmid6606682-0.

A solubilization solution (usually either dimethyl sulfoxide, an acidified ethanol solution, or a solution of the detergent sodium dodecyl sulfate in diluted hydrochloric acid) is added to dissolve the insoluble purple formazan product into a colored solution. The absorbance of this colored solution can be quantified by measuring at a certain wavelength (usually from 500 and 600 nm) by a spectrophotometer. The absorption maximum is dependent on the solvent employed.

Culture medium, culture plates, and additives are prepared as described in part A of this example. Pre-warm the medium in a 37° C. thermostat water bath. Remove the dish from a 37° C./$CO_2$ incubator. Check the cell name and complete medium and passage number marked on the dish. Aspirate the medium carefully and add 1 ml PBS to rinse the cells. Remove and discard the solution and add 1 ml of 0.25% Trypsin/0.02% EDTA. Rinse the cells with the added Trypsin/EDTA to ensure all the cells have been rinsed. Remove the Trypsin/EDTA with a vacuum pump and incubate at 37° C. for 3-5 minutes. Examine the cell morphology under an inverted microscope until single cell suspension is clearly visible. Add 3 ml of complete medium to the dish and suspend the cell by gentle pipetting. Count the cell numbers with a hematometer. Adjust cell density to 100 k/ml by adding appropriate volume of the complete medium. Add 100 μl of cell suspension to each well of a 96-well white plate; the cell density is thus 10 k per well. Mark the plate with cell name, passage number, seeding density, date and the name of the operator. Place the 96-well assay plate in 37° C./5% $CO_2$ incubator for 24 hours.

Compounds are prepared or provided at 25 mM in 100% DMSO. This is the compound stock solution. The dilution procedure should be performed in a cell culture hood. Dispense the stock solution into the second column of a 96-well plate. Prepare 9-step (10 concentrations total), 5-fold serial dilutions by transferring 10 μl of the compound into the next well containing 90 μl of DMSO. Repeat for all compounds. Aspirate 2 μl of the above compound solution from each well and add into 198 μl complete media using a 12-channel pipetter to obtain the 10-fold concentration compound solution with 1% DMSO, mix well. Remove the 96-well assay plate from 37° C. 15% $CO_2$ incubator, examine the cell morphology under an inverted microscope. In a cell culture hood, add 10 µl of the 10× concentration compound solution into each well on the 96-well assay plate. All compound's dose responses are done in duplicate. The starting final concentration of the compounds is 25 µM, and DMSO final concentration 0.1%.

Mark the plate with compound code(s) and concentrations. Place the 96-well assay plate into $CO_2$ incubator for 48 hours. Add 10 µl of 5 mg/ml MTT to each well and incubate in the 37° C./$CO_2$ incubator for 4 hours. Add 100 µl of testing solution (10% SDS+5% isobutyl alcohol+10 mmol/L HCl) to each well directly and incubate in the 37° C./5% $CO_2$ incubator overnight. Measure the absorbance at 580/680 nm on SpectraMax Plus 384 (MDC). Record and analyze the results.

C. HCV Genotype 2a Infectious Clone Assay

In an embodiment, the replication assay protocol can include the following stages. It should be noted that the following replication assay protocol is non-limiting, and is presented as an illustrative embodiment of a replication assay protocol. The assays in parts A and B were used to generate the genotype 1b inhibitory activity and related cell toxicity (viability) data. This assay has been used to generate the genotype 2a inhibitory activity data.

Stage 1: RNA Transcription

1) Linearize the FL-J6/JFH-5'Cl9Rluc2A Ubi plasmid with XbaI at 37° C. for 2 hrs, and run on 1% agarose gel to check completeness of digestion. 2) Digest the 5' overhangs by treatment with mung bean nuclease at 30° C. for 30 min. 3) For linearization of the Bart79I-luc plasmid (similar to Bart79I plasmid as described in Elazar et al. J. Virol. 2003, 77(10):6055-61 except that the neomycinphosphotransferase gene has been replaced with the gene encoding firefly luciferase) use SeaI restriction endonuclease, then examine the linearized template DNA on a gel to confirm that cleavage is complete, follow this with proteinase k digestion. 4) Purify templates by digestion with proteinase K for 30 min, phenol-chloroform extraction, ethanol precipitation, and then resuspend at 1 µg/µl. 5) For the transcription reaction, use 1 µg of purified template by using the T7 Megascript kit for FL-J6/JFH-5'Cl9Rluc2AUbi (Ambion, Austin, Tex.) or the RiboMax™ kit for Bart79I-luc (Promega, Madison, Wis.). Incubate reactions at 37° C. for 4 h. 6) Add DNAse for 15 min. 7) Extract with an equal volume of phenol/chloroform and then with an equal volume of chloroform. Recover aqueous phase and transfer to new tube. 8) Precipitate the RNA by adding 1 volume of isopropanol and mixing well. 9) Chill the mixture for at least 15 min at −20° C. Centrifuge at 4° C. for 15 min at maximum speed to pellet the RNA. 10) Carefully remove the supernatant solution and resuspend the RNA in RNase/DNase-free Water at 1 µg/µl. 11) Run on a gel and check RNA concentration. 12) Make aliquots and store in −80° C.

Stage 2: Electroporating Huh7.5 Cells

1) Wash cells once with PBS, trypsinize. 2) Resuspend cells in a total volume of 5 ml per 10 cm plate of complete medium (pull all together) in 50 ml tubes. 3) Pellet cells at 1000×RPM for 5 min at 4° C. Aspirate supernatant and resuspend in 10 ml ice cold RNAse free filtered 1×PBS (BioWhitaker)—pipette up and down ~5 times gently to get rid of cell clumps. 4) Pellet cells again at 1000×RPM as before and again resuspend in 10 ml ice cold PBS (BioWhitaker). 5) Remove a 10 µl aliquot to determine cell concentration. 6) Pellet cells again and resuspend in a final concentration of $1.5 \times 10^7$ cells/ml in ice cold RNAse free-PBS. Need: $6 \times 10^6$ cells in 0.4 ml per each electroporation (ep) and 5 µg of FL-J6/JFH-5'C19Rluc2A Ubi RNA or Bart79I-luc RNA. 7) Place 5 µg RNA aliquot in an eppendorf tube (1 tube per ep). 8) Remove 0.4 ml of the cell suspension and add to the RNA. Mix twice by pipetting. 9) Immediately transfer 0.4 ml to a 2 mm gap ep cuvette. 10) Pulse the cells: 820 v, 5 pulses, 99 µsec, 220 ms interval, unipolar. 11) Allow cells to rest for 15 min. 12) Transfer cells using the Pasteur pipette in the cuvette package to medium. Make a common stock from all tubes. 13) Plate 10,000 cells/well in 96 well plates. 14) Rotate plate a little for even cell plating. 15) Incubate for 24 hr before treatment.

Stage 3: Treating plates

1) About 24 hr following electroporation prepare medium with the desired concentration of the drug. 2) Aspirate the medium and add 100 µl of fresh medium and drug. Leave untreated wells at the beginning and again at the end. 3) Repeat daily for 2 more days.

Stage 4: Harvesting (Day 5 from Electroporation)

1) Alamar blue assay—a) Include medium for background subtraction (and also for seeing change in color easily). b) Aspirate medium. c) Make a stock of medium plus 10% Alamar blue. Total volume per well is 100 µl. d) Incubate for 2-2.5 hrs at 37° C. (or until there is a color change). c) Read plates at flex station.

2) *Renilla* Luciferase assay—a) Aspirate medium with Alamar blue. b) Wash with 1×PBS. c) Aspirate completely (aspirate, then tilt and aspirate remainders of buffer again). d) Make sure which lysis buffer is needed: firefly or *renilla*. e) Add 30 µl of 1× lysis buffer (add 1 volume of 5× lysis buffer to 4 volumes of sterile water). f) Shake the plate for 15 min. g) Freeze at −80° C. At this point, one can stop or continue to the next phase.

Stage 5: Reading by Luminometer. a) Thaw the plate. b) Leave plate on ice until ready to read. c) Prepare substrate reagent you need; for the *renilla*: thaw *renilla* buffer, make 1 volume 100× *Renilla* luc substrate plus 100 vol luc assay buffer+2 ml for priming luminometer (e.g., for 4 ml *Renilla* lucsubstrate, add 40 ul assay buffer). For the firefly; thaw 10 ml firefly buffer and add to the luciferase reagent. d) Read plates using a standard luminometer according to the manufacturer's directions.

D. HERG Channel Assay:

Drugs belonging to different classes have been shown to be associated with QT prolongation and in some cases serious ventricular arrhythmias. The most common mechanism for these adverse events is the inhibition of one or more cardiac potassium channels, in particular hERG. This current is important for cardiac myocyte repolarization and is a common target for drugs that prolong the QT interval. Test articles in this study were therefore characterized to determine their ability to inhibit the hERG channel. Ion channel activity was measured using a stably transfected Chinese Hamster Ovary (CHO) cell line expressing the hERG mRNA. The pharmacology of this cloned channel expressed in the CHO cell line is very similar to that observed in native tissue.

Cells: AVIVA's CHO cell line, which stably expresses hERG channels, was used for the study. Cells were cultured in DMEM/F12 containing 10% FBS, 1% penicillin/streptomycin and 500 µg/ml G418. Before testing, cells were harvested using Accumax (Innovative Cell Technologies).

Solutions: For electrophysiological recordings, the following solutions were used. External Solution: 2 mM $CaCl_2$; 2 mM $MgCl_2$; 4 mM KCl; 150 mM NaCl; 10 mM Glucose; 10 mM HEPES; 310-320 mOsm; pH 7.4 (adjusted with 1M NaOH). Internal Solution: 140 mM KCl; 10 mM $MgCl_2$; 6 mM EGTA; 5 mM HEPESNa; mM ATP-Mg; 300-320 mOsm; pH 7.25 (adjusted with 1M KOH).

Electrophysiology: Whole cell recordings were performed using PX 7000A (Axon Instruments) with VIVA's Seal-Chip™ technology. Cells were voltage clamped at a holding potential of −80 mV. The hERG current was then activated by a depolarizing step to −50 mV for 300 ms. This first step at −50 mV was used as a baseline for measuring peak amplitude of the tail current. Next, a voltage step to +20 mV was applied for 5 s to activate the channels. Finally a step back to −50 mV for 5 seconds removed activation and the deactivating tail current was recorded.

Compound Handling and Dilutions: All compounds were prepared from either 10 or 30 mM DMSO stock solutions. Solutions were mixed by sonication for 20 min, followed by vigorous vortexing. Prior to testing, compounds were diluted to test concentrations in glass vials using External Solution. Dilutions were prepared no longer than 20 min prior to use. Equal amounts of DMSO (0.1%) were present in all final dilutions.

Electrophysiology Procedures: After achieving whole cell configuration, cells were monitored for 90 s to assess stability and then washed with External Solution for 66 s. The voltage protocol described above was then applied to the cells every 12 s throughout the procedure. Only stable cells with recording parameters above threshold (see Quality Control section) were allowed to enter the drug addition procedure. External solution containing 0.1% DMSO (vehicle) was applied to the cells to establish a baseline. After allowing the current to stabilize for 3 to 5 min, test articles were applied. Test article solutions were added to cells in 4 separate additions. Cells were kept in test solution until effect of the test article reached steady state, to a maximum of 12 min. Next, 1 μM cisapride (positive control) was added. Finally, washout with External Solution was performed until the recovery current reached a steady state.

Data Analysis: Data analysis was performed using DataXpress (Axon Instruments), Clampfit (Axon Instruments) and Origin (Originlab Corporation) software.

Quality Control: Data included in the report originated from experiments that satisfied all of the following criteria: a) Recording Parameters: membrane resistance (Rm): >200 MΩ; access resistance (Ra): <15MΩ; tail current amplitude: >150pA; b) Pharmacological Parameters: 1 μM cisapride: >95% inhibition.

Following these procedures, several compounds provided by the present invention are found to lack substantial cross reactivity with hERG channel.

Example 2

Treatment of HCV-Infected Patients with Clemizole and Clemizole in Combination with Ribavirin and/or Interferon To demonstrate the in vivo efficacy of clemizole in treating patients infected with HCV, 3 patients chronically-infected with HCV (genotype 4) were treated with clemizole 100 milligrams, p.o. BID for 8 weeks. After the first four weeks of clemizole monotherapy, pegylated interferon (180 micrograms Pegasus (Roche) s.q. per week) was added. Thereafter the patients are continued on the pegylated interferon and nitazoxanide (500 mg. (Romark) p.o. BID. The baseline characteristics and serial HCV viral loads in the serum decreased significantly on treatment with clemizole alone, becoming completely, or nearly, undetectable after 4 weeks of treatment. These results demonstrate that clemizole is effective in treating patients infected with HCV.

A second study (CLEAN-1) was conducted in HCV genotypes 1 and 2-infected patients, in which clemizole was administered 100 mg po BID for one month, after which the patients were treated with standard of care (SOC; interferon with ribavirin). Ten patients were enrolled (7 genotype 1b and 3 genotype 2a), and while no reduction of viral load was observed after one month of therapy, ALT levels did decline over the treatment period. PK analysis indicated that the plasma levels of clemizole were below the EC50 for both genotype 1 (>20 μM) and genotype 2 (8 μM) for the entire treatment period and theoretical levels of clemizole in the liver (estimated to be 100× blood levels) were below the EC50 for genotype 1b (>20 μM) at all times and below the EC50 for genotype 2a (EC50=8 μM) for about 60% of the dosing period. One patient (infected with genotype 2) was dosed at 200 mg BID, and viral loads did not decrease after one month of therapy.

A third study (CLEAN 1.5) was initiated in HCV genotype 4-infected patients, in which either (i) clemizole 100 mg po BID and placebo (the "clemizole arm", or (ii) clemizole 100 mg po BID and ribavirin 800-1200 mg po QD (weight based dosing) (the "clemizole/ribavirin arm", was administered for one month (28 days); and after the first month of treatment, all patients (both arms) received SOC (PEG Intron by Schering plus ribavirin 800-1200 mg, both weight based dosing) plus clemizole 100 mg po BID for one month. There were two patients treated in the clemizole arm and three patients in clemizole/ribavirin arm of the study. In the clemizole/ribavirin arm, the results were as follows: Patient 1 Viral Load at Day 1=170,000 IU/mL, Day 28=79,000 IU/mL, Day 56=undetectable; Patient 2 Viral Load at Day 1=35,000 IU/mL, Day 28=2,000 IU/mL, Day 56=undetectable; Patient 3 Viral Load at Day 1=1,400,000 IU/mL, Day 28=13,000 IU/mL, Day 56=undetectable. In the clemizole only arm, the results were as follows: Patient 1 Viral Load at Day 1=330,000 IU/mL, Day 28=530,000 IU/mL, Day 56=undetectable; Patient 2 Viral Load at Day 1=150,000 IU/mL, Day 28=480,000 IU/mL, Day 56=undetectable. These results demonstrate that, in these HCV genotype 4 patients, while clemizole alone at the dose administered was not effective to reduce viral load after 28 days of treatment, coadministration of clemizole and ribavirin was effective, and triple therapy with clemizole, ribavirin, and interferon alpha was most effective. The efficacy results for triple therapy demonstrate that this therapy should be efficacious against any HCV genotype. In addition to these results, the ALT level of one patient in the clemizole/ribavirin arm whose ALT level was above the upper limit of normal (normal is 5-60 IU/L) decreased into the normal range after one month of treatment.

A fourth study was initiated in HCV genotype 1-infected patients, in which patients received either (i) clemizole 100 mg po BID and PEG-interferon (Pegasys by Roche, given per the manufacturers recommended dosing) for two months, followed by clemizole 100 mg po BID plus SOC (Pegasys by Roche plus weight-based ribavirin) ("triple therapy") for one month, or (ii) clemizole 100 mg po BID and ribavirin 800-1200 mg po QD (per manufacturers recommended weight based dosing) was administered for one month, followed by clemizole 200 mg po BID and ribavirin 800-1200 mg po QD (per manufacturers recommended weight based dosing) administered for one month, followed by SOC (Pegasys by Roche plus weight-based ribavirin) plus clemizole 200 mg BID. This study is ongoing, but in the 4 patients initially treated in the clemizole plus ribavirin arm, while viral loads did not decrease significantly, ALT levels in the two patients whose levels were above the upper limit of normal range (defined as 5-60 IU/L) decreased to within the normal range by the end of the first month of treatment. In the clemizole plus Pegasys arm, two of the four patients treated exhibited significant decreases in viral load (6.4 Log 10 IU/ml to 3.1 Log 10 IU/ml and 5.1 Log 10 IU/ml to undetectable), and the ALT levels in the one patient whose levels were above the upper limit of normal range decreased to within the normal range by Day 28.

Collectively, these results demonstrate that, while clemizole 100 mg po BID administration can be effective as single agent therapy, it is most effective against genotype 4, and it is more efficacious when administered with ribavirin and/or interferon. In addition, these results demonstrate that higher clemizole dosing, i.e., 200 mg po BID, 200 mg po TID, 300 mg po BID, 300 mg po TID, 400 mg po BID, 400 mg po TID, 500 mg po BID, and 500 mg po TID, alone and in combination with ribavirin and/or interferon, is more efficacious than 100 mg po BID administration, and that these higher doses should be administered to, e.g., genotype 1, genotype 2, and genotype 4-infected patients when clemizole is administered as single agent therapy.

Example 3

Chemical Synthesis

FIG. 4A of U.S. patent application publication no. 20100028299, and incorporated herein by reference, illustrates a method that can be used to produce 5-6-disubstituted clemizole analog compounds. In particular, the methods can produce Compound 1 (disubstituted with methyl groups at the 5 and 6 positions (FIG. 4B)) and Compound 2 (disubstituted with Cl groups at the 5 and 6 positions (FIG. 4C)). Such methods are generally useful, with appropriate modification, in preparing clemizole analogs of the invention.

The disubstituted clemizole can be synthesized by: condensation of 4,5-disubstituted-benzene-1,2-diamine (A) and 2-chloro-acetimidic acid ethyl ester (B) yields 2-chloromethyl-5,6-disubstituted-1H-benzoimidazole (C); followed by alkylation with 1-bromomethyl-4-chloro-benzene (D) affords 1-(4-chloro-benzyl)-2-chloromethyl-5,6-disubstituted-1H-benzoimidazole (E); and the final alkylation of 1-(4-chloro-benzyl)-2-chloromethyl-5,6-disubstituted-1H-benzoimidazole (E) with pyrrolidine yields the 5,6-disubstituted Clemizole (1-(4-Chloro-benzyl)-5,6-disubstituted-2-pyrrolidin-1-ylmethyl-1H-benzoimidazole) (G).

Synthetic Method 1. {1-[1'-(4-Chloro-benzyl)-1H-benzoimidazol-2-ylmethyl]-pyrrolidin-2-yl}-(S)-methanol

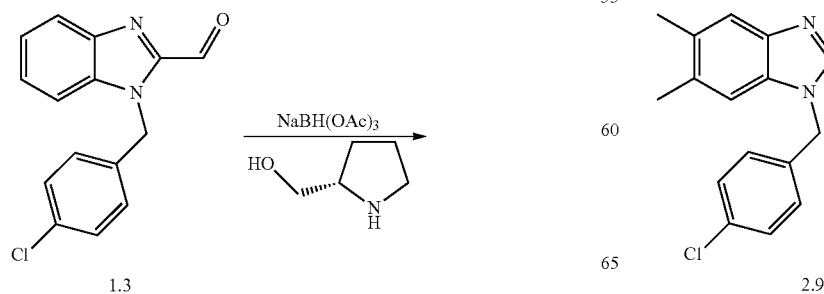

1.3

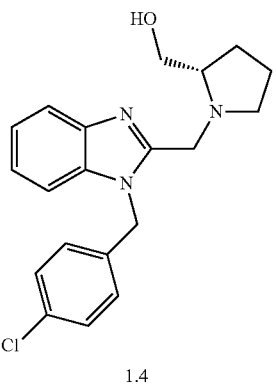

1.4

To a solution of 1-(4-chlorobenzyl)-1H-benzimidazole-2-carbaldehyde 1.3 (0.050 g, 0.18 mmol,) and (S)-(+)-2-pyrroidine-methanol (0.22 g, 0.20 mmol) in $CH_2Cl_2$ (10 mL) was added 1 drop AcOH and $NaBH(OAc)_3$ (0.50 g, 0.24 mmol). After stirring for 30 min, the reaction solution was diluted with $CH_2Cl_2$ (5 mL) and washed with aqueous saturated $NaHCO_3$ (2×5 mL). The organic layer was dried with $Na_2SO_4$ and concentrated in vacuo. The crude residue was purified by reverse phase preparative HPLC to provide the title compound.

Synthetic Method 2. {1-[1-(4-Chloro-benzyl)-5,6-dimethyl-1H-benzoimidazol-2-ylmethyl]-pyrrolidin-2-yl}-methanol

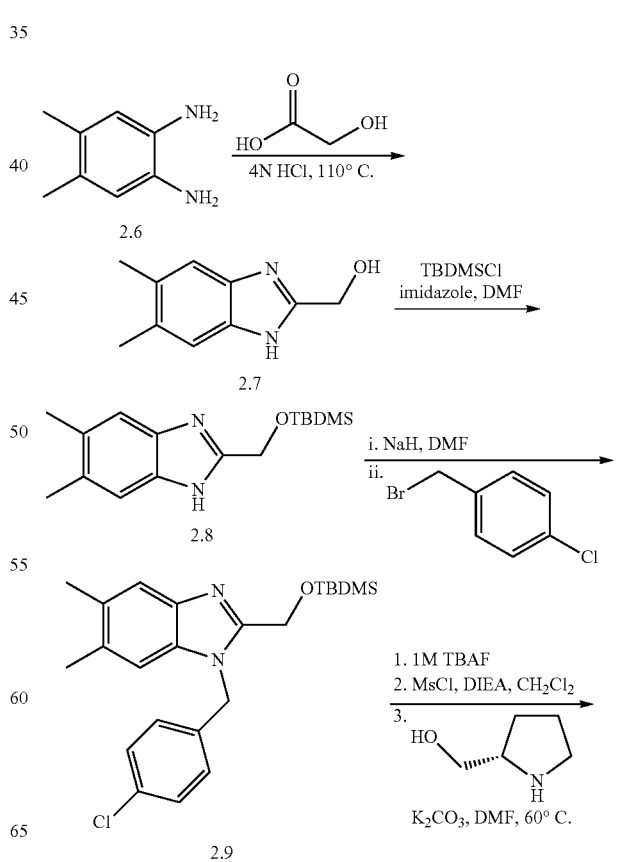

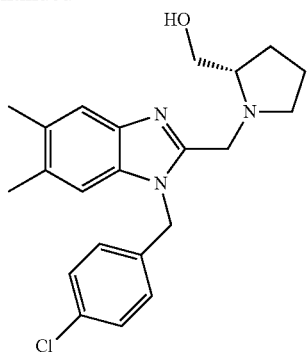

2.10

To a solution of 4,5-dimethyl-1,2-phenylenediamine 2.6 (1.5 g, 11 mmol) in 4 N HCl (60 mL) was added glycolic acid (2.5 g, 33 mmol). After heating at 110° C. for 3 h, the solution was cooled to room temperature and basified with solid NaOH until basic by pH paper. The resulting precipitate was filtered and washed with water to provide 2.7 which was used without further purification.

To a solution of 2.7 (6.7 g, 38 mmol) in DMF (125 mL) was added TBDMSCl (6.3 g, 42 mmol) and imidazole (2.9 g, 42 mmol). After stirring for 6 h, the reaction solution was diluted with EtOAc (100 mL) and washed with water (2×50 mL). The aqueous layers were back-extracted with EtOAc (3×50 mL). The combined organic layers were dried with $Na_2SO_4$ and concentrated in vacuo to provide crude silylated alcohol which was purified via silica gel chromatography (20% EtOAc in hexanes) to provide 2.8.

To a solution of 2.8 (1.59 g, 5.5 mmol) in DMF (20 mL) was added 60% NaH (0.204 g, 6.1 mmol). After stirring for 30 min, 4-chloro-benzylbromide (1.25 g, 6.1 mmol) was added and the solution was heated to 60° C. for 2 h. The reaction solution was diluted with EtOAc (100 mL) and washed with water (2×50 mL). The combined organic layers were dried with $Na_2SO_4$ and concentrated in vacuo to provide crude alkylated intermediate which was purified via silica gel chromatography (20% EtOAc in hexanes) to provide 2.9.

To a solution of 2.9 (0.750 g, 1.8 mmol) in THF (5 mL) was added 1 M THF (2 mL, 2 mmol). After stirring for 1 h, the solvent was removed in vacuo, and the crude residue was diluted with EtOAc (20 mL) and washed with water (2×10 mL). The organic layer was dried with $Na_2SO_4$ and concentrated in vacuo to provide the crude alcohol. To a solution of the crude alcohol (0.54 g, 1.8 mmol) in $CH_2Cl_2$ (10 mL) was added methanesulfonyl chloride (0.152 mL, 2.0 mmol) and DIEA (0.345 mL, 2.0 mmol). After stirring for 15 min, the solvent was removed in vacuo to provide crude mesylate. To a solution of the crude mesylate (0.10 g, 0.30 mmol) in DMF (5 mL) was added (S)-(+)-2-pyrroidine-methanol (0.061 g, 0.60 mmol) and $K_2CO_3$ (0.124 g, 0.90 mmol). After heating at 60° C. for 2 h, the reaction mixture was cooled to rt, diluted with MeOH (1 mL), filtered, and purified by reverse phase preparative HPLC to provide the title compound 2.10.

Synthetic Method 3. N-[1-(4-Chloro-benzyl)-5,6-dimethyl-1H-benzoimidazol-4-yl]-methanesulfonamide

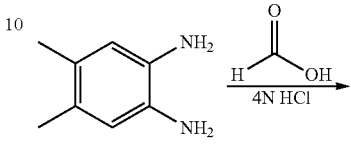

2.6

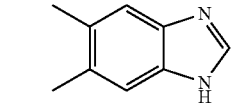

3.6

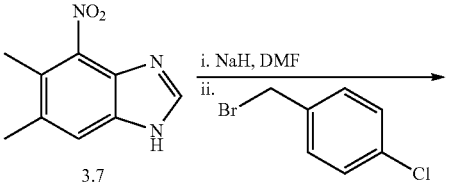

3.7

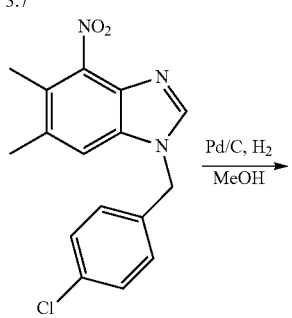

3.8

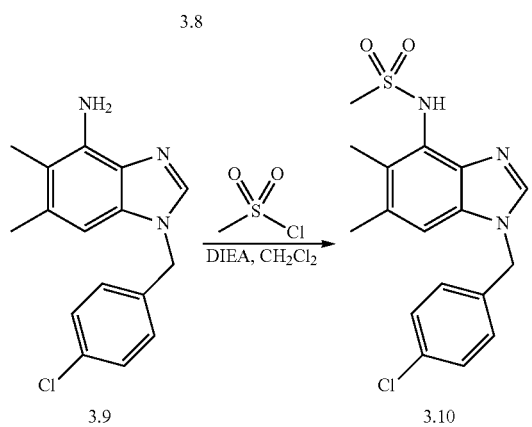

3.9     3.10

To a solution of 4,5-dimethyl-1,2-phenylenediamine 2.6 (3.0 g, 22 mmol) in 4 N HCl (30 mL) was added formic acid (3.0 g, 66 mmol). After heating at 110° C. for 3 h, the solution was cooled to rt and basified with solid NaOH until basic by pH paper. The resulting precipitate was filtered and washed with water (3×50 mL) to provide 3.6 which was used without further purification.

To a solution of 3.6 (0.474 g, 7.1 mmol) in 1:1 THF/$Et_2O$ (20 mL) at 0° C. was dropwise added 70% nitric acid (0.291 g, 7.1 mmol). After stirring for 1 h, the resulting white precipitate (nitric acid salt of 3.6) was filtered and washed with Et₂O. To a suspension of the nitric acid salt of 3.6 in CH₂Cl₂ at 0° C. was dropwise added concentrated H₂SO₄ (6 mL). After stirring for 1 h at 0° C., the reaction solution was slowly added to 10 mL of cold water and then basified with 28% NH₄OH solution until pH 10. The mixture was then extracted with CH₂Cl₂. The organic layer was dried with Na₂SO₄ and concentrated in vacuo to provide 3.7, which was used without further purification.

To a solution of 3.7 (0.8 g, 4.2 mmol) in DMF (15 mL) was added 60% NaH (0.218 g, 5.5 mmol). After stirring for 30 min, 4-chlorobenzylbromide (0.946 g, 4.6 mmol) was added and the solution was heated to 60° C. for 2 h. The solution was then cooled to rt, diluted with EtOAc (20 mL) and washed with water (3×10 mL). The organic layer was dried with Na₂SO₄ and concentrated in vacuo to provide 3.8.

To a solution of 3.8 (4.2 mmol) in MeOH (20 mL) was added 50% w/w palladium on carbon (0.200 g) in water. A balloon of hydrogen was then placed on the reaction flask and the reaction was stirred for 2 h. The reaction mixture was then filtered and washed with MeOH over a pad of Celite. The filtrate was concentrated in vacuo to provide 3.9.

To a solution of 3.9 (0.100 g, 0.3 mmol) in CH₂Cl₂ (10 mL) was added MSCl (0.086 mL, 0.4 mmol) and DIEA (0.069 mL, 0.4 mmol). After stirring for 15 min, the reaction solution was concentrated in vacuo to provide crude 3.10, which was purified by reverse-phase preparative HPLC to provide the title compound.

Synthetic Method 4. 1-(4-chlorobenzyl)-5,6-dimethyl-2-(2-(pyrrolidin-3-yl)ethyl)-1H-benzo[d]imidazole

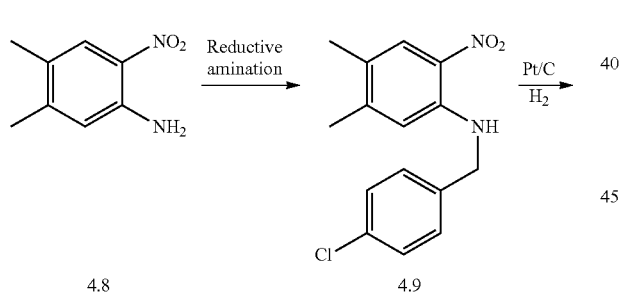

4.8    4.9

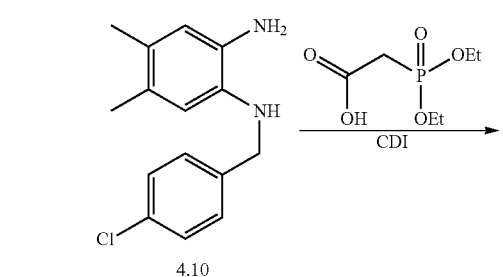

4.10

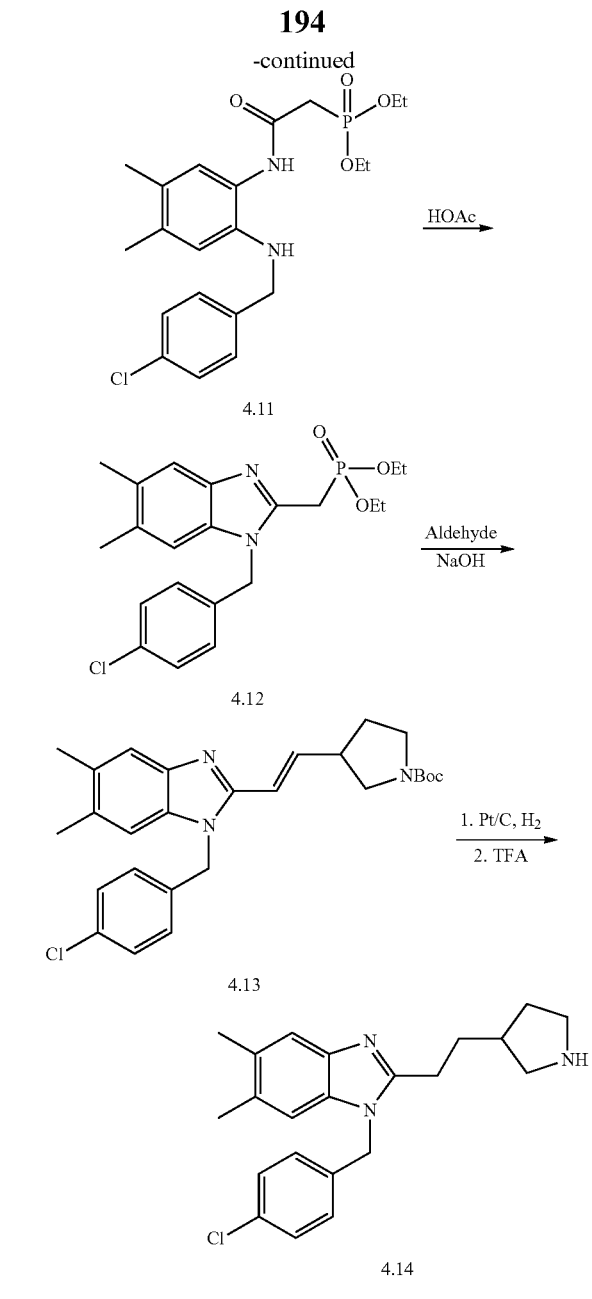

To a solution of 2-nitro-3,4-dimethylaniline 4.8 (8.3 g, 50 mmol) in 200 mL of dichloroethane was added a solution of p-chlorobenzealdehyde (7.7 g, 55 mmol). To this solution was added NaBH(OAc)₃ (12 g, 55 mmol) and 1 mL a 5 N NaOH aqueous solution. The organic layer was separated and was washed with 1 M HCl (100 mL) and then with brine (100 mL). The organic layer was dried over MgSO₄ and concentrated under reduced pressure. 200 mL of hexanes was added and the resulting solid was collected followed by recrystallization with 10% hexane in EtOAc to get a red solid (12.5 g, 86.3%).

To a solution of 4.9 (2.9 g, 10 mmol) in 100 mL of EtOH was added 140 mg of 5% Pt on carbon. After stirring at room temperature under H₂ atmosphere for three hours, the mixture was filtered and the filtrate was concentrated to provide a pale solid 4.10 (2.5 g, 96.2%).

To a solution of CDI (1.05 g, 6.5 mmol) in 20 mL of THF was added diethylphosphate acetic acid (1.27 g, 6.5 mmol). After stirring at 40° C. for 30 min, a solution of 4.10 (1.3 g, 5 mmol) in 20 mL of THF was added at 40° C. The resulting mixture was stirred at 30° C. for 2 h followed by concentration to give a brown residue which was purified through flash column chromatography on silica gel (100% EtOAc) to afford 4.11 (1.95 g, 89%).

A solution of 4.11 (0.438 g, 1 mmol) in 10 mL of toluene and 0.5 mL of HOAc was stirred at 120° C. for 10 h. The resulting mixture was concentrated and purified through flash column chromatography on silica gel (100% EtOAc) to provide 4.12 (0.380 g, 90%).

To a mixture of 4.12 (0.05 mg, 0.12 mmol) and aldehyde (2 eq) in 2 mL of THF was added 0.2 mL of 2 N NaOH. The resulting mixture was stirred at room temperature for 5 h and then diluted with 5 mL of EtOAc. The organic layer was washed with brine and dried with $MgSO_4$. Concentration and purification through preparative TLC or HPLC gave 4.13.

To a solution of 4.13 (0.1 mmol) in 5 mL of methanol was added 10 mg of 5% Pt on carbon. After stirring the mixture at rt under $H_2$ atmosphere for 4 h, filtration and concentration followed by treatment with TFA provided crude 4.14 which was purified by reverse-phase prepatory HPLC.

Synthetic Method 5. 1-(4-Chloro-benzyl)-6-methoxy-2-pyrrolidin-1-ylmethyl-1H-benzoimidazole

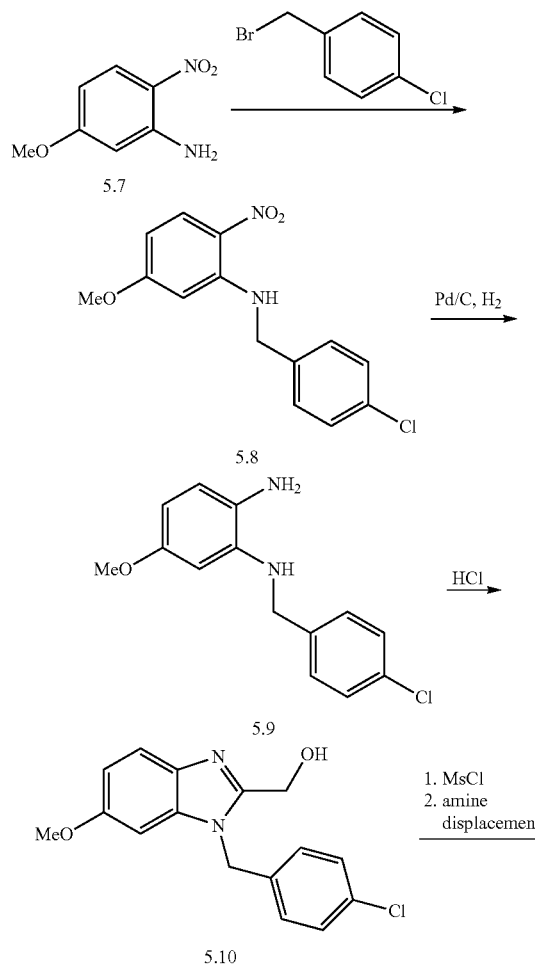

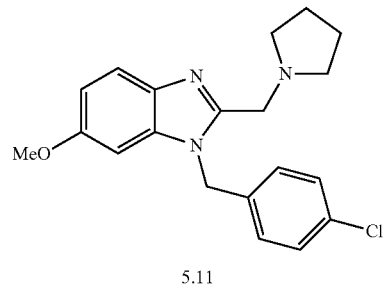

5.11

To a solution of nitroaniline 5.7 (1 eq) in DMF was added alkylator (1.1 eq), $K_2CO_3$ (3 eq). After stirring at 60° C. for 2 h, the reaction was diluted with EtOAc and washed with $H_2O$. The organic layer was dried and the solvent removed under reduced pressure to provide 5.8 which was purified by silica gel chromatography (30% EtOAc in hexanes).

To a solution of 5.8 (1 eq) in EtOH was added Pd/C (0.2 eq). The reaction was purged of $N_2$ and the reaction was stirred under a balloon of $H_2$ for 6 h. The reaction was filtered over a pad of Celite, and the filtrate was concentrated in vacuo to provide 5.9.

To a solution of 5.9 (1 eq) in 4 N HCl was added glycolic acid (3 eq). After stirring at 100° C. for 2 h, the reaction was basified with solid NaOH until pH 10. The resulting precipitate was filtered and washed with water to provide 5.10.

To a solution of 5.10 (1 eq) was added MsCl (1.5 eq) and DIEA (2 eq) in $CH_2Cl_2$. After 15 min, the solvent was removed in vacuo to provide the mesylate. To a solution of mesylate (1 eq) in DMF was added $K_2CO_3$ (3 eq) and heated to 60° C. for 3 h. The crude reaction was diluted with 1 mL MeOH and then directly purified by reverse-phase HPLC to provide 5.11.

Synthetic Method 6

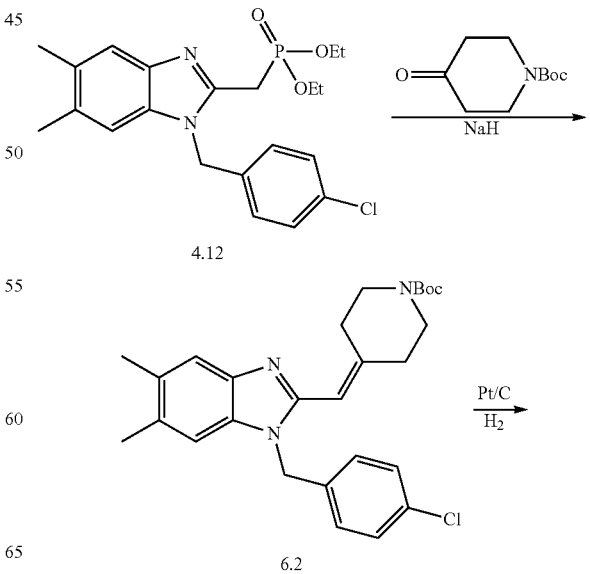

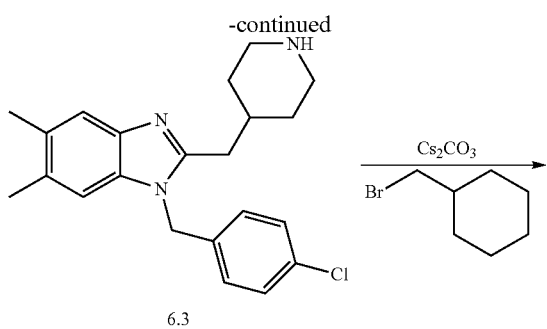

6.3

6.4

To a mixture of 4.12 and Boc-piperidinone (2 eq) in 2 mL of THF was added 0.2 mL of 2 N NaOH. The resulting mixture was stirred at room temperature for 5 h and then diluted with 5 mL of EtOAc. The organic layer was washed with brine and dried with $MgSO_4$. Concentration and purification through preparative TLC or HPLC gave 6.2.

To a solution of 6.2 (0.1 mmol) in 5 mL of methanol was added 10 mg of 5% Pt on carbon. After stirring the mixture at rt under $H_2$ atmosphere for 4 h, filtration and concentration followed by treatment with TFA provided crude 6.3 which was purified by reverse-phase prepatory HPLC. To a solution of 6.3 in DMF was added $Cs_2CO_3$, (3 eq) followed by (bromomethyl)cyclohexane (1.1 eq). After heating at 50° C. for 2 h, the crude reaction was diluted with MeOH and then directly purified by reverse-phase HPLC to provide 6.4.

Example 4

Demonstration of Antiviral Activity

This Example presents the results of testing illustrative compounds of the invention in the assays described in Example 1. The compounds are divided into two tables: Table A presents "1b Active Analogs"; and Table B presents "Clemizole Like Analogs". Each of these categories is discussed below.

Table A presents results for compounds that demonstrate significant activity against HCV in the 1b replicon assay (EC50 under 25 micromolar). Because clemizole does not show significant activity in this assay, the compounds in Table A should be more effective than clemizole against most HCV genotypes and at lower doses as compared to clemizole used in single agent therapy. In the 1b replicon assay, test compounds were tested at 3-fold serial dilutions from concentrations of 25 μM to 0.001 μM. The results are reported as micromolar activity against inhibition of 50% of replication of the 1b replicon (EC50). A high value of >25 μM means that >25 μM of test compound is required to inhibit 50% of replication of the 1b replicon. A low value of 1 μM means that 1 μM of test compound is required to inhibit 50% of replication of the 1b replicon. Thus, lower EC50 values correspond to higher potency. To illustrate, see compound EBP933 from Table A, which shows for this assay an EC50 value of 1.8 μM, indicating that this compound is a relatively potent inhibitor against 1b replicon replication. In addition, Table A lists only compounds with test results demonstrating cell viability >10 μM and activity in 1b replicon assay of <10 μM. Compounds were tested for cell toxicity at 3-fold serial dilutions from concentrations of 25 μM to 0.001 μM. The results are reported as micromolar activity. A high value of >25 μM indicates that no toxicity was observed at 25 μM.

In addition, activity against hERG potassium channel was tested on representative compounds. In this assay, the results are reported as micromolar activity against inhibition of hERG channel repolarization activity. A low value of <1 μM means that <1 μM of compound is required to inhibit 50% of hERG channel activity. A high value of >10 μM means that >10 μM of compound is required to inhibit 50% of hERG channel activity. To illustrate, see compound EBP467 in Table A, which shows for this assay a value of 1.1 nM, indicating that plasma concentrations of at least 1 μM would likely be required to cause potential QT prolongation in humans. Compounds having a structure similar to that of EBP467 (compounds that contain, in R2, a C-attached heterocycle where the heterocycle is nitrogen, and the nitrogen is optionally substituted with alkyl, cycloalkyl, amide, sulfonamide or the like) should have a similar activity in this assay. To illustrate further, compound EBP461 in Table A, which shows for this assay a value of 8.8 μM, indicating that a much higher plasma concentration of 8 μM would be required to cause QT prolongation. Compounds having a structure similar to that of EBP461 (compounds that contain, in R2, a C-attached heteroaryl, aryl, cycloalkyl or heterocycle where heteroatom is acylated N) should have a similar activity in this assay. Finally, compound EBP714 in Table A, which shows for this assay a value of 10 μM, indicating that a much higher plasma concentration of 10 μM would be required to cause QT prolongation. Compounds having a structure similar to that of EBP714 (compounds that contain, in R2, a N-attached heterocycle with electron deficient substituents such as fluorine) would similarly show no activity in the hERG assay at 10 μM. Generally, compounds that show no or only low activity in the hERG assay are preferred.

TABLE A

1b Active Analogs

| Structure | Compound ID | 1b EC50 (μM) | Cell Viability EC50 (μM) | hERG IC50 (μM) |
|---|---|---|---|---|
| 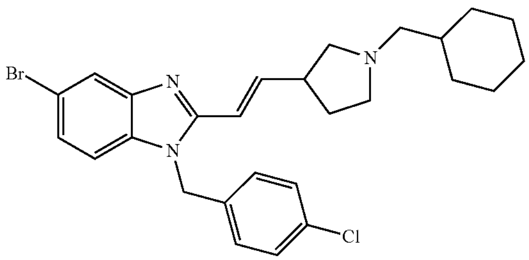 [SMILES: Clc1ccc(Cn2c(/C=C/C3CCN(CC4CCCCC4)C3)nc3cc(Br)ccc32)cc1] | EBP933 | 1.8 | >25 | 1.1 |
| 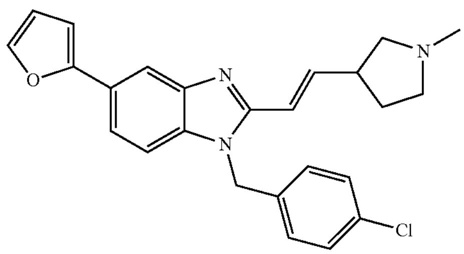 [SMILES: CN1CCC(/C=C/c2nc3cc(-c4ccco4)ccc3n2Cc2ccc(Cl)cc2)C1] | EBP801 | 2.1 | 23 | |
| 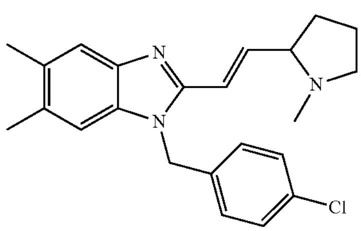 [SMILES: Cc1cc2nc(/C=C/C3CCCN3C)n(Cc3ccc(Cl)cc3)c2cc1C] | EBP470 | 2.5 | 9.2 | 0.98 |
| 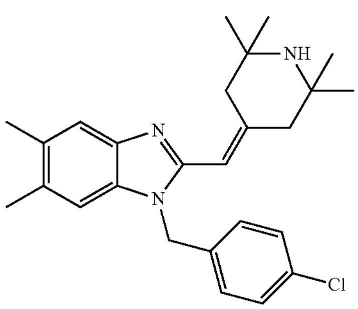 | EBP871 | 2.7 | | |
| 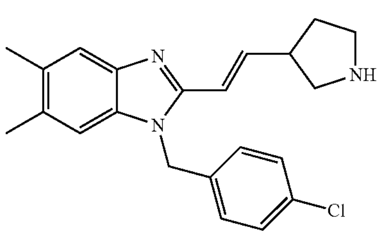 [SMILES: Cc1cc2nc(/C=C/C3CCNC3)n(Cc3ccc(Cl)cc3)c2cc1C] | EBP372 | 2.8 | >25 | 1.6 |

TABLE A-continued
1b Active Analogs
| Structure | Compound ID | 1b EC50 (μM) | Cell Viability EC50 (μM) | hERG IC50 (μM) |
|---|---|---|---|---|
| 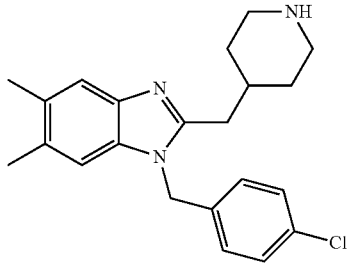 [SMILES: Cc1cc2nc(CC3CCNCC3)n(Cc3ccc(Cl)cc3)c2cc1C] | EBP467 | 3.2 | >25 | 1.1 |
| 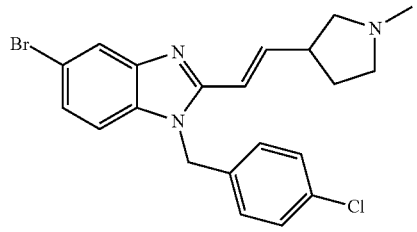 [SMILES: CN1CCC(/C=C/c2nc3cc(Br)ccc3n2Cc2ccc(Cl)cc2)C1] | EBP773 | 3.5 | >25 | |
| 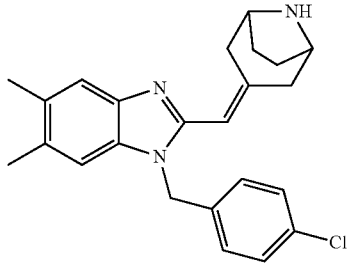 [SMILES: Cc1cc2nc(C=C3CC4CCC(C3)N4)n(Cc3ccc(Cl)cc3)c2cc1C] | EBP870 | 3.7 | 6.3 | |
| 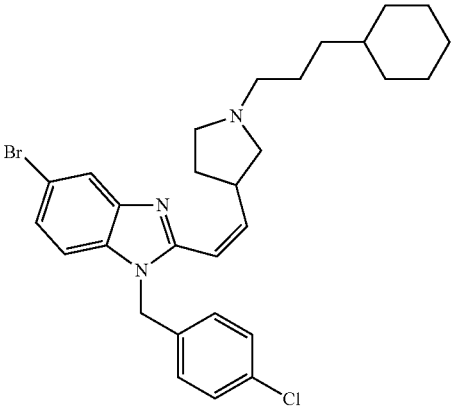 [SMILES: Clc1ccc(Cn2c(/C=C\C3CCN(CCCC4CCCCC4)C3)nc3cc(Br)ccc32)cc1] | EBP937 | 3.7 | >25 | |
| 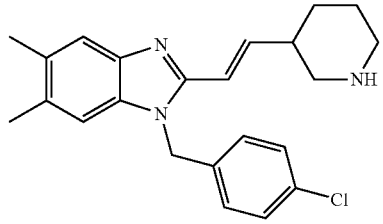 [SMILES: Cc1cc2nc(/C=C/C3CCCNC3)n(Cc3ccc(Cl)cc3)c2cc1C] | EBP378 | 4 | >25 | |

TABLE A-continued
1b Active Analogs
| Structure | Compound ID | 1b EC50 (μM) | Cell Viability EC50 (μM) | hERG IC50 (μM) |
|---|---|---|---|---|
| 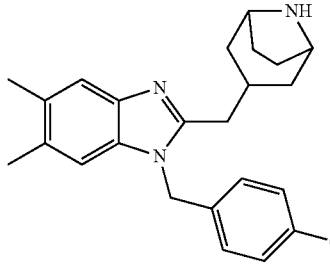 | EBP882 | 4.3 | | 4.3 |
| 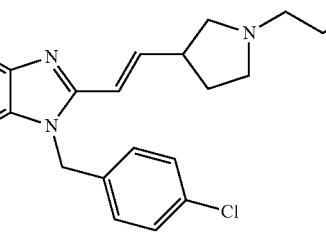 | EBP936 | 4.5 | 9.9 | |
| 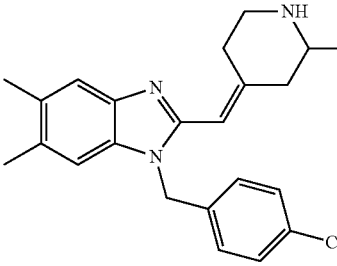 | EBP869 | 4.6 | >25 | |
| 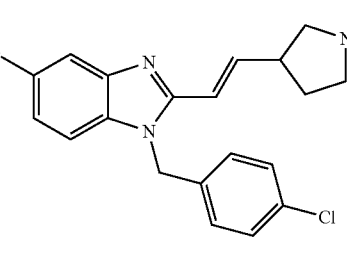 | EBP772 | 4.7 | >25 | |
| 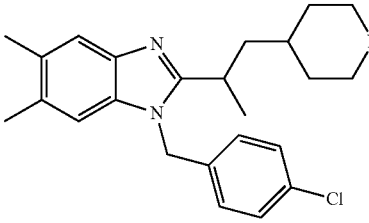 | EBP796 | 4.7 | >25 | |
| 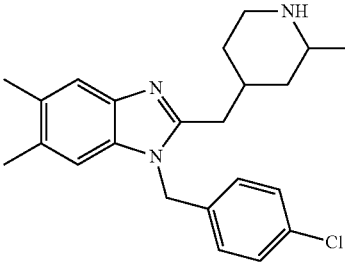 | EBP881 | 4.7 | | 0.58 |

TABLE A-continued
1b Active Analogs
| Structure | Compound ID | 1b EC50 (µM) | Cell Viability EC50 (µM) | hERG IC50 (µM) |
|---|---|---|---|---|
| 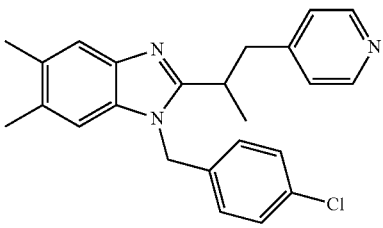 [SMILES: Cc1cc2nc(C(C)Cc3ccncc3)n(Cc3ccc(Cl)cc3)c2cc1C] | EBP461 | 4.9 | >25 | 8.8 |
| 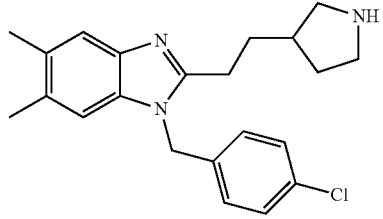 [SMILES: Cc1cc2nc(CCC3CCNC3)n(Cc3ccc(Cl)cc3)c2cc1C] | EBP463 | 4.9 | >25 | |
| 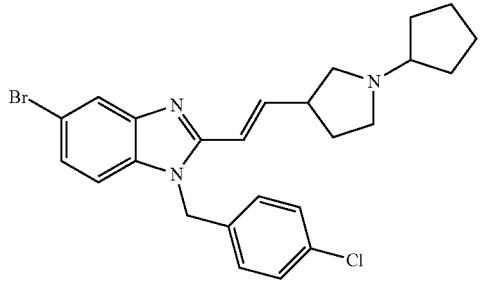 [SMILES: Clc1ccc(Cn2c(/C=C/C3CCN(C4CCCC4)C3)nc3cc(Br)ccc32)cc1] | EBP934 | 5 | >25 | |
| 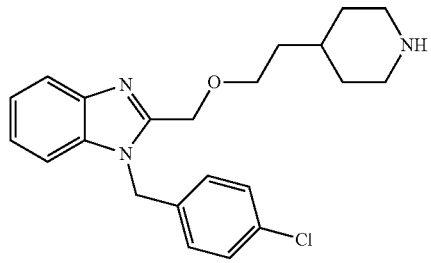 [SMILES: Clc1ccc(Cn2c(COCCC3CCNCC3)nc3ccccc32)cc1] | EBP995 | 5.3 | | |
| 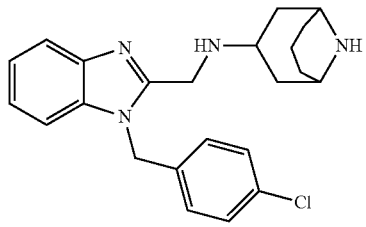 [SMILES: Clc1ccc(Cn2c(CNC3CC4CCCC(C3)N4)nc3ccccc32)cc1] | EBP926 | 5.4 | >25 | |
| 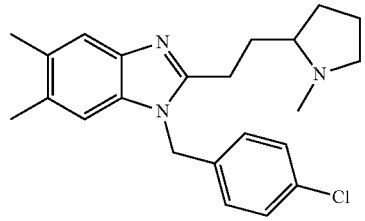 [SMILES: Cc1cc2nc(CCC3CCCN3C)n(Cc3ccc(Cl)cc3)c2cc1C] | EBP480 | 5.6 | >25 | |

TABLE A-continued
1b Active Analogs
| Structure | Compound ID | 1b EC50 (μM) | Cell Viability EC50 (μM) | hERG IC50 (μM) |
|---|---|---|---|---|
| 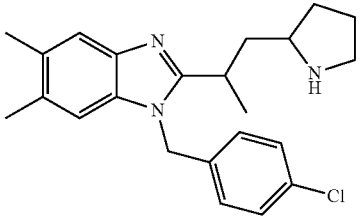 [SMILES: Cc1cc2nc(C(C)CC3CCCN3)n(Cc3ccc(Cl)cc3)c2cc1C] | EBP799 | 6 | >25 | |
| 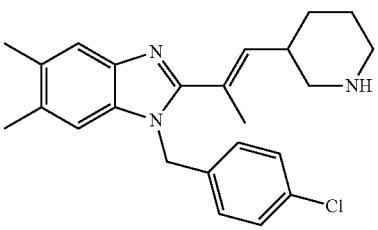 [SMILES: C/C(=C\C1CCCNC1)c1nc2cc(C)c(C)cc2n1Cc1ccc(Cl)cc1] | EBP797 | 6.3 | >25 | |
| 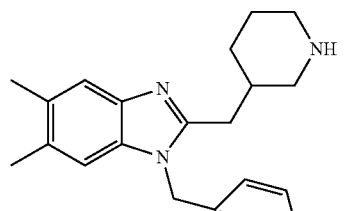 | EBP660 | 6.5 | >25 | 0.49 |
| 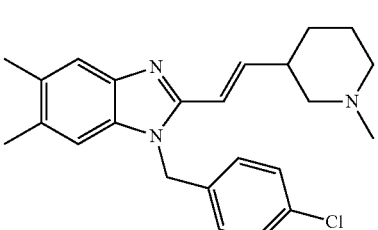 | EBP549 | 7.5 | >25 | |
| 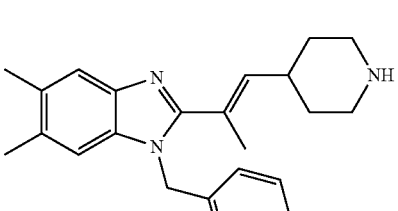 | EBP771 | 7.5 | >25 | |

TABLE A-continued

1b Active Analogs

| Structure | Compound ID | 1b EC50 (μM) | Cell Viability EC50 (μM) | hERG IC50 (μM) |
|---|---|---|---|---|
| 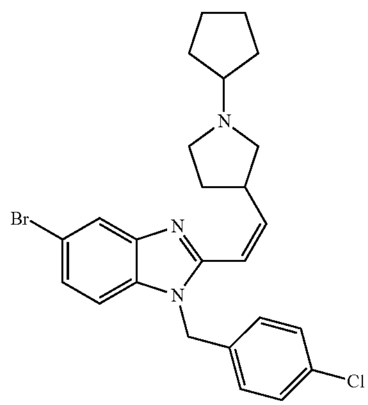 [SMILES: Clc1ccc(Cn2c(/C=C\C3CCN(C4CCCC4)C3)nc3cc(Br)ccc32)cc1] | EBP935 | 7.7 | >25 | |
| 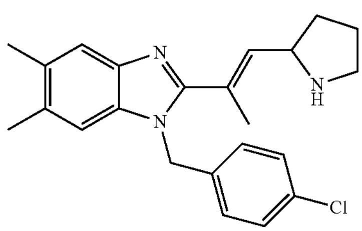 [SMILES: C/C(=C\C1CCCN1)c1nc2cc(C)c(C)cc2n1Cc1ccc(Cl)cc1] | EBP800 | 7.9 | >25 | |
| 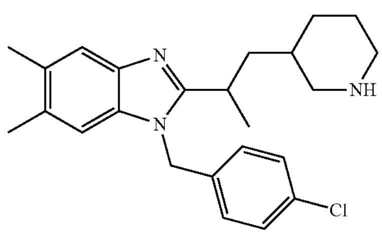 [SMILES: Cc1cc2nc(C(C)CC3CCCNC3)n(Cc3ccc(Cl)cc3)c2cc1C] | EBP847 | 7.9 | | |
| 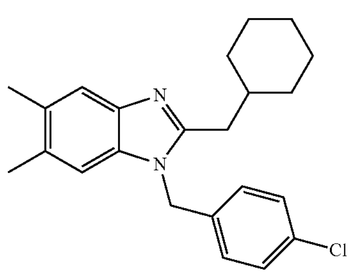 [SMILES: Cc1cc2nc(CC3CCCCC3)n(Cc3ccc(Cl)cc3)c2cc1C] | EBP468 | 8 | >25 | >10 |
| 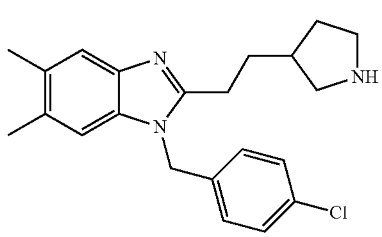 [SMILES: Cc1cc2nc(CCC3CCNC3)n(Cc3ccc(Cl)cc3)c2cc1C] | EBP553 | 8.1 | >25 | |

TABLE A-continued

1b Active Analogs

| Structure | Compound ID | 1b EC50 (μM) | Cell Viability EC50 (μM) | hERG IC50 (μM) |
|---|---|---|---|---|
| 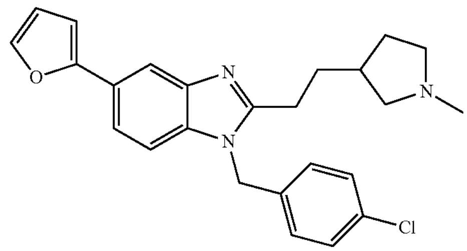 [SMILES: CN1CCC(CCc2nc3cc(-c4ccco4)ccc3n2Cc2ccc(Cl)cc2)C1] | EBP802 | 8.1 | 21 | |
| 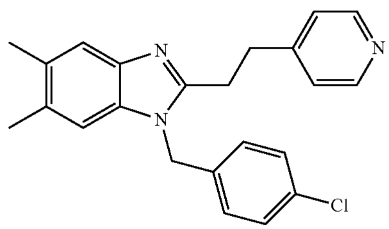 [SMILES: Cc1cc2nc(CCc3ccncc3)n(Cc3ccc(Cl)cc3)c2cc1C] | EBP417 | 8.1 | >25 | |
| 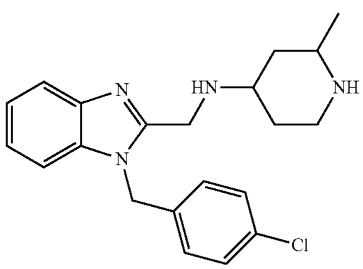 [SMILES: CC1CC(NCc2nc3ccccc3n2Cc2ccc(Cl)cc2)CCN1] | EBP809 | 8.3 | >25 | |
| 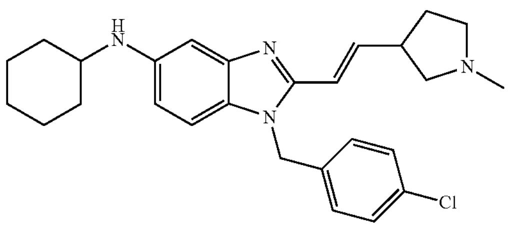 [SMILES: CN1CCC(/C=C/c2nc3cc(NC4CCCCC4)ccc3n2Cc2ccc(Cl)cc2)C1] | EBP848 | 8.4 | | |
| 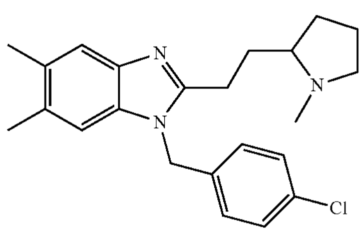 [SMILES: Cc1cc2nc(CCC3CCCN3C)n(Cc3ccc(Cl)cc3)c2cc1C] | EBP661 | 8.7 | >25 | 0.26 |
| 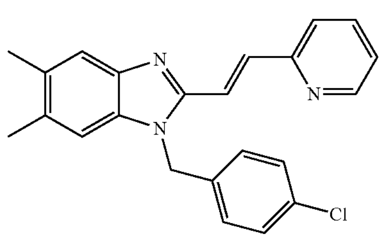 [SMILES: Cc1cc2nc(/C=C/c3ccccn3)n(Cc3ccc(Cl)cc3)c2cc1C] | EBP375 | 8.7 | >25 | |

TABLE A-continued
1b Active Analogs
| Structure | Compound ID | 1b EC50 (μM) | Cell Viability EC50 (μM) | hERG IC50 (μM) |
|---|---|---|---|---|
| 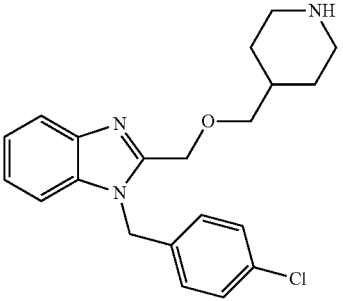 [SMILES: Clc1ccc(Cn2c(COCC3CCNCC3)nc3ccccc32)cc1] | EBP977 | 8.9 | | |
| 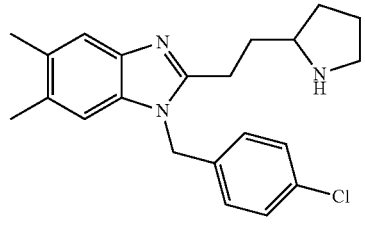 [SMILES: Cc1cc2nc(CCC3CCCN3)n(Cc3ccc(Cl)cc3)c2cc1C] | EBP418 | 9.1 | >25 | |
| 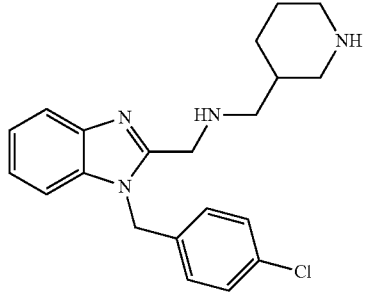 [SMILES: Clc1ccc(Cn2c(CNCC3CCCNC3)nc3ccccc32)cc1] | EBP928 | 9.2 | >25 | |
| 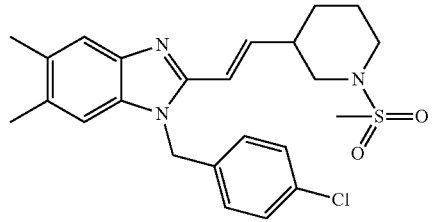 [SMILES: Cc1cc2nc(/C=C/C3CCCN(S(C)(=O)=O)C3)n(Cc3ccc(Cl)cc3)c2cc1C] | EBP550 | 9.3 | >25 | |
| 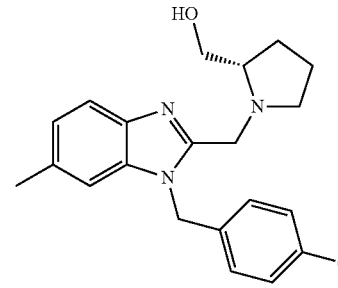 | EBP426 | 10 | >25 | |

TABLE A-continued

| 1b Active Analogs | | | | |
|---|---|---|---|---|
| Structure | Compound ID | 1b EC50 (μM) | Cell Viability EC50 (μM) | hERG IC50 (μM) |
| | EBP805 | 11 | >25 | |
| | EBP978 | 12 | | |
| | EBP558 | 11 | >25 | |

Table B presents results for Clemizole Like Analogs, i.e., compounds that do not demonstrate significant activity against HCV in the 1b replicon assay but do demonstrate significant activity against HCV in the 2a infectious clone assay. Thus, these compounds should demonstrate potency against HCV similar to clemizole. In the 2a infectious clone assay, test compounds are tested at two concentrations of 5 μM and 10 μM. Only the results from testing at 5 μM are shown in Table B. The results are reported as % replication activity of a control sample with no test compound present. A low value of 40% indicates that, at 5 μM of test compound, 40% of replication activity remains, indicative of a compound of high potency. A high value of 90% indicates that, at 5 μM of test compound, 90% of replication activity remains, indicative of a compound of low potency. In addition, Table B lists only compounds with test results demonstrating cell viability levels of >85% at 5 μM and >80% at 10 μM, and activity in 2a infectious clone assay of <90%. Compounds were tested for cell toxicity at concentrations of 5 μM and 10 μM. The results are reported as % cell survival. High values of >85% at 5 μM and >80% at 10 μM indicate that at 5 μM, greater than 85% of cells are viable and at 10 μM, greater than 80% of cells are viable.

TABLE B

| Clemizole Like Analogs | | | | |
|---|---|---|---|---|
| Structure | Eiger ID | 2a % activity @ 5 μM | 2a Cell Viability @ 5, 10 μM | hERG IC50 (μM) |
| | EBP475 | 38 | 100, 95 | >10 |

TABLE B-continued

Clemizole Like Analogs

| Structure | Eiger ID | 2a % activity @ 5 μM | 2a Cell Viability @ 5, 10 μM | hERG IC50 (μM) |
|---|---|---|---|---|
| (structure) | EBP315 | 39 | 86, 81 | <1 |
| (structure) | EBP462 | 45 | 95, 91 | >10 |
| (structure) | EBP325 | 49 | >100, >100 | >10 |
| (structure) | EBP003 | 50 | 85, 100 | 7 |
| (structure) | EBP059 | 50 | 86, 79 | |
| (structure) | EBP106 | 50 | 93, 83 | 5 |

TABLE B-continued

Clemizole Like Analogs

| Structure | Eiger ID | 2a % activity @ 5 µM | 2a Cell Viability @ 5, 10 µM | hERG IC50 (µM) |
|---|---|---|---|---|
| 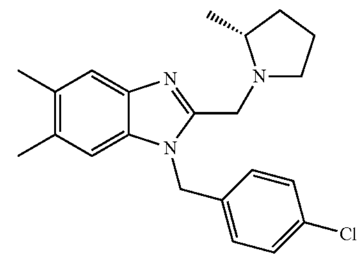 [SMILES: Cc1cc2nc(CN3CCC[C@H]3C)n(Cc3ccc(Cl)cc3)c2cc1C] | EBP273 | 50 | 95, 82 | |
| 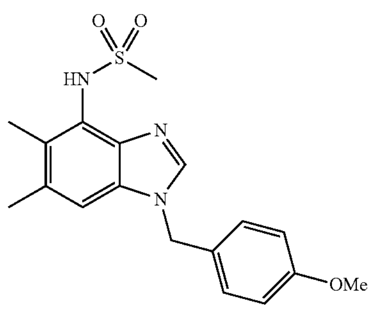 [SMILES: COc1ccc(Cn2cnc3c(NS(C)(=O)=O)c(C)c(C)cc32)cc1] | EBP304 | 53 | >100, 93 | |
| 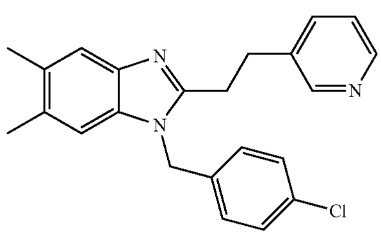 [SMILES: Cc1cc2nc(CCc3cccnc3)n(Cc3ccc(Cl)cc3)c2cc1C] | EBP416 | 53 | 100, 91 | |
| 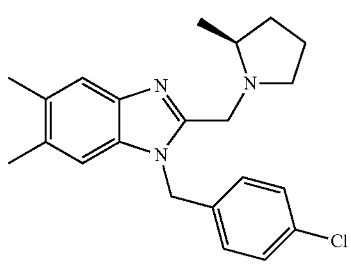 [SMILES: Cc1cc2nc(CN3CCC[C@@H]3C)n(Cc3ccc(Cl)cc3)c2cc1C] | EBP272 | 56 | 98, 69 | |
| 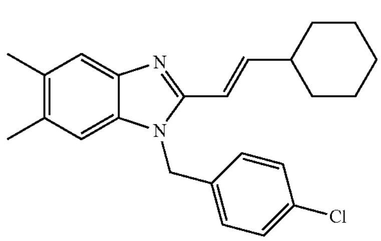 [SMILES: Cc1cc2nc(/C=C/C3CCCCC3)n(Cc3ccc(Cl)cc3)c2cc1C] | EBP321 | 56 | >100, >100 | |
| 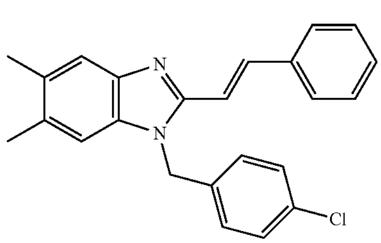 [SMILES: Cc1cc2nc(/C=C/c3ccccc3)n(Cc3ccc(Cl)cc3)c2cc1C] | EBP101 | 57 | >100, 95 | 4 |

TABLE B-continued

| Clemizole Like Analogs | | | | |
|---|---|---|---|---|
| Structure | Eiger ID | 2a % activity @ 5 μM | 2a Cell Viability @ 5, 10 μM | hERG IC50 (μM) |
| | EBP299 | 57 | 85, 81 | |
| | EBP062 | 59 | 89, 80 | |
| | EBP317 | 59 | 96, 82 | |
| | EBP476 | 60 | 95, 76 | |
| | EBP001 | 70 | 100, 90 | <1 |

TABLE B-continued

Clemizole Like Analogs

| Structure | Eiger ID | 2a % activity @ 5 μM | 2a Cell Viability @ 5, 10 μM | hERG IC50 (μM) |
|---|---|---|---|---|
| 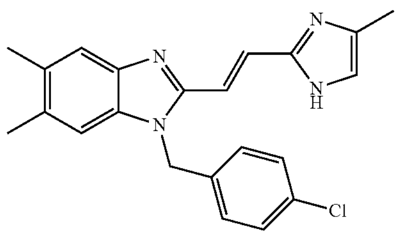 | EBP362 | 71 | 100, 100 | |
| 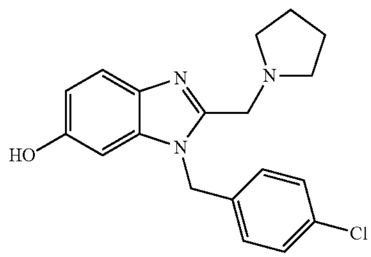 [SMILES: Oc1ccc2nc(CN3CCCC3)n(Cc3ccc(Cl)cc3)c2c1] | EBP483 | 75 | 90, 80 | |
| 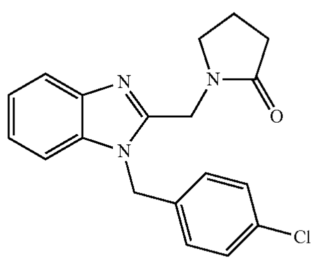 [SMILES: O=C1CCCN1Cc1nc2ccccc2n1Cc1ccc(Cl)cc1] | EBP144 | 77 | >100, >100 | 7 |
| 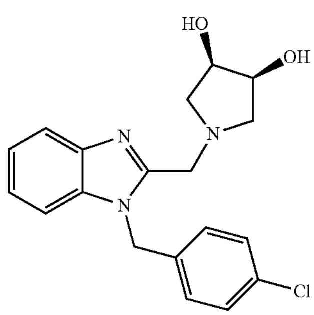 [SMILES: O[C@@H]1CN(Cc2nc3ccccc3n2Cc2ccc(Cl)cc2)C[C@@H]1O] | EBP412 | 81 | 100, 100 | |
| 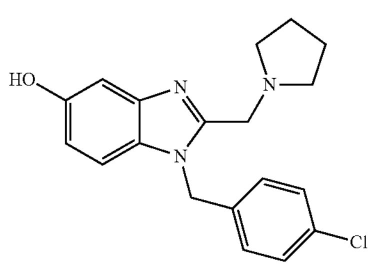 [SMILES: Oc1ccc2c(c1)nc(CN1CCCC1)n2Cc1ccc(Cl)cc1] | EBP366 | 89 | 100, 100 | |

TABLE B-continued

Clemizole Like Analogs

| Structure | Eiger ID | 2a % activity @ 5 μM | 2a Cell Viability @ 5, 10 μM | hERG IC50 (μM) |
|---|---|---|---|---|
| 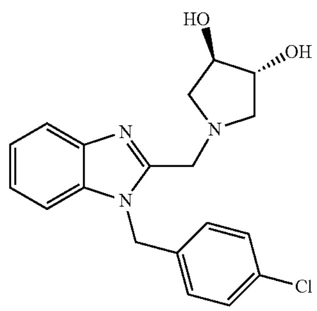 [SMILES: O[C@@H]1CN(Cc2nc3ccccc3n2Cc2ccc(Cl)cc2)C[C@H]1O] | EBP491 | 90 | 94, 100 | |
| 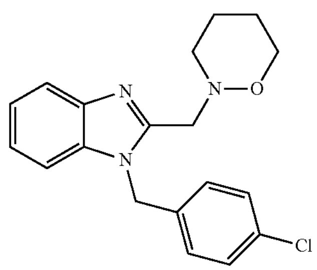 [SMILES: Clc1ccc(Cn2c(CN3CCCCO3)nc3ccccc32)cc1] | EBP481 | 93 | 91, 87 | |
| 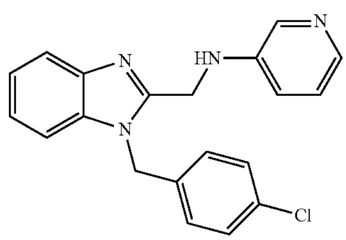 [SMILES: Clc1ccc(Cn2c(CNc3cccnc3)nc3ccccc32)cc1] | EBP804 | | | |
| 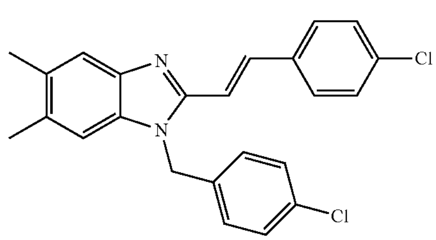 [SMILES: Cc1cc2nc(/C=C/c3ccc(Cl)cc3)n(Cc3ccc(Cl)cc3)c2cc1C] | EBP344 | | | |
| 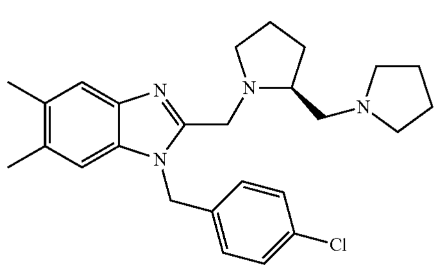 [SMILES: Cc1cc2nc(CN3CCC[C@H]3CN3CCCC3)n(Cc3ccc(Cl)cc3)c2cc1C] | EBP232 | 0.39 | ND | |

TABLE B-continued
Clemizole Like Analogs
| Structure | Eiger ID | 2a % activity @ 5 μM | 2a Cell Viability @ 5, 10 μM | hERG IC50 (μM) |
|---|---|---|---|---|
| 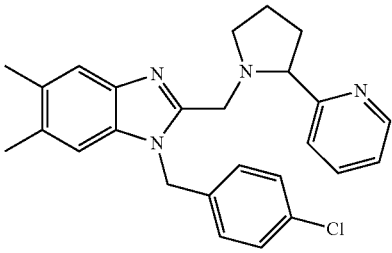 [SMILES: Cc1cc2nc(CN3CCCC3c3ccccn3)n(Cc3ccc(Cl)cc3)c2cc1C] | EBP233 | 1.9 | ND | |
| 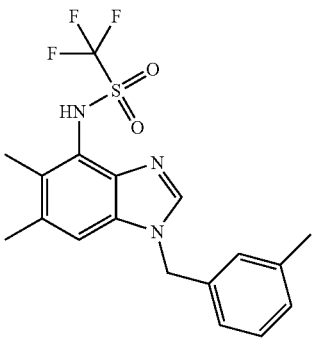 | EBP170 | 33 | 94, 97 | |
| 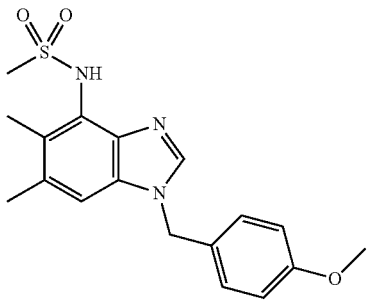 | EBP103 | 35 | 100, 100 | >30 |
| 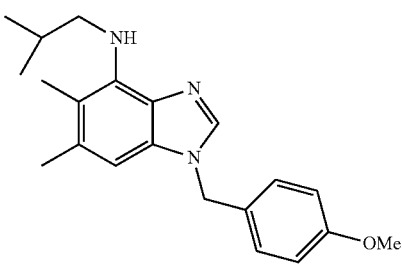 [SMILES: COc1ccc(Cn2cnc3c(NCC(C)C)c(C)c(C)cc32)cc1] | EBP308 | 45 | 93, 82 | |
| 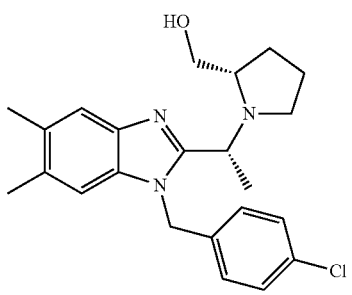 [SMILES: Cc1cc2nc([C@@H](C)N3CCC[C@H]3CO)n(Cc3ccc(Cl)cc3)c2cc1C] | EBP267 | 46 | 88, 73 | |

TABLE B-continued

Clemizole Like Analogs

| Structure | Eiger ID | 2a % activity @ 5 μM | 2a Cell Viability @ 5, 10 μM | hERG IC50 (μM) |
|---|---|---|---|---|
| (structure) | EBP307 | 48 | 97, 71 | |
| (structure) | EBP231 | 49 | >100, 89 | |
| (structure) | EBP156 | 57 | 89, 93 | |
| (structure) | EBP423 | 59 | 98, 71 | |
| (structure) | EBP197 | 60 | 96, 95 | |

TABLE B-continued

| Clemizole Like Analogs | | | | |
|---|---|---|---|---|
| Structure | Eiger ID | 2a % activity @ 5 μM | 2a Cell Viability @ 5, 10 μM | hERG IC50 (μM) |
| | EBP108 | 61 | 100, 96 | >30 |
| | EBP271 | 61 | 100, 90 | 1.3 |
| | EBP017 | 62 | 81, 88 | |
| | EBP370 | 62 | 93, 78 | |
| | EBP196 | 63 | >100, 98 | |
| | EBP207 | 63 | >100, 88 | |

TABLE B-continued

Clemizole Like Analogs

| Structure | Eiger ID | 2a % activity @ 5 μM | 2a Cell Viability @ 5, 10 μM | hERG IC50 (μM) |
|---|---|---|---|---|
| (5,6-dimethylbenzimidazole, N-(4-chlorobenzyl), 2-(1-(2-hydroxymethyl-pyrrolidinyl)ethyl)) | EBP265 | 63 | 94, 75 | |
| (5-methylbenzimidazole, N-(4-chlorobenzyl), 2-((2-hydroxymethyl-pyrrolidinyl)methyl)) | EBP318 | 63 | 93, 77 | |
| (5-methoxybenzimidazole, N-(4-chlorobenzyl)) | EBP209 | 64 | >100, 85 | |
| (5,6-dimethoxybenzimidazole, N-(4-chlorobenzyl)) | EBP210 | 65 | >100, 90 | |
| (5-methyl-6-chlorobenzimidazole, N-(4-chlorobenzyl)) | EBP218 | 65 | >100, 88 | |
| (5,6-dimethylbenzimidazole, N-(4-chlorobenzyl), 2-(pyrrolidinylmethyl)) | EBP126 | 65 | >100, 77 | |

TABLE B-continued
Clemizole Like Analogs
| Structure | Eiger ID | 2a % activity @ 5 μM | 2a Cell Viability @ 5, 10 μM | hERG IC50 (μM) |
|---|---|---|---|---|
| 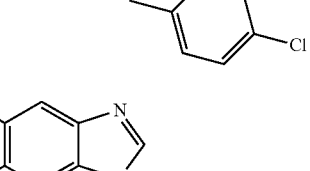 | EBP428 | 65 | 100, 100 | |
| 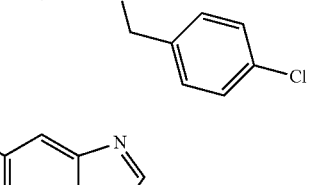 | EBP268 | 66 | 86, 74 | |
| 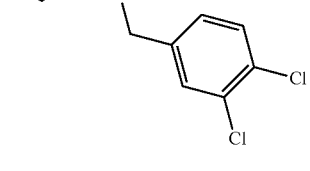 | EBP048 | 67 | 100, 89 | |
| 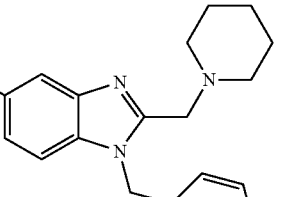 | EBP314 | 67 | 97, 84 | |
| 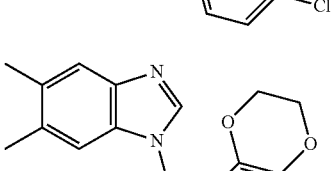 | EBP113 | 68 | 92, 90 | |
| 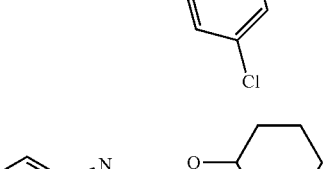 | EBP324 | 68 | >100, >100 | |

TABLE B-continued

Clemizole Like Analogs

| Structure | Eiger ID | 2a % activity @ 5 μM | 2a Cell Viability @ 5, 10 μM | hERG IC50 (μM) |
|---|---|---|---|---|
| (structure) | EBP346 | 68 | 103, 99 | |
| (structure) | EBP364 | 68 | 100, 100 | |
| (structure) | EBP411 | 68 | 93, 99 | |
| (structure) | EBP137 | 69 | >100, >100 | |
| (structure) | EBP165 | 69 | >100, >100 | |

TABLE B-continued

Clemizole Like Analogs

| Structure | Eiger ID | 2a % activity @ 5 µM | 2a Cell Viability @ 5, 10 µM | hERG IC50 (µM) |
|---|---|---|---|---|
| (5,6-dichloro-1-(4-chlorobenzyl)benzimidazole) | EBP211 | 69 | 93, 91 | |
| (4-amino-5,6-dimethyl-1-(4-chlorobenzyl)benzimidazole) | EBP238 | 69 | 100, 100 | |
| (N-(1-(4-methoxybenzyl)-2,5,6-trimethylbenzimidazol-4-yl)-4-fluorobenzenesulfonamide) | EBP132 | 70 | 93, 79 | |
| (2-((2-(hydroxymethyl)pyrrolidin-1-yl)methyl)-1-(4-chlorobenzyl)-6-hydroxybenzimidazole) | EBP485 | 70 | 87, 78 | |
| (2-((2-(hydroxymethyl)pyrrolidin-1-yl)methyl)-1-(4-chlorobenzyl)benzimidazole) | EBP163 | 71 | >100, >100 | <1 |

TABLE B-continued

| Clemizole Like Analogs | | | | |
|---|---|---|---|---|
| Structure | Eiger ID | 2a % activity @ 5 μM | 2a Cell Viability @ 5, 10 μM | hERG IC50 (μM) |
| | EBP195 | 71 | >100, >100 | |
| | EBP225 | 71 | >100, >100 | |
| | EBP131 | 71 | 94, 61 | |
| | EBP306 | 71 | >100 (3 uM), 93 (6 uM) | |
| | EBP104 | 72 | 98, 96 | |
| | EBP012 | 73 | >100, 93 | |

TABLE B-continued

Clemizole Like Analogs

| Structure | Eiger ID | 2a % activity @ 5 μM | 2a Cell Viability @ 5, 10 μM | hERG IC50 (μM) |
|---|---|---|---|---|
| (MeO-benzimidazole with 4-chlorobenzyl and (S)-2-methylpyrrolidinylmethyl) | EBP489 | 73 | 100, 97 | |
| (4-NO2, 5,6-dimethylbenzimidazole with 4-methoxybenzyl) | EBP303 | 74 | 95, 74 | |
| (5,6-dimethylbenzimidazole with 4-chlorobenzyl and 3-methylbut-1-enyl) | EBP322 | 74 | >100, 95 | |
| (6-methoxybenzimidazole with 4-chlorobenzyl and 2-(hydroxymethyl)piperidinylmethyl) | EBP488 | 74 | 89, 84 | |
| (5,6-dimethylbenzimidazole with 4-chlorobenzyl and N-SO2Me-pyrrolidinyl vinyl) | EBP471 | 75 | 95, 100 | |
| (6-hydroxybenzimidazole with 4-chlorobenzyl and (S)-2-methylpyrrolidinylmethyl) | EBP487 | 75 | 93, 92 | |

TABLE B-continued
Clemizole Like Analogs
| Structure | Eiger ID | 2a % activity @ 5 μM | 2a Cell Viability @ 5, 10 μM | hERG IC50 (μM) |
|---|---|---|---|---|
| 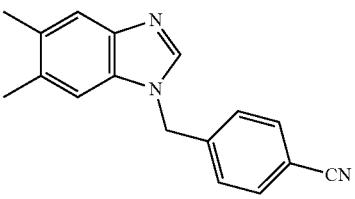 [SMILES: Cc1cc2ncn(Cc3ccc(C#N)cc3)c2cc1C] | EBP061 | 76 | 86, 88 | |
| 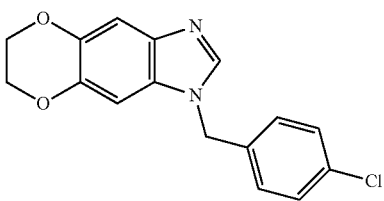 [SMILES: Clc1ccc(Cn2cnc3cc4c(cc32)OCCO4)cc1] | EBP217 | 76 | >100, 94 | |
| 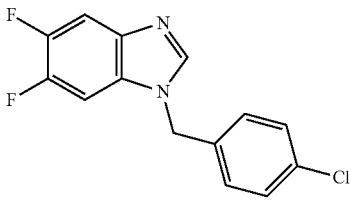 [SMILES: Fc1cc2ncn(Cc3ccc(Cl)cc3)c2cc1F] | EBP269 | 76 | 97, 85 | |
| 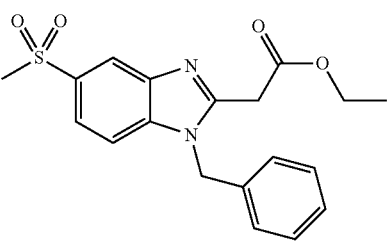 [SMILES: CCOC(=O)Cc1nc2cc(S(C)(=O)=O)ccc2n1Cc1ccccc1] | EBP109 | 76 | 100, 100 | |
| 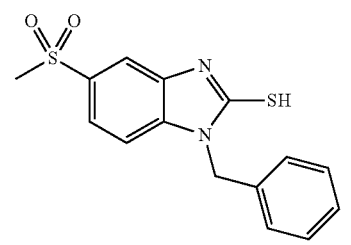 [SMILES: CS(=O)(=O)c1ccc2c(c1)nc(S)n2Cc1ccccc1] | EBP110 | 76 | 98, 90 | |
| 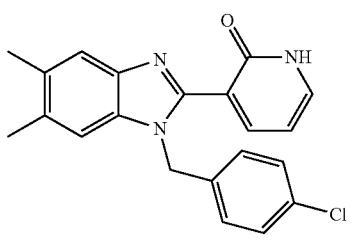 [SMILES: Cc1cc2nc(-c3ccc[nH]c3=O)n(Cc3ccc(Cl)cc3)c2cc1C] | EBP128 | 76 | 92, 94 | |

TABLE B-continued

Clemizole Like Analogs

| Structure | Eiger ID | 2a % activity @ 5 μM | 2a Cell Viability @ 5, 10 μM | hERG IC50 (μM) |
|---|---|---|---|---|
| (structure) | EBP363 | 76 | 100, 100 | |
| (structure) | EBP376 | 76 | 105, 98 | >10 |
| (structure) | EBP486 | 76 | 100, 100 | |
| (structure) | EBP142 | 77 | >100, >100 | |
| (structure) | EBP152 | 77 | >100, >100 | |
| (structure) | EBP193 | 77 | >100, >100 | |

TABLE B-continued

Clemizole Like Analogs

| Structure | Eiger ID | 2a % activity @ 5 µM | 2a Cell Viability @ 5, 10 µM | hERG IC50 (µM) |
|---|---|---|---|---|
| (5,6-dimethyl benzimidazole, N1-(4-chlorobenzyl), C2-CH2-pyrrolidine-2-CH2OH) | EBP229 | 77 | 90, 79 | |
| (5,6-dihydroxy benzimidazole, N1-(4-chlorobenzyl)) | EBP215 | 77 | 97, 95 | |
| (5,6-dimethyl benzimidazole, N1-(4-chlorobenzyl), C2-CH2-(2-oxopyrrolidine)) | EBP216 | 77 | 97, 95 | |
| (4-diethylamino-5,6-dimethyl benzimidazole, N1-(4-chlorobenzyl)) | EBP246 | 77 | >100, 98 | |
| (6-methoxy benzimidazole, N1-(4-chlorobenzyl), C2-CH2-pyrrolidine) | EBP482 | 77 | 100, 100 | |
| (benzimidazole, N1-(5-chlorothiophen-2-ylmethyl), C2-CH2-pyrrolidine) | EBP187 | 78 | >100, 99 | |

TABLE B-continued

Clemizole Like Analogs

| Structure | Eiger ID | 2a % activity @ 5 μM | 2a Cell Viability @ 5, 10 μM | hERG IC50 (μM) |
|---|---|---|---|---|
| (HOOC-benzimidazole-CH2-4-chlorophenyl) | EBP226 | 78 | >100, >100 | |
| (5,6-dimethyl-benzimidazole-2-CH2-prolinamide, N-4-chlorobenzyl) | EBP234 | 78 | ND | |
| (5,6-dimethyl-benzimidazole-2-CH2-O-iPr, N-4-chlorobenzyl) | EBP326 | 78 | >100, >100 | |
| (5,6-dimethyl-benzimidazole-2-piperidinylidene, N-4-chlorobenzyl) | EBP422 | 78 | 89, 80 | |
| (benzimidazole-2-CH2-pyrrolidine, N-4-isopropylbenzyl) | EBP198 | 79 | >100, 100 | |
| (5,6-dimethyl-benzimidazole-2-(2-oxo-1,2-dihydropyridin-5-yl), N-4-chlorobenzyl) | EBP129 | 79 | 90, 78 | |

TABLE B-continued

| | | Clemizole Like Analogs | | |
|---|---|---|---|---|
| Structure | Eiger ID | 2a % activity @ 5 μM | 2a Cell Viability @ 5, 10 μM | hERG IC50 (μM) |
| | EBP323 | 79 | >100, 99 | |
| | EBP431 | 79 | 100, 92 | |
| | EBP020 | 80 | >100, 68 | |
| | EBP186 | 80 | >100, 99 | |
| | EBP194 | 80 | >100, >100 | |

TABLE B-continued
Clemizole Like Analogs
| Structure | Eiger ID | 2a % activity @ 5 μM | 2a Cell Viability @ 5, 10 μM | hERG IC50 (μM) |
|---|---|---|---|---|
| 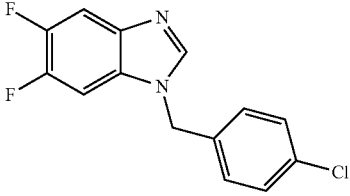 [SMILES: Fc1cc2ncn(Cc3ccc(Cl)cc3)c2cc1F] | EBP208 | 80 | >100, >100 | |
| 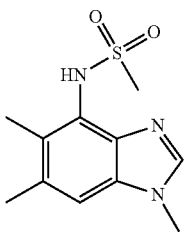 [SMILES: Cc1cc2c(ncn2C)c(NS(C)(=O)=O)c1C] | EBP171 | 80 | >100, >100 | |
| 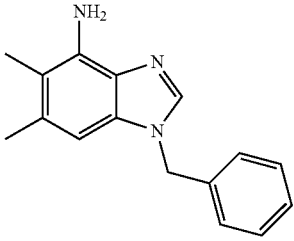 [SMILES: Cc1cc2c(ncn2Cc2ccccc2)c(N)c1C] | EBP102 | 80 | 100, 100 | |
| 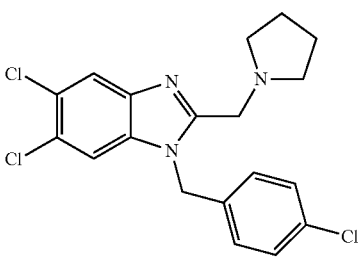 [SMILES: Clc1ccc(Cn2c(CN3CCCC3)nc3cc(Cl)c(Cl)cc32)cc1] | EBP127 | 80 | >100, >100 | |
| 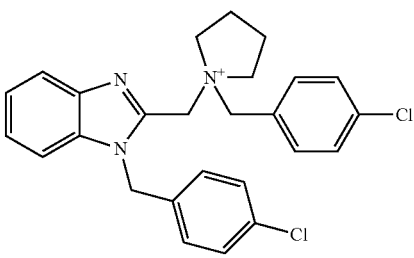 [SMILES: Clc1ccc(Cn2c(C[N+]3(Cc4ccc(Cl)cc4)CCCC3)nc3ccccc32)cc1] | EBP310 | >10 | >100, >100 | |
| 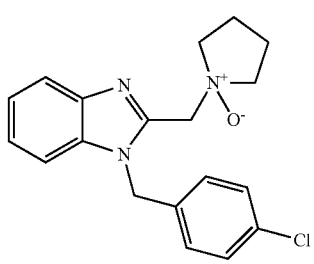 [SMILES: [O-][N+]1(Cc2nc3ccccc3n2Cc2ccc(Cl)cc2)CCCC1] | EBP405 | >10 | 100, 96 | |

TABLE B-continued

Clemizole Like Analogs

| Structure | Eiger ID | 2a % activity @ 5 μM | 2a Cell Viability @ 5, 10 μM | hERG IC50 (μM) |
|---|---|---|---|---|
| 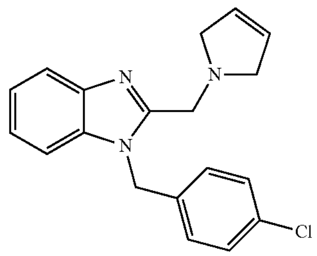 [SMILES: Clc1ccc(Cn2c(CN3CC=CC3)nc3ccccc32)cc1] | EBP409 | 80 | 100, 98 | |
| 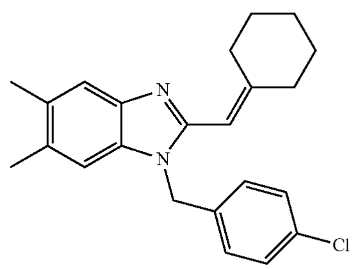 [SMILES: Cc1cc2nc(C=C3CCCCC3)n(Cc3ccc(Cl)cc3)c2cc1C] | EBP466 | 80 | 100, 100 | |
| 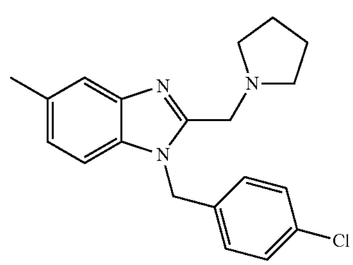 [SMILES: Cc1ccc2c(c1)nc(CN1CCCC1)n2Cc1ccc(Cl)cc1] | EBP183 | 81 | >100, 99 | |
| 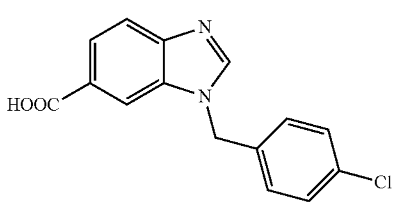 [SMILES: O=C(O)c1ccc2ncn(Cc3ccc(Cl)cc3)c2c1] | EBP227 | 81 | >100, >100 | |
| 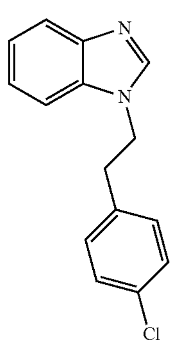 [SMILES: Clc1ccc(CCn2cnc3ccccc32)cc1] | EBP228 | 81 | TBD | |

TABLE B-continued

Clemizole Like Analogs

| Structure | Eiger ID | 2a % activity @ 5 μM | 2a Cell Viability @ 5, 10 μM | hERG IC50 (μM) |
|---|---|---|---|---|
| (structure) | EBP484 | 81 | 87, 83 | 5 |
| (structure) | EBP052 | 82 | 91, 82 | |
| (structure) | EBP184 | 82 | >100, 90 | |
| (structure) | EBP199 | 82 | 90, 93 | |
| (structure) | EBP479 | 82 | 91, 91 | |
| (structure) | EBP008 | 83 | 91, 82 | |

TABLE B-continued

| Structure | Eiger ID | 2a % activity @ 5 μM | 2a Cell Viability @ 5, 10 μM | hERG IC50 (μM) |
|---|---|---|---|---|
| 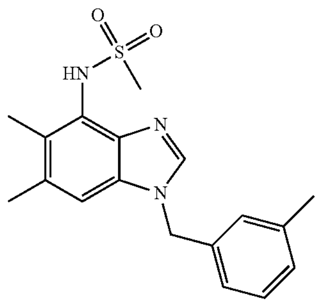 | EBP167 | 83 | >100, >100 | |
| 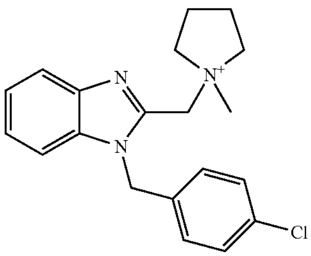 [SMILES: C[N+]1(Cc2nc3ccccc3n2Cc2ccc(Cl)cc2)CCCC1] | EBP311 | 83 | >100, >100 | |
| 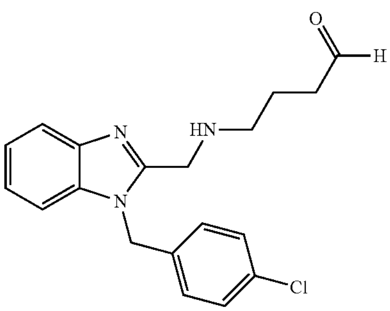 [SMILES: O=CCCCNCc1nc2ccccc2n1Cc1ccc(Cl)cc1] | EBP499 | 83 | 100, 100 | |
| 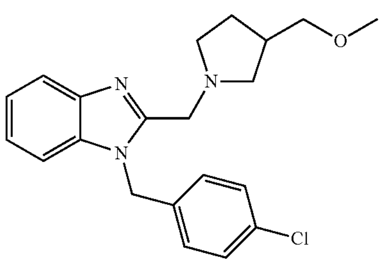 [SMILES: COCC1CCN(Cc2nc3ccccc3n2Cc2ccc(Cl)cc2)C1] | EBP138 | 84 | 98, 98 | |
| 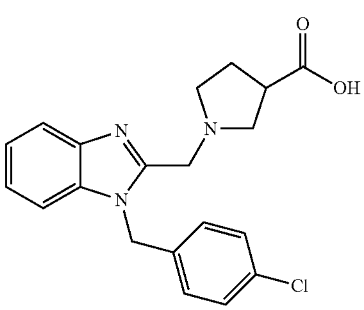 [SMILES: O=C(O)C1CCN(Cc2nc3ccccc3n2Cc2ccc(Cl)cc2)C1] | EBP141 | 84 | >100, >100 | |

TABLE B-continued

Clemizole Like Analogs

| Structure | Eiger ID | 2a % activity @ 5 μM | 2a Cell Viability @ 5, 10 μM | hERG IC50 (μM) |
|---|---|---|---|---|
| (benzimidazole with 2-CH2-pyrrolidine and N1-CH2-C6H4-4-COOH) | EBP153 | 84 | >100, >100 | |
| (benzimidazole with 2-CH2-pyrrolidine and N1-CH2-C6H4-3-COOH) | EBP155 | 84 | >100, >100 | |
| (benzimidazole with 2-CH2OH and N1-CH2-C6H4-4-Cl) | EBP143 | 85 | >100, >100 | >30 |
| (benzimidazole with 2-CH2-piperidine and N1-CH2-C6H4-4-Cl) | EBP133 | 86 | >100, >100 | |
| (benzimidazole with 2-CH2-pyrrolidine and N1-CH2-cyclohexyl) | EBP160 | 86 | >100, >100 | |

TABLE B-continued

Clemizole Like Analogs

| Structure | Eiger ID | 2a % activity @ 5 μM | 2a Cell Viability @ 5, 10 μM | hERG IC50 (μM) |
|---|---|---|---|---|
| 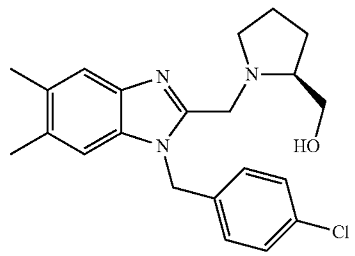 [SMILES: Cc1cc2nc(CN3CCC[C@H]3CO)n(Cc3ccc(Cl)cc3)c2cc1C] | EBP230 | 86 | 94, 85 | |
| 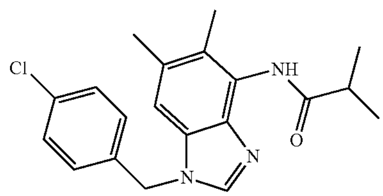 [SMILES: Cc1cc2c(ncn2Cc2ccc(Cl)cc2)c(NC(=O)C(C)C)c1C] | EBP240 | 86 | >100, 99 | |
| 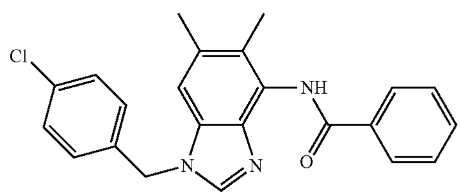 [SMILES: Cc1cc2c(ncn2Cc2ccc(Cl)cc2)c(NC(=O)c2ccccc2)c1C] | EBP242 | 86 | >100, >100 | |
| 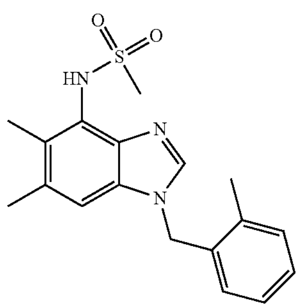 [SMILES: Cc1ccccc1Cn1cnc2c(NS(C)(=O)=O)c(C)c(C)cc21] | EBP166 | 86 | 97, 91 | |
| 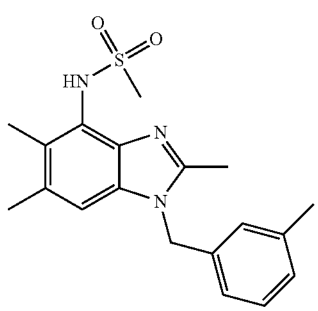 | EBP169 | 86 | >100, 97 | |
| 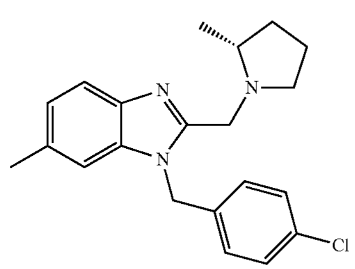 [SMILES: Cc1ccc2nc(CN3CCC[C@H]3C)n(Cc3ccc(Cl)cc3)c2c1] | EBP427 | 86 | 100, 91 | |

TABLE B-continued

Clemizole Like Analogs

| Structure | Eiger ID | 2a % activity @ 5 μM | 2a Cell Viability @ 5, 10 μM | hERG IC50 (μM) |
|---|---|---|---|---|
| 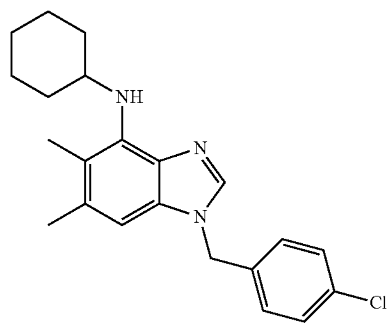 [SMILES: Cc1cc2c(ncn2Cc2ccc(Cl)cc2)c(NC2CCCCC2)c1C] | EBP435 | 86 | 100, 93 | |
| 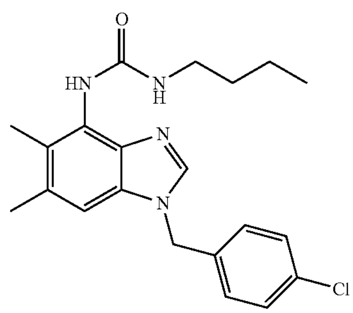 [SMILES: CCCCNC(=O)Nc1c(C)c(C)cc2c1ncn2Cc1ccc(Cl)cc1] | EBP245 | 87 | 96, 93 | |
| 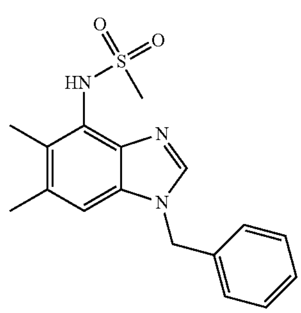 [SMILES: Cc1cc2c(ncn2Cc2ccccc2)c(NS(C)(=O)=O)c1C] | EBP168 | 87 | >100, 96 | |
| 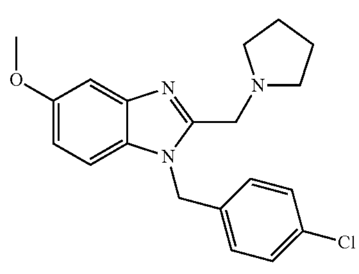 [SMILES: COc1ccc2c(c1)nc(CN1CCCC1)n2Cc1ccc(Cl)cc1] | EBP365 | 87 | 100, 100 | |
| 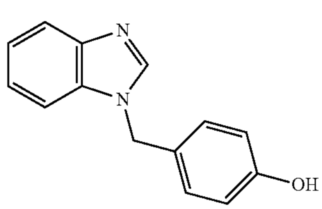 [SMILES: Oc1ccc(Cn2cnc3ccccc32)cc1] | EBP067 | 88 | 85, 88 | |

TABLE B-continued

Clemizole Like Analogs

| Structure | Eiger ID | 2a % activity @ 5 μM | 2a Cell Viability @ 5, 10 μM | hERG IC50 (μM) |
|---|---|---|---|---|
| (benzimidazole with 2-(pyrrolidin-1-ylmethyl) and N-(3-methoxycarbonylbenzyl)) | EBP154 | 89 | >100, >100 | |
| (benzimidazole with 2-((2S)-2-hydroxymethylpyrrolidin-1-ylmethyl) and N-(4-chlorobenzyl)) | EBP270 | 89 | >100, 98 | |
| (5,6-dimethyl-4-(cyclopropanesulfonamido)benzimidazole with N-(4-chlorobenzyl)) | EBP430 | 89 | 98, 92 | |
| (benzimidazole with 2-(pyrrolidin-1-ylmethyl) and N-(2-chlorobenzyl)) | EBP157 | 90 | >100, >100 | |
| (5,6-dimethyl-4-(methanesulfonamido)benzimidazole with N-(4-chlorobenzyl)) | EBP243 | 90 | >100, >100 | |

TABLE B-continued

Clemizole Like Analogs

| Structure | Eiger ID | 2a % activity @ 5 μM | 2a Cell Viability @ 5, 10 μM | hERG IC50 (μM) |
|---|---|---|---|---|
| (structure) | EBP316 | 90 | 97, 93 | |
| (structure) | EBP408 | 90 | 100, 100 | |
| (structure) | EBP425 | 90 | 100, 100 | 0.65 |
| (structure) | EBP432 | 90 | 93, 94 | |

Tables A and B demonstrate, without being bound by theory, that a basic amine (even pyridyl is basic enough) in $R_2$ typically confers activity in the 1b replicon assay, and the basic amine is at least part of a C-linked heteroalkyl or heteroaryl. While not wishing to be bound by theory, in certain embodiments of the present invention, the basic amine, that is part of a compound of the present invention, may need to be positioned further from the benzimidazole core than it is in clemizole to have activity in the 1b assay, as evidenced by those analogs where $R_2$ is an N-linked heterocycle, which are generally inactive in the 1b replicon assay, perhaps due to the amine being too close to the benzimidazole.

Compounds of the invention that are less preferred due to high hERG activity, high cell toxicity, or low activity in the 2a infectious clone assay are listed below:

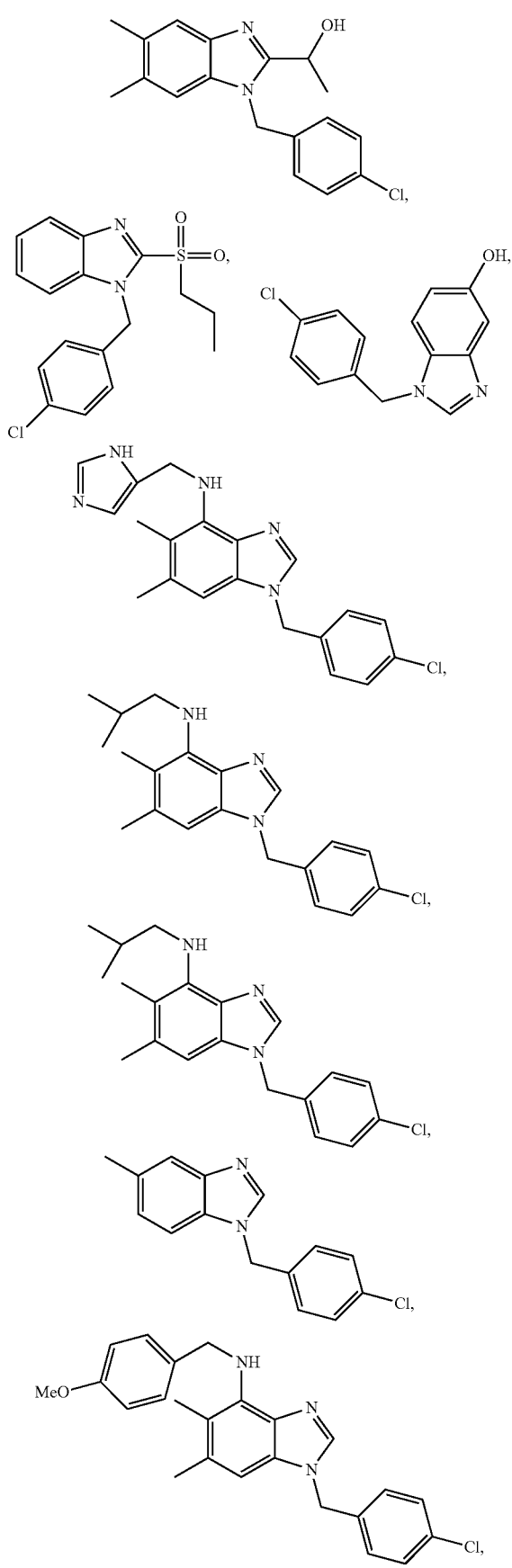

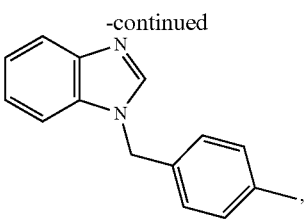

-continued

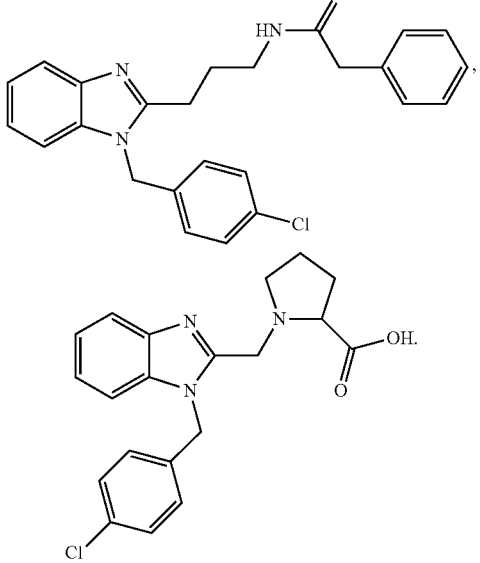

Example 5

Synergy Studies

Combination studies were conducted in the 1b replicon assay, combining at least two compounds at several concentrations (below, at, and above its EC50 value in the 1b replicon assay). Luciferase values were then analyzed using MacSynergy™ to determine whether the affects of the drug combinations were strongly synergistic (synergy volume>100), moderately synergistic (50<synergy volume<100), mildly synergistic (25<synergy volume<50), additive (−25<synergy volume<25), mildly antagonistic (−50<synergy volume<−25), moderately antagonistic (−100<synergy volume<−50) or strongly antagonistic (synergy volume<−100). To illustrate, see combinations of EBP1 and boceprevir (EBP520) (Entry 1) in Table D, which shows a synergy volume of 100 $\mu M^2$ for 1b and 207 $\mu M^2$ for 2a, indicating strong synergism for both genotype 1b and 2a.

Additional synergistic combinations between boceprevir (EBP520) and other benzimidazole analogs were identified as exemplified in entries 9 (boceprevir and EBP490), (boceprevir and EBP273), and 11 (boceprevir and EBP317). EBP490, EBP273 and EBP317 have $EC_{50}$ values greater than 25 μM in the 48 hour 1b replicon assay; however, all three compounds demonstrate<50% replication activity at 5 μM of test compound in the 2a infectious clone assay (in other words, all three compounds have an EC50<5 μM in the 2a assay, in which clemizole has an $EC_{50}$ of 8 μM).

In the table or results below, EBP520 is boceprivir, EBP521 is ITMN-191 (also known as RG7227), EBP883 is a compound in development by BMS, and EBP954 is ribavirin.

TABLE C
Synergy Study

| Entry | Combo | | MacSynergy | | |
|---|---|---|---|---|---|
| | Cmpd #1 | Cmpd #2 | Lab | Results (μM²) | Comments |
| 1 | EBP1 | EBP520 | 1b/2a | 100 (1b) 207 (2a) | Strong synergy |
| 2 | EBP1 | EBP521 | 1b | −35 | Additivity |

TABLE C-continued

Synergy Study

| Entry | Cmpd #1 | Combo Cmpd #2 | Lab | MacSynergy Results (μM²) | Comments |
|---|---|---|---|---|---|
| 3 | EBP1 | MK7009 | 1b | TBD | Mar. 5, 2010 |
| 4 | EBP1 | VX-750 | 1b | TBD | Mar. 5, 2010 |

TABLE C-continued

Synergy Study

| Entry | Combo | | Lab | MacSynergy Results (μM²) | Comments |
|---|---|---|---|---|---|
| | Cmpd #1 | Cmpd #2 | | | |
| 5 | EBP1 | EBP883 | 1b | −49 | Mild antagonism |
| 6 | EBP1 | EBP954 | 1b/2a | n/a | Additivity |
| 7 | EBP1 | HCV796, ViroPharma | 2a | n/a | Additivity |
| 8 | EBP1 | IFN-2a | 2a | n/a | Additivity |
| 9 | EBP1 | EBP520 (EBP490) | 1b | 135 | Strong synergy |

TABLE C-continued

Synergy Study

| Entry | Combo | | MacSynergy | | |
|---|---|---|---|---|---|
| | Cmpd #1 | Cmpd #2 | Lab | Results (µM²) | Comments |
| 10 | EBP273 | EBP520 | 1b | 73 | Moderate synergy |
| 11 | EBP317 | EBP520 | 1b | 35 | Mild synergy |
| 12 | EBP714 | EBP520 | 1b | 18 | Additivity |

TABLE C-continued

Synergy Study

| Entry | Combo | | MacSynergy | | |
|---|---|---|---|---|---|
| | Cmpd #1 | Cmpd #2 | Lab | Results (μM²) | Comments |
| 13 | EBP882 | EBP520 | 1b | −68 | Moderate antagonism |
| 14 | EBP467 | EBP521 | 1b | −110 | Strong antagonism |

TABLE C-continued
Synergy Study
| Entry | Combo | | MacSynergy | | |
|---|---|---|---|---|---|
| | Cmpd #1 | Cmpd #2 | Lab | Results (µM²) | Comments |
| 15 | 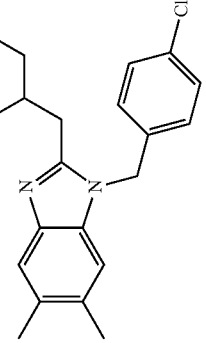 EBP467 | EBP520 | 1b | 9 | Additivity |
| 16 | 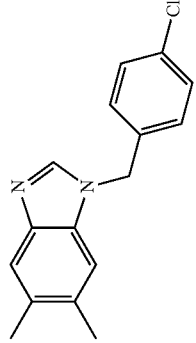 EBP3 | EBP520 | 1b | −90 | Strong antagonism |
| 17 | 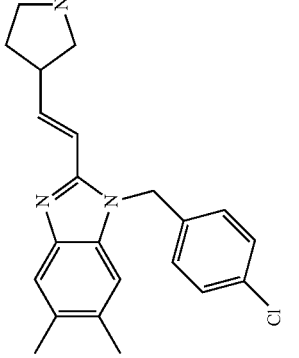 EBP372 | EBP520 | 1b | 2 | Additivity |

TABLE C-continued
Synergy Study
| Entry | Combo Cmpd #1 | Cmpd #2 | MacSynergy Lab | Results (µM²) | Comments |
|---|---|---|---|---|---|
| 18 |  EBP461 | EBP520 | 1b | 28 | Additivity |
| 19 |  EBP933 | EBP520 | 1b | −25 | Additivity |
| 20 |  EBP809 | EBP520 | 1b | −62 | Mild antagonism |

TABLE C-continued
Synergy Study
| | Combo | | MacSynergy | | |
|---|---|---|---|---|---|
| Entry | Cmpd #1 | Cmpd #2 | Lab | Results (μM²) | Comments |
| 21 | 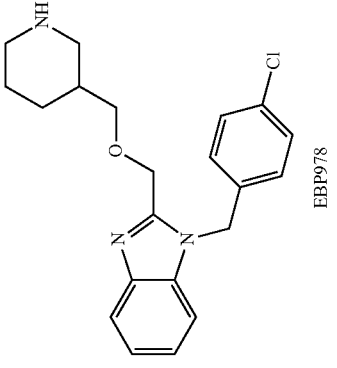<br>EBP978 | EBP520 | 1b | −19 | Additivity |

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, +2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

The invention claimed is:

1. A compound having the structure shown in Formula III-C

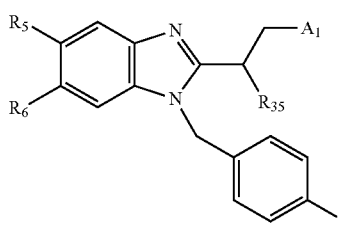

Formula III-C or a pharmaceutically acceptable salt, a tautomer, or a prodrug thereof,
  $A_1$ is a substituted or an unsubstituted, 5 or 6 membered, non aromatic heterocycle containing one basic nitrogen atom or a substituted or an unsubstituted 6 membered heteroaryl containing one basic nitrogen atom, wherein substituted refers to a substitution selected from the group consisting of: alkyl, alkenyl, oxo, aryl, heterocyclo, carbocyclo, halo, hydroxy, alkoxy, aryloxy, alkanoyl, aroyl, alkylester, arylester, cyano, nitro, amido, amino, substituted amino, lactam, urea, urethane, and sulfonyl;
  wherein $R_5$ is a substituted or an unsubstituted $C_1$-$C_3$ alkyl or 5 membered heteroaryl group, wherein substituted refers to a substitution selected from the group consisting of: aryl, heteroaryl, heterocyclo, carbocyclo, halo, hydroxy, protected hydroxy, alkoxy, acyl, aryloxy, alkylester, arylester, alkanoyl, aroyl, carboxy, protected carboxy, cyano, nitro, amino, substituted amino, (monosubstituted)amino, (disubstituted)amino, protected amino, amido, lactam, urea, urethane, and sulfonyl;
  $R_6$ is hydrogen or a substituted or an unsubstituted $C_1$-$C_3$ alkyl, wherein substituted refers to a substitution selected from the group consisting of: aryl, heteroaryl, heterocyclo, carbocyclo, halo, hydroxy, protected hydroxy, alkoxy, acyl, aryloxy, alkylester, arylester, alkanoyl, aroyl, carboxy, protected carboxy, cyano, nitro, amino, substituted amino, (monosubstituted) amino, (disubstituted)amino, protected amino, amido, lactam, urea, urethane, and sulfonyl; and
  $R_{35}$ is hydrogen or a substituted or an unsubstituted $C_1$-$C_3$ alkyl, wherein substituted refers to a substitution selected from the group consisting of: aryl, heteroaryl, heterocyclo, carbocyclo, halo, hydroxy, protected hydroxy, alkoxy, acyl, aryloxy, alkylester, arylester, alkanoyl, aroyl, carboxy, protected carboxy, cyano, nitro, amino, substituted amino, (monosubstituted) amino, (disubstituted)amino, protected amino, amido, lactam, urea, urethane, and sulfonyl.

2. A composition, comprising the following compound,

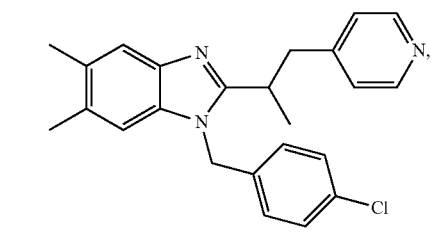 [SMILES: Cc1cc2nc(C(C)Cc3ccncc3)n(Cc3ccc(Cl)cc3)c2cc1C]

or a pharmaceutically acceptable salt, a tautomer, or a prodrug thereof.

3. A compound having the structure shown in Formula III-C

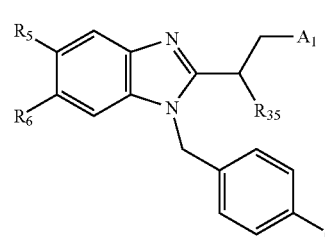

Formula III-C or a pharmaceutically acceptable salt, a tautomer, or a prodrug thereof,
  wherein $A_1$ is a 6 membered, non aromatic heterocycle containing one basic nitrogen atom;
  wherein $R_5$ is a $C_1$-$C_4$ alkyl or 5 membered heteroaryl group;
  wherein $R_6$ is hydrogen or a $C_1$-$C_4$ alkyl; and
  wherein $R_{35}$ is hydrogen or a $C_1$-$C_3$ alkyl.

4. A compound having the structure shown in Formula III-C

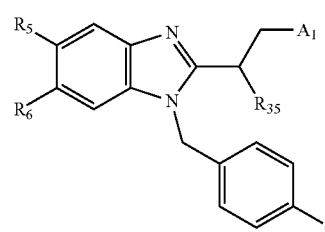

Formula III-C or a pharmaceutically acceptable salt, a tautomer, or a prodrug thereof,
  wherein $A_1$ is a 6 membered heteroaryl containing one basic nitrogen atom;

wherein $R_5$ is a $C_1$-$C_4$ alkyl or 5 membered heteroaryl group;
wherein $R_6$ is hydrogen or a $C_1$-$C_4$ alkyl; and
wherein $R_{35}$ is hydrogen or a $C_1$-$C_3$ alkyl.

5. A compound having the structure shown in Formula III-C

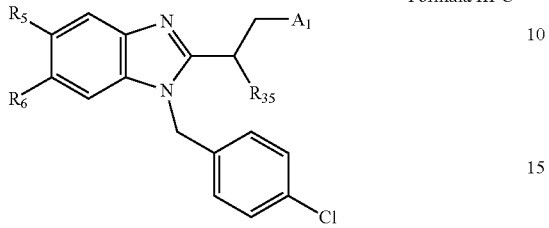

Formula III-C or a pharmaceutically acceptable salt, a tautomer, or a prodrug thereof,
wherein $A_1$ is a 5 or 6 membered, non aromatic heterocycle containing one basic nitrogen atom or a 6 membered heteroaryl containing one basic nitrogen atom;
wherein $R_5$ is a $C_1$-$C_4$ alkyl;
wherein $R_6$ is a $C_1$-$C_4$ alkyl; and
wherein $R_{35}$ is a $C_1$-$C_3$ alkyl.

* * * * *